US006406880B1

(12) United States Patent
Thornton

(10) Patent No.: US 6,406,880 B1
(45) Date of Patent: Jun. 18, 2002

(54) BETAINES AS ADJUVANTS TO SUSCEPTIBILITY TESTING AND ANTIMICROBIAL THERAPY

(75) Inventor: Charles G. Thornton, Gaithersburg, MD (US)

(73) Assignee: Integrated Research Technology, LLC

( * ) Notice: Subject to any disclaimer, the term of this patent is extended or adjusted under 35 U.S.C. 154(b) by 0 days.

(21) Appl. No.: 09/429,614

(22) Filed: Oct. 29, 1999

Related U.S. Application Data

(63) Continuation of application No. PCT/US98/08760, filed on May 1, 1998.
(60) Provisional application No. 60/045,512, filed on May 2, 1997.

(51) Int. Cl.[7] .............................. C12Q 1/18; C12N 1/20; C12N 1/06; A01N 33/02; C07G 11/00

(52) U.S. Cl. ....................... 435/32; 435/253.1; 435/259; 536/16.8; 514/77; 514/192

(58) Field of Search ..................... 514/77, 192; 435/32, 435/253.1, 259; 536/16.8

(56) References Cited

U.S. PATENT DOCUMENTS

| | | | |
|---|---|---|---|
| 3,987,053 A | 10/1976 | Cavalleri et al. ........... | 260/309 |
| 4,075,350 A | 2/1978 | Michaels .................... | 424/316 |
| 4,107,328 A | 8/1978 | Michaels .................... | 424/316 |
| 4,622,297 A | 11/1986 | Kappner et al. .............. | 435/32 |
| 5,399,558 A | 3/1995 | Baker et al. ............. | 514/232.5 |
| 5,523,288 A | 6/1996 | Cohen et al. ................. | 514/12 |
| 5,543,417 A | 8/1996 | Waldstreicher ............. | 514/284 |
| 5,610,198 A | 3/1997 | Barry, III et al. ........... | 514/712 |
| 5,629,288 A * | 5/1997 | Lattrell et al. ................. | 514/9 |
| 5,658,749 A | 8/1997 | Thornton .................... | 435/29 |

FOREIGN PATENT DOCUMENTS

| | | |
|---|---|---|
| WO | WO 95/27076 | 10/1995 |
| WO | WO 98/50576 | 11/1998 |

OTHER PUBLICATIONS

Brennan, P.J., "The Envelope of Mycobacteria," *Annu. Rev. Biochem.* 64:29–63, Annual Reviews, Inc. (1995).
Chambers, H.F., et al., "Can Penicillins and Other β–Lactam Antibiotics Be Used To Treat Tuberculosis?" *Antimicrob. Agents Chemother.* 39:2620–2624, American Society for Microbiology (1995).
Connell, N.D. and Nikaido, H., "Chapter 22: Membrane Permeability and Transport in *Mycobacterium tuberculosis*," in: *Tuberculosis, Pathogenesis, Protection. and Control*, Bloom, B.R., ed., American Society for Microbiology, Washington, D.C., pp. 333–352 (1994).
Cynamon, M.H. and Klemens, S.P., "Chapter 5: Drug Susceptibility Tests for *Mycobacterium fortuitum* and *Mycobacterium chelonae*," in:*Drug Susceptibility in the Chemotherapy of Mycobacterial Infections*, Heifets, L.B., ed., CRC Press, Boca Raton, Florida, pp. 147–159 (1991).
Dubos, R.J. and Davis, B.D., "Factors Affecting the Growth of Tubercle Bacilli in Liquid Media," *J. Exp. Med.* 83:409–423, Rockefeller Institute for Medical Research (1946).
Eng, R.H.K., et al., "Inoculum Effect of New β–Lactam Antibiotics on *Pseudomonas aeruginosa*," *Antimicrob. Agents Chemother.* 26:42–47, American Society for Microbiology (1984).
Heifets, L.B., "Chapter 1: Antituberculosis Drugs: Antimicrobial Activity In Vitro," in: *Drug Susceptibility in the Chemotherapy of Mycobacterial Infections*, Heifets, L.B., ed., CRC Press, Boca Raton, Florida, pp. 13–57 (1991).
Hugo, W.B., "Some Aspects of the Action of Cationic Surface–Active Agents on Microbial Cells with Special Reference to Their Action of Enzymes," in: *Surface Activity and the Microbial Cell*, Staples Printers Ltd., Rochester, England, pp. 67–83 (1965).
Hui, J., et al., "Permeability Barrier to Rifampin in Mycobacteria," *Antimicrob. Agents Chemother.* 11:773–779, American Society for Microbiolgy (1977).
Inderlied, C.B. and Salfinger, M., "Antimicrobial Agents and Susceptibility Tests: Mycobacteria," in: *Manual of Clinical Microbiology*, Murray, P.R. et al., eds., ASM Press Washington, D.C., pp. 1385–1404 (1995).
Jarlier, V. and Nikaido, H., "Permeability Barrier to Hydophilic Solutes in *Mycobacterium chelonei*," *J. Bacteriol*.172:1418–1423, American Society for Microbiology (1990).
Jorgensen, J.H. and Sahm, D.F., "Antimicrobial Susceptibility Testing: General Considerations," in: *Manual of Clinical Microbiology*, Murray, P.R. et al., eds., ASM Press Washington, D.C., pp. 1277–1280 (1995).
Liu, J., et al., "Mycolic Acid Structure Determines the Fluidity of the Mycobacterial Cell Wall," *J. Biol. Chem.* 271:29545–29551, American Society for Biochemistry and Molecular Biology, Inc. (Nov. 1996).
National Committee for Laboratory Standards,"Development of In Vitro Susceptibility Testing Criteria and Quality Control Parameters; Approved Guideline," NCCLS Document M23–A, Villanova, PA (1994).
National Committee for Laboratory Standards, "Performance Standards for Antimicrobial Disk Suscebtibility Tests–Sixth Edition; Approved Standard," NCCLS Document M2–A6, Villanova, PA (Jan. 1997).

(List continued on next page.)

*Primary Examiner*—Michael P. Woodward
*Assistant Examiner*—Marjorie A. Moran
(74) *Attorney, Agent, or Firm*—Sterne, Kessler, Goldstein & Fox P.L.L.C.

(57) ABSTRACT

The present invention is related to methods and compositions for susceptibility testing of bacteria containing mycolic acid structures using betaine-like detergents, and inducing the susceptibility of such bacteria using the same.

64 Claims, 55 Drawing Sheets-

OTHER PUBLICATIONS

National Committee for Laboratory Standards, "Methods for Dilution Antimicrobial Susceptibility Tests for Bacteria that Grow Aerobically–Fourth Edition; Approved Standard," NCCLS Document M7–A4, Villanova, PA (Jan. 1997).

Nikaido, H. and Jarlier, V., "Permeability of the mycobacterial cell wall," *Res. Microbiol.* 142:437–443, Elsevier Science (1991).

Rastogi, N., et al., "Enhancement of Drug Susceptibility of *Mycobacterium avium* by Inhibitors of Cell Envelope Synthesis," *Antimicrob. Agents Chemother.* 34:759–764, American Society for Microbiology (1990).

Roberts, G.D., et al., "Evaluation of the BACTEC Radiometric Method for Recovery of Mycobacteria and Drug Susceptibility testing of *Mycobacterium tuberculosis* from Acid–Fast Smear–Positive Specimens," *J. Clin. Microbiol.* 18:689–696, American Society for Microbiology (1983).

Siddiqi, S.H., et al., "Evaluation of a Rapid Radiometric Method for Drug Susceptibility Testing of *Mycobacterium tuberculosis*," *J. Clin. Microbiol.* 13:908–912, American Society for Microbiology (1981).

Snider Jr., D.E., et al., "Rapid Drug–Susceptibility Testing of *Mycobacterium tuberculosis*," *Am. Rev. Respir. Dis.* 123:402–406, American Lung Association (1981).

Stinson, M.W., et al., Interaction of Tween 80 Detergent with Mycobacteria in Synthetic Medium, *Am. Rev. Respir. Dis.* 104:717–727, American Lung Association (1971).

Tarrand, J.L. and Gröschel, D.H.M., "Evaluation of the BACTEC Radiometric Method for Detection of 1% Resistant Populations of *Mycobacterium tuberculosis*," *J. Clin. Microbiol.* 21:941–946, American Society for Microbiology (1985).

Tsubone, K., et al., "Relation between Structure and Antimicrobial Activity of 2–(N.N.N–Trialkylammonio)alkyl HydrogenPhosphates," *J. Pharm Sci.* 80:441–444, American Pharmaceutical Association (1991).

Tsubone, K., "Correlation between Antimicrobial Activity and Chelating Ability of 2–(N,N,N–Trialkylammonio)alkyl HydrogenPhosphates," *J. Pharm. Sci.* 80:1051–1054, American Pharmaceutical Association (1991).

Vincké, G., et al., "Rapid Susceptibility of *Mycobacterium tuberculosis* by a radiometric technique," *J. Antimicrob. Chemother.* 10:351–354, Academic Press, Inc. (1982).

Woods, G.L. and Washington, J.A., "Antibacterial Susceptibility Tests: Dilution and Disk Diffusion Methods," in: *Manual of Clinical Microbiology*, Murray, P.R. et al., eds., ASM Press Washington, D.C., pp. 1327–1384 (1995).

Yamori, S. and Tsukamura, M., "Paradoxical Effect of Tween 80 between the Susceptibility to Rifampicin and Streptomycin and the Susceptibility to Ethambutol and Sulfadimethoxine in the *Mycobacterium avium–Mycobacterium intracellulare* Complex," *Microbiol. Immunol.* 35:921–926, Center for Academic Publications Japan (1991).

* cited by examiner

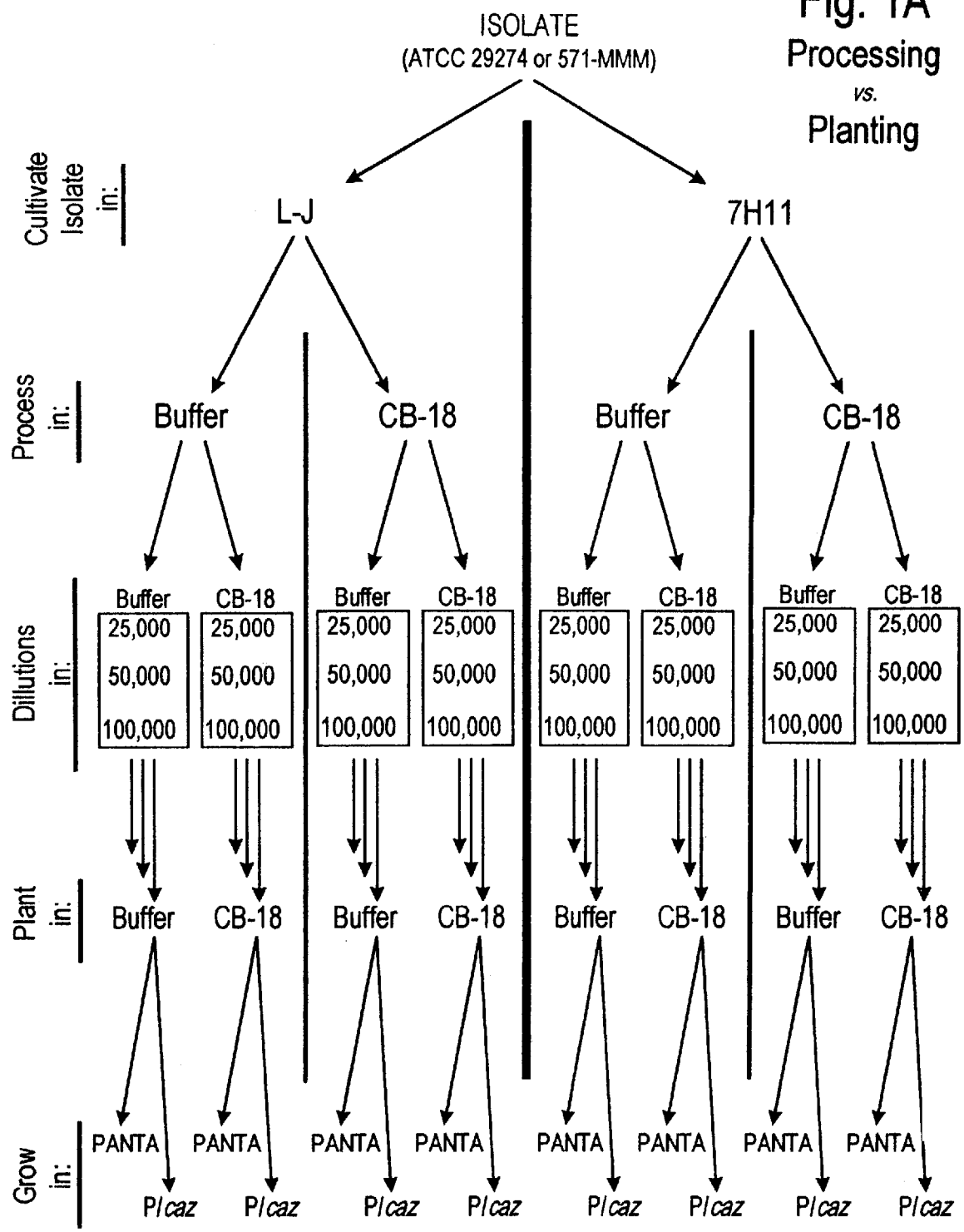

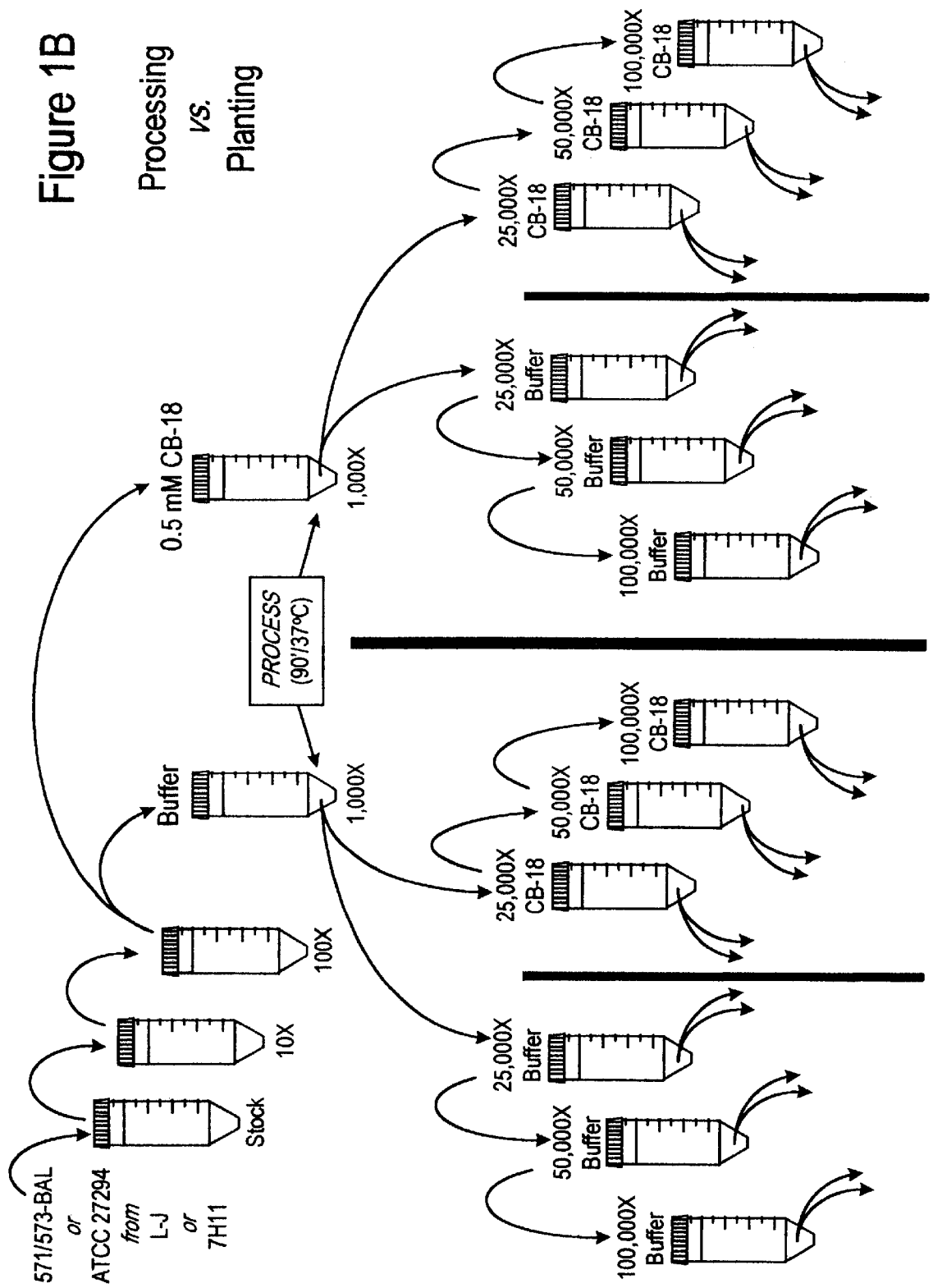

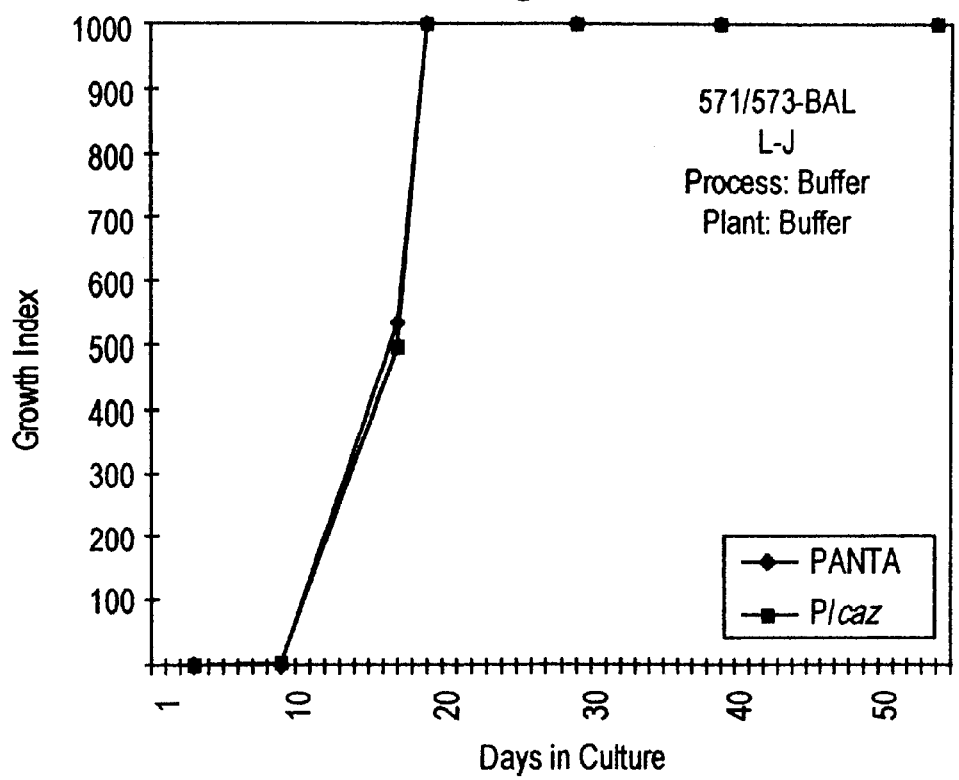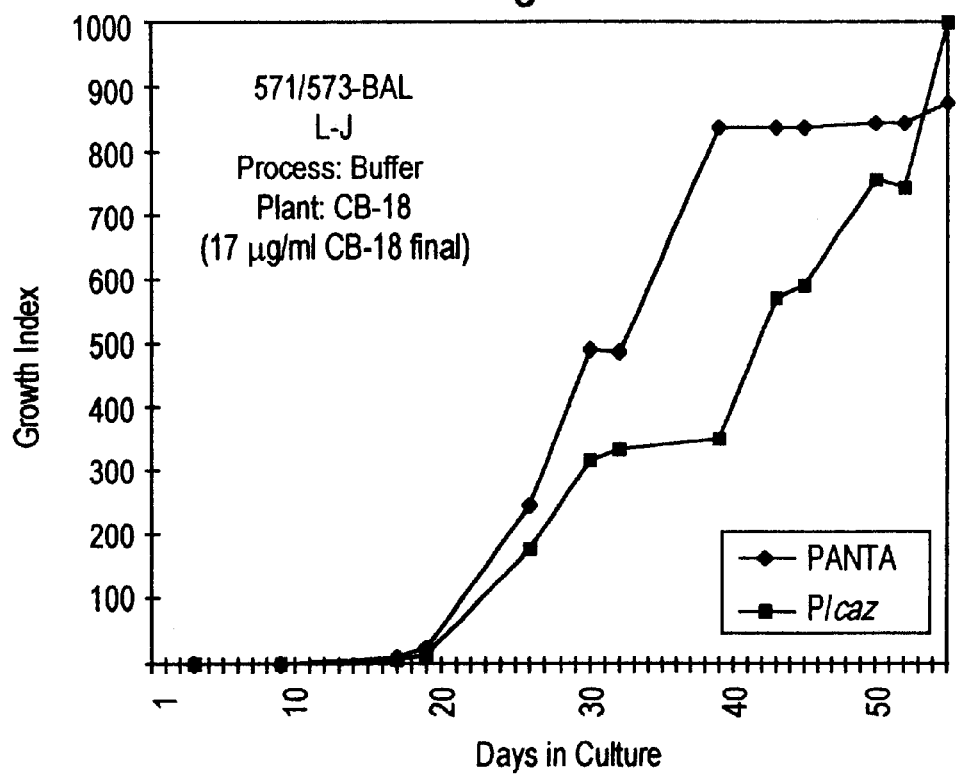

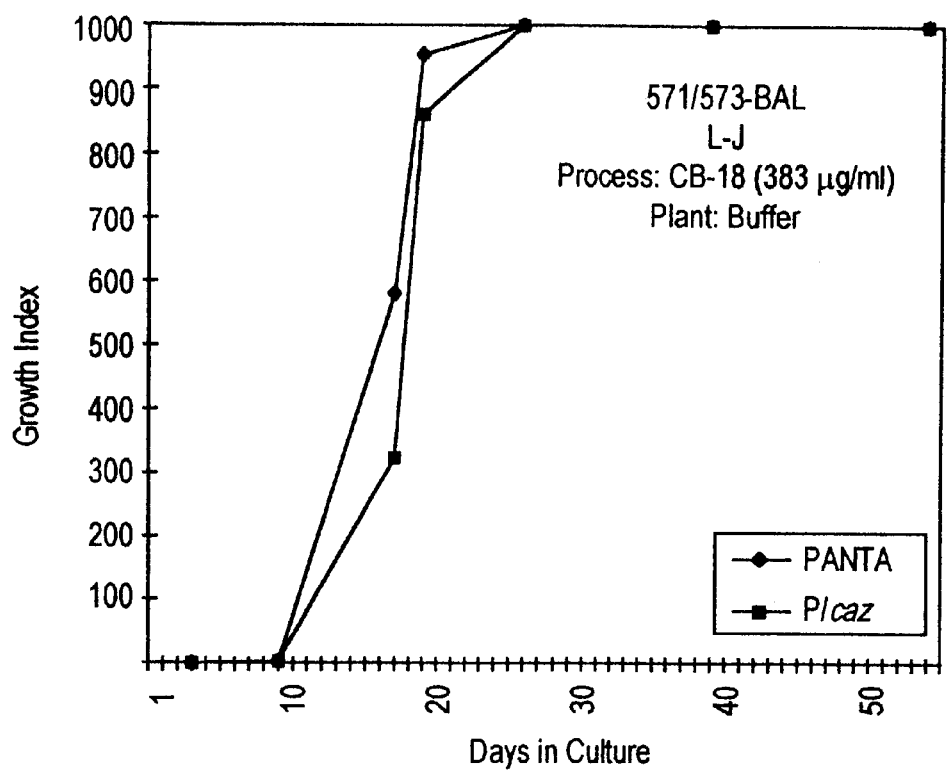
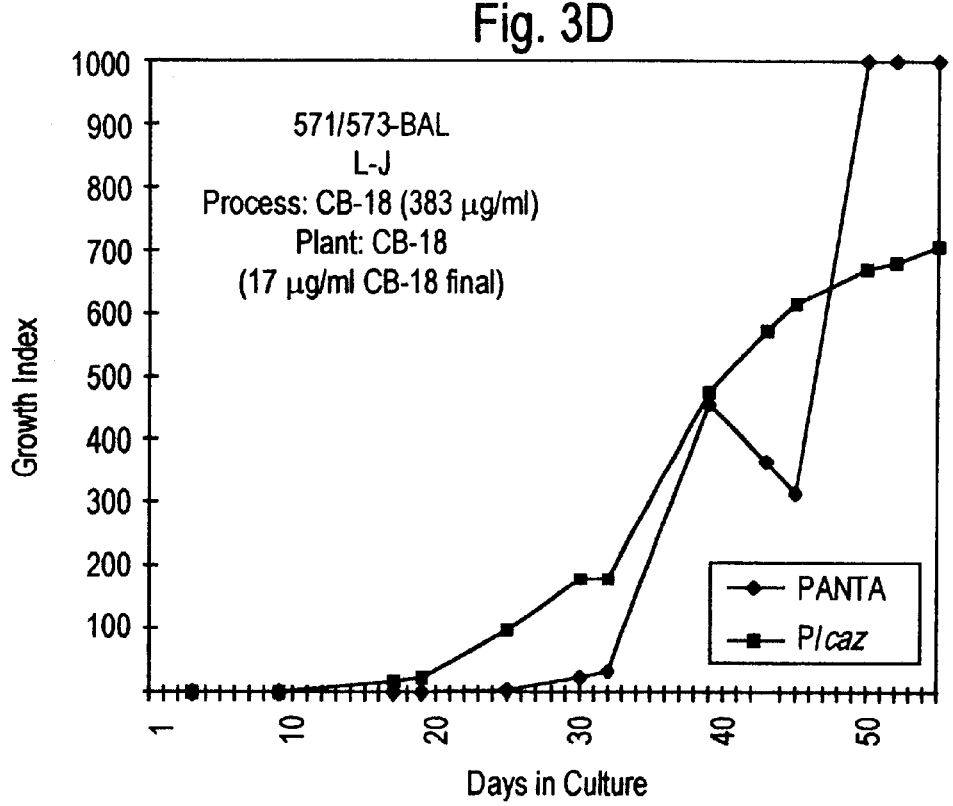

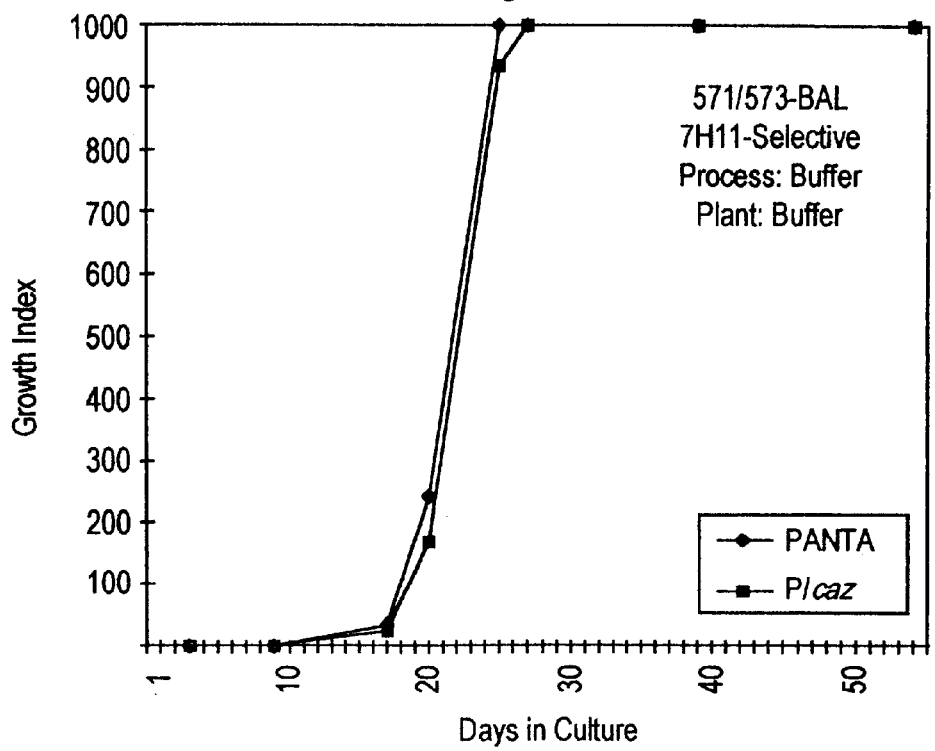
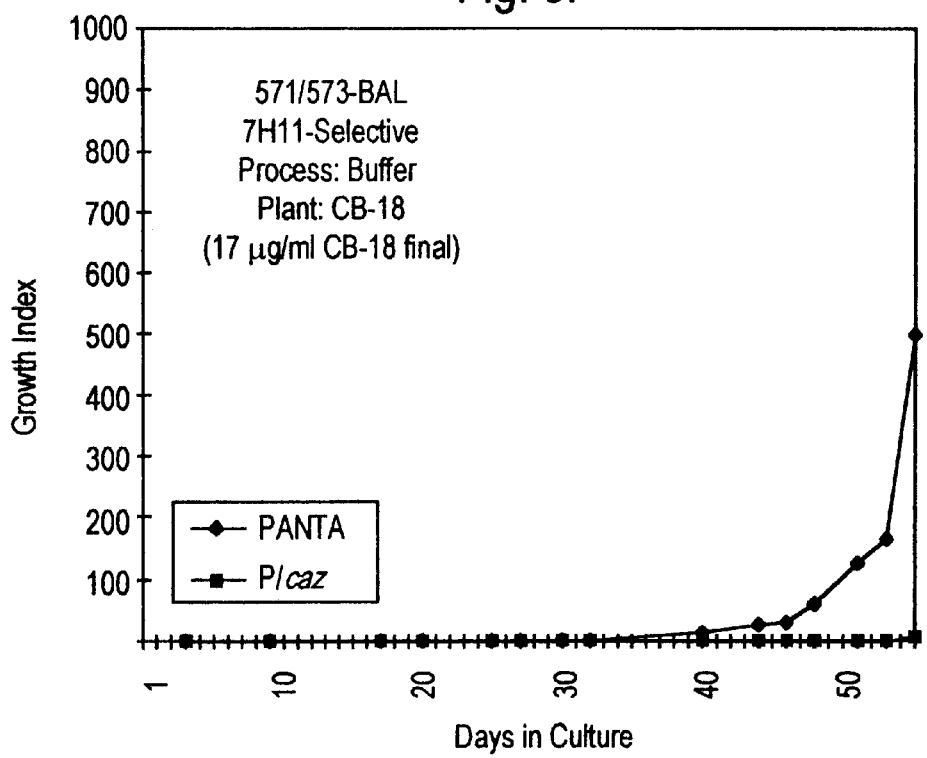

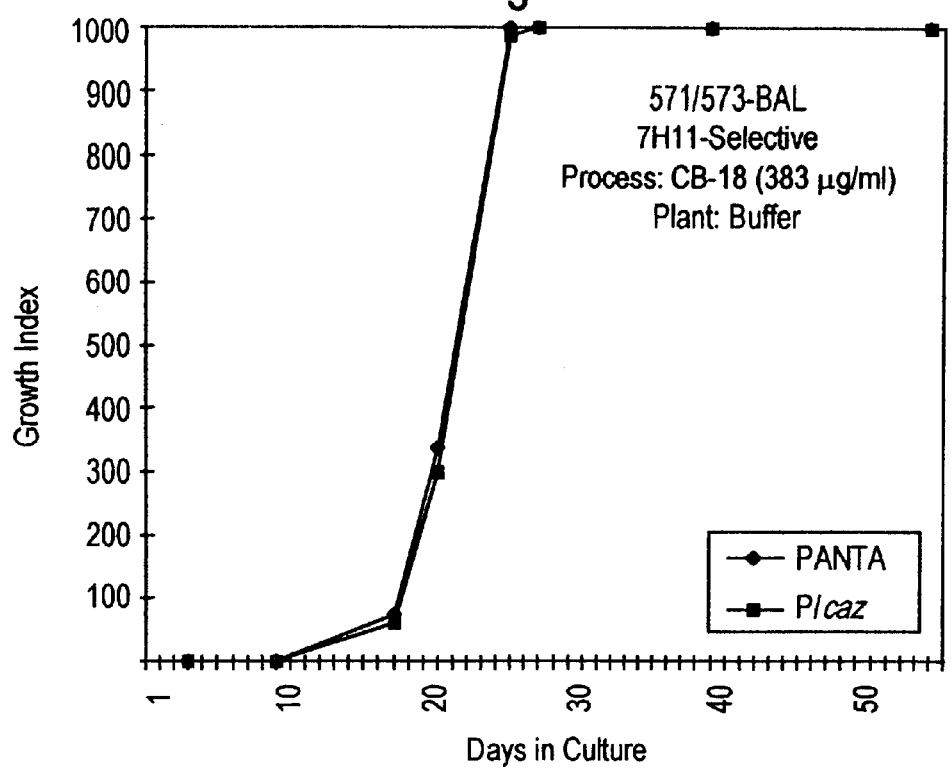
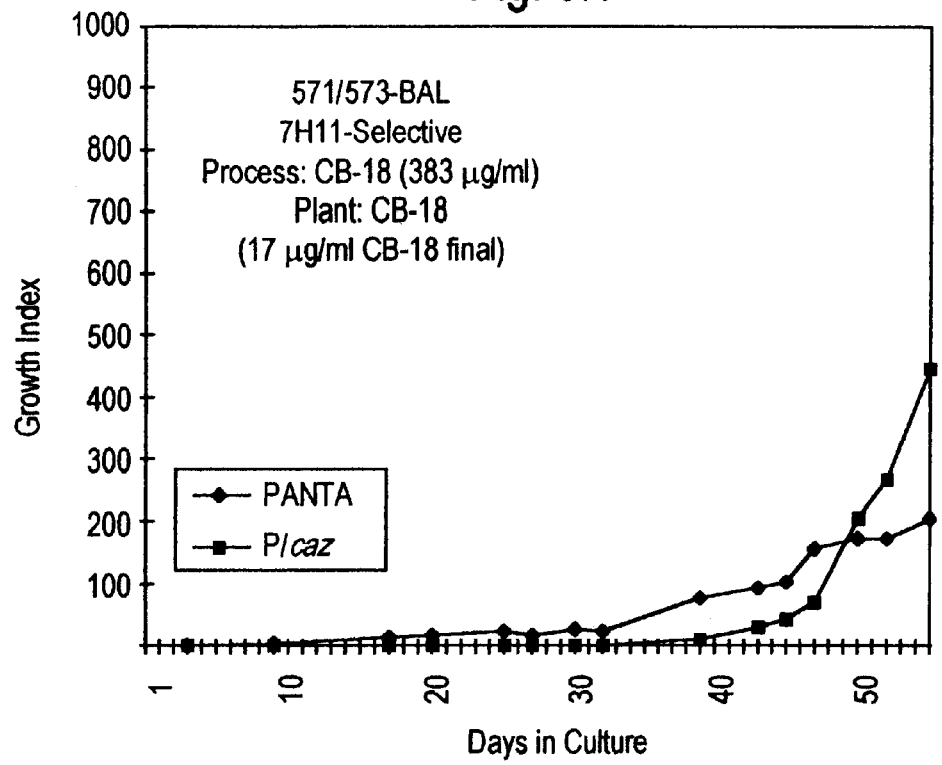

Planting in Lecithin at Low Inocula

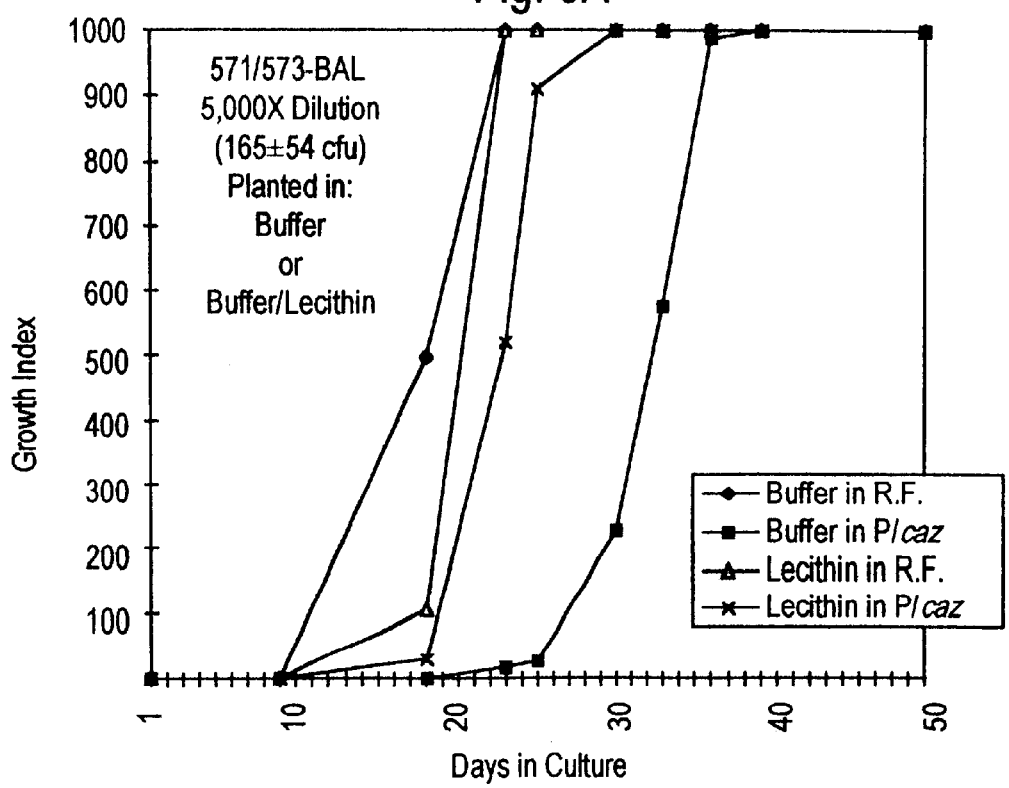
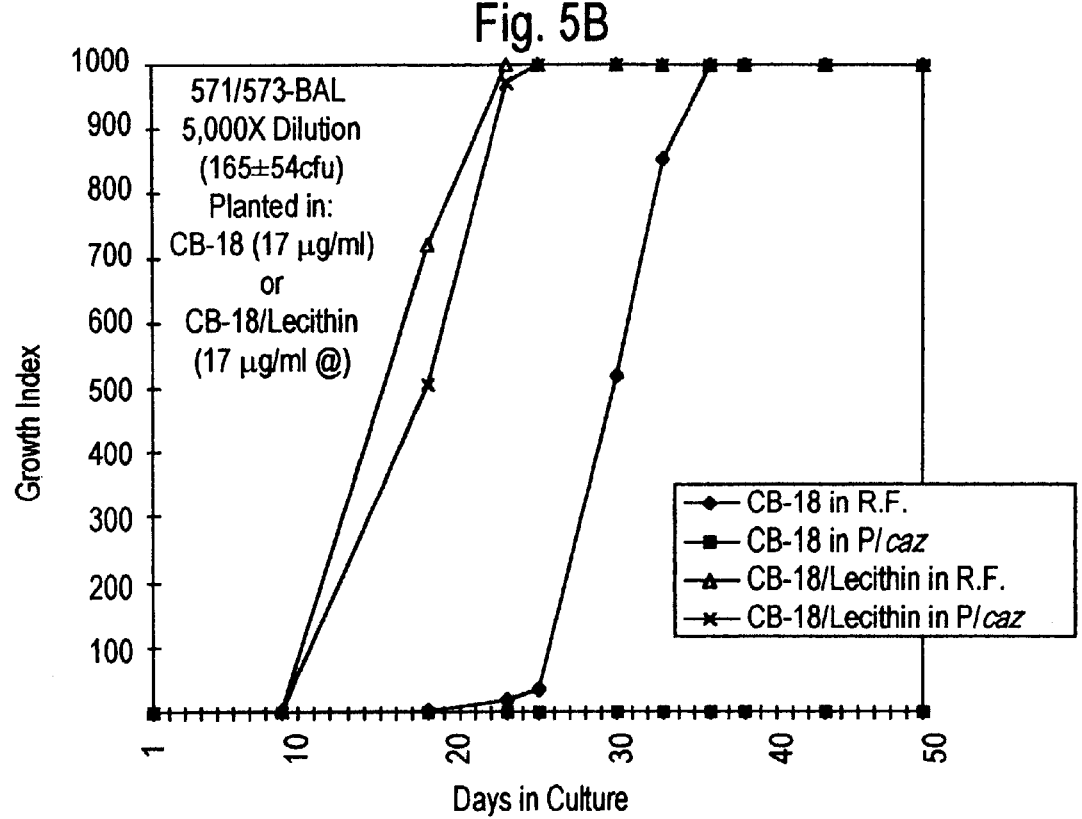

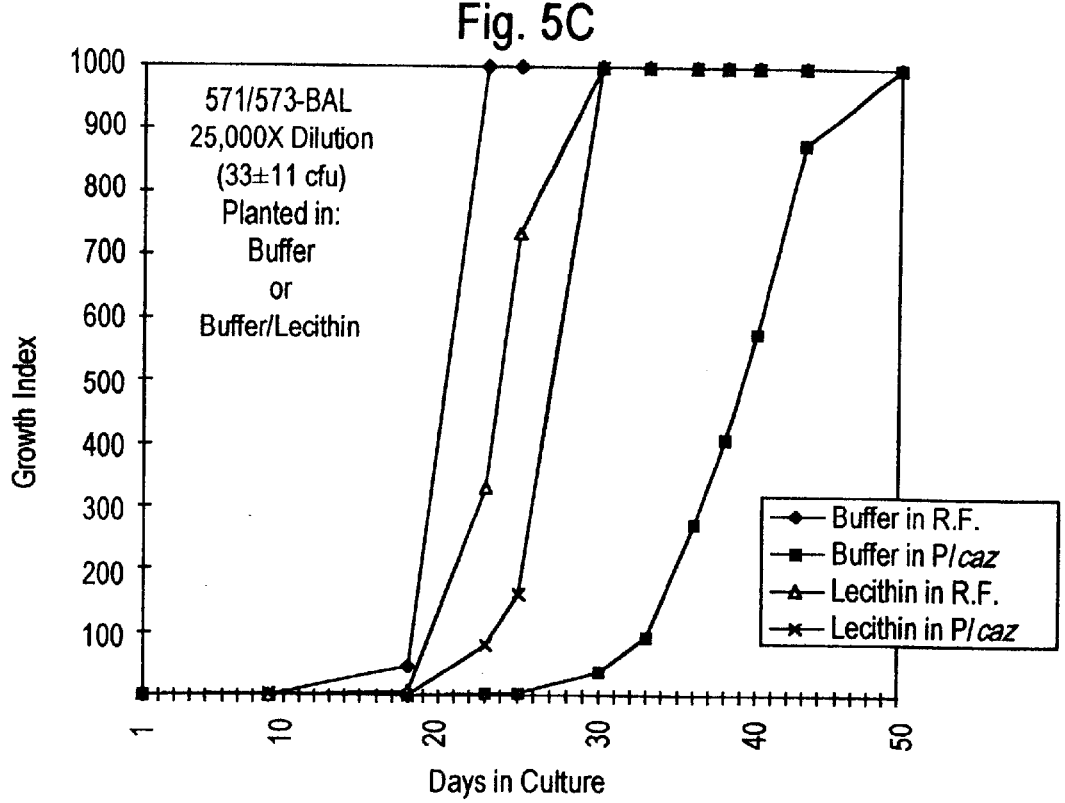
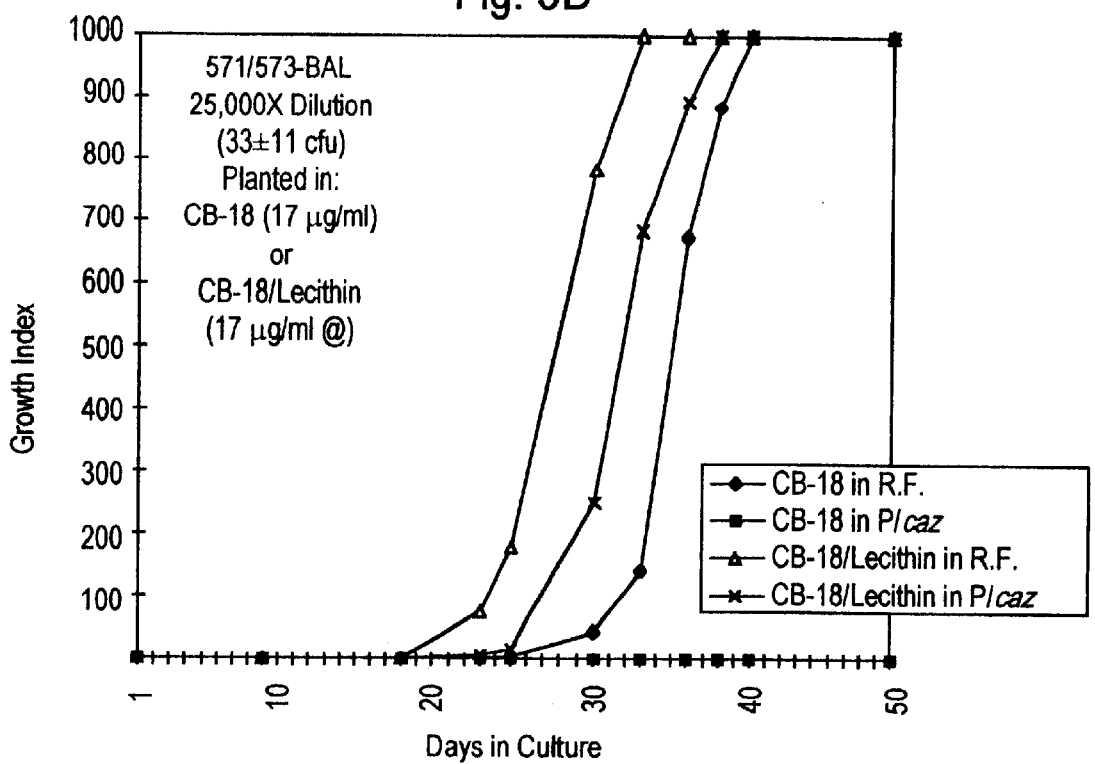

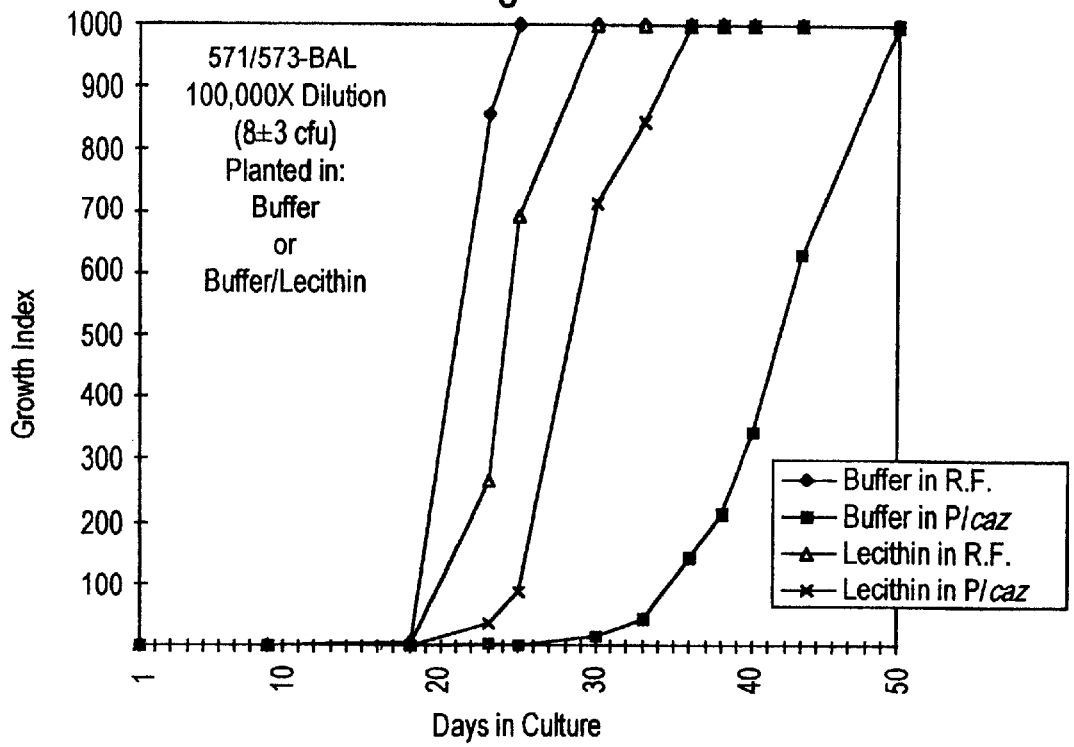
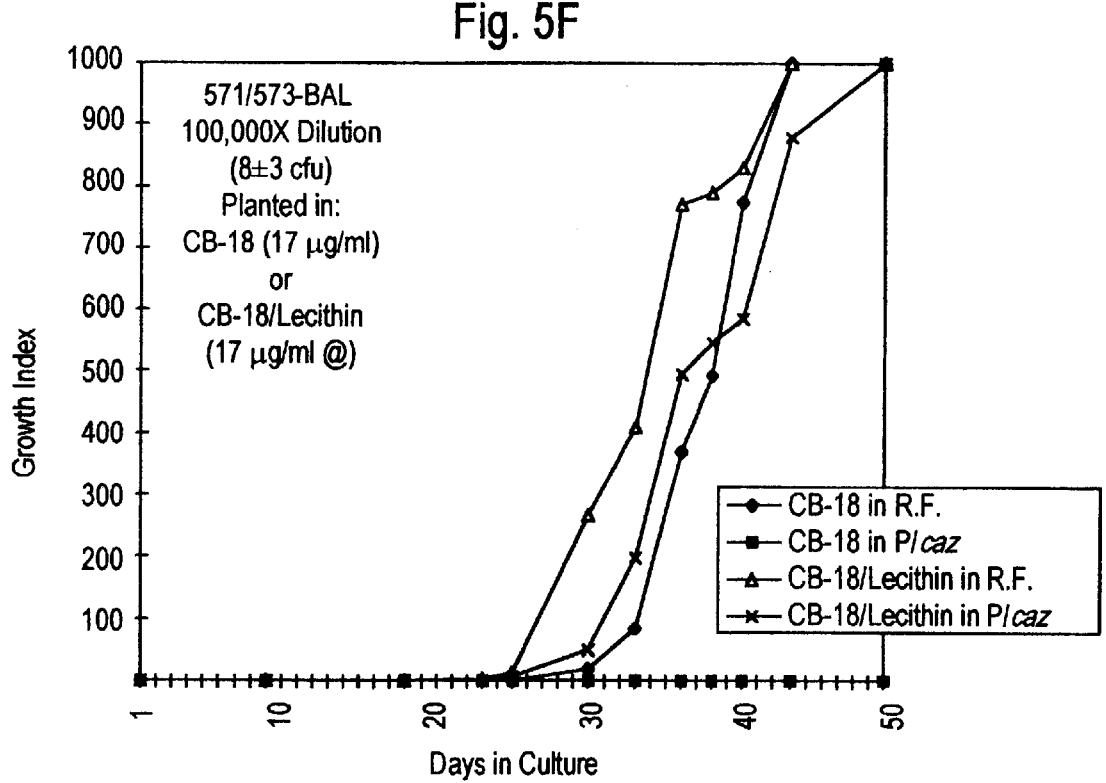

CB-18 & TMA-18 Titration

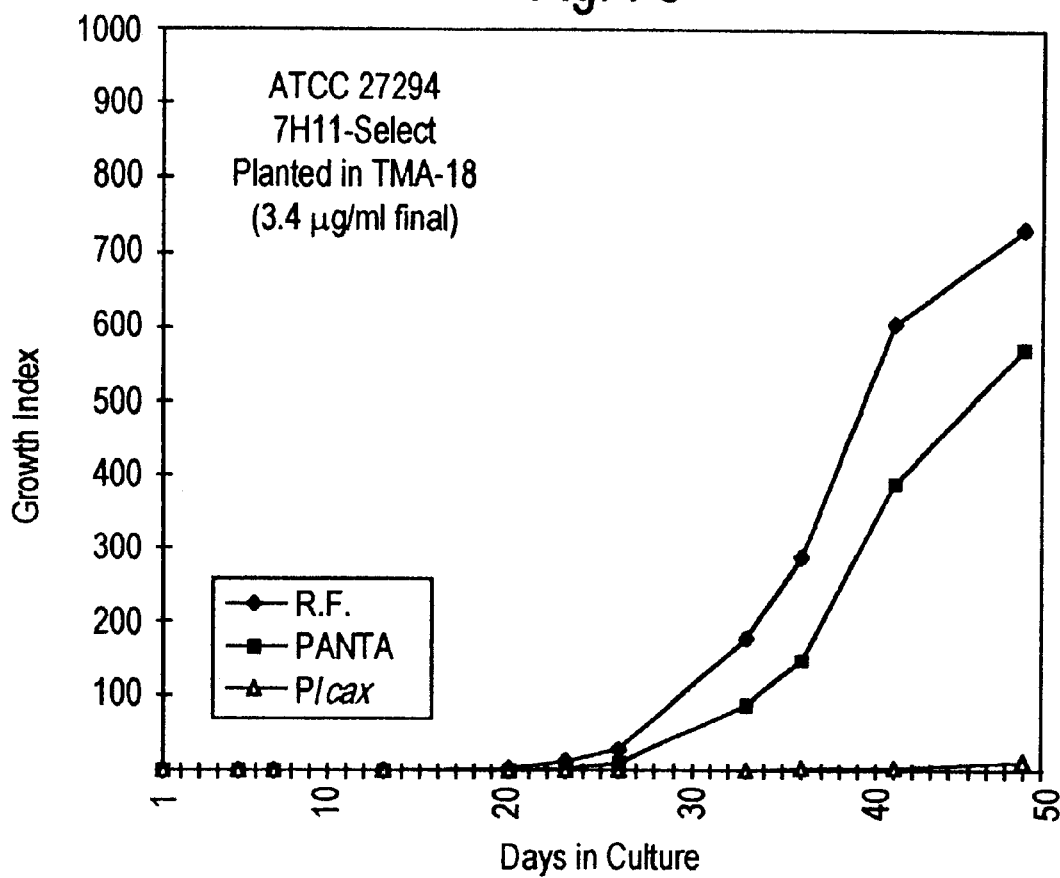

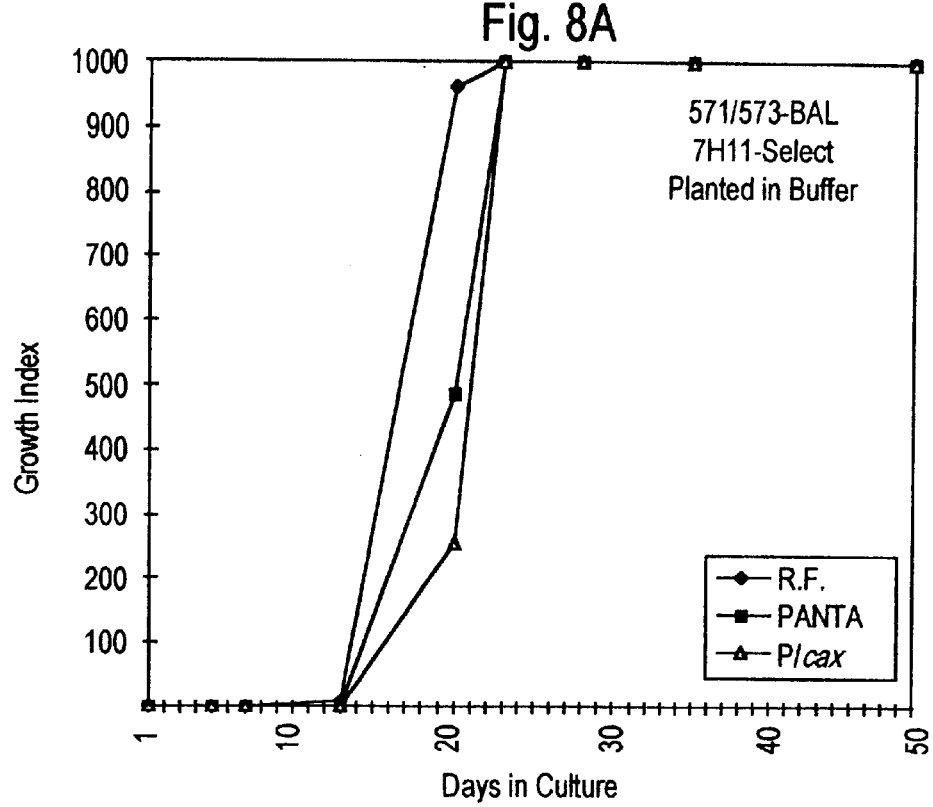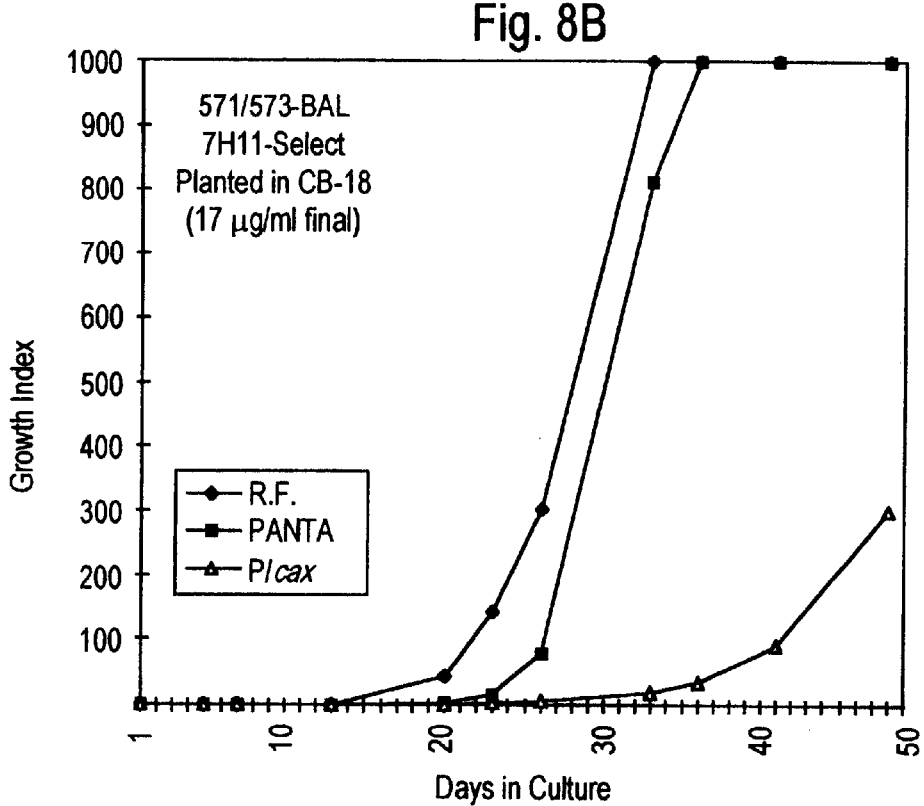

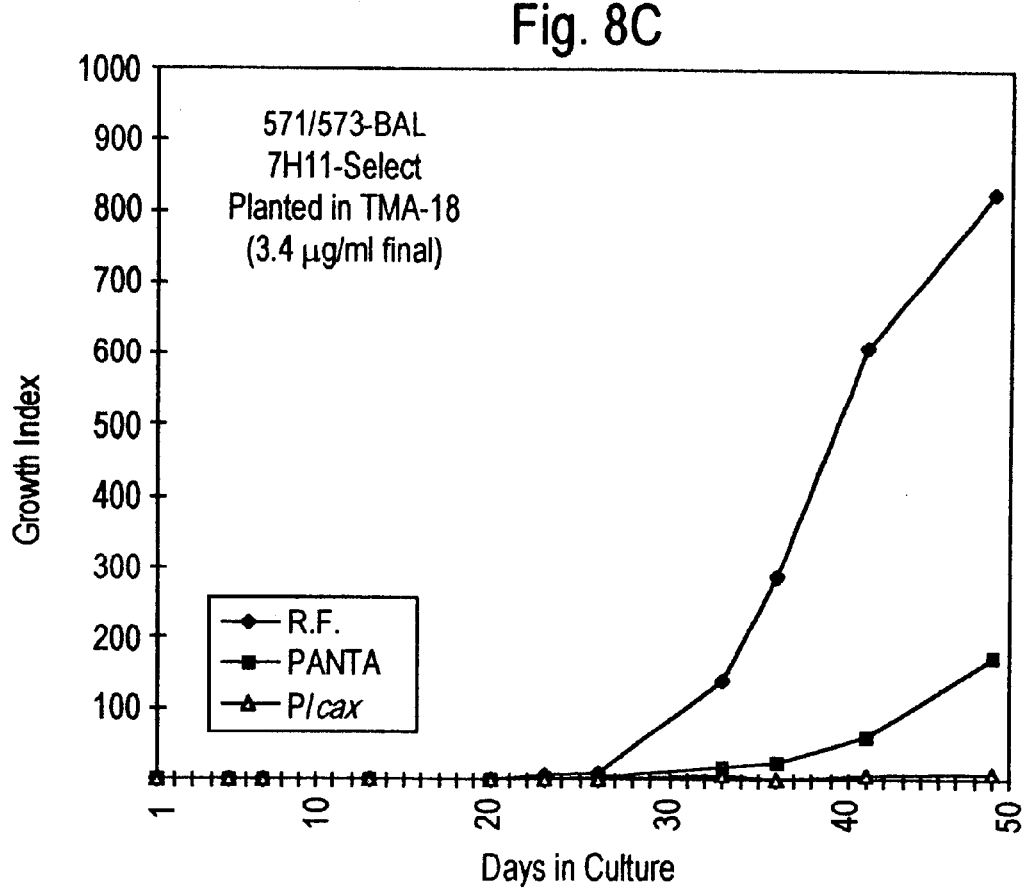

CB-18 Titrations

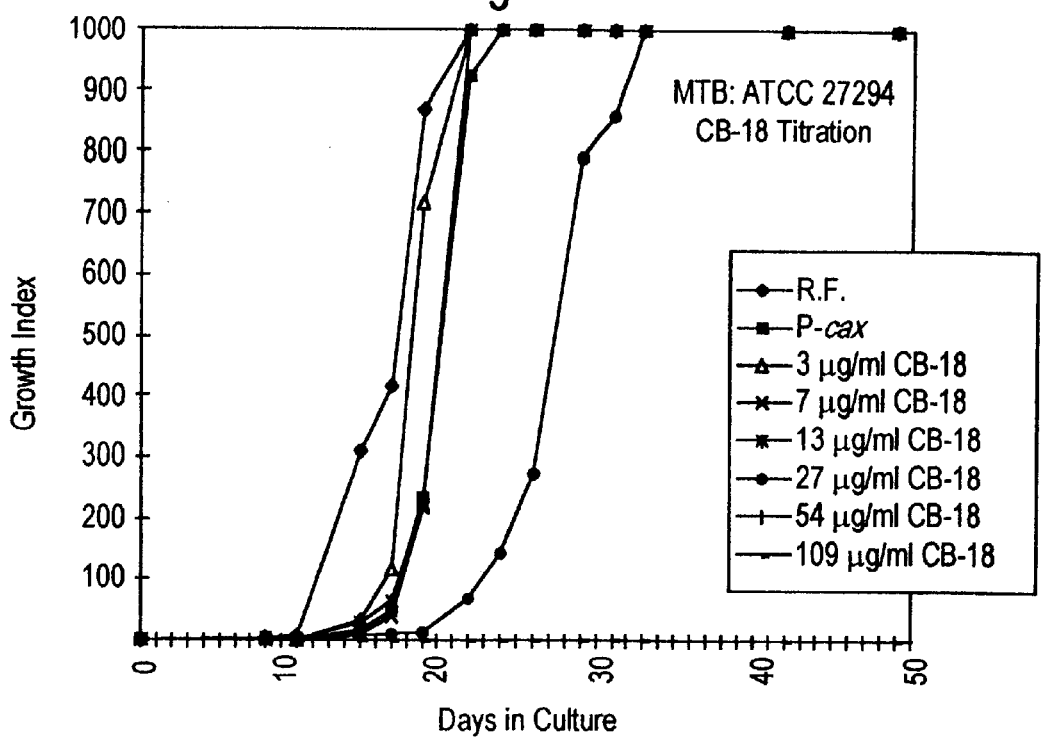
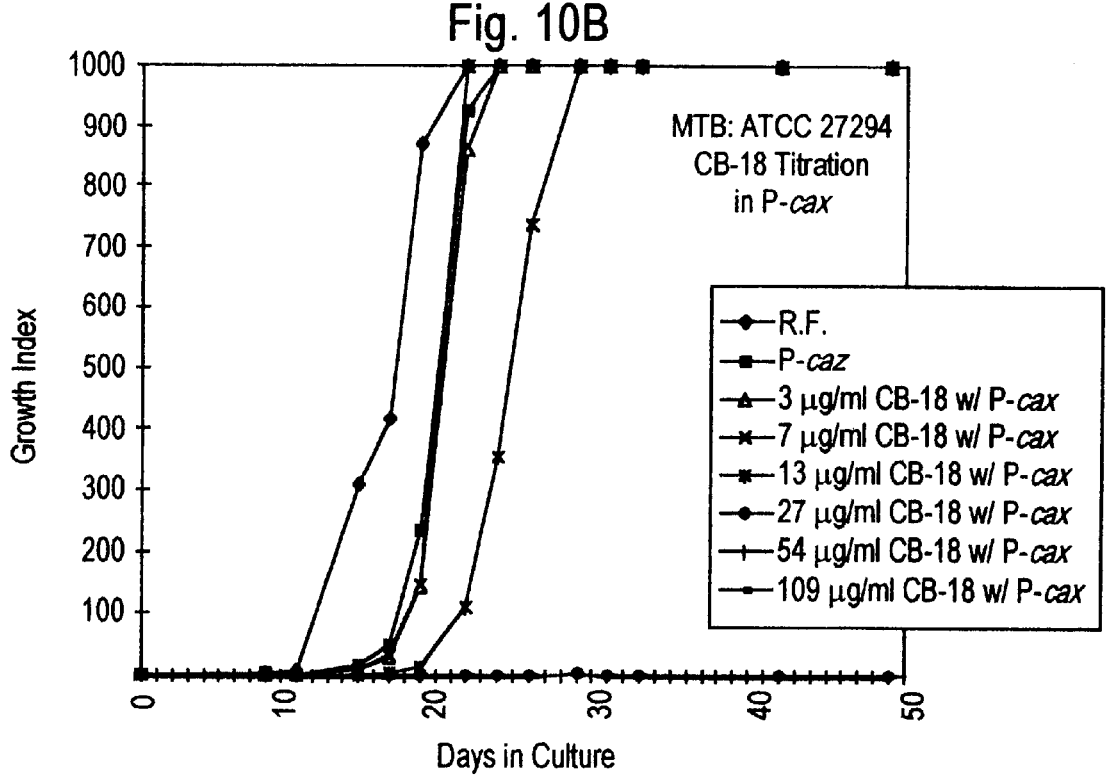

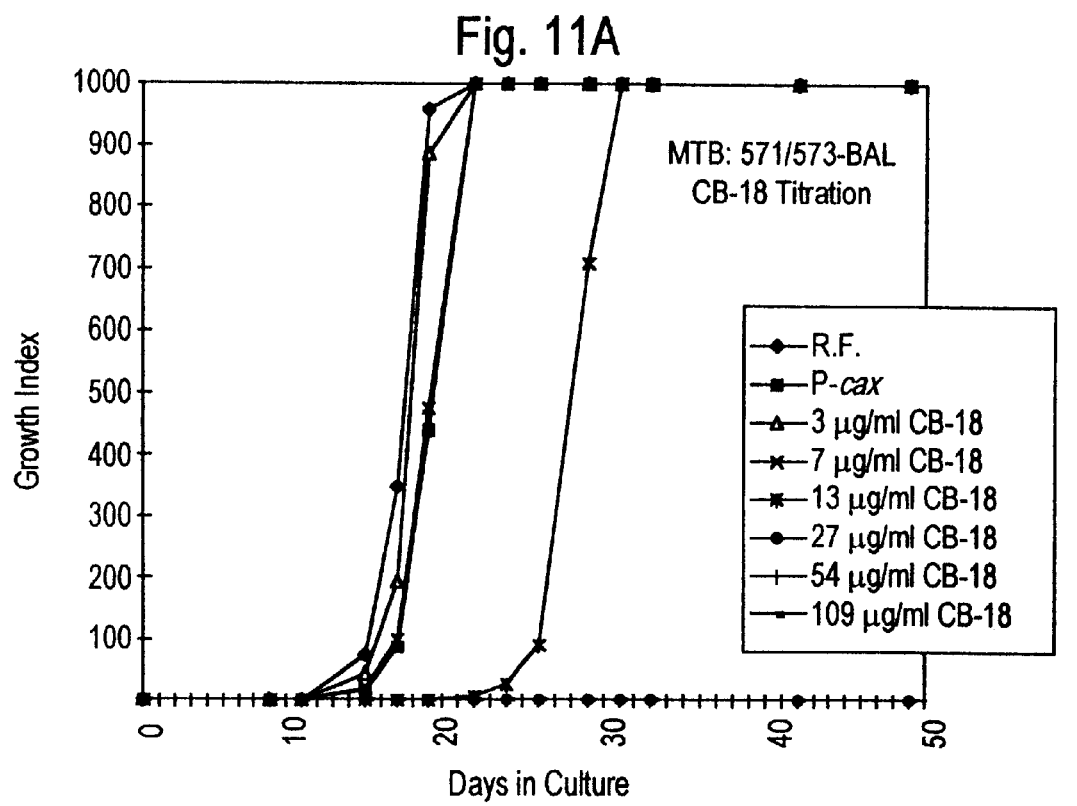
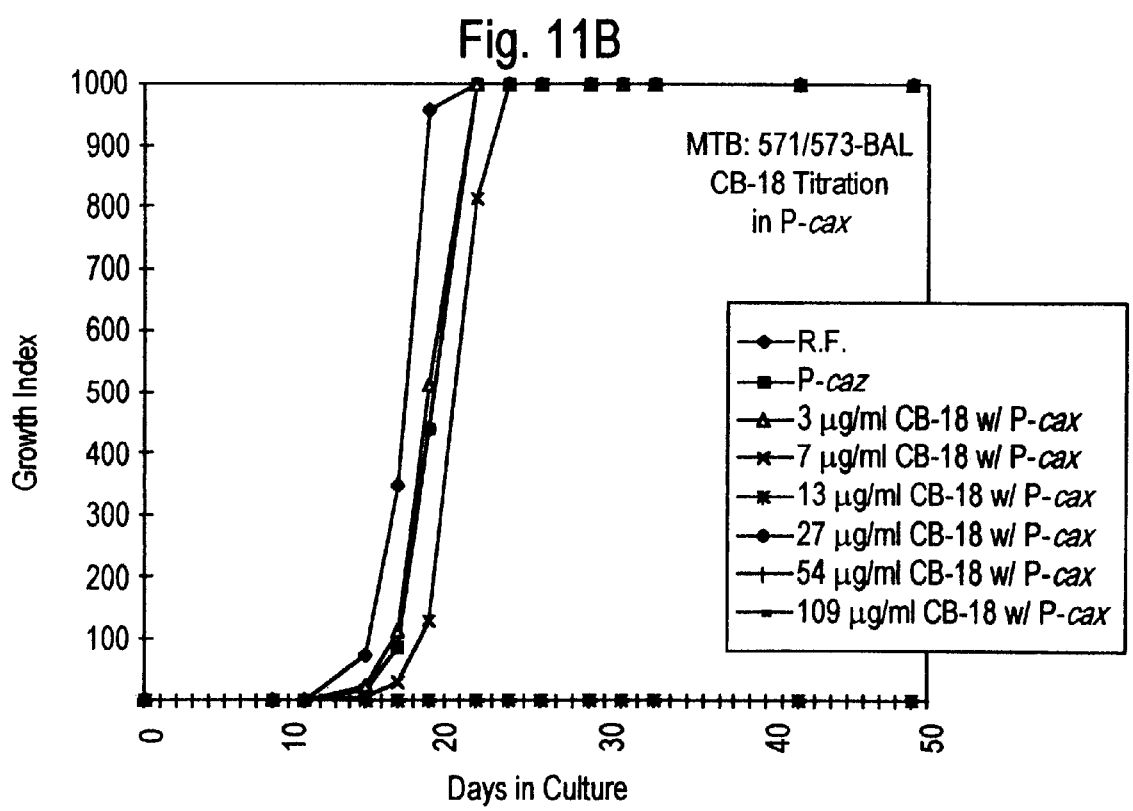

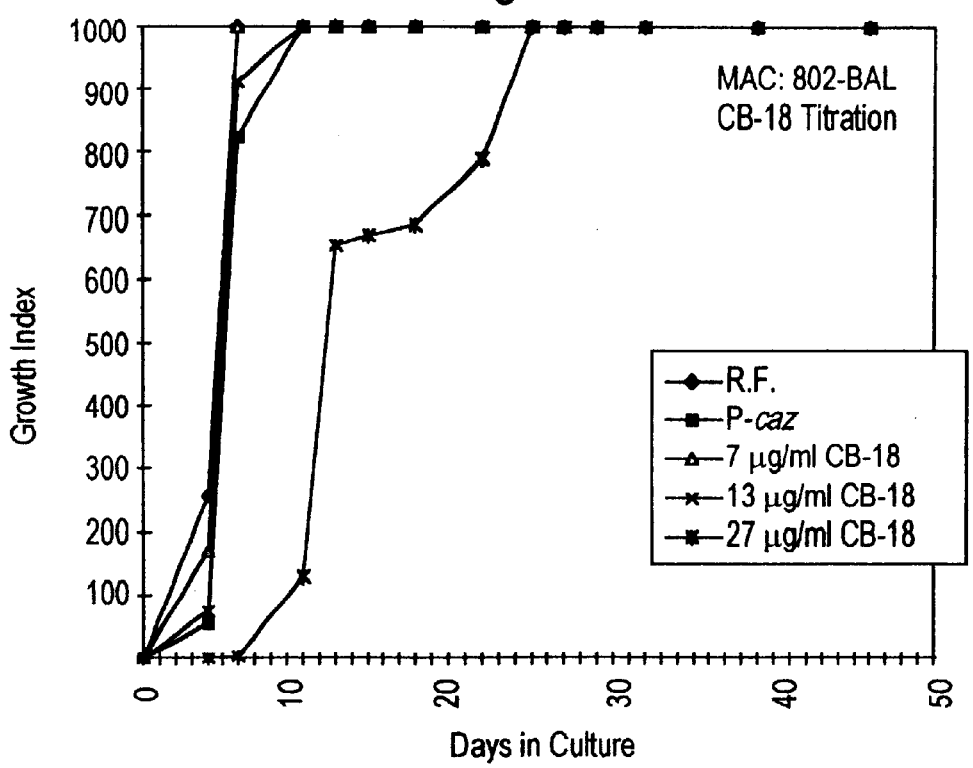
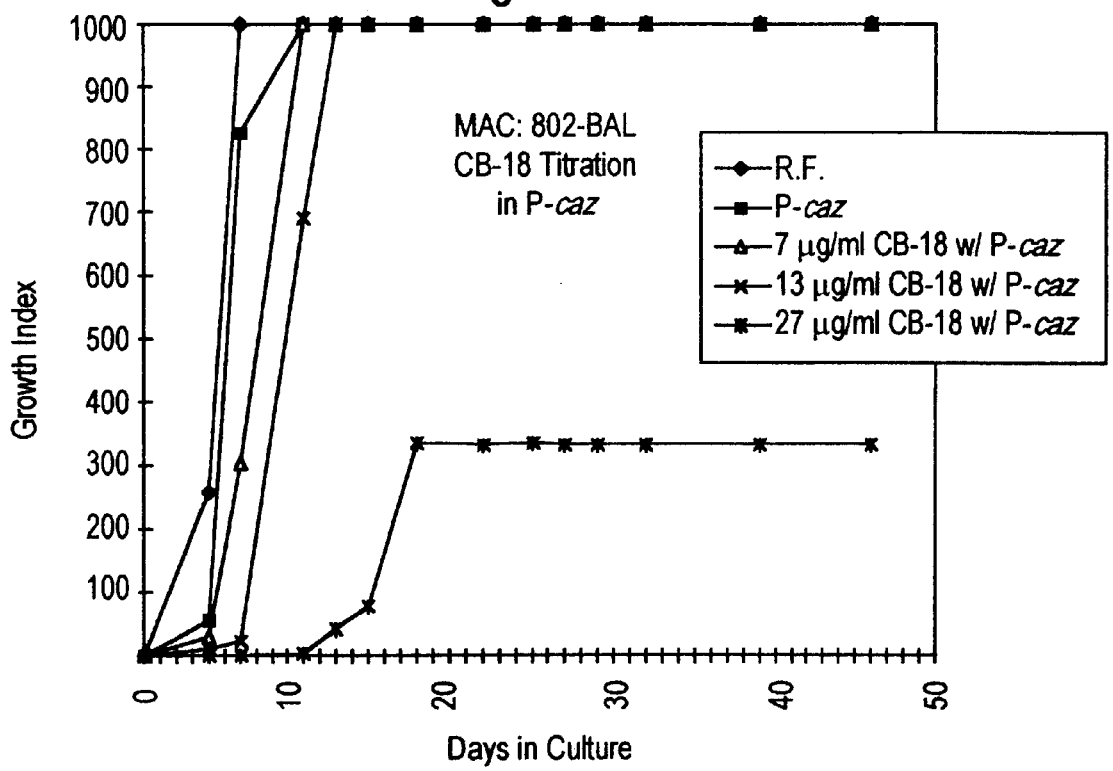

MTB Isolates
vs.
Antibiotic Screen

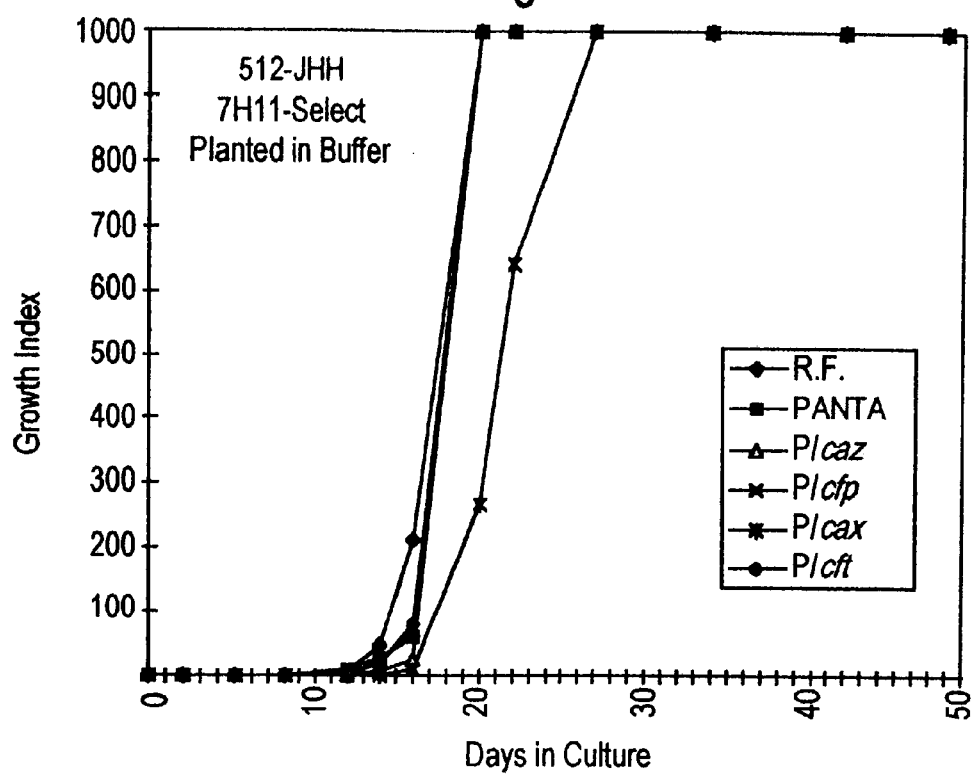
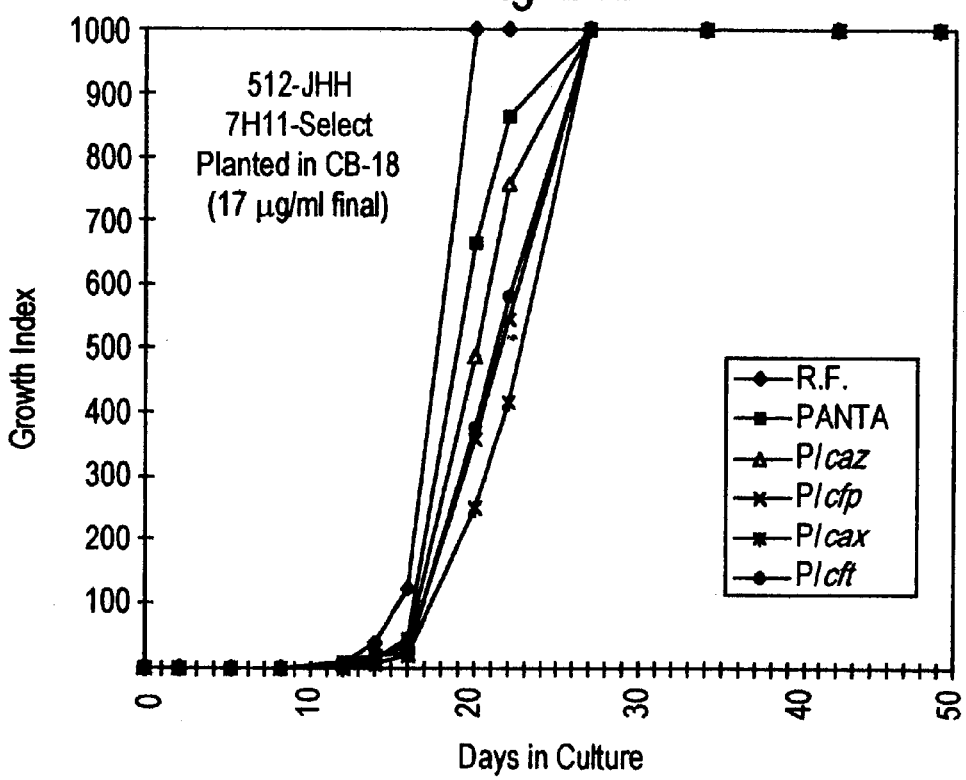

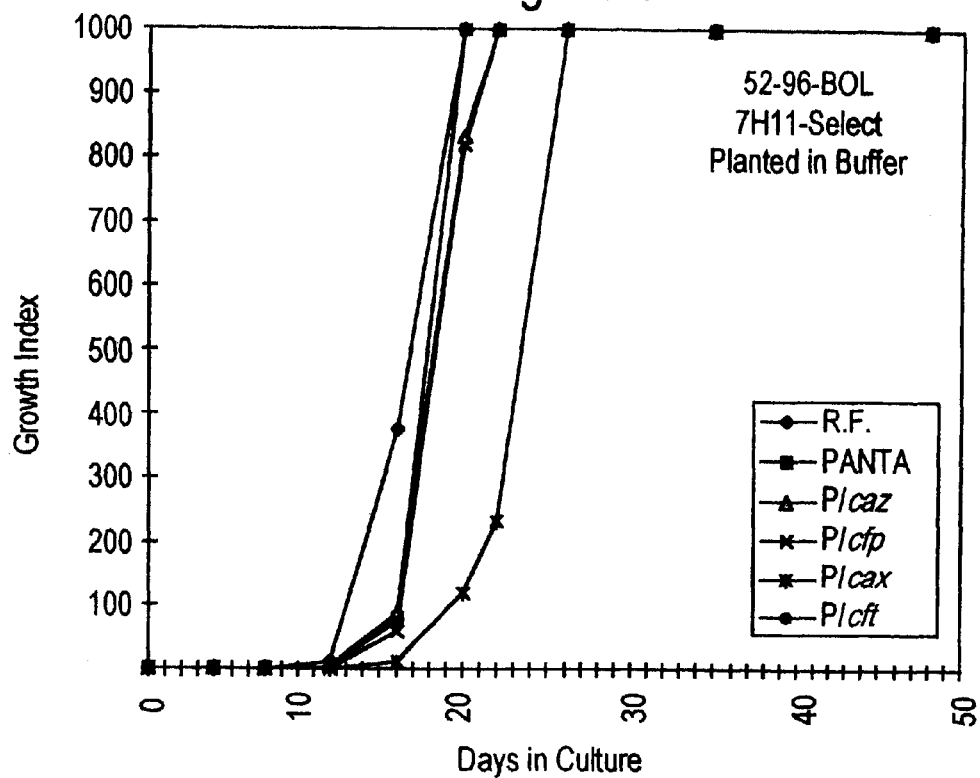
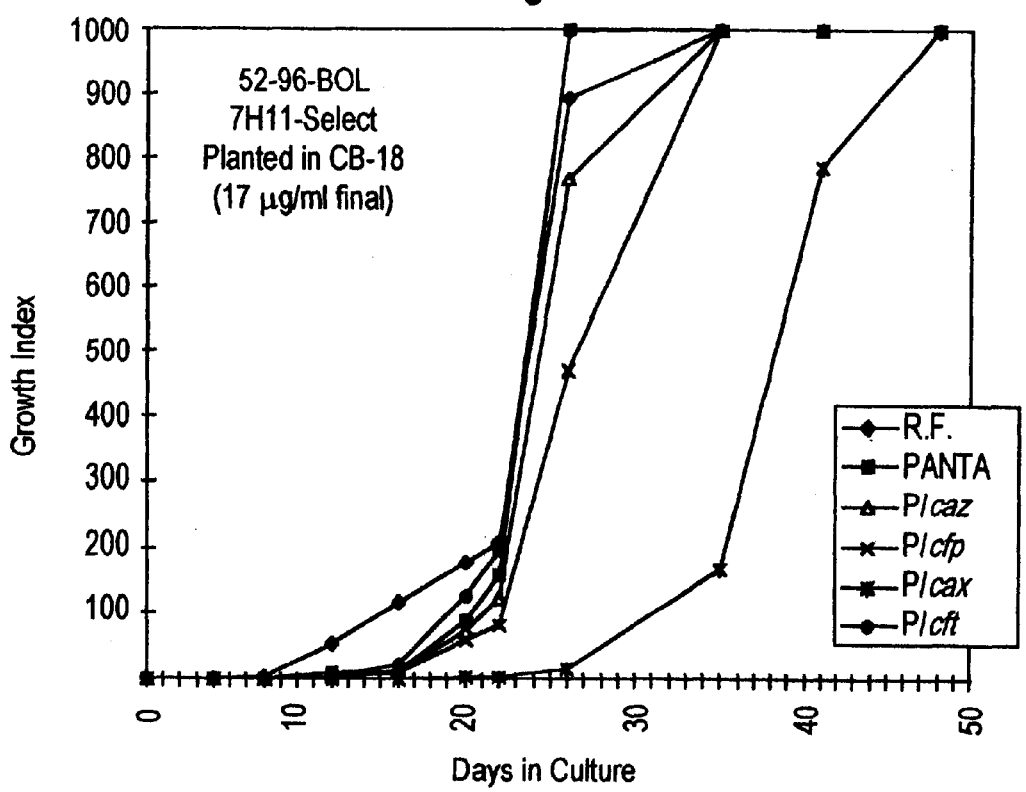

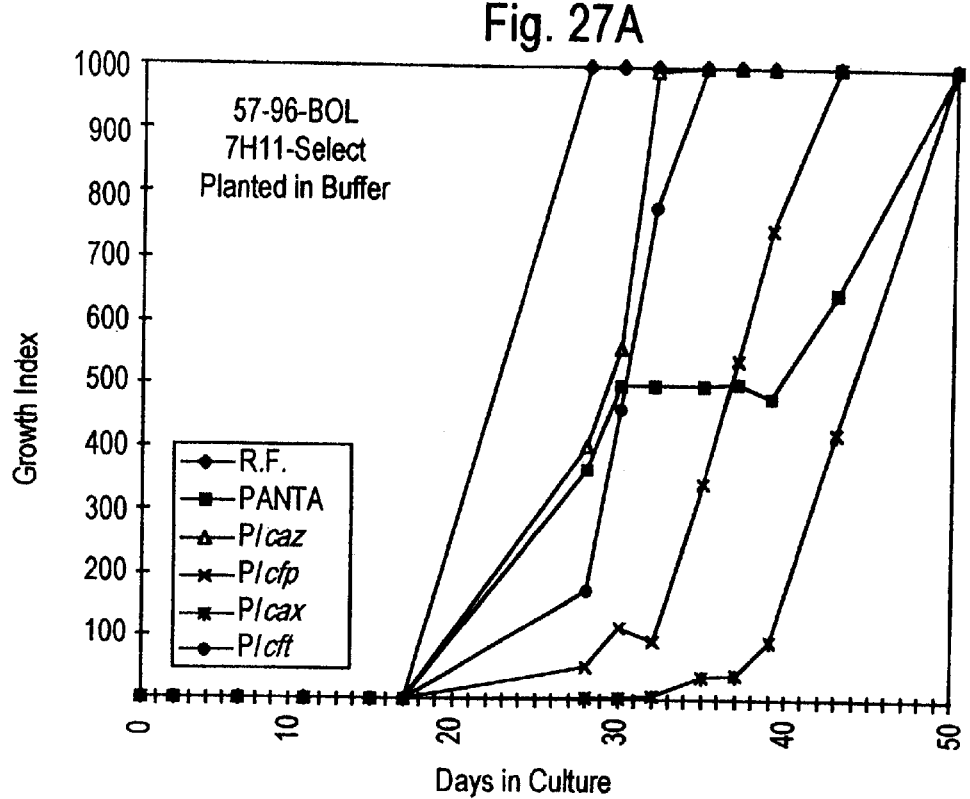
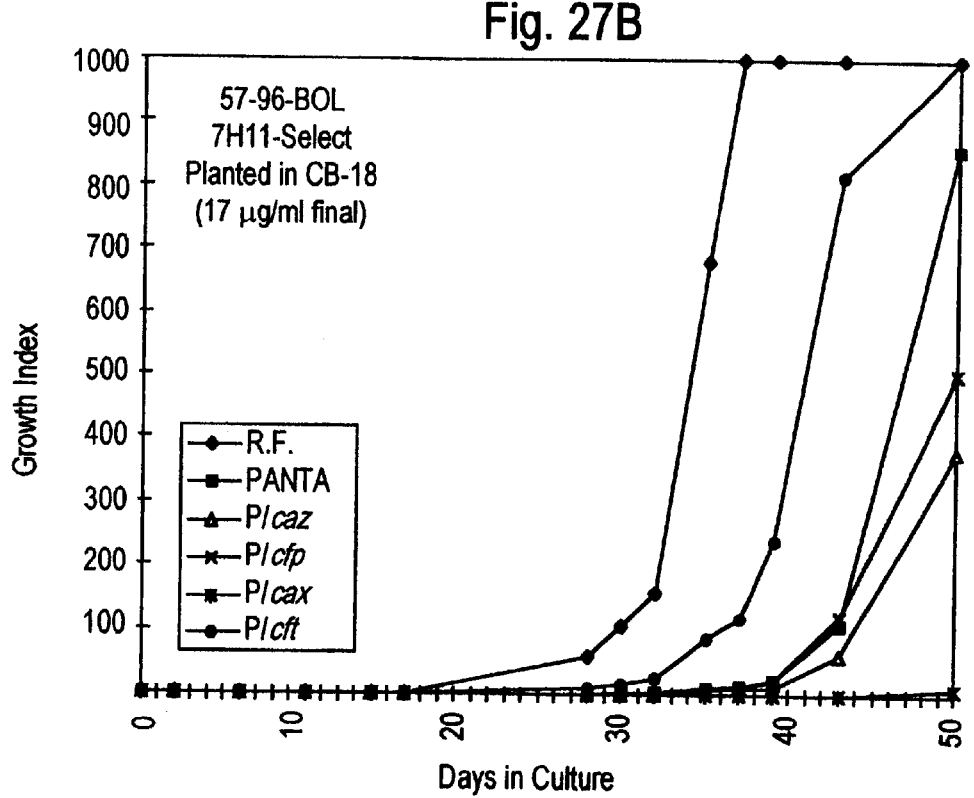

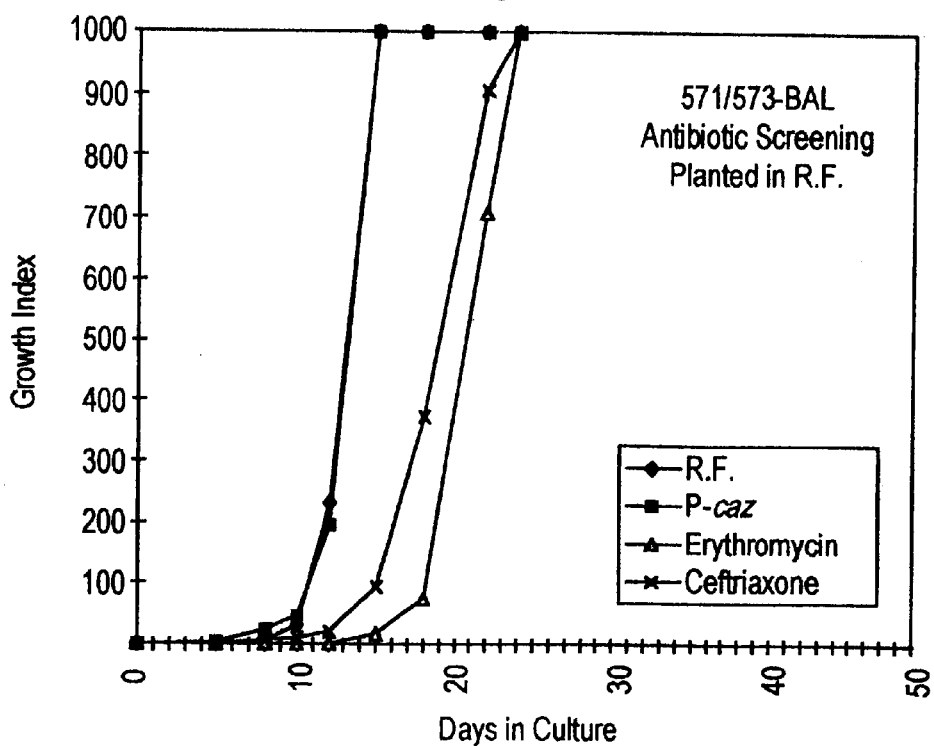
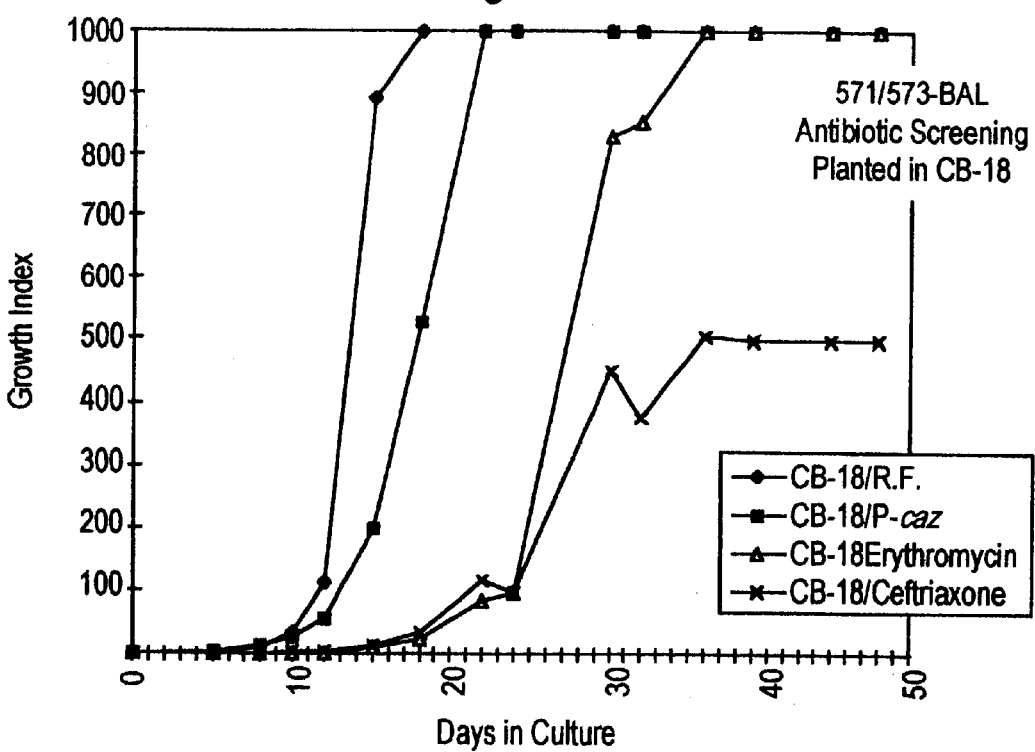

Detergent Screen

CB-18 vs. EDTA

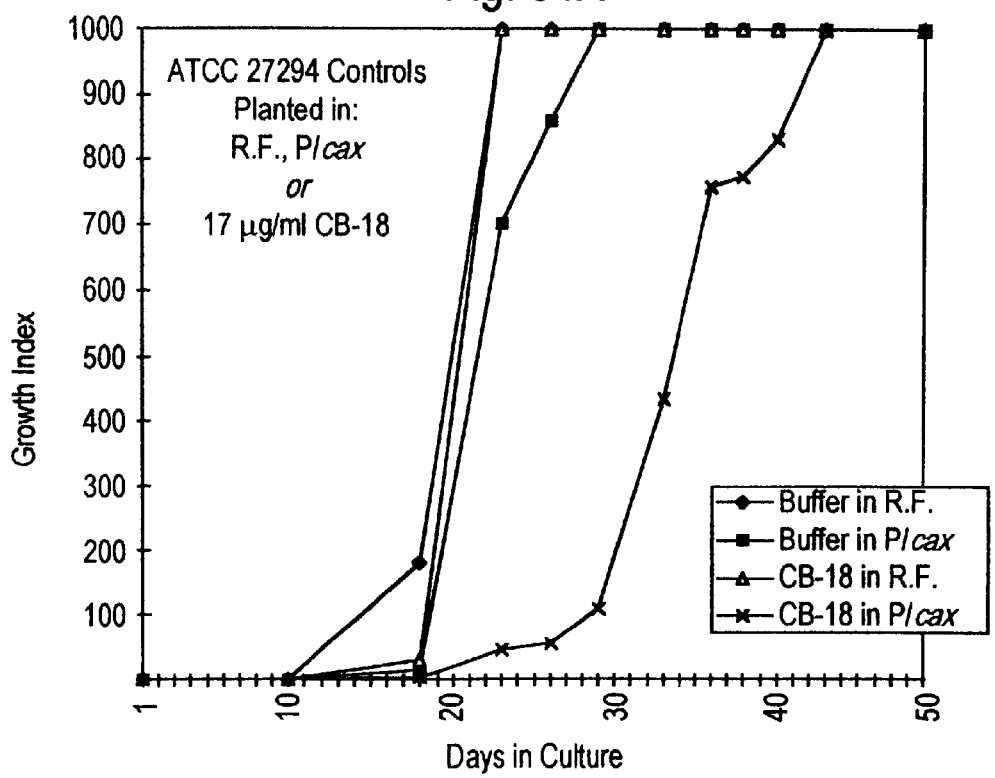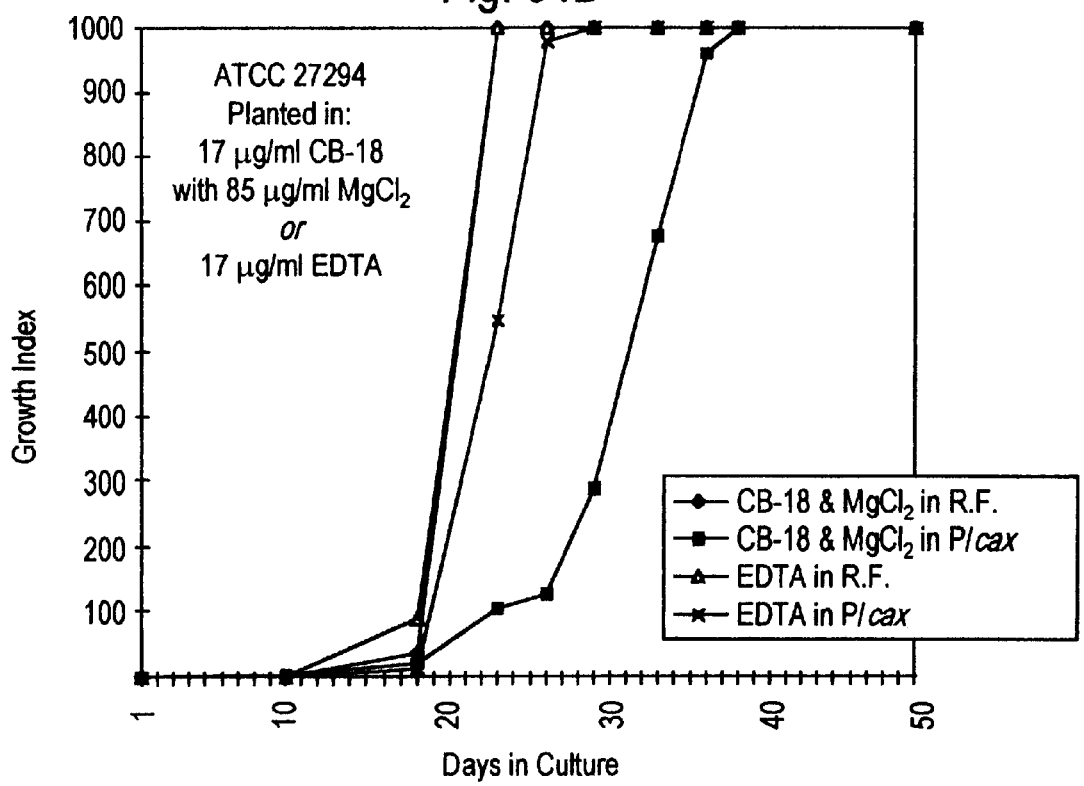

Mycobacterial Susceptibility Testing

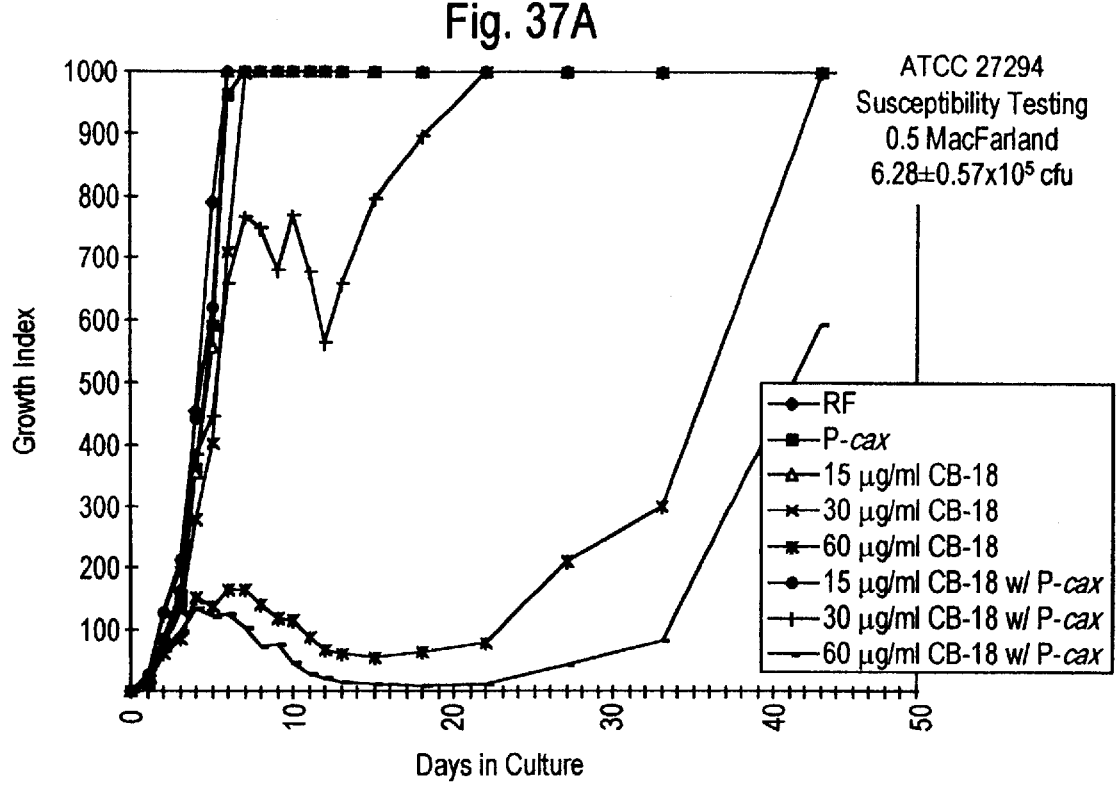
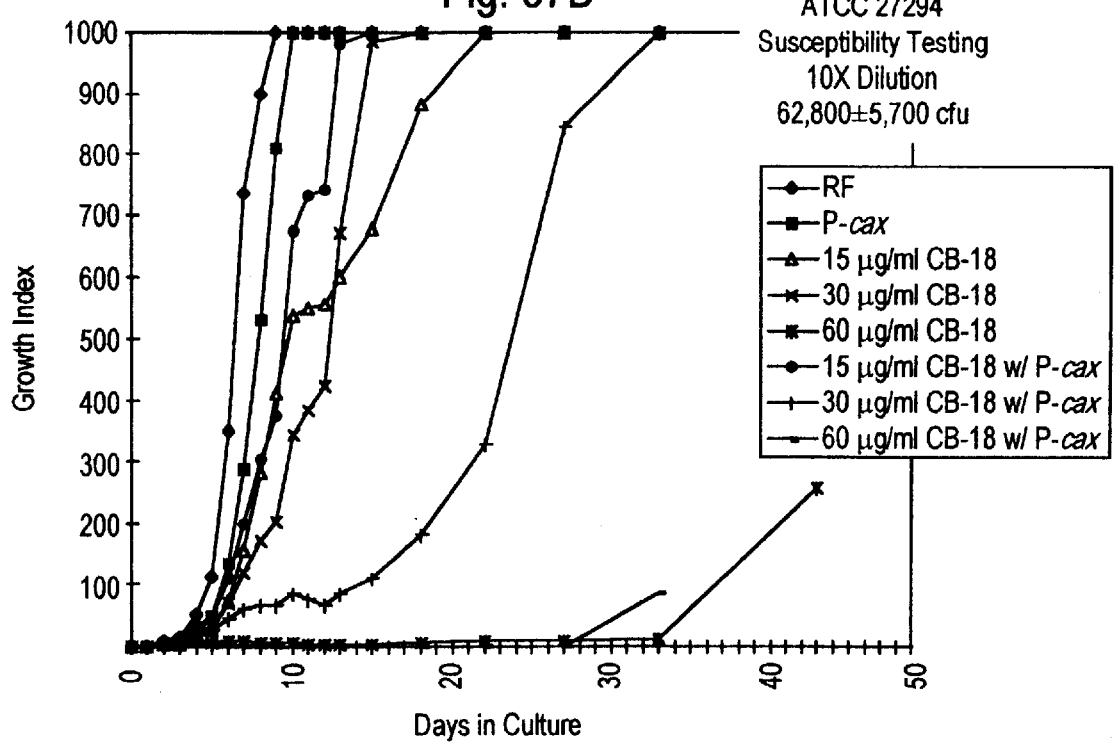

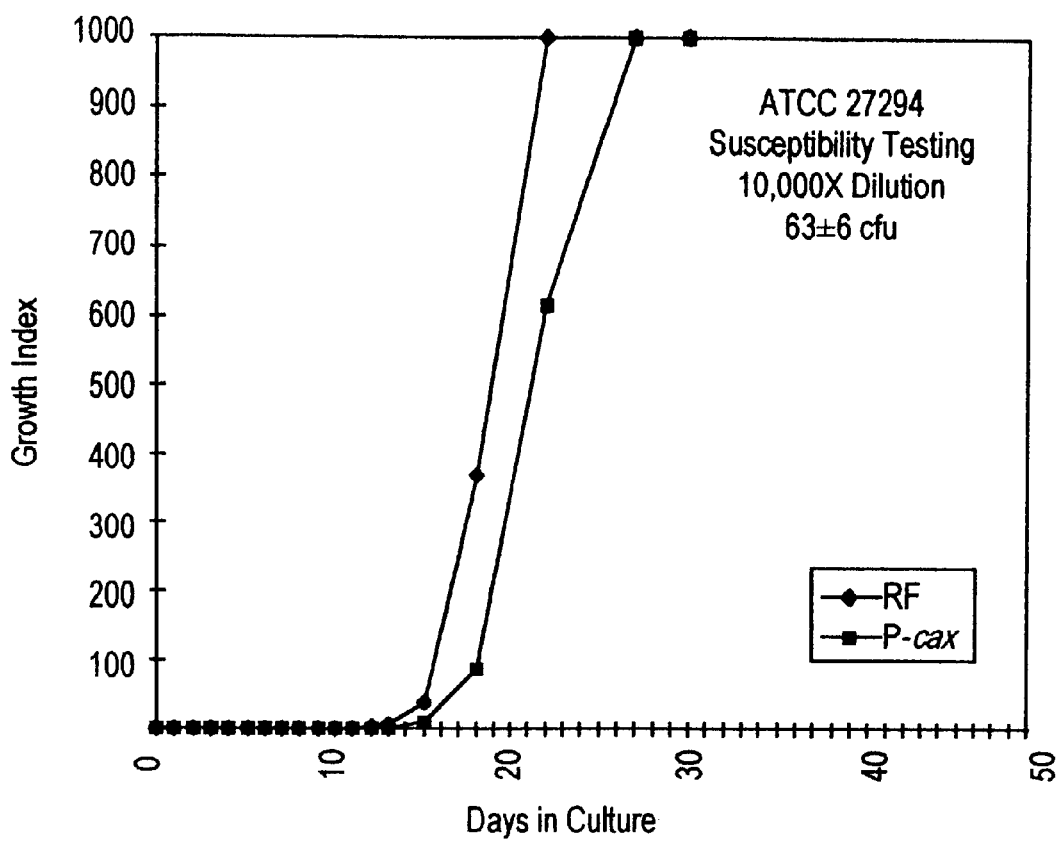

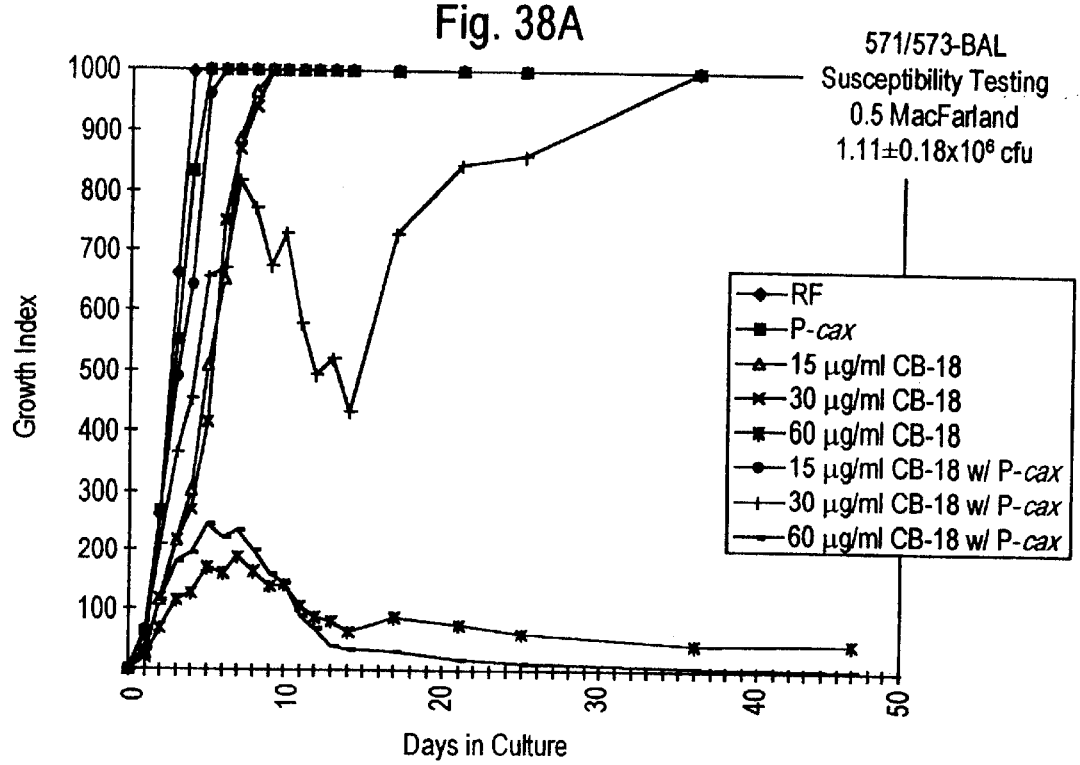
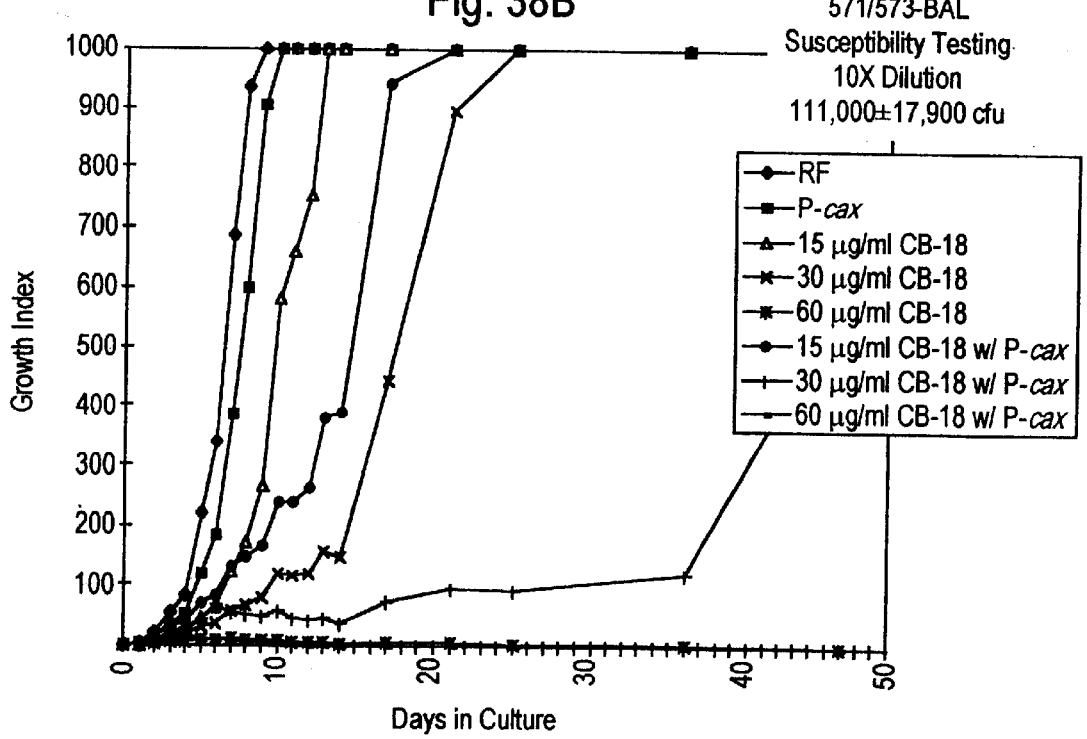

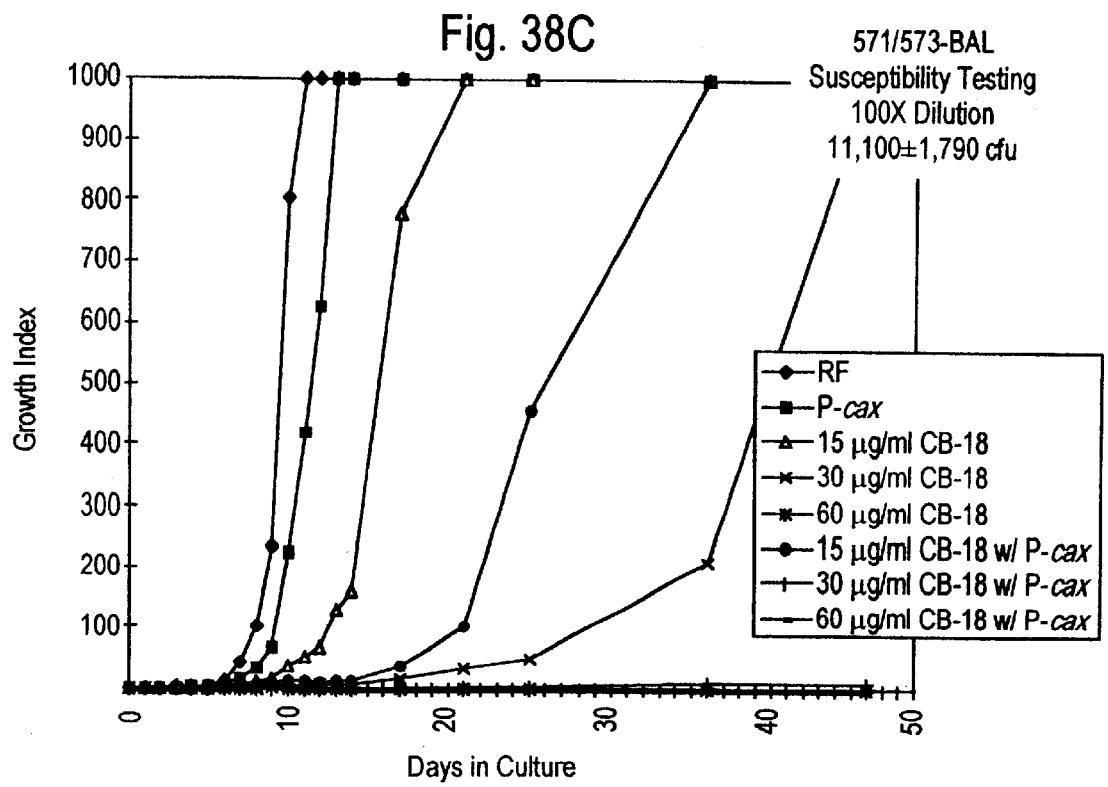
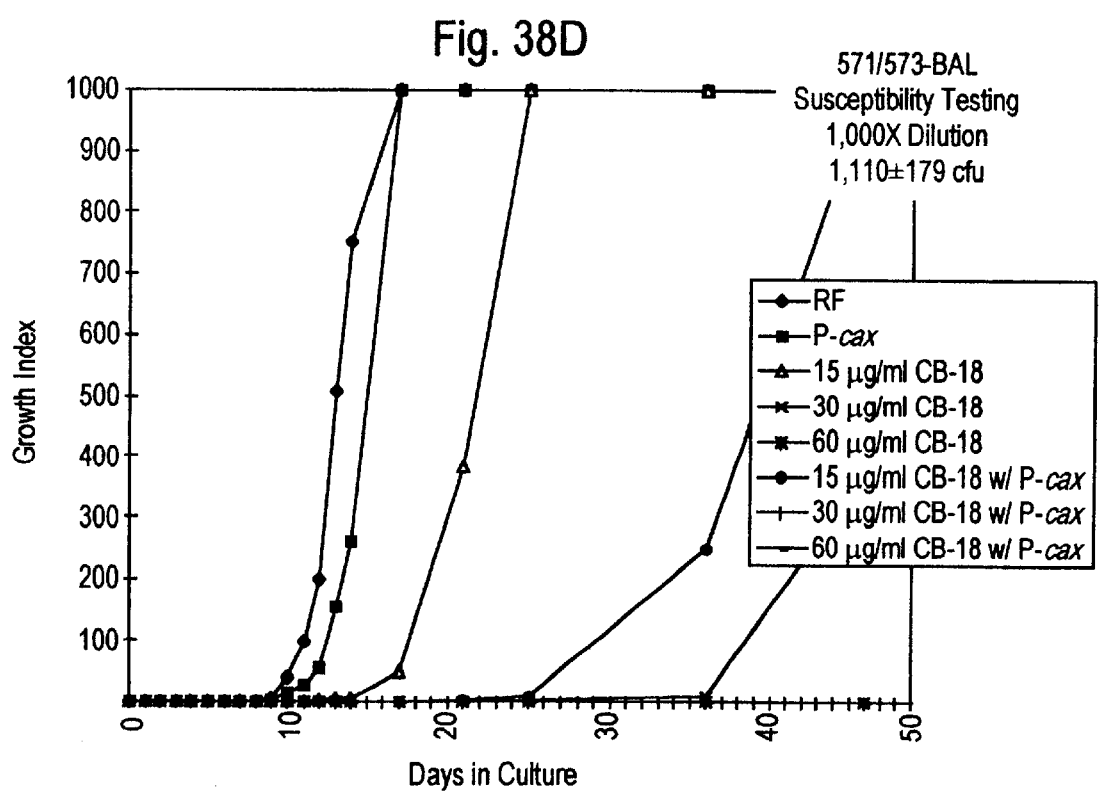

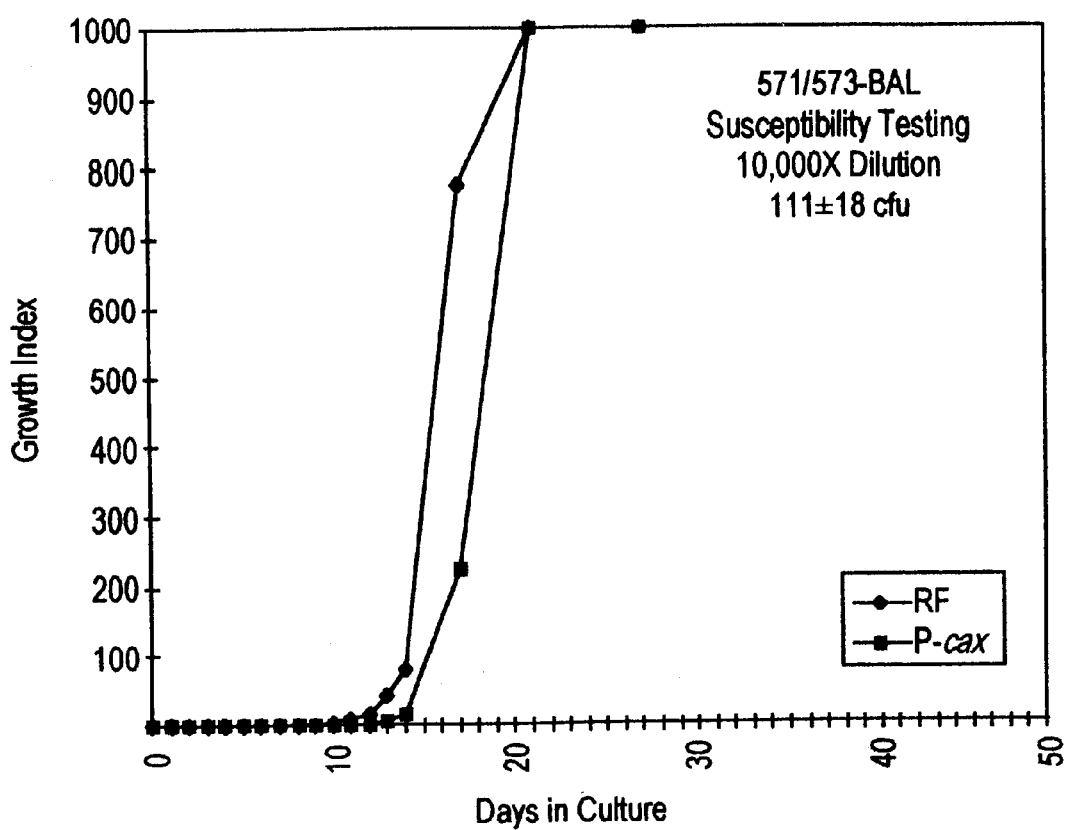

BETAINES AS ADJUVANTS TO SUSCEPTIBILITY TESTING AND ANTIMICROBIAL THERAPY

CROSS REFERENCE TO RELATED APPLICATIONS

This application is a continuation of PCT/US98/08760, filed May 1, 1998, which claims the benefit of U.S. application Ser. No. 60/045,512, filed May 2, 1997.

FIELD OF THE INVENTION

The present invention is related to compositions and methods for ascertaining susceptibility characteristics of bacteria that contain mycolic acid structures. The compositions and methods of the invention are especially useful as adjuvants to susceptibility testing and antimicrobial therapy, most especially testing or therapy involving the β-lactam family of antibiotics.

BACKGROUND OF THE INVENTION

Contemporary methods for treating patients infected with bacteria involve selecting antibiotics for therapy. Most conventional therapy is based on the physician's experience. In simplistic terms, the physician simply chooses a broad spectrum antibiotic thought to be effective against the most common infectious agents associated with the patient's symptoms. In some instances, however, selection of the appropriate therapeutic is based on susceptibility testing. Susceptibility testing guides the medical practitioner by defining which therapeutics will have the highest probability of successfully treating a particular pathogen, and which antimicrobial agents will most probably be impotent. Susceptibility testing is an important tool, especially when a patient is identified as having a mycobacterial infection, and most especially when the patient presents with tuberculosis (TB: caused by *Mycobacterium tuberculosis* complex bacteria (MTB)). Current federal recommendations include susceptibility testing on all new cases of TB (Tenover, F. C. et al., *Jour. Clin. Micro.* 31:767–770 (1993)). Susceptibility testing is an invaluable tool that virtually all physicians rely on at one time or another to select the appropriate antibiotic therapy for their patients.

Methods of treating bacterial infections are constrained by the spectrum of activity of a particular compound. For example, not all bacteria are susceptible to a given antimicrobial compound. Different classes of bacteria are resistant to the action of the different classes of antibiotics. Generally speaking the spectrum of activity of a given antibiotic falls into discrete groups with respect to the class of organisms it affects (e.g., mycologic vs. bacterial, or gram positive bacteria vs. gram negative bacteria).

Antibiotics exert their effect by interfering with a variety of cellular functions. For example, different classes of antibiotics are known to interfere with various aspects of cell wall synthesis, RNA/DNA synthesis, DNA replication, or protein synthesis. Bacteria are resistant to different antibiotics for a variety of reasons. Quintiliani, R. et al., In: Murray, P. R. et al., eds. *Manual of Clinical Microbiology*, ASM Press, Washington, D.C. (1995) pp.1308–1326 review several of these resistence mechanisms and point out that the antibiotic must first enter the cell, and only then can it exert its effect at the site of action. The basis for resistance can either be due to the permeability of the organism, or the molecular configuration of the site of action might either be incompatible or nonexistent. In addition, the bacteria might modify, destroy or eliminate the agent.

Resistance can either be innate or acquired. Acquiring resistance can be either by acquisition of genetic material (e.g., transposable elements), or by the inherent infidelity of DNA replication (e.g., point mutations). Mycobacteria appear to have an additional mechanism of resistance. Heifets, L. B. In: *Drug Susceptibility in the Chemotherapy of Mycobacterial Infections*, Heifets, L. B. ed. CRC Press, Boston, Mass. (1991), pp. 13–57 classifies subpopulations of infecting MTB cells as either actively growing, or in different stages of dormancy. Dormancy permits these subpopulations to survive during patient therapy.

Treating mycobacterial infections is further complicated by the complex pattern of susceptibility. For example, while MTB infections can usually be treated effectively with isoniazide (INH) and/or pyrazinamide (PZA), MAC isolates are typically resistant to these drugs, and *M. fortuitiim* and *M. chelonae* isolates are usually resistant to all the front line antituberculosis agents.

Tuberculosis is the most prevalent infectious disease in the world today, infecting approximately one-third of the world's population, some 1.7 billion people (Kochi, A. *Tubercle* 72:1–6 (1991)). In addition, tuberculosis kills more people worldwide (approximately 3 million annually) than any other single infectious disease (Morbidity and Mortality Weekly Report 42:961–964 (1993)). The vast majority of TB cases are in developing countries, however, multi-drug resistant (MDR) strains of MTB (MDR-TB) have become a significant problem globally (World Health Organization (document WHO/TB/96.198) Groups at Risk, *WHO Report on the Tuberculosis Epidemic* 1996 (1996)). Unless something is done to stem the rise in MDR-TB, a return of the past where tuberculosis was the most common cause of death in both developing and industrialized countries is inevitable.

Other mycobacteria such as *Mycobacterium avium* complex (MAC), *M. paratuberculosis*, *M. ulcerans*, *M. leprae*, *M. kansasii*, and *M. fortuitum* complex are commonpathogens aswell (see: Wayne, L. G. *Clin. Micro. Rev.* 5:1–25 (1992) or Falkinham, J. O. *Clin. Micro. Rev.* 9:177–215 (199) for reviews of the different mycobacterial pathogens). MAC causes disseminated disease in almost half of all late stage AIDS patients (Nightingale, S. D. et al., *Jour. Infect. Dis.* 165:1082–1085 (1992)). The World Health Organization estimates that by the year 2000 the number of people infected with human immunodeficiency virus (HIV) could exceed 40 million (World Health Organization (document WHO/GPA/CNP/EVA/93.1) Global Programme on AIDS (1993)). *M. paratuberculosis* (a subspecies of *M. avium*) causes Johne's disease in ruminants. It has been estimated that Johne's disease costs the U.S. farming industries (e.g., diary and beef) in excess of $1.5 billion annually due to lower productivity and fecundity (Whitlock, R. *Proceedings of the Third International Colloquium on Paratuberculosis*, pp.514–522 (1991); Whitlock, R. et al, *Proceedings of the 89[th] Annual Meeting of the United States Animal Health Association*, pp.484–490 (1985)). Mycobacterial diseases extract an enormous social cost.

The most common and best characterized class of antibiotic compounds is by far the β-lactams. Due to the depth and breadth of these antibiotics, the ability to treat mycobacterial infections with these agents would provide significant advantages. Application of the β-lactams in therapeutic regimes designed to treat mycobacterial infections has been tried with limited success (Chambers, H. F. et al., *Antimicrob. Agents Chemo.* 39:2620–2624 (1995)). The ability to broaden the susceptibility of the mycobacteria, especially to the β-lactams by addressing resistance mechanisms, has significant potential in effectively treating mycobacterial infections.

The invention described herein outlines novel methods and compositions wherein the susceptibility of the mycobacteria can be characterized. These methods and compositions alter the susceptibility of these bacteria to enhance the efectiveness of antibiotics, especially the β-lactam antibiotics. Such methods and compositions will permit the same to be used as part of an effective therapy for defining and/or treating such infections.

SUMMARY OF THE INVENTION

In an effort to control the undesirable growth of contaminating bacteria in liquid culture bottles derived from biological specimens that had been processed by the methods of Thornton WO 95/27076 and U.S. Pat. No. 5,658,749, the inventor supplemented standard antimicrobial formulations (i.e., PANTA) with a third generation cephalosporin, ceftazidime (CAS® No. 72558-82-8). The inventor surprisingly and unexpectedly found that when $C_{18}$-carboxypropylbetaine (CB-18) was employed as the processing reagent as per Thornton WO 95/27076 and U.S. Pat. No. 5,658,749, and used in combination with this antimicrobial formulation there was a marked and dramatic loss in liquid culture sensitivity. In seeking to maintain the advantages in diagnostic sensitivity provided by Thornton WO 95/27076 and U.S. Pat. No. 5,658,749 the inventor undertook studies to characterize and negate this loss in liquid culture sensitivity. These studies resulted in methods and compositions wherein the sensitivity of the mycobacteria to antibiotics, especially the β-lactam family of antibiotics, could be altered using the betaine-like compounds of Thornton WO 95/27076 and U.S. Pat. No. 5,658,749. The methods are useful for characterizing and altering the susceptibility of bacteria, especially the mycobacteria, and most especially *M. tuberculosis* complex bacteria, to antimicrobial compounds, and as adjuvants to antimicrobial therapy.

The invention further comprises a composition for susceptibility testing, said composition comprising one or more antibiotics in admixture with one or more betaine-like detergents.

The invention further comprises a kit for determining the susceptibility of a micoorganism, said kit comprising one or more betaine-like detergents and one or more antibiotics in close confinement or proximity.

BRIEF DESCRIPTION OF THE DRAWINGS

FIGS. 1A and 1B outline the experimental design used to characterize important growth/processing parameters of *Mycobacterium tuberculosis* isolates ATCC 27294 and 571/573-BAL in the CB-18/12B/PANTA/caz culture system.

FIG. 2A: ATCC 27294, L–J, process in buffer, plant in buffer. FIG. 2B: ATCC 27294, L–J, process in buffer, plant in CB-18 (17 μg/ml CB-18 final); FIG. 2C: ATCC 27294, L–J, process in CB-18 (383 μg/ml), plant in buffer; FIG. 2D: ATCC 27294, L–J, process in CB-18 (383 μg/ml), plant in CB-18 (17 μg/ml CB-18 final); FIG. 2E: ATCC 27294, 7H11-Selective, process in buffer, plant in buffer; FIG. 2F: ATCC27294, 7H11-Selective, process in buffer, plant in CB-18 (17 μg/ml CB-18 final).

FIGS. 3A–3H present the growth curves when the *M. tuberculosis* isolate 571/573-BAL was tested using the experimental design shown in FIGS. 1A and 1B. Diamonds: PANTA; Squares: P/caz. FIG. 3A: 571/573-BAL, L–J, process in buffer, plant in buffer; FIG. 3B: 571/573-BAL, L–J, process in buffer, plant in CB-18 (17 μg/ml CB-18 final); FIG. 3C: 571/573-BAL, L–J, process in CB-18 (383 μg/ml), plant in buffer; FIG. 3D: 571/573-BAL, L–J, processin CB-18 (383 μg/ml), plant in CB-18 (17 μg/ml CB-18 final); FIG. 3E: 571/573-BAL, 7H11-Selective, process in buffer, plant in buffer; FIG. 3F: 571/573-BAL, 7H11-Selective, process in buffer, plant in CB-18 (17 μg/ml CB-18 final); FIG. 3G: 571/573-BAL, 7H11-Selective, process in CB-18 (383 μg/ml), plant in buffer; FIG. 3H: 571/573-BAL, 7H11-Selective, process in CB-18 (383 μg/ml), plant in CB-18 (17 μg/ml CB-18 final);

FIGS. 5A–5F present the growth curves when the *M. tuberculosis* isolate 571/573-BAL was tested using the experimental design shown in FIG. 4. FIGS. 5A and 5B examine a 5,000 fold dilution of the bacterial stock (approximately 165±54 cfu). FIGS. 5C and 5D examine a 25,000 fold dilution of the bacterial stock (approximately 33±11 cfu), and FIGS. 5E and 5F examine a 100,000 fold dilution of the bacterial stock (approximately 8±3 cfu). Diamonds: buffer in R.F.; squares: buffer in P/caz; triangles: lecithin in R.F.; "x": lecithin in P/caz. FIG. 5A: planted in buffer or buffer/lecithin; FIG. 5B: planted in CB-18 (17 μg/ml) or CB-18/lecithin (17 μg/ml @; FIG. 5C: planted in buffer or buffer/lecithin; FIG. 5D: planted in CB-18 (17 μg/ml) or CB-18/lecithin (17 μg/ml @); FIG. 5E: planted in buffer or buffer/lecithin; FIG. 5F: planted in CB-18 (17 μg/ml) or CB-18/lecithin (17 μg/ml @).

FIGS. 7A–7C present the growth curves when the *M. tuberculosis* isolate ATCC 27294 was tested using the experimental design shown in FIG. 6. Diamonds: R.F.; squares: PANTA; triangles: P/caz. FIG. 7A: 7H11-Select, planted in buffer. FIG. 7B: 7H11-Select, planted in CB-18 (17 μg/ml final). FIG. 7C: 7H11-Select, planted in TMA-18 (3.4 μg/ml final).

FIGS. 8A–8C present the growth curves when the *M. tuberculosis* isolate 571/573-BAL was tested using the experimental design shown in FIG. 6. Diamonds: R.F.; squares: PANTA; triangles: P/caz. FIG. 8A: 7H11-Select, planted in buffer. FIG. 8B: 7H11-Select, planted in CB-18 (17 μg/ml final). FIG. 8C: 7H11-Select, planted in TMA-18 (3.4 μg/ml final).

FIGS. 10A and 10B present the growth curves when the *M. tuberculosis* isolate ATCC 27294 was tested using the CB-18 titration experiment presented in FIG. 9. Diamonds: R.F.; squares: P-cax; triangles: 3 μg/ml CB-18; "x": 7 μg/ml CB-18; "*" 13 μg/ml CB-18; circles: 27 μg/ml CB-18; vertical hatches: 54 μg/ml CB-18; horizontal dashed line: 109 μg/ml CB-18. FIG. 10A, titration in the absence of P-cax. FIG. 10B, each titration performed in the presence of P-cax.

FIGS. 11A and 11B present the growth curves when the *M. tuberculosis* isolate 571/573-BAL was tested using the CB-18 titration experiment presented in FIG. 9. Diamonds:

R.F.; squares: P-cax; triangles: 3 µg/ml CB-18; "x": 7 µg/lml CB-18; "*" 13 µg/ml CB-18; circles: 27 µg/ml CB-18; vertical hatches: 54 µg/ml CB-18; horizontal dashed line: 109 µg/ml CB-18. FIG. 11A, titration in the absence of P-cax. FIG. 11B, each titration performed in the presence of P-cax.

FIG. 12A, titration in the absence of P-caz. FIG. 12B, each titration performed in the presence of P-caz.

FIGS. 13A and 13B present the growth curves when the *M. avium* complex isolate 802-BAL was tested using the CB-18 titration experiment presented in FIG. 9. Diamonds: R.F.; squares: P-caz; triangles: 7 µg/ml CB-18; "x": 13 µg/ml CB-18; "*" 27 µg/ml CB-18. FIG. 13A, titration in the absence of P-caz. FIG. 13B, each titration performed in the presence of P-caz.

FIG. 14A, titration in the absence of P-cft. FIG. 14B, each titration performed in the presence of P-cft FIG. 15A, titration in the absence of P-cft. FIG. 15B, each titration performed in the presence of P-cft.

FIG. 17A: 7H11-select, planted in buffer. FIG. 17B: 7H11 -select, planted in CB-18 (17 µg/ml final).

FIG. 18A: 7H11-select, planted in buffer. FIG. 18B: 7H11-select, planted in CB-18 (17 µg/ml final).

FIG. 19A: 7H11-select, planted in buffer. FIG. 19B: 7H11-select, planted in CB-18 (17 µg/ml final).

FIG. 20A: 7H11-select, planted in buffer. FIG. 20B: 7H11-select, planted in CB-18 (17 µg/ml final).

FIG. 21A: 7H11-select, planted in buffer. FIG. 21B: 7H11-select, planted in CB-18 (17 µg/ml final).

FIG. 22A: 7H11-select, planted in buffer. FIG. 22B: 7H11-select, planted in CB-18 (17 µg/ml final).

FIG. 23A: 7H11-select, planted in buffer. FIG. 23B: 7H11-select, planted in CB-18 (17 µg/ml final).

FIGS. 24A and 24B present the growth curves when the *M. tuberculosis* isolate 512-JHH was tested using the antibiotic screening experiment presented in FIG. 16. Diamonds: R.F.; squares: PANTA; triangles: P-caz;"x": P/cfp; "*" P/cax; circles: P/cft. FIG. 24A: 7H11-select, planted in buffer. FIG. 24B: 7H11-select, planted in CB-18 (17 µg/ml final).

FIG. 25A: 7H11-select, planted in buffer. FIG. 25B: 7H11-select, planted in CB-18 (17 µg/ml final).

FIGS. 26A and 26B present the growth curves when the *M. tuberculosis* isolate 52-96-BOL was tested using the antibiotic screening experiment presented in FIG. 16. Diamonds: R.F.; squares: PANTA; triangles: P-caz;"x": P/cfp; "*" P/cax; circles: P/cft. FIG. 26A: 7H11-select, planted in buffer. FIG. 26B: 7H11-select, planted in CB-18 (17 µg/ml final).

FIGS. 27A and 27B present the growth curves when the *M. tuberculosis* isolate 57-96-BOL was tested using the antibiotic screening experiment presented in FIG. 16. Diamonds: R.F.; squares: PANTA; triangles: P-caz;"x": P/cft; "*" P/cax; circles: P/cft. FIG. 27A: 7H11-select, planted in buffer. FIG. 27B: 7H11-select, planted in CB-18 (17 µg/ml final).

FIGS. 28A and 28B present the growth curves when the *M. tuberculosis* isolate 572/573-BAL was tested using a modified version of the antibiotic screening experiment presented in FIG. 16. In these experiments additional, non-β-lactam antibiotics were tested. Diamonds: R.F.; squares: P-caz;diamonds: erythromycin; "x": ceftriaxone. FIG. 28A: antibiotic screening, planted in R.F. FIG. 28B: antibiotic screening; planted in CB-18.

FIG. 29A: antibiotic screening, planted in R.F., FIG. 29B: antibiotic screening, planted in CB-18.

Figure 2A:
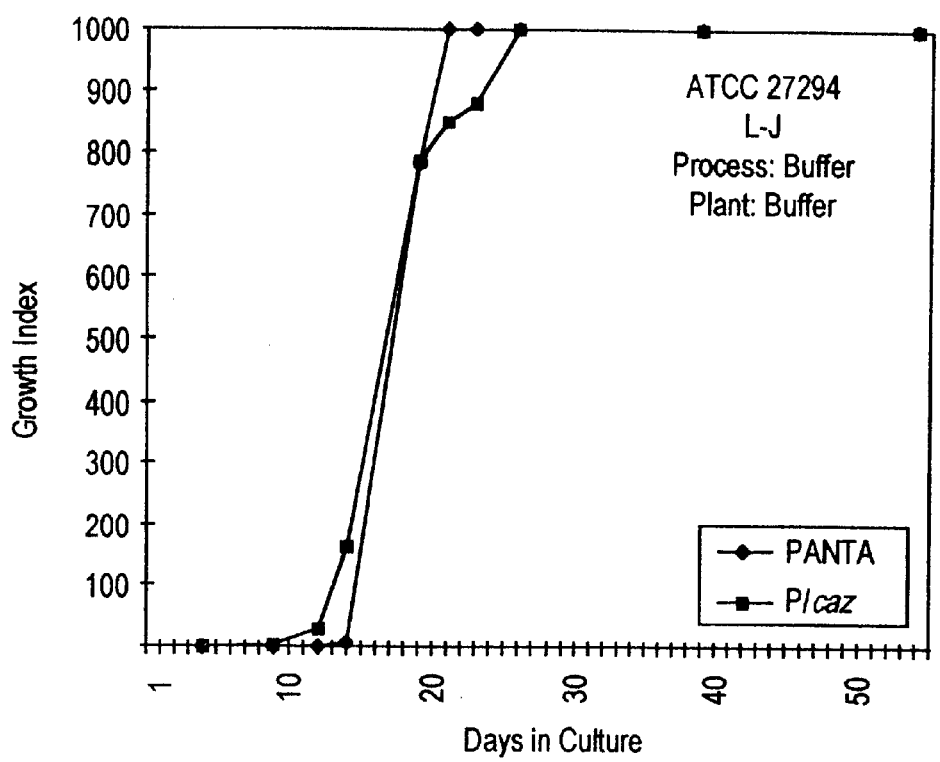
FIGS. 2A–2F present the growth curves when the *M. tuberculosis* isolate ATCC 27294 was tested using the experimental design shown in FIGS. 1A and 1B. Diamonds: PANTA; Squares: P/caz.
Figure 2B:
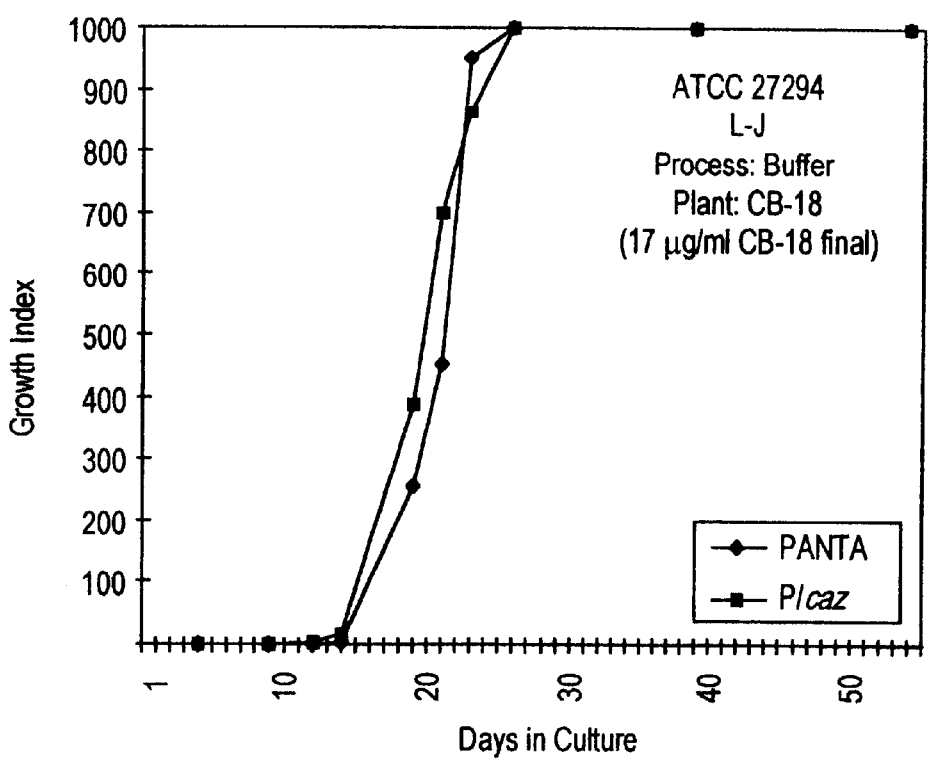
Figure 2C:
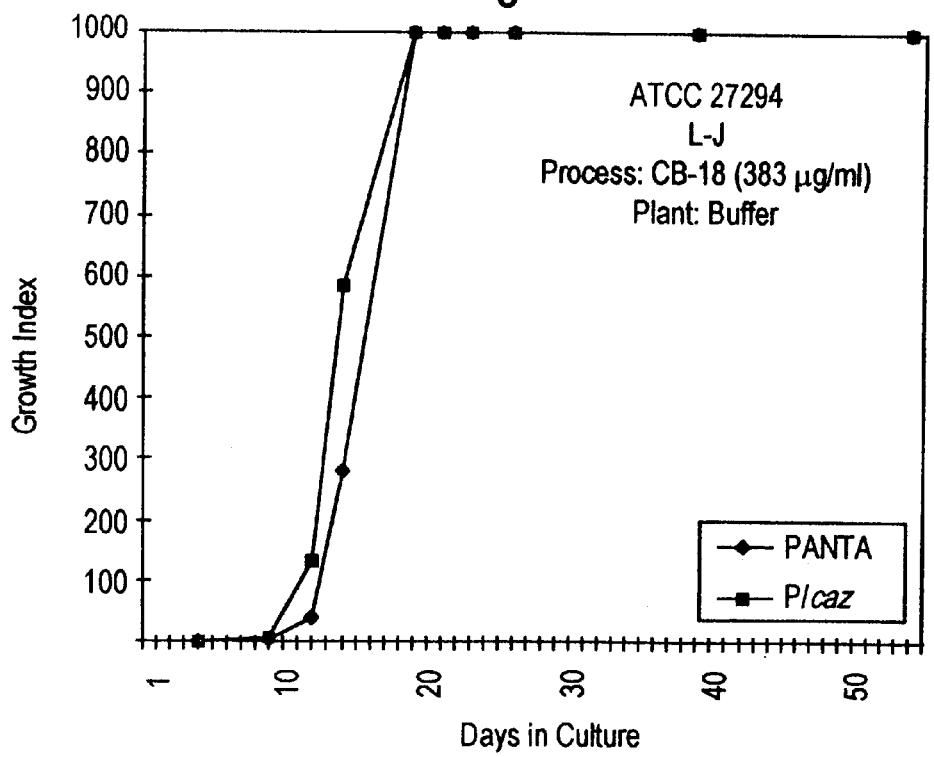
Figure 2D:
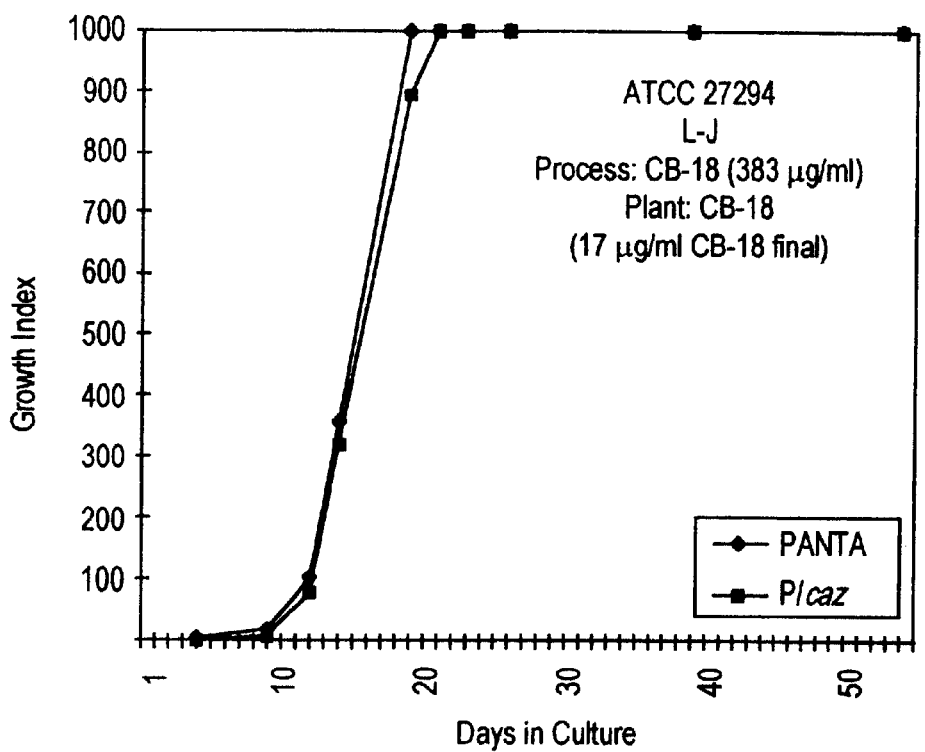
Figure 2E:
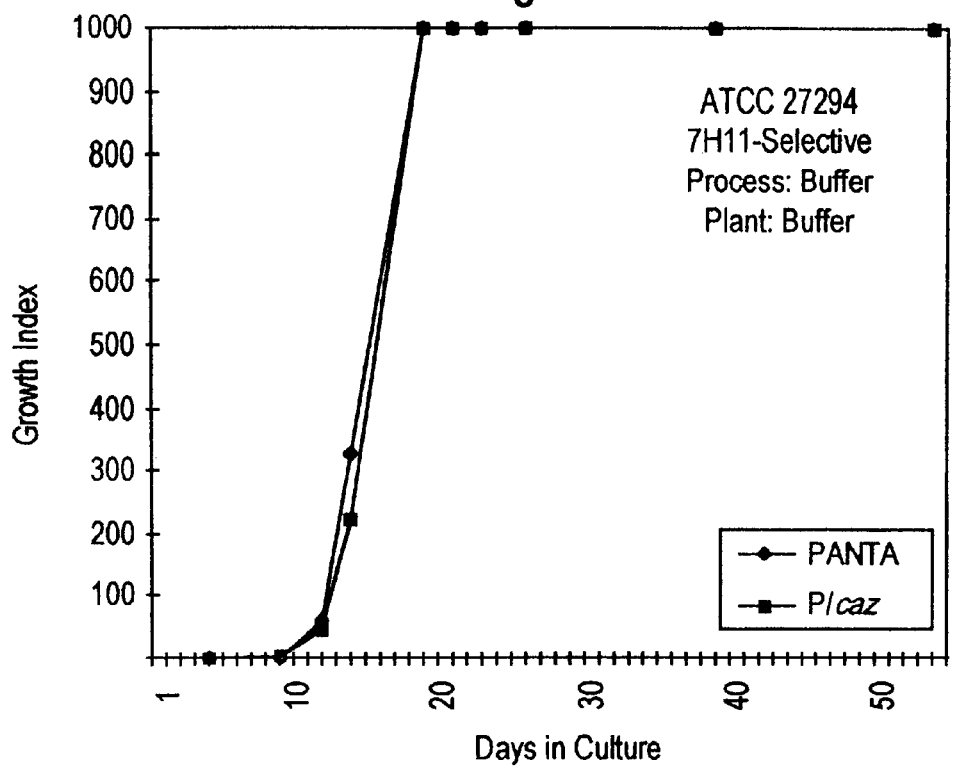
Figure 2F:
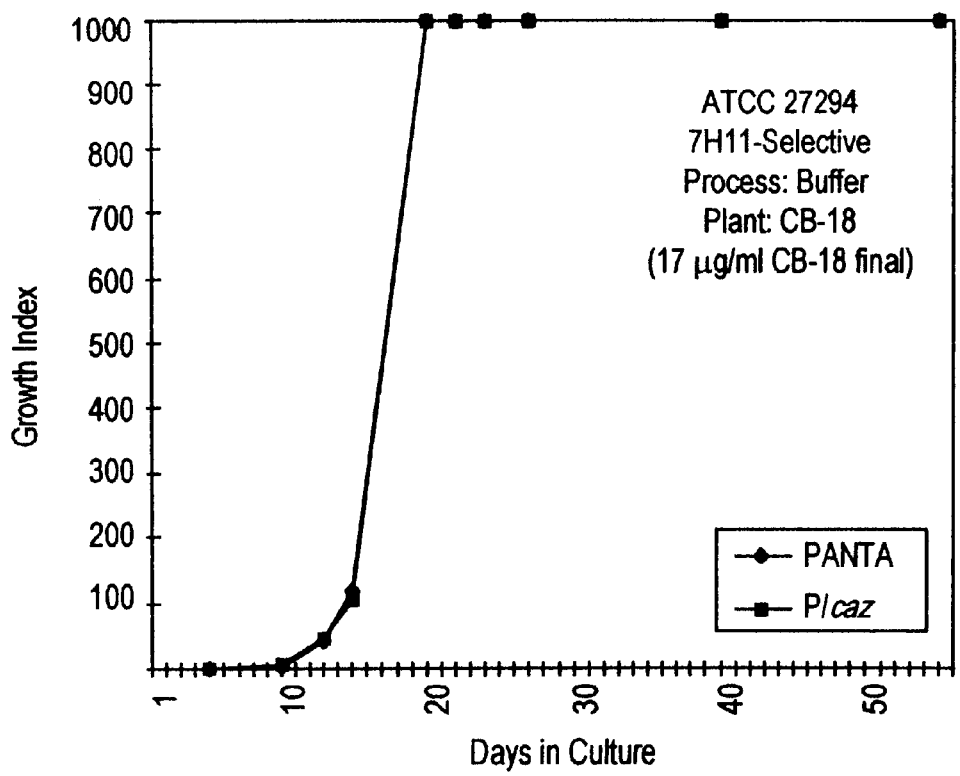

By a microorganism, such as a clinical isolate or infectious agent, being "susceptible" is meant that the microorganism, (for example, a Mycobacterium), is deleteriously affected by an antibiotic in such a manner that such clinical isolate or infectious agent is rendered incompetent, noninfectious or non-viable as understood in the art (Yao, J. D. C. et al., In: Murray, P. R. el al., eds. *Manual of Clinical Microbiology*, ASM Press, Washington, D.C. (1995) pp.1281–1307 (incorporated herein by reference)). Susceptible, as used herein, is synonymous with "susceptibility." When a microorganism, such as a clinical isolate or infectious agent, is determined to be susceptible to a given antibiotic, the antibiotic is said to have "activity" against, or be "active" against such isolate or infectious agent.

By "susceptibility testing" is meant an in vitro assay whereby the susceptibility of a microorganism, such as a clinical isolate or an infectious agent, to a series of antimicrobial compounds is determined, as understood in the art (Jorgensen, J. H. et al., In: Murray, P. R et al., eds. *Manual of Clinical Microbiology*, ASM Press, Washington, D.C. (1995) pp.1277–1280; Woods, G. L. et al., In: Murray, P. R. et al, eds. *Manual of Clinical Microbiology*, ASM Press, Washington, D.C. (1995) pp.1327–1404; National Committee for Laboratory Standards. *Methods for Dilution Antimicrobial Susceptibility Tests for Bacteria that Grow Aerobicall—Fourth Edition.* Approved Standard M7-A4 Villanova, Pa. (1997); National Committee for Laboratory Standards. *Performance Standards for Antimicrobial Disk Susceptibility Tests—Sixth Edition.* Approved Standard M2-A6 Villanova, Pa. (1997); National Committee for Laboratory Standards. *Development of In Vitro Susceptibility Testing Criteria and Quality Control Parameters.* Approved Standard M23-A Villanova, Pa. (1994); National Committee for Laboratory Standards. *Antimycobacterial Susceptibility Testing for Mycobacterium tuberculosis;* Tentative Standard M24-T Villanova, Pa. (1995) (all incorporated herein by reference)). The goal of any susceptibility testing is to more accurately predict a successful therapeutic intervention.

By "antibiotic" is meant any of the compounds known in the art that have a deleterious effect on the viability, integrity, infectivity or competence of an infectious agent, as understood in the art (see: Murray, P. R. et al., eds. *Manual of Clinical Microbiology*, ASM Press, Washington, D.C. (1995) pp.1281–1307 and 1385–1404; Kucers, A. et al., *The Use of Antibiotics* $4^{th}$ ed. J. B. Lippincott Co. Philadelphia, Pa. (1987); and Lorian, V. ed. *Antibiotics in Laboratory Medicine* $2^{nd}$ Edition, Williams & Wilkins, Baltimore, Md., all incorporated herein by reference). Examples of the different classes of antibiotics would include the β-lactam antibiotics, the β-lactamase inhibitors, the aminoglycosides and aminocyclitols, the quinolones, tetracyclines, macrolides, and lincosamides, as well as the glycopeptides, lipopeptides and polypeptides, the sulfonamides and trimethoprim, chloramphenicol, isoniazid, nitroimidazoles, rifampicins, nitrofurans, methenamine, and mupirocin, all of which would be useful in conjunction with the methods of the invention. The term antibiotic is synonymous with "antimicrobial," "therapeutic," or "drug" as used herein. All antibiotics are drugs or therapeutics, but not all drugs or therapeutics are antibiotics.

By "adjuvant" is meant a chemical compound that may or may not have antimicrobial activity in and of itself, but when taken in combination (i.e., simultaneously) with one or more of the antibiotics, the compound acts synergistically to enhance the effect of these antibiotic(s). Adjuvant(s) can be used to enhance either susceptibility testing or antimicrobial therapy. An example of a therapeutic adjuvant would be a β-lactamase inhibitor (infra). The methods and compositions described herein do not speak to the use of the β-lactamase inhibitors as adjuvants per se, but rather to the use of betaine-like detergents as adjuvants; however, the betaine-like detergents can be used alone or in combination with other adjuvants, including the β-lactamase inhibitors.

The term "betaine-like" is synonymous with "SB-18-like" as used in WO 95/27076, and in U.S. Pat. No. 5,658,749, both incorporated herein by reference. Betaine-like detergents according to WO 95/27076 and U.S. Pat. No. 5,658,749 have the ability to disperse cords (and clumps) of mycobacteria and/or compensate buoyancy of the mycobacteria. Dispersion of mycobacteria that cord, such as, for example, *Mycobacterium tuberculosis* complex (MTB) organisms, facilitates detection by increasing the probability that aliquots taken for detection are representative of the whole sample. Betaine-like detergents that disperse cords have an alkyl chain length that is greater than 16 carbon atoms, and alkyl chains with 18–20 carbon atoms are most preferred. Betaine-like detergents also have the ability to facilitate collection of mycobacteria, such as, for example, *Mycobacterium avium* complex (MAC) organisms, that do not grow in clumps, by compensating, to some degree, the natural buoyancy of such organisms. Such compensation preferably occurs by a mechanism that involves movement of the detergent into the bacterial cell. Betaine-like detergents that compensate buoyancy preferably have an alkyl chain length greater than 12 carbon atoms, and most preferably 16–20 carbon atoms. Therefore, "betaine-like," as used herein includes structures as described in Tables 2 and 3 of WO 95/27076, and U.S. Pat. No. 5,658,749, both incorporated herein by reference, including, for example, the CB-like, SB-like, HSB-like, PB-like, StB-like, PhB-like, SoB-like, RevB-like, AO-like, cAB-like, and ImB-like compounds that possess SB-18-like activity, as described in WO 95/27076 and in U.S. Pat. No. 5,658,749. "Betaine-like" detergents include zwitterionic compounds of the structure shown in Table 1. These structures are expected to be the most useful in the methods of the invention.

TABLE 1

The Most Useful Betaine-Like Detergents
The general structure of the most useful betaines is shown. $R_1$ is the hydrophobic alkyl chain, and α is the "linkage" connecting $R_1$ to the cation, β. $R_2$ and $R_3$ modify the cation, when required. $R_4$ is the "bridge" that connects the cation to the anion, γ.

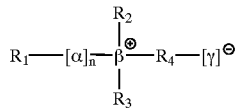

| | |
|---|---|
| $R_1$ | $C_8$–$C_{22}$ |
| α | —$CH_2$—, —CH(OH)—, —(CO)—NH—$CH_2CH_2CH_2$—, —O—, —C(O)— |
| n | 0 or 1 |
| β | —$N^\oplus$—, —$P^\oplus$—, or —$S^\oplus$— |
| $R_2$ | —H, —$CH_3$, —$C_2H_5$, —$C_3H_7$, —$C_4H_9$ |
| $R_3$ | —H, —$CH_3$, —$C_2H_5$, —$C_3H_7$, —$C_4H_9$ |
| $R_4$ | —$CH_2$—, —$C_2H_4$—, $C_3H_6$—, $C_4H_8$—, —$C_5H_{10}$—, —$C_6H_{12}$—, —$CH_2$—$C_6H_4$—, $C_mH_{2m}$—, —CH(OH)$CH_2CH_2$—, —$CH_2$CH(OH)$CH_2$—, or —$C_mH_{2m-1}$(OH)—; where m is ≧1 |
| γ | —$COO^\ominus$, —$SO3^\ominus$, —$OSO3^\ominus$, $OPO3^\ominus$, $PO3^\ominus$, $PO2^\ominus$— |

By "CB-like" is meant those betaine-like detergents having a carboxylate (—$COO^\ominus$) moiety as the anion (e.g., carboxybetaine-like). By "SB-like" is meant those betaine-like detergents having a sulfonate (—$SO_3^\ominus$) moiety as the anion (e.g., sulfobetaine-like). By "HSB-like" is meant those betaine-like detergents having a sulfonate moiety as the anion, and a hydroxyl group (—OH) in the bridge (e.g., hydroxysulfobetaine-like). By "PB-like" is meant those betaine-like detergents having either a phosphate (—$OPO_3^\ominus$), phosphonate (—$PO_3^\ominus$), or a phosphinate (—$PO_2^\ominus$) moiety as the anion (e.g., phosphobetaine-like). By "StB-like" is meant those betaineike detergents having a sulfate (—$OSO_3^\ominus$) moiety as the anion (e.g., sulfatobetaine-like). By "AO-like" is meant those betaine-like detergents having an oxide radical (—$O^\ominus$) as the anion (e.g., amine oxide-like). By "PhB-like" is meant those betaine-like detergents having a phosphonium (—$P^\oplus$—) moiety as the cation (e.g., phosphoniumbetaine-like). By "SoB-like" is meant those betaine-like detergents having a sulphonium (—$S^\oplus$—) moiety as the cation (e.g., sulphoniumbetaine-like). By "n-alkyl betaine" is meant those betaine-like detergents having an ammonium (—$N^\oplus$—) moiety as the cation (e.g., n-alkyl betaine-like). By "ImB-like" is meant those betaine-like detergents having a imidazolinium moiety as the cation (e.g., imidazoliniumbetaine-like). By "RevB-like" is meant those betaine-like detergents wherein the alkyl chain is covalently attached to the anion, as opposed to the cation (e.g., reverse betaine-like). By "cAB-like" is meant those betaine-like detergents wherein the alkyl chain is covalently attached to the bridge, as opposed to either the cation or the anion (e.g., c-alkyl betaine-like).

By "CB-18" is meant N-(3-carboxypropyl)-N,N-dimethyl-1-octadecanaminium, inner salt. CB-18 is also known as N,N-dimethyl-N-(n-octadecyl)-N-(3-carboxypropyl)ammonium inner salt, or $C_{18}$-carboxypropylbetaine. CB-18 has been assigned the CAS®No. 78195-27-4.

By "SB-18" is meant N-octadecyl-N,N-dimethyl-3-ammonio-1-propane-sulfonate (CAS®No. 13177-41-8).

By "SB-16" is meant N-hexadecyl-N,N-dimethyl-3-ammonio-1-propane-sulfonate (CAS®No. 2281-11-0).

By "SB-14" is meant N-tetradecyl-N,N-dimethyl-3-ammonio-1-propane-sulfonate (CAS®No. 14933-09-6), and by "SB-12" is meant N-dodecyldecyl-N,N-dimethyl-3-ammonio-1-propane-sulfonate (CAS®No. 14933-08-5).

By "clinical isolate" is meant a purified strain of a bacterial agent that causes infection, such clinical isolate being derived from a patient infected with such infectious agent. One or more clinical isolates could be derived from the same patient, or the same isolate might be derived from different patients, such as is seen during nosocomial outbreaks (Pittet, D. et al., *Archives of Internal Medicine* 155:1177–1184, (1995)). Such clinical isolates are typically purified by a combination of specimen processing and culture methods. As such these clinical isolates are viable and, therefore, available for further analysis and testing with respect to susceptibility to antibiotics in an in vitro assay such as a susceptibility test. Procedures for purifying these clinical isolates include methods and procedures known in the art, especially those described by Kent, P. T. et al., "Public Health Mycobacteriology: A Guide for the Level III Laboratory", U.S. Department of Health and Human Service, Centers for Disease Control, Atlanta, Ga. (1985) pp. 31–70, and Nolte, F. S. et al., In: Murray, P. R. et al., eds. *Manual of Clinical Microbiology,* ASM Press, Washington, D.C. (1995) pp.400–437, for the isolation of Mycobacterium, or the methods outlined by Clarridge, J. E. et al., In: Murray, P. R. et al., eds. *Manual of Clinical Microbiology,* ASM Press, Washington, D.C. (1995) pp.357–379, and Beaman, B. L. et al., In: Murray, P. R. et al., eds. *Manual of Clinical Microbiology,* ASM Press, Washington, D.C. (1995) pp.379–399 for the isolation of Corynebacterium and Nocardia, respectively (all incorporated herein by reference).

By "infectious agent" is meant an infectious microorganism, especially an infectious bacterium as understood in the art. Infectious agents of special interest according to the methods of the invention include those that contain mycolic acid structures, for example, the mycobacteria, and most especially *Mycobacterium tuberculosis* complex bacteria, that cause disease (Isenberg, H. D. et al., In: Murray, P. R. et al., eds. *Manual of Clinical Microbiology,* ASM Press, Washington, D.C. 1995 pp 5–18 (incorporated herein by reference)). A human or animal patient having a disease caused by such an infectious agent is said to have an "infection" caused by such an agent, or to be "infected with" such agent. An infectious agent that causes disease is said to be "pathogenic." Bacteria that are typically not pathogenic, and part of the patient's normal bacterial flora, are said to be saprophytic. Under some circumstances, such as when the patient is immune compromised or immune suppressed (e.g., being infected with HIV, or having AIDS complex, or after having undergone an organ transplant), such saprophytic microorganisms can cause infection. A patient can be infected with one or more infectious agents.

By "mycolic acid structure(s)" is meant a β-hydroxy acid substituted at the α-position with a moderately long aliphatic chain, as understood in the art (Goren, M. B. *Bact. Rev.* 36:33–64(1966), incorporated herein by reference). An example of an organism having corynomycolic acid is *Corynebacterium diphtheria;* an example of an organism having nocardomycolic acid is *Nocardia asteroides;* and an example of an organism having mycolic acid is *Mycobacterium tuberculosis* (see also Funke, G. et al., *Clin. Micro. Rev.* 10:125–159 (1997) for further discussions on coryneform bacteria (incorporated herein by reference)) Such mycolic acid-like molecules are herein collectively termed "mycolic acid structures." Additional tables of representative mycolic acid structures, including some that are unsaturated, cyclopropanoid, methoxylated and ketonic acids, may also be found, for example, in Lederer, E. *Chem. Phys, Lipids* 1:294–315 (1967); Lederer, E. *Pure Appl.*

Chem. 25:135–165 (1971), both incorporated herein by reference. "Mycolic acid structures" are acid-stable molecules.

By "antimicrobial therapy" is meant treating a patient, either human or animal, in vivo, with efficacious levels of an antibiotic-containing composition by any appropriate means; for example, by ingesting, injecting, applying or inhaling such antibiotic. Delivery of the compositions of the invention, that include the antibiotic, might also include, but not be limited to, introduction of the drug via intravenous means, as the active component of an ointment, or by swallowing. The goal of antimicrobial therapy is to compromise the viability, integrity or competence of the infectious agent such that the patient or animal infected rids, eliminates, or overcomes the infection. Antimicrobial therapy can be taken to mean that one or more of the classes of drugs, or one or more of the drugs within a given class of antibiotics, is taken alone or in combination, that is to say, either simultaneously or in series. Antimicrobial therapy is synonymous with "antibiotic therapy" or simply "therapy" as used herein.

By an "efficacious amount" is meant an amount sufficient to achieve a desired end. For example, when used in the context of antimicrobial therapy, an efficacious amount is an amount that results in the amelioration of a microbiological infection. Such amelioration can be a direct effect on the microorganism, or an indirect effect whereby exposure to the efficacious amount compromises the microorganism in a manner that increases the susceptibility of the microorganism to a second agent.

A material is said to be "substantially free of contaminants" if it has been substantially purified from materials with which it has previously been associated before such purification, to a degree necessary to perform a desired procedure or analysis. Therefore, such contaminants are either completely absent or are otherwise present at such low concentrations that their presence (1) does not interfere with the desired therapeutic effect when a preparation containing such material is administered to a patient in need of the same and (2) does not harm the patient as the result of the administration of such preparation.

By "administration" or "administering" to a patient is intended the introduction of a desired substance into or onto a desired site, such as a site in or on human or an animal in need of the same, by any appropriate means known to the medical art appropfiate for achieving the desired purpose, including, but not limited to, enteral, parenteral (e.g., intravenous) and iontophoretic administration. Administration can also be in the form of a bandage that is placed locally at the site of an infection, the bandage being designed to provide efficacious release of the antibiotic(s) and betaine-like detergents of the invention.

By "coadministration" or "coadministering" two or more agents, such as an antibiotic and a betaine-like detergent, to a patient is intended the administering of such agents either together in a single preparation, or separately in individual preparations.

A "pharmaceutically acceptable salt" is intended to include salts formed from pharmaceutically acceptable acids or bases, such as, for example, but not limited to, acids such as sulfuric, hydrochloric, nitric, phosphoric, etc., or bases such as alkali or alkaline earth metal hydroxides, ammonium hydroxides, alkyl ammonium hydroxides, etc.

The term "pharmaceutically acceptable vehicle" is intended to include pharmaceutically acceptable solvents, carriers, diluents, and the like, which are utilized as additives to preparations of the invention so as to provide a carrier or adjuvant for the administration of such compounds.

The term "treatment" or "treating" is intended to include the administration of efficacious amounts of one or more desired agents to a subject or object in need of such agents for purposes which may include prophylaxis, amelioration, prevention or cure of a disorder, or eradication of a microorganism, thought to be susceptible to such agents.

By "exposing" a sample containing a microorganism to a composition of the invention is intended mixing the microorganism and the composition, or otherwise providing for contact between the microorganism and the composition.

The inventor serendipitously discovered that when at least one betaine-like detergent such as $C_{18}$-carboxypropylbetaine (CB-18) was combined with antimicrobial compounds, clinical isolates of mycobacteria could be differentiated based on an induced susceptibility. The inventor recognized that this phenomenon might be useful for characterizing such clinical isolates, and also, microorganisms and infectious agents in general, with respect to susceptibility to such antimicrobial compounds. In addition, the inventor also recognized that this phenomenon might be useful for enhancing the susceptibility of such mycobacteria to these antimicrobial compounds in a synergistic fashion during in vivo therapy.

Thus, in its broadest embodiment, the invention is directed to a method for characterizing the susceptibility of microorganisms to antimicrobial compounds. In a preferred embodiment, the microorganism being tested is an infectious agent or clinical isolate. In a further preferred embodiment, the susceptibility of a microorganism to the β-lactam antibiotics is characterized and determined. In a further preferred embodiment, the microorganism to be tested is obtained from a sample taken from a patient suspected of being, or at risk of being, or identified as being infected with undesired bacteria that contain mycolic acid structures. The susceptibility test of the invention is herein referred to as a betaine susceptibility test. The results of such susceptibility testing characterize the microorganisms under investigation that are present in a sample, such as a clinical isolate or infectious agent, with respect to the CB-18 effect described herein. That is, the susceptibility test of the invention identifies whether or not a microorganism(s) that is present in a sample is susceptible to the antibiotic(s) that are tested. Preferably, as a result of the susceptibility test of the invention, one or more antibiotics, or combinations of the same with other efficacious agents such as the betaine-like detergents, are identified to which the microorganisms present in the sample are susceptible. However, it is also important that, as a result of the susceptibility test of the invention, one or more antibiotics, or combinations of the same with other agents such as betaine-like detergents, are identified to which the microorganisms present in the sample are not susceptible. The result allows the health professional to more effectively select an appropriate antimicrobial therapy to treat patients, or otherwise sterilize the desired site from which the sample was taken with respect to this microorganism(s).

In a second preferred embodiment, the invention is directed to a method for treating patients during antibiotic therapy using betaine-like detergents as adjuvants, such patients being suspected of being, or at risk of being, or identified as being infected with undesired bacteria. In a preferred embodiment, such undesired bacteria contain mycolic acid structures. Such antibiotic therapy can be designed to treat such infection with a combination of one or more antibiotic(s) and one or more betaine-like detergent(s) of the invention. The combination of antibiotic and betaine-like detergent more effectively treats the patient than antibiotic therapy alone by compromising the integrity of such bacteria in such a manner that the infecting organisms are rendered either incompetent, noninfectious or non-viable more rapidly or more effectively than they would be using the antibiotic in the absence of the betaine-like detergent.

In a third preferred embodiment, the invention is directed to a method for sterilizing or otherwise preventing the growth of an undesired microorganism by providing a combination of one or more antibiotics with one or more betaines to the site of infection, and or the environment suspected of containing such microorganisms.

The susceptibility test of the present invention is especially useful for characterizing, assessing and establishing the susceptibility of a microorganism, especially a clinical isolate and/or infectious agent, to antimicrobial agents. Disease caused by such microorganisms can be treated with efficacious amounts of the combination of one or more of the antibiotics and betaine-like detergent(s) that the susceptibility test of the invention demonstrates as being a rational component of a therapeutic course for the treatment of such infection caused by such microorganism(s).

In the susceptibility method of the invention, use of a range of concentrations of a given betaine-like detergent provides useful information regarding the efficacy of such detergent, and testing with more than one betaine-like detergent is preferred. As many betaine-like detergents as desired, or combinations of the same, can be tested. Preferably at least five are tested, although any number, for example, 10, 15, 20, 25 or 30 or more are also easily tested in varying dilutions. The susceptibility test provides additional information regarding the effect of the combination of such concentration of betaine-like detergent with the selected antibiotic(s). The working or useful concentration of a given betaine-like detergent will depend on the detergent used. In general, useful concentrations range from 0.1 µg/ml for the most potent structures, to 1 mg/ml for the most innocuous, with 1 µg/ml to 100 µg/ml being the most useful concentrations for most betaine-like detergents. Such betaine-like detergents can be used alone or in combination with other betaine-like detergents in the susceptibility test methods of the invention.

While at least one antibiotic is necessary to provide susceptibility information in the methods of the invention, it is anticipated that more than one antibiotic will be used in the betaine susceptibility test. As many antibiotics or combinations of antibiotics as desired can be tested. Preferably at least five are tested, although any number, for example, 10, 15, 20, 25 or 30 or more are also easily tested in varying dilutions. The concentration of a given antibiotic will depend on the antibiotic used. In general, useful concentrations range from 0.1 µg/ml for the most potent antimicrobials, to 100 µg/ml for the most benign compounds, with 0.5 µg/ml to 64 µg/ml being the most useful concentrations for most antibiotics. Such antibiotics can be used alone or in combination with other antibiotics in the methods of the invention.

As with other susceptibility tests (Woods, G. L. et al., In: Murray, P. R. et al., eds. *Manual of Clinical Microbiology*, ASM Press, Washington, D.C. (1995) pp. 1327–1404), it would be reasonably expected that variations in inoculum would affect the outcome or results generated by the betaine susceptibility test. The inoculum is manufactured by a standard method including picking colonies or comparison with a MacFarland standard as known in the art. The experimental results presented in FIGS. 5A–5F and Example 8 show that the CB-18 effect is comparable for inocula between a few cells and several thousand cells. In general, between 1 cell and $10^5$ cells are useful in this regard, with 100 to 10,000 cells being most useful, and approximately 1,000 cells being preferred. Below 10 cells, sampling issues (e.g., sampling error) may obscure performance of the assay, and above $10^5$ cells, performance is affected due to overwhelming the system. Inocula between 1,000 and 10,000 cells allow growth of the controls in a timely fashion. However, any inoculum that provides for observing the CB-18 effect can be used, and, in this regard, the betaine susceptibility test of the invention is similar to other in vitro susceptibility assays.

The information provided by betaine susceptibility assay described herein is a result of the dynamic interaction of the isolate, the betaine-like detergent(s), and the antibiotic(s). The betaine susceptibility test combines these three components and allows the artisan to identify and adjust the concentration of the antibiotic(s) and betaine-like detergent (s) with the appropriate inoculum in such a manner as to produce the CB-18 effect, thereby providing the most useful information regarding the character and/or susceptibility of the clinical isolate under investigation.

Example 7 shows that some betaine-like detergents may be more useful than others in both the susceptibility and therapeutic methods of the invention. For example, structures that include modifications to the linkage show reduced activity in the susceptibility and thus therapeutic assays herein. In addition, betaine-like detergents that have modifications in the bridge also show attenuated activity in the susceptibility and thus therapeutic assays herein. Table 1 shows those structures that are most useful in the methods of the invention.

The most useful betaine-like detergents are those without modification, for example, wherein $R_1$ is a simple alkyl, the linkage (α) is a simple methylene, $R_2$ and $R_3$ are either hydrogen or methyl groups (depending on the cation employed), and $R_4$ has no constituents.

Toxicity of the betaine-like detergents against mycolic acid containing bacteria is dependent on the anion (γ), the bridge length ($R_4$), and alkyl chain length ($R_1$). In general, a balance between the surface active nature of the betaine and its action as an adjuvant must be considered in this regard. For example, the surface active properties are dependent on the acid-base character of the anion, and the alkyl chain length. The most ionic detergents are the phosphobetaines ($PO_4^{\ominus}$), and the most non-ionic are the sulfatobetaines ($SO_4^{\ominus}$). It is expected that phosphobetaines would be exceptionally toxic, and sulfatobetaines would have solubility problems. Hence, sulfobetaines and carboxybetaines are preferred, and carboxybetaines are the most preferred. Based on the permeability discussion (Example 9), the carboxybetaines are predicted to posses the most preferred anion, and whereas CB-18 possesses the ammonium cation, the sulfoniumbetaines are reasonably predicted to posses the most preferred cation. Therefore, the preferred structures include n-alkyl sulfobetaines, and especially preferred structures are n-alkyl carboxybetaines, with the most preferred structures the alkyl-sulfoniumcarboxybetaines.

The surface active properties of betaines change with increasing chain length. Longer alkyl chains have lower critical micellar concentrations (CMC), or conversely, shorter alkyl chains require higher concentrations to achieve the CMC. The length of the alkyl chain can be varied according to the use. For example, since shorter alkyl chains require higher concentrations to achieve the CMC, then when used in the second embodiment (i.e., during antimicrobial therapy) shorter chains are preferred, especially for use in the therapeutic methods of the invention when delivery is by an intravenous route. Alternatively, therapeutic delivery via inhalation may be used as compositions useful for such delivery are less restricted by the relationship between concentration and CMC; as such, longer alkyl chains can be employed. In the first embodiment (i.e., in the in vitro susecptility assay), correlation of the chain length can be varied to identify that detergent capable of maximizing the observable CB-18 effect. Betaine-like detergents having alkyl chain lengths of 8 to 22 carbon atoms are preferred, alkyl chain lengths of 12 to 18 carbon atoms are especially preferred, and alkyl chain lengths of 16 to 18 carbon atoms are most preferred.

In order to guarantee the ability to salt in, the minimum bridge length should be a propylene. Toxicity to the microorganism is also a function of the bridge length (Tsubone, K. et al., *Jour. Pharm. Sci.* 80:441–444 (1991)). For example, both the ethylene and butylene bridges show greater toxicity than the propylene bridge. It is possible that the ethylene bridge could have solubility problems, depending on the ions employed. Therefore, further consideration would require matching the appropriate alkyl chain length with the ions and bridge structure to avoid such problems. For example, longer alkyl chains require ion combinations with stronger polarity ($SO_4^\ominus < SO_3^\ominus < CO_2^\ominus < PO_4^\ominus$) and a bridge structure that facilitates salting-in. A bridge structure of the type $-C_mH_{2m}-$ (where $m \geq 1$) is preferred, and a bridge with the same structure having $6 \geq m \geq 3$ is most preferred. As per Tsubone, K. et al., *Jour. Pharm. Sci.* 80:441–444 (1991), the constituents used to modify the cation would also impact toxicity (e.g., toxicity was inversely related to the length of $R_2$ and $R_3$ (see Table 1)).

The length of the bridge and the cation constituents can be varied according to use. For example, since shorter alkyl chains might be used in the second embodiment (i.e., during antimicrobial therapy), bridge structures wherein $m \geq 2$ are acceptable because solubility is of less concern with shorter chains. Alternatively, delivery via inhalation would necessitate that the betaine-like detergent be soluble: and bridge structures wherein $m \geq 3$ would be required. As discussed above, the polarity of the betaine could be further modified by varying the anion. Again, correlation of the bridge length and the constituents used to modify the cation could be varied to maximize the observable CB-18 effect in the first embodiment (i.e., in the in vitro assay).

Several carboxybetaines have been tested and show the CB-18 effect in the methods of the invention. These include: $C_{16}$-carboxymethylbetaine (CAS®No. 693-33-4), $C_{18}$-carboxyethylbetaine (CAS®No. 30612-73-8), $C_{18:1}$-carboxymethylbetaine (CAS®No. 871-37-4), and $C_{18}$-carboxypropylbetaine (CAS®No. 78195-27-4).

Examples of CB-like detergents, but not limited to, are: N-(carboxymethyl)-N,N-dimethyl-1-hexadecanaminium, inner salt (CAS®No. 693-33-4), cococarboxymethylbetaine and (CAS®No. 68424-94-2), N-(carboxymethyl)-N,N-dimethyl-9-octadecenyl-1-miniumm, inner salt (CAS®No. 871-37-4), N-(carboxymethyl)-N,N-dimethyl-3-((1-oxooctadecyl)amino)-1-propanaminium, inner salt (CAS®No. 6179-44-8), 3-amino-N(carboxymethyl)-N,N-dimethyl-1-propanaminium —$C_8$–$C_{22}$ acyl derivatives, inner salt (CAS®No. 84082-44-0), N-(carboxymethyl)-3-((12-hydroxy-1-oxo-9-octadecenyl)amino)-N,N-dimethyl-1-propanainium, inner salt (CAS®No. 71850-81-2), cocoa-midopropyl carboxymethylbetaine (CAS®No. 61789-39-7 and CAS®No. 61789-40-0), N-(2-carboxyethyl)-N,N-dimethyl-1-dodecanaminium, inner salt (CAS®No. 16527-85-8), N-(2-carboxyethyl)-N,N-dimethyl-1-tridecanaminium, inner salt (CAS®No. 132621-79-5), N-(2-carboxyethyl)-N,N-dimethyl-1-tetradecanaminium, inner salt (CAS®No. 69725-38-3), N-(2-carboxyethyl)-N,N-dimethyl-1-hexadecanaminium, inner salt (CAS®No. 42416-43-3), N-(2-carboxyethyl)-N,N-dimethyl-1-octadecanaminium, inner salt (CAS®No. 30612-73-8), N-dodecyl-beta-alanine (CAS®No. 1462-54-0), N-(3-carboxypropyl)-N,N-dimethyl-1-undecanaminium, inner salt (CAS®No. 150147-53-8), N-(3-carboxypropyl)-N,N-dimethyl-1-dodecanaminium, inner salt (CAS®No. 15163-30-1), N-(3-carboxypropyl)-N,N-dimethyl-1-tetradecanaminium, inner salt (CAS®No. 146959-90-2), N-(3-carboxypropyl)-N,N-dimethyl-1-pentadecanaminium, inner salt (CAS®No. 146959-91-3), N-(3-carboxypropyl)-N,N-dimethyl-1-hexadecanaminium, inner salt (CAS®No.71695-32-4), N-(3-carboxypropyl)-N,N-dimethyl-1-octadecanaminium, inner salt (CAS®No. 78195-27-4), N-(4-carboxybutyl)-N,N-dimethyl-1-dodecanaminium, inner salt (CAS®No. 120139-51-7), N-(5-carboxypentyl)-N,N-dimethyl-1-dodecanaminium, inner salt (CAS®No. 76392-97-7), N-(5-carboxypentyl)-N,N-dimethyl-1-hexadecanaminium, inner salt (CAS®No. 73565-98-7), N-(6-carboxyhexyl)-N,N-dimethyl-1-dodecanaminium, inner salt (CAS®No. 132621-80-8), 4-carboxy-N-dodecyl-N,N-dimethyl-benzenemethanaminium, inner salt (CAS®No. 71695-31-3), 2-carboxy-N-dodecyl-N,N-dimethyl-benzenemethanaminium, inner salt (CAS®No. 71695-34-6), 4-carboxy-N-hexadecyl-N,N-dimethyl-benzenemethanaminium, inner salt (CAS®No. 71695-33-5), 2-carboxy-N-hexadecyl-N,N-dimethyl-benzenemethanaminium, inner salt (CAS®No. 71695-35-7), tallow glycinate (CAS®No. 70750-46-8), soyamidopropyl carboxymethylbetaine, and babassuamidopropyl carboxymethylbetaine.

Examples of the most useful carboxybetaines that utilize a methylene bridge ("carboxymethylbetaines": $R_4$=—$CH_2$—), or a methylene linkage ($\alpha$=—$CH_2$—), and that vary based solely on alkyl chain length are: $C_{10}$ (CAS®No. 2644-45-3), $C_{11}$ (CAS®No. 2956-38-9), $C_{12}$ (CAS®No. 683-10-3), CAS®$C_{13}$ CAS®No. 23609-76-9), $C_{14}$ (CAS®No. 2601-33-4), $C_{15}$ (CAS®No. 23609-77-0), $C_{16}$ (CAS®No. 693-33-4), and $C_{18}$ (CAS®No. 820-66-6). There is a $C_{12}$-carboxymethylbetaine (CAS®No. 6232-16-2) example that is N,N diethyl ($R3=R_4$=—$CH_2CH_3$); and an example in which the alkyl has a double bond: $C_{18:1}$ (CAS®No. 871-37-4). Examples of the most useful carboxybetaines that utilize an ethyl bridge ("carboxyethylbetaine": $R_4$=—$CH_2CH_2$—), a methylene linkage ($\alpha$=—$CH_2$—), and vary based solely on alkyl chain length include: $C_{12}$ (CAS®No. 16527-85-8), $C_{13}$ (CAS®No. 132621-79-5), $C_{14}$ (CAS®No. 69725-38-3), $C_{16}$ (CAS®No. 42416-43-3), and $C_{18}$ (CAS®No. 30612-73-8). An example of a carboxyethylbetaine in which $R_2$ and $R_3$ are hydrogen atoms, under the appropriate conditions, is CAS®No. 1462-54-0 ($C_{12}$-beta alanine). Examples of the most useful carboxybetaines that utilize a propyl bridge ("carboxypropylbetaine": $R_4$=—$CH_2CH_2CH_2$—), a methylene linkage ($\alpha$=—$CH_2$—), and vary based solely on alkyl chain length include: $C_{11}$ (CAS®No. 150147-53-8), $C_{\gamma2}$ (CAS®No. 15163-30-1), $C_{14}$ (CAS®No. 146959-90-2), $C_{15}$ (CAS®No. 146959-91-3), $C_{16}$ (CAS®No. 71695-32-4), and $C_{18}$ (CAS®No. 78195-27-4). An example of a useful carboxybetaine that utilizes a butyl bridge ("carboxybutylbetaine": $R_4$=—$CH_2CH_2CH_2CH_2$—), and a methylene linkage ($\alpha$=—$CH_2$—), is: $C_{12}$ (CAS®No. 120139-51-7). Two examples of the most useful carboxybetaines that utilize a pentyl bridge ("carboxypentylbetaine": $R_4$=—$CH_2CH_2CH_2CH_2CH_2$—), and a methylene linkage ($\alpha$=—$H_2$—), is: $C_{12}$ (CAS®No. 76392-97-7), and C16 (CAS®No. 73565-98-7). An example of a useful carboxybetaine that utilizes a hexyl bridge ("carboxyhexylbetaine": $R_4$=—$CH_2CH_2CH_2CH_2CH_2CH_2$—), and a methylene linkage ($\alpha$=—$CH_2$—), is: $C_{12}$ (CAS®No. 132621-80-8). There as several carboxybetaine examples in which a benzyl group is used as the bridge function ($R_4$=—$CH_2$—$C_6H_4$—). There are two $C_{12}$ examples, one in which the carboxy function is in the 4, or para, position (CAS®No. 71695-31-3), and one in which the carboxy function is in the 2, or ortho, position (CAS®No. 71695-34-6). There are two $C_{16}$ examples, one in which the carboxy function is in the 4, or para, position (CAS®No. 71695-33-5), and one in which the carboxy function is in the 2, or ortho, position (CAS®No. 71695-35-7). Therefore, "carboxybetaine-like" ("CB-like") not only includes those structures that utilize a carboxyl group as the anion ($\gamma$=—$COO^{\ominus}$) as defined in WO 95/27076 and U.S. Pat. No. 5,658,749, but most especially refers to those betaine-like structures that are shown in Table 1, and shall include all possible combinations of $R_1$, $\alpha$, $R_2$, $R_3$, $\beta$, and $R_4$, as hereinbefore defined.

In addition to the carboxybetaines, other readily available betaines useful in conjunction with the methods of the invention include the sulfobetaines, for example, the highly purified (i.e., research grade) "SB"-series of detergents and especially, SB-18 (N-octadecyl-N,N-dimethyl-3-ammonio-1-propane-sulfonate (CAS®No. 13177-41-8)), SB-16 (N-hexadecyl-N,N-dimethyl-3-ammonio-1-propane-sulfonate (CAS®No. 2281-11-0)), SB-14 (N-tetradecyl-N,N-dimethyl-3-ammonio-1-propane-sulfonate (CAS®No. 14933-09-6)), and SB-12 (N-dodecyldecyl-N,N-dimethyl-3-ammonio-1-propane-sulfonate (CAS®No.14933-08-5)).

Most commercially available betaines are used to manufacture detergents, shampoos, cosmetics, and other toiletries. These betaines are derived primarily from natural oils such as coconut oil, tallow, wheat germ, babassu oil, castor oil, canola oil, soy bean oil, and rapeseed oil. It would be reasonably expected that all these betaine-like detergents would be useful in conjunction with the methods of the invention.

The present invention is especially useful for characterizing and testing clinical isolates or treating disease caused by infectious microorganisms, especially microorganisms that are lipophilic, or encased in a wax-like capsule characterized by having mycolic acid structures in their outer cell wall (outer membrane) such as, for example, corynomycolic acids, nocardomycolic acids and mycolic acids, among others.

The methods of the invention are directed to a method wherein a microorganism, such as a Mycobacterium is tested for susceptibility to antibiotics. In a highly preferred embodiment, the microorganism is a clinical isolate. The methods of the invention are also directed to a therapeutic method wherein a patient (either human or animal) is treated by antibiotic therapy, using betaine-like detergents in combination with antibiotics. The betaines that are ultimately used in testing or treatment in the methods of the invention will depend upon the microorganism, preferably the bacterium, that is present in the sample.

Such testing procedures or therapeutic regimes are useful for any desired microorganism, and especially, any desired bacterium. In a highly preferred embodiment, the microorganism is a Mycobacterium group or complex or member of the same. For example, the bacterium being tested can include any desired Mycobacterium group or complex or Mycobacterium species, and most preferred, a Mycobacterium complex such as M. tuberculosis (MTB) complex, M. avium (MAC) complex, MAIS complex and M. fortuitum complex. The bacterium being tested can also include as fast growing and slow growing mycobacteria including specified and unspecified photochromogens, nonphotochromogens, scotochromogens. Any of the mycobacteria can be characterized or treated according to the invention, including M. agri, M. abscessus, M. acetamidolyticum, M. africanum, M. aichiense, M. asiaticum, M. aurum, M. atistroafricanum, M. avium, M. bovis, M. bovis (BCG), M. chelonae, M. chitae, M. chubuense, M. cookii, M. diernhoferi, M. duvalii, M. fallax, M. farcinogenes, M. flavescens, M. fortuitum, M. gadium, M. gastri, M. gilvum, M. gordonae, M. haemophilum, M. intracellulare, M. kansasii, M. komossense, M. leprae, M. lepraemurium, M. marinum, M. malmoense, M. microti, M. moriokaense, M. neoaurum, M. nonchromogenicum, M. obuense, M. parafortuitum, M. paratuberculosis, M. peregrinum, M. phlei, M. porcinum, M. poriferae, M. pulveris, M. rhodesiae, M. scrofulaceum, M. senegalense, M. shimoidei, M. simiae, M. smegmatis, M. sphagni, M. szulgai, M. terrae, M. thermoresistible, M. tokaiense, M. triviale, M. tuberculosis, M. ulcerans, M. vaccae, M. xenopi, and serovars thereof M. tuberculosis, M. africanum, M. bovis, M. bovis (BCG), and M. microti are the members of the Mycobacterium tuberculosis complex (TB). M. terrae, M. triviale, and M. nonchromogenicum are members of the M. terrae complex. M. avium and M. intracellulare are the members of the Mycobacterium avium complex (MAC); there are at least three distinct serologic groups of M. avium, and more than 25 serovars of M. intracellulare. The MAIS group (M. avium-intracellulare-scrofulaceum) encompasses mycobacteria that have biochemical properties of both M. avium complex and M. scrofulaceum mycobacteria, but that do not hybridize with nucleic acids probes (e.g., AccuProbe (Gen-Probe, San Diego, Calif.)) homologous to the M. avium complex mycobacteria.

M. kansasii, M. marinum, M. simiae and M. asiaticutm are examples of photochromogens. M. scrofulaceum, M. szulgai, M. xenopi, M. gordonae and M. flavescens are examples of scotochromogens. M. avium, M. intracellulare, M. gastri, M. malmoense, M. terrae and M. triviale are all examples of nonphotochromogens.

M. africanum, M. asiaticum, M. avium, M. bovis, M. bovis (BCG), M. cookii, M. gastri, M. gordonae, M. haemophilum, M. intracellulare, M. kansasii, M. leprae, M. lepraemurium, M. marinum, M. malmoense, M. microti, M. nonchromogenicum, M. paratuberculosis, M. scrof laceum, M. shimoidei, M. simiae, M. szulgai, M. terrae, M. triviale, M. tuberculosis, M. ulcerans, and M. xeniopi are all examples of slow-growing (requiring more than seven days) mycobacterial species. M. agri, M. abscessus, M. acetamidolyticum, M. aichiense, M. aurum, M. austroafricanum, M. chelonae, M. chitae, M. chuibuense, M. diernhoferi, M. duvalii, M. falkw, M. farcinogenes, M. flavescens, M. fortuitum, M. gadium, M. gilvum, M. komossense, M. moriokaense, M. neoaurum, M. peregrinum, M. obuense, M. parafortuitum, M. phlei, M. porcinum, M. poriferae, M. pulveris, M. rhodesiae, M. senegalense, M. smegmatis, M. sphagni, M. thermoresistible, M. tokajense, and M. vaccae are all examples of rapid-growing (requiring less than seven days) mycobacterial species.

Examples of the diseases and conditions in which various mycobacterial species are present and that can be treated according to the invention include especially tuberculosis (*M. tuberculosis* complex), leprosy (*M. leprae* (human leprosy) and *M. lepraemurium* (rodent leprosy)), bird diseases caused by *Mycobacterium avium* complex bacteria, opportunistic and superinfections of AIDS patients and others by *M. avium* (Nightingale, S. D. et al., *Jour. Infect. Dis.* 165:1082–1085 (1992)), and any infections due to a specific mybacterial agent such as, for example, *M. bovis* (of special importance in veterinary medicine), *M. fortuitum* (a soil bacterium that has been isolated from lesions in animals and humans), *M. intracellulare* (an opportunistic infection especially seen in patients infected with the AIDS virus), *M. paratuberculosis* (especially of interest in the diagnosis of Crohnrs disease (regional ileitis) in humans), *Mycobacterium kansasii* (is a rare but devastating agent, generally associated with pulmonary disease, *Mycobacterium marinum* (which infects cold-blooded animals and fish; it has also been isolated from superficial granulomas on the extremities of humans), *Mycobacterium paratuberculosis* (the causative agent of Johne's disease in cattle; it is very slow growing and cultures must be held for 16 weeks before it can be assured that they are negative), and *M. ulcerans* (the cause of *Buruli ulcer*). Many of the above and others have been discussed by Wayne, L. G. et al., *Clin. Micro. Rev.* 5:1–25 (1992), and Falkinham, O., *Clin. Micro. Rev.* 9:177–215 (1996) both incorporated herein by reference.

The betaine-like detergents can be used as adjuvants either alone (if the detergent has antimicrobial activity) or in combination with antibiotics. For example, in the first preferred embodiment the betaine-like detergent(s) are part of a susceptibility testing panel (such as that described in Example 10) wherein such detergent(s) are used both alone and in combination with antibiotics, or other betaine-like detergents, to characterize the susceptibility of a clinical isolate. In a second preferred embodiment, the betaine-like detergents of the invention are used alone or in combination with antibiotic(s) during antimicrobial therapy. While the betaine-like detergents may be used alone in lieu of antibiotics, they are more preferably used in conjunction with such antibiotics. In any of the embodiments, use of the betaine-like detergents can be alone or in combination with other adjuvants, either simultaneously or in series. For example, the betaine-like detergents can be used in combination with other betaine-like detergents, or with other adjuvants, such as the β-lactamase inhibitors.

In the second embodiment the methods of the invention provide for treating a patient, either human or animal, in need of such treatment, with an efficacious amount of a composition of the invention comprising either the betaine-like detergent alone, or an antibiotic in combination with a betaine-like detergent. Antimicrobial therapy as used herein is also taken to include such a combination. Delivery of the betaine-like detergent can be by any route that will provide such efficacious levels to the patient, for example, ingestion or intramuscular injection, or especially by intravenous drip, and most especially inhaling or applying such compositions.

The antibiotic can be provided in a separate manner and solution than the betaine-like detergent, or they can be provided together. Betaine-like detergents would probably not be well tolerated by ingestion or intramuscular injection, whereas intravenous drip might be a viable route of delivery; however, care must be taken with respect to the concentration of the betaine in the blood. While addition of the betaine above the critical micellar concentration (CMC) might be feasible, complications might result if the overall blood level rose above the CMC due to solubilization of blood components. Injection at the site of infection would reasonably be expected to be viable means of delivery, however, this may be possible only in rare instances. It is preferable that the composition or at least the betaine-like detergent, be delivered by the most direct route or directly to the site of infection if possible. In that regard, for those mycobacterial infections, especially tuberculosis, that are respiratory infections, inhalation would be the most preferred method of delivery. An example of an inhalation device for delivery for the betaine-like detergents of the invention would be similar in design to that currently in use for the delivery of albuterol, a β-blocker for asthmatics (e.g., Ventolin® sold by Allen & Hanburys, a division of Glaxo, Research Triangle Park, N.C.). Mycobacterial infections such as those caused by *M. ulcerans* (*Buruli ulcer*) are preferably treated by applying the betaine-like detergent directly to the lesion (with or without antibiotics) in the form of an ointment.

Amounts and regimens for the administration of a given betaine-like detergent to a patient can be determined readily by those with ordinary skill in the clinical art of treating such microbial infections. Generally, the dosage of the antibiotic and betaine-like compound will vary depending upon considerations such as: type of antibiotic and betaine-like compound employed; age; health; conditions being treated; kind of concurrent treatment, if any, frequency of treatment and the nature of the effect desired; extent of tissue damage; gender; duration of the symptoms; and, contraindications, if any, and other variables to be adjusted by the individual physician. Dosage can be administered in one or more applications to obtain the desired results. In general, useful concentrations include a range from 0.1 $\mu$g/kg for the most potent structures (for example, the carboxyethylbetaines), to 1 mg/kg for the most innocuous (for example, those carboxybetaines listed in Table 10 as having "no effect"), with 1 $\mu$g/kg to 100 $\mu$g/kg being the most useful concentrations for most betaine-like detergents. When using the betaine-like detergents of the invention in the form of an ointment useful concentrations would be from 0.1 $\mu$g/ml for the most potent structures, to 1 mg/ml for the most innocuous, with 1 $\mu$g/ml to 100 $\mu$g/ml being the most useful concentrations for most betaine-like detergents. Such betaine-like detergents can be used alone or in combination with other betaine-like detergents in the therapeutic methods of the invention. Preferably, the betaine is administered for the same length of time that the antibiotic is administered.

The concentration of a given antibiotic will depend on the antibiotic used. The antibiotics may be provided in the methods of the invention at those doses known in the art to be therapeutic or at those concentrations identified in the susceptibility test of the invention as being therapeutically efficacious. Examples of the different classes of antibiotics useful in the methods of the invention include the β-lactam antibiotics, the β-lactamase inhibitors in combination with the β-lactam antibiotics, the aminoglycosides and aminocyclitols, quinolones, tetracyclines, macrolides, and lincosamides, as well as the antibiotic glycopeptides, lipopeptides and polypeptides, the sulfonamides and trimethoprim, chloramphenicol, isoniazid, nitroirnidazoles, rifampins, nitrofurans, methenamine, and mupirocin.

Antibiotics known to have significant activity against the mycobacteria include, but are not be limited to, amikacin, azithromycin, any β-lactam in combination with any of the β-lactamase inhibitors, capreomycin, cefinetazole, cefoxitin, ciprofloxacin, clarithromycin, clofazamine, cycloserine, dapsone, erythromycin, ethambutol (EMB), ethionamide, imipenem, isoniazid (INH), kanamycin, minocycline, ofloxacin, para-amino salicylic acid, prothionamide, pyrazinamide (PZA), rifampin (RMP), rifabutin, sparfloxacin, sulfamethoxazole with trimethoprim, streptomycin (SM), tetracycline, thiacetazole and viomycin (Inderlied, C. B. et al., In: Murray, P. R. et al., eds. *Manual of Clinical Microbiology,* ASM. Press, Washington, D.C. (1995) pp.1385–1404; and Kucers, A. et al., *The Use of Antibiotics* 4$^{th}$ ed. J. B. Lippincott Co. Philadelphia, Pa. (1987) pp.1352–1437)). All would be useful in the methods of the invention.

By "β-lactam" is meant any of the penicillin, cephalosporin, monobactam and carbapenem antibiotics having as a component of its structure the β-lactam ring as understood in the art (Yao, J. D. C. et al., In: Murray, P. R et al., eds. *Manual of Clinical Microbiology,* ASM. Press, Washington, D.C. 1995 pp 1281–1286; Kucers, A. et al., *The Use of Antibiotics* 4$^{th}$ ed J. B. Lippincott Co. Philadelphia, Pa. (1987) pp.3–584). All β-lactams are useful in the methods of the invention.

By "penicillin" is meant an antibiotic having the 6-aminopenicillanic acid chemical nucleus as understood in the art (Yao, J. D. C. et al., In: Murray, P. R. et al., eds. *Manual of Clinical Microbiology,* ASM. Press, Washington, D.C. (1995) pp.1281–1282). Examples of penicillins include, but are not limited to, methicillin, nafcillin, cloxacillin, dicloxacillin, oxacillin, ampicillin, bacampicillin, carbenicillin, ticarcillin, mezlocillin, and piperacillin, and especially azlocillin. It is reasonably expected that penicillins with chemical structures homologous to any of the above named penicillin compounds will also be useful in the methods of the invention.

By "cephalosporin" is meant an antibiotic having the 7-aminocephalosporanic acid chemical nucleus as understood in the art (Yao, J. D. C. et al., In: Murray, P. R. et al., eds. *Manual of Clinical Microbiology,* ASM. Press, Washington, D.C. (1995) pp.1282–1285). Examples of cephalosporins useful in the methods of the invention include, but are not be limited to, cefadroxil, cefazolin, cephalexin, cephaloridine, cephalothin, cephapirin, cephradine, cefaclor, cefamandole, cefonicid, ceforanide, cefprozil, cefuroxime, loracarbef, cefinetazole, cefotetan, cefixime, cefotaxime, cefpodoxime, and ceftizoxime, and especially cefoxitin, cefoperazone, and ceftazidime, and most especially cettriaxone. It is reasonably expected that cephalosporins with chemical structures homologous to any of the above named cephalosporin compounds will also be useful in the methods of the invention.

By "monobactam" is meant an antibiotic having the β-lactam ring as the chemical nucleus, and having various side chains as understood in the art (Yao, J. D. C. et al., In:. Murray, P. R. et al.., eds. *Manual of Clinical Microbiology,* ASM Press, Washington, D.C. (1995) p.1285). An example of a monobactam that is useful in the methods of the invention includes but is not limited to, aztreonam. It is reasonably expected that monobactams with chemical structures homologous to the above named monobactam compound will also be useful in the methods of the invention.

By "carbapenem" is meant an antibiotic having the β-lactam ring as the chemical nucleus, and having a hydroxyethyl side chain at the 6 position (in the trans configuration) and lacking a sulfur or oxygen atom in the nucleus as understood in the art (Yao, J. D. C. el al., In: Murray, P. R. et al, eds. *Manual of Clinical Microbiology,* ASM. Press, Washington, D.C. (1995) pp. 1285–1286). Examples of carbapenems that are useful in the methods of the invention include, but are not limited to, imipenem, meropenem, panipenem, and biapenem, It is reasonably expected that carbapenems with chemical structures homologous to any of the above named carbapenem compounds will also be useful in the methods of the invention.

By "β-lactamase inhibitor" is meant an antibiotic having a modified β-lactam structure as the chemical nucleus as understood in the art (Yao, J. D. C. et al., In: Murray, P. R. et al., eds. *Manual of Clinical Microbiology,* ASM. Press, Washington, D.C. (1995) pp. 1286–1287). These compounds, having limited antibacterial activity in isolation, are known to act synergistically with the β-lactams. The β-lactamase inhibitors interfere with the enzymes that degrade β-lactams (e.g., β-lactamases). For example, β-lactamases degrade β-lactams. In doing so, the microorganism effectively evades the action of the β-lactam, thus conferring resistance on the infectious agent. Consequently, the β-lactamase inhibitors are useful in conjunction with the β-lactam antibiotics, as adjuvants to β-lactam therapy. Example of β-lactamase inhibitors that are useful in the methods of the invention when a β-lactam is also used, but are not limited to, clavulanic acid, sulbactam, and tazobactam. It is reasonably expected that β-lactamase inhibitors with chemical structures homologous to any of the above named β-lactamase inhibitor compounds will also be useful in the methods of the invention.

By "aminoglycoside" or "aminocyclitol" is meant an antibiotic having amino sugars linked by glycosidic bonds to an aminocyclitol nucleus as understood in the art (Yao, J. D. C. et al., In: Murray, P. R. et al., eds. *Manual of Clinical Microbiology,* ASM. Press, Washington, D.C. (1995) pp. 1287–1288; and Kucers, A. et al., *The Use of Antibiotics* 4$^{th}$ ed. J. B. Lippincott Co. Philadelphia, Pa. (1987) pp.585–750). Examples of aminoglycosides and aminocyclitols that are useful in the methods of the invention include, but are not limited to, streptomycin, kanamycin, gentamicin, tobramycin, amikacin, sisomicin, netilmicin, neomycin, framycetin and paromomycin. It is reasonably expected that aminoglycosides and aminocyclitols with chemical structures homologous to any of the above named aminoglycoside and aminocyclitol compounds will also be useful in the methods of the invention.

By "quinolone" or "fluoroquinolone" is meant an antibiotic having a naphthyridine nucleus with different side chains as understood in the art (Yao, J. D. C. etal., In: Murray, P. R. et al., eds. *Manual of Clinical Microbiology,* ASM Press, Washington, D.C. (1995) pp. 1288–1290; and Kucers, A. et al., *The Use of Antibiotics* 4$^{th}$ ed. J. B. Lippincott Co. Philadelphia, Pa. (1987) pp. 1203–1275). Examples of quinolones that are useful in the methods of the invention include, but are not limited to, oxolinic acid, cinoxacin, flumequine, miloxacin, rosoxacin, pipemidic acid, norfloxacin, enoxacin, ciprofloxacin, ofloxacin, lomefloxacin, temafloxacin, fleroxacin, pefloxacin, amifloxacin, sparfloxacin, levofloxacin, clinafloxacin and especially nalidixic acid. It is reasonably expected that quinolones or fluoroquinolones with chemical structures homologous to any of the above named quinolone or fluoroquinolone compounds will also be useful in the methods of the invention.

By "tetracycline" is meant an antibiotic having as a nucleus a hydronaphthacene structure as understood in the art (Yao, J. D. C. et aL, In: Murray, P. R. et al., eds. *Manual of Clinical Microbiology,* ASM. Press, Washington, D.C. (1995) pp.1290–1291; and Kucers, A. et al., *The Use of Antibiotics* 4$^{th}$ ed. J. B. Lippincott Co. Philadelphia, Pa. (1987) pp.979–1044). Examples of tetracyclines that are useful in the methods of the invention include, but are not limited to, tetracycline, chlortetracycline, oxytetracycline, dimethylchlortetracycline demeclocycline, methacycline, lymecycline, clomocycline, doxycycline, and minocycline. It is reasonably expected that tetracyclines with chemical structures homologous to any of the above named tetracycline compounds will also be useful in the methods of the invention.

By "macrolide" is meant an antibiotic having a macrocyclic lactone ring with two attached sugars, desosamine and cladinose, and various substitutions as understood in the art (Yao, J. D. C. et al., In: Murray, P. R. et al., eds. *Manual of Clinical Microbiolog*, ASM. Press, Washington, D.C. (1995) pp.1291–1292; and Kucers, A. et al., *The Use of Antibiotics* 4$^{th}$ ed J. B. Lippincott Co. Philadelphia, Pa. (1987) pp.851–892). Examples of macrolides that are useful in the methods of the invention include, but are not limited to, erthromycin, oleandomycin, spiramycin, josamycin, rosaramicin, clarithromycin, azithromycin (also known as a azalide), dirithromycin, roxithromycin, flurithromycin, and rokitamycin. It is reasonably expected that macrolides with chemical structures homologous to any of the above named macrolide compounds will also be useful in the methods of the invention.

By "lincosamide" is meant an antibiotic having an amino acid linked to an amino sugar as understood in the art (Yao, J. D. C. et al., In: Murray, P. R. et al., eds. *Manual of Clinical Microbiology*, ASM. Press, Washington, D.C. (1995) pp.1292–1293; and Kucers, A. et al., *The Use of Antibiotics* 4$^{th}$ ed. J. B. Lippincott Co. Philadelphia, Pa. (1987) pp.819–850). Examples of lincosamides that are useful in the methods of the invention include, but are not limited to, lincomycin and clindamycin. It is reasonably expected that lincosamides with chemical structures homologous to any of the above named lincosamide compounds will also be useful in the methods of the invention.

By "glycopeptide" or "lipopeptide" is meant an antibiotic having a combination of peptide with either carbohydrate or lipid constituents, or both, as understood in the art (Yao, J. D. C. et al., In: Murray, P. R. et al., eds. *Manual of Clinical Microbiology*, ASM. Press, Washington, D.C. (1995) p. 1293; and Kucers, A. et al., The Use of Antibiotics 4$^{th}$ ed J. B. Lippincott Co. Philadelphia, Pa. (1987) pp.1045–1072). Examples of glycopeptides and lipopeptides that are useful in the methods of the invention include, but are not limited to, vancomycin, teicoplanin, daptomycin (also known as YL 146032) and ramoplanin (also known as MDL 62198). It is reasonably expected that glycopeptides and lipopeptides with chemical structures homologous to any of the above named glycopeptide or lipopeptide compounds will also be useful in the methods of the invention.

By a "polypeptide antibiotic" is meant an antibiotic having a cyclic polypeptide structure, or peptide linked amino acids, as understood in the art (Yao, J. D. C. et al., In: Murray, P. R. et al., eds. *Manual of Clinical Microbiology*, ASM. Press, Washington, D.C. (1995) p.1295–1296; and Kucers, A. et al., *The Use of Antibiotics* 4$^{th}$ ed. J. B. Lippincott Co. Philadelphia, Pa. (1987) pp.899–913 and 751–753). Examples of polypeptide antibiotics that are useful in the methods of the invention include, but are not limited to, polymixins A, B, C, D and E, and bacitracin and gramicidin. It is reasonably expected that polypeptide antibiotics with chemical structures homologous to any of the above named polypeptide antibiotic compounds will also be useful in the methods of the invention.

By "sulfonamide" is meant an antibiotic having a core structure similar to para-aminobenzoic acid as understood in the art, and by "trimethoprim" is meant an antibiotic that is a pyrimidine analog as understood in the art (Yao, J. D. C. et al., In: Murray, P. R. et al, eds. *Manual of Clinical Microbiology*, ASM. Press, Washington, D.C. (1995) pp.1293–12$^{95}$; and Kucers, A. et al., *The Use of Antibiotics* 4$^{th}$ ed. J. B. Lippincott Co. Philadelphia, Pa. (1987) pp.1075–1117).

Examples of sulfonamides that are useful in the methods of the invention include, but are not limited to, sulfanilamide, sulfacetarnide, sulfapyridine, sulfathiazole, sulfadiazine, sulfamerazine, sulfadimidine, sulfasomidine, sulfasalazine, mafenide, sulfamethoxazole, sulfamethoxypyridazine, sulfadimethoxine, sulfasymazine, sulfadoxine, sulfametopyrazine, sulfaguanidine, succinylsulfathiazole, and phthalylsulfathiazole. Trimethoprim is useful in the methods of the invention alone or in combination with any of the sulfonamides. It is reasonably expected that sulfonamides and trimethoprim analogs with chemical structures homologous to any of the above named sulfonamide compounds will also be useful in the methods of the invention.

By "nitroimidazole" antibiotic is meant an antibiotic having a nitroimidazole nucleus as understood in the art (Yao, J. D. C. et al., In: Murray, P. R. et al., eds. *Manual of Clinical Microbiology*, ASM. Press, Washington, D.C. (1995) p.1297; and Kucers, A. et al., *The Use of Antibiotics* 4$^{th}$ ed J. B. Lippincott Co. Philadelphia, Pa. (1987) pp.1290–1343). Examples of nitroimidazoles that are useful in the methods of the invention include, but are not limited to, metronidazole, tinidazole, nimorazole, ornidazole, camidazole, and secnidazole. It is reasonably expected that nitroimidazoles with chemical structures homologous to any of the above named nitroimidazole compounds will also be useful in the methods of the invention.

By "chloramphenicol" antibiotic is meant an antibiotic having a nitrobezene ring as its structural core as understood in the art (Yao, J. D. C. et al., In: Murray, P. R. et al., eds. *Manual of Clinical Microbiology*, ASM. Press, Washington, D.C. (1995) pp.1296–1297; and Kucers, A. et al., *The Use of Antibiotics* 4$^{th}$ ed. J. B. Lippincott Co. Philadelphia, Pa. (1987) pp.757–807). Examples of chloramphenicols that are useful in the methods of the invention include, but are not limited to, chloramphenicol and thiamphenicol. It is reasonably expected that chloramphenicols with chemical structures homologous to any of the above named chloramphenicol compounds will be useful in the methods of the invention.

By "rifampicin" is meant an antibiotic having an ansa, or macrocyclic, structural core (ansamycin antibiotics) as understood in the art (Yao, J. D. C. et al., In: Murray, P. R. et al., eds. *Manual of Clinical Microbiology*, ASM. Press, Washington, D.C. (1995) p.1298; and Kucers, A. et al., *The Use of Antibiotics* 4$^{th}$ ed. J. B. Lippincott Co. Philadelphia, Pa. (1987) pp.914–970). Examples of rifampicins that are useful in the methods of the invention include, but are not limited to, rifampin, rifamycin SV rifamycin B (rifamide) and rifabutin. It is reasonably expected that rifampicins with chemical structures homologous to any of the above named rifampicin compounds will also be useful in the methods of the invention.

By "nitrofuran" is meant an antibiotic having a heterocyclic ring with a nitro group as understood in the art (Yao, J. D. C. et al., In: Murray, P. R. et al., eds. *Manual of Clinical Microbiology*, ASM. Press, Washington, D.C. (1995) pp.1298–1299; and Kucers, A. et al., *The Use of Antibiotics* 4$^{th}$ ed. J. B. Lippincott Co. Philadelphia, Pa. (1987) pp.1276–1289). Examples of nitrofurans that are useful in the methods of the invention include, but are not limited to, nifuratel, nitrofurazone, furazolidone and nitrofurantoin. It is reasonably expected that nitrofurans with chemical structures homologous to any of the above named nitrofuran compounds will also be useful in the methods of the invention.

By "methenamine" is meant an antibiotic having a tertiary amine as understood in the art (Yao, J. D. C. et al., In: Murray, P.R et al., eds. *Manual of Clinical Microbiology*, ASM. Press, Washington, D.C. (1995) pp.1299; and Kucers, A. et al., *The Use of Antibiotics* 4$^{th}$ ed. J. B. Lippincott Co. Philadelphia, Pa. (1987) pp.1344–1348). Examples of tertiary amines that are useful in the methods of the invention include, but are not limited to, methenamine, mandelate, methenamine hippurate. It is reasonably expected that tertiary amines with chemical structures homologous to any of the above named methenamine compounds are also useful in the methods of the invention.

By "mupirocin" (also known as pseudomonic acid) is meant an antibiotic having a unique 9-hydroxy-nonanoic acid moiety as understood in the art (Yao, J. D. C. et al., In: Murray, P. R. et al., eds. *Manual of Clinical Microbiology*, ASM Press, Washington, D.C. (1995) pp.1299–1300; and Kucers, A. et al., *The Use of Antibiotics* 4$^{th}$ ed J. B. Lippincott Co. Philadelphia, Pa. (1987) pp.754–756). It is reasonably expected that compounds with chemical structures homologous to the above named mupirocin compounds will also be useful in the methods of the invention.

Therapy for patients infected with *Mycobacterium tuberculosis* complex bacteria (MTB) typically includes one or a combination of drugs. The preferred primary drugs ("front line" drugs) for treating TB include isoniazide (INH), rifampin (RMP), pyrazinamide (PZA) streptomycin (SM) and ethambutol (EMB); and secondary (or "second line") drugs include ciprofloxacin, ofloxacin, ethionamide, and cycloserine. Additional drugs under investigation include amikacin, rifabutin, rifapentine, and sparfloxacin (Inderlied, C. B. et al., In: Murray, P. R. et al., eds. *Manual of Clinical Microbiology*, ASM. Press, Washington, D.C. (1995) pp.1385–1404). Any drug having activity against a bacteria containing mycolic acid structures would be useful in the methods of the invention.

Antimicrobial therapy for patients infected with *Mycobacterium avium* complex (MAC) bacteria typically also includes one or a combination of a limited number of drugs. Front line drugs to treat MAC infections include azithromycin, clarithromycin and EMB. Second line drugs include amikacin, clofazamine, ciprofloxacin, and rifabutin. Alternate drugs include cycloserine and SM (Inderlied, C. B. et al., In: Murray, P. R. et al., eds. *Manual of Clinical Microbiology*, ASM. Press, Washington, D.C. (1995) pp.1385–1404). All would be useful in the methods of the invention.

Other important mycobacterial pathogens, *M. kansasii* for example, are typically treated with one or a combination of the drugs used to treat TB or MAC infections as discussed above. Infections by the rapid growers (e.g., *M. fortuitum* and *M. chelonae*) can be treated with amikacin or clarithromycin, as well as some of the β-lactams, especially the cephalosporins (Inderlied, C. B. et al., In: Murray, P. R. et al., eds. *Manual of Clinical Microbiology*, ASM. Press, Washington, D.C. (1995) pp.1385–1404). All would be useful in the methods of the invention.

The betaine-like detergents and/or antibiotics used in the methods of the invention, especially the therapeutic method, can be administered in any appropriate pharmacologically acceptable or pharmaceutically acceptable form, including a pharmaceutically acceptable salt or vehicle if desired. They can be administered in any form that effects prophylactic, palliative, preventative or curing conditions for microbial infection in humans and animals. The doses of antibiotics that are useful in the therapeutic methods of the invention are those recommended by the manufacturer. Such doses are found, for example, in the Physician's Desk Reference (PDR), Medical Economics Company, Montvale, N.J., USA. Dosages for veterinary usage are found, for example, in The Merck Veterinary Manual, Merck & Co., Inc., Rahway, N.J., USA.

When the antibiotic(s) and betaine-like detergent(s) are administered to a patient in need of the same in individual preparations, each agent is preferably provided to the patient so as to be present in said patient at efficacious levels at the same time. That is, the microorganism at the site of the infection in said patient is preferably exposed to efficacious levels of both the antibiotic(s) and the betaine-like detergent (s) at the same time, no matter how such agents were individually provided to the patient. Therefore, for example, a patient can be treated by coadministration of an antibiotic and a betaine-like detergent, for example, by the oral administration of the antibiotic and the inhalation or intravenous administration of the betaine-like detergent. A patient can be treated by coadministration can also occur by providing both the betaine-like detergent(s) and antibiotic(s) at the same time, in the same preparation, for example, in an ointment or bandage that provides both the antibiotic(s) and the betaine-like Idetergent(s).

Additionally, a patient can be treated by "pretreating" the patient with either the antibiotic or betaine-like detergent in the absence of the other, and then "treating" the patient with both the antibiotic or betaine-like detergent, or with just the "other" that was absent in the pretreatment—either the antibiotic or the betaine-like detergent, as long as the effect of the pretreatment on the microorganism has not been lost at the time of the treatment. Therefore, for example, a patient can be pretreated with the betaine-like detergent to compromise the permeability and/or viability of the microorganism prior to administering the antibiotic with or without the betaine-like detergent. Alternatively, a patient can be pretreated with the antibiotic prior to administering the betaine-like detergent with or without the antibiotic.

When in admixture, the antibiotic(s) and betaine-like detergent(s) can each be in solution, or each be in solid form (and especially a suspension). Alternatively, one or more of the antibiotics and/or one or more of the betaine-like detergents can be in solution any other antibiotics or detergents in the same preparation are in solid form.

Useful preparations of the compositions of the invention for parenteral administration includes sterile aqueous or non-aqueous solvents, suspensions and emulsions. Examples of useful non-aqueous solvents include propylene glycol, polyethylene glycol, vegetable oil, fish oil, and injectable organic esters. Examples of aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Examples of intravenous vehicles include fluid and nutrient replenishers, electrolyte replenishers, such as those based upon Ringer's dextrose and the like.

Injectable preparations, such as oleaginous solutions, suspensions or emulsions, may be formulated according to known art, using suitable dispersing or wetting agents and suspending agents, as needed. When the active compounds are in water-soluble form, for example, in the form of water soluble salts, the sterile injectable preparation may employ a nontoxic parenterally acceptable diluent or solvent as, for example, sterile nonpyrogenic water or 1,3-butanediol. iAmong the other acceptable vehicles and solvents that may be employed are 5% dextrose injection, Ringer's injection and isotonic sodium chloride injection (as described in the USP/NF). When the active compounds are in a non-water soluble form, sterile, appropriate oily suspensions containing suitable lipophilic solvents or vehicles, such as fatty oil, for example, sesame oil, or synthetic fatty acid esters, for example, ethyl oleate or triglycerides, are used. Alternatively, aqueous injection suspensions which contain substances which increase the viscosity, for example, sodium carboxymethyl cellulose, sorbitol, and/or dextran, and optionally also contain stabilizers may be used.

Pharmaceutical preparations for oral use can be obtained by combining the active compounds with solid excipients, optionally granulating a resulting mixture and processing the mixture or granules, after adding suitable auxiliaries, if desired or necessary, to give tablets of dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders, such as starch, pastes, using, for example, maize starch, wheat starch, rice starch, or potato starch, gelatine, tragacanth, methyl cellulose, hydroxypropylmethyl cellulose, sodium carboxymethyl cellulose, and/or polyvinyl pyrrolidone, and/or, if desired, disintegrating agents, such as the above-mentioned starches, and also carboxymethyl-starch, cross-linked polyvinyl pyrrolidone, agar or alginic acid or a salt thereof, such as sodium alginate. Auxiliaries are, above all, flow-regulating agents and lubricants, for example, silica, talc, stearic acid or salts thereof, such as magnesium stearate or calcium stearate, with suitable coating, which if desired, are resistant to gastric juices and for this purpose, infer alia concentrated sugar solutions, which optionally contain gum arabic, talc, polyvinyl pyrrolidone, polyethylene glycol and/or titanium dioxide, lacquer solutions and suitable organic solvents or solvent mixtures. In order to produce coatings resistant to gastricjuices, solutions of suitable cellulose preparations such as acetyl cellulose phthalate or hydroxypropylmethyl cellulose phthalate, are used. Dyestuffs or pigments may be added to the tablets or dragee coatings, for example, for identification or in order to characterize different combinations of active compound doses.

Other pharmaceutical preparations which can be used orally are push-fit capsules made of gelatin, as well as soft, sealed capsules made of gelatin and a plasticizer such as glycerol or sorbitol. The push-fit capsules can contain the active compounds in the form of granules, for example, mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin or liquid polyethylene glycols, it also being possible to add stabilizers.

Suppositories for rectal administration of the compound of this invention can be prepared by mixing the drug with suitable suppository bases such as a nonirritating excipient, for example, cocoa butter, natural or synthetic triglycerides, paraffin hydrocarbons, polyethylene glycols, or higher alkanols, and especially bases which are solid at ordinary temperature but liquid at body temperature and which therefore melt in the rectum and release the drug. In addition, it is possible to use gelatin rectal capsules which consist of a combination of the active compounds with a base; possible base materials are, for example, liquid triglycerides, polyethylene glycols, or paraffin hydrocarbons.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying, suspending, sweetening, flavoring and perfuming agents.

The compositions of the invention may also be administered by means of pumps, or in sustained-release form. The compounds of the invention may also be delivered to specific organs in high concentration by means of suitably inserted catheters, or by providing such molecules as a part of a chimeric molecule (or complex) which is designed to target specific organs.

Administration in a sustained-release form is more convenient for the patient when repeated injections for prolonged periods of time are indicated so as to maximize the comfort of the patient.

The betaine-like detergents or antibiotics that are used in the compositions and methods of the invention can be employed in dosage forms such as tablets, capsules, powder ointments, packets, or liquid solutions for oral administration if the biological activity of the material is not destroyed by the digestive process and if the characteristics of the compound allow it to be absorbed across the intestinal tissue.

The pharmaceutical compositions of the present invention can be manufactured in a manner which is in itself know, for example, by means of conventional mixing, granulating, dragee-making, dissolving, lyophilizing or similar processes.

The methods of the invention, especially the susceptibility test, are also conveniently practiced by providing the agents used in such method in the form of a kit. Such a kit preferably contains appropriate buffers, salts, betaine-like detergents or combinations thereof, antibiotic(s) or combinations thereof, and if desired, water of the appropriate purity. In a preferred embodiment, a collection of different betaine-like detergents and a collection of different antibiotics are provided. The betaine-like detergents and/or antibiotics in the collection can be one that is not tailored for a particular microorganism, or one that is specifically tailored to a particular microorganism. Preferably at least five different betaine-like detergents are provided although in preferred embodiment, a larger selection than 5, for example, 10, 15, 20, 25 or 30, or any number in between, are provided. Preferably at least five different antibiotics are provided although in preferred embodiment, a larger selection than 5, for example, 10, 15, 20, 25 or 30, or any number in between, are provided. Specific kits may, if desired, contain, inter alia, particular microbacteria, especially, Mycobacterium, to use, preferably, as standards. In such a kit, if the non-bacterial components are not already mixed together as they might be, such components are generally in close proximity to each other, even if confined in separate containers or packages, and in close proximity to any microbacterial samples provided in the kit.

The CB-18 Pilot Study

The invention herein stems from observations surrounding application of the invention described in Thornton WO 95/27076 and U.S. Pat. No. 5,658,749 (the method is described in Example 1). In Example 2 the results of a study using this processing procedure showed that the sensitivity of liquid culture was dramatically affected by combining CB-18 with the antimicrobial supplement PANTA that had been fortified with ceftazidime (caz) (Table 6). Table 6 showed that the NALC/NaOH culture sensitivities of liquid and solid media were 98.4% and 75.4%, respectively, while the sensitivities of liquid and solid media for the same set of specimens processed by CB-18 were 64.0% and 83.1%, respectively. In other words the CB-18 liquid culture sensitivity was depressed even though CB-18 provided a 46% increase in overall culture sensitivity (Table 3). More significant was the observation that, whereas the difference in liquid culture sensitivity for smear positive vs. smear negative specimens was only 4% for NALC/NaOH sediments (i.e., 100% vs. 95.8%), the same comparison for CB-18 showed a 65% difference (i.e., 75.0% vs. 45.4%). Since the difference between solid media sensitivities of smear positive and negative specimens for the two different methods was comparable (34% vs 39% for NALC/NaOH and CB-18, respectively), the fortification of PANTA with caz was originally thought to be solely responsible for the loss in liquid culture sensitivity. Example 3 (FIGS. 3A–3H), however, revealed that CB-18 not only had the capacity to affect the growth characteristics of the test isolate (571/573-BAL: see Table 8), but that PANTA, both alone and in combination with caz, also had the capacity to affect the growth characteristics of this isolate. This effect, the so-called CB-18 effect, was a synergistic and graded effect when CB-18 was added in combination with antibiotics.

Figure 29A:
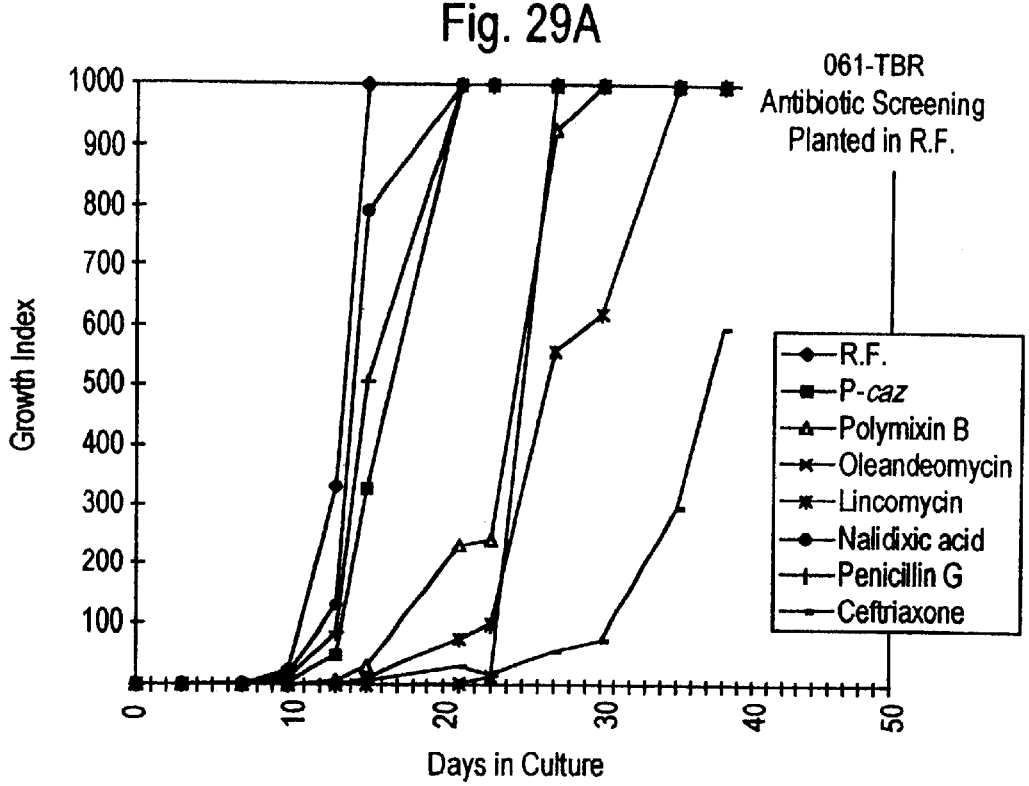
FIGS. 29A and 29B present the growth curves when the *M. tuberculosis* isolate 061-TBR was tested using a modified version of the antibiotic screening experiment presented in FIG. 16. In these experiments additional, non-β-lactam antibiotics were tested. Diamonds: R.F.; squares: P-caz; triangles: polymixin B; "x": oleandeomycin; "*" lincomycin; circles: nalidixic acid; vertical hatches: penicillin G; horizontal dashed line: ceftriaxone.
Figure 29B:
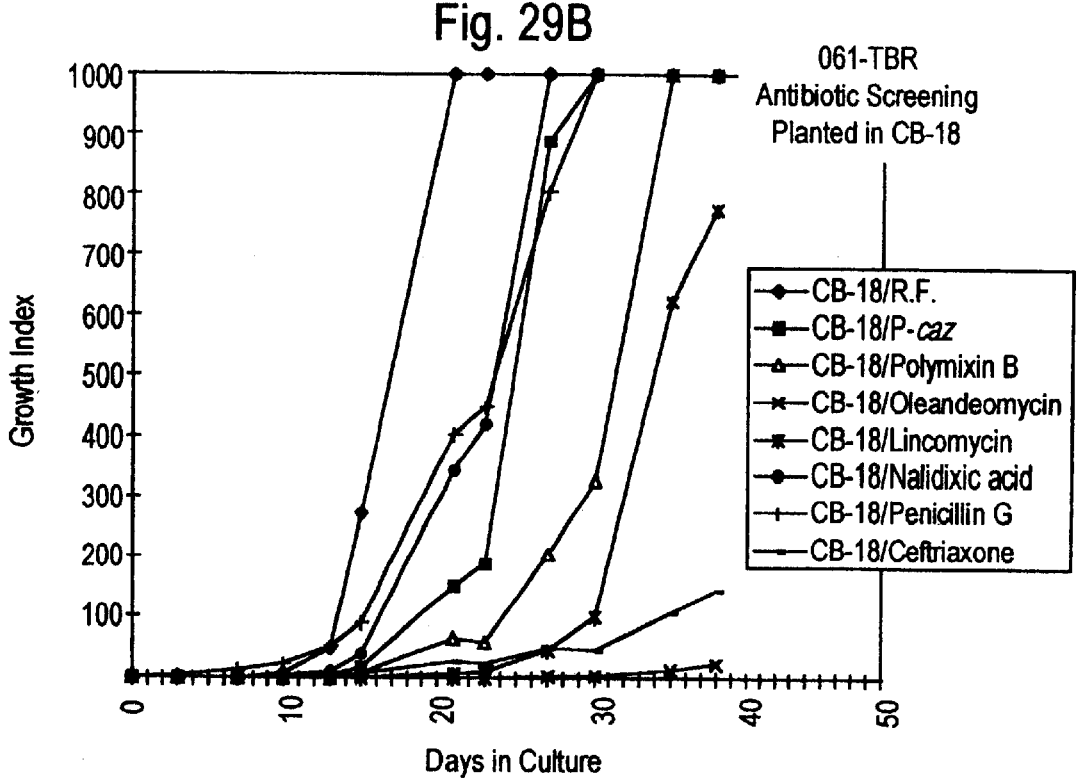
Figure 30A:
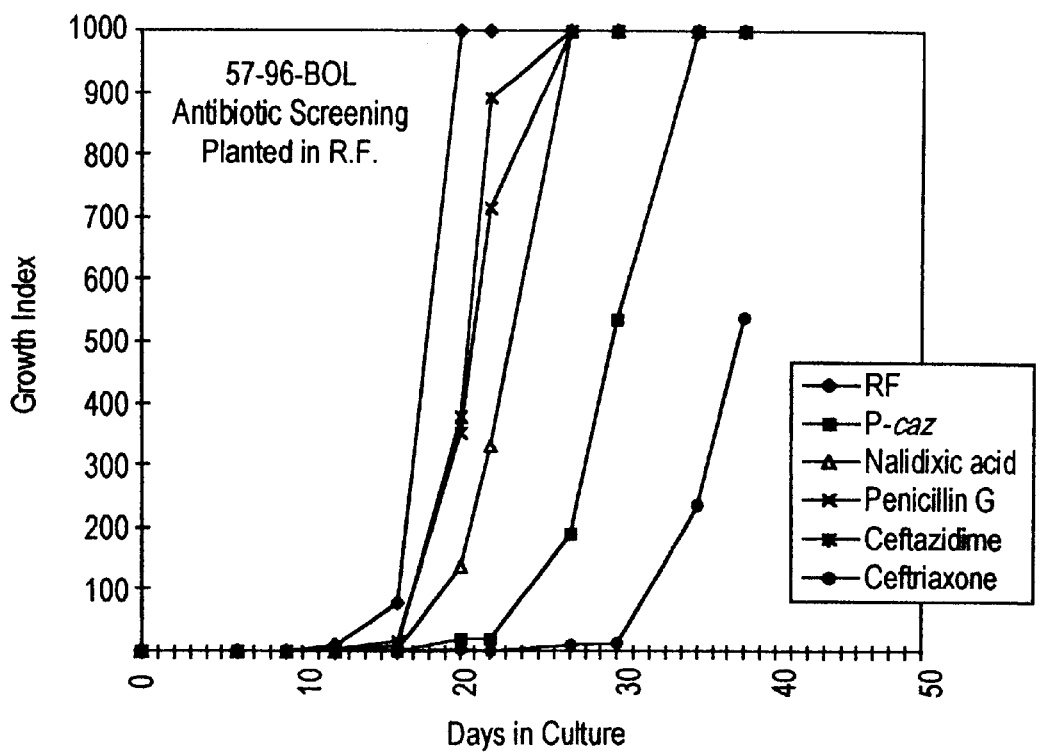
FIGS. 30A and 30B present the growth curves when the *M. tuberculosis* isolate 57-96-BOL was tested using a modified version of the antibiotic screening exper microorganism, for example, a homogeneous population of microorganisms or a mixture of types/variants/isolates, etc. of microorganisms, is exposed to a composition comprising an antibiotic and a betaine-like detergent, and the susceptibility of the microorganism in the sample to said antibiotic is determined based upon the viability of the microorganism in the sample. The betaine susceptibility test is a first embodiment of the methods of the invention. Such betaine susceptibility testing can be accomplished in a microtiter format, in culture bottles, or on plates containing solid media as understood in the art. Examples of standard liquid media formats include BACTEC (Becton-Dickinson, Cockeysville, Md.), ESP Myco System II™ (DIFCO Laboratories, Detroit, Mich.) or MT/BacT™ (Organon Teknika, Durham, N.C.). Examples of standard solid media include Mueller-Hinton agar as known in the art, or other equivalent media. Such culture formats would necessarily be supplemented with the appropriate antibiotic(s) and betaine-like detergent(s) in the appropriate combinations and at the appropriate concentrations as discussed herein. As with any susceptibility test, the purpose of such testing is to identify the antibiotic(s), that has the highest probability of successfully ridding the patient of the infection.
Figure 30B:
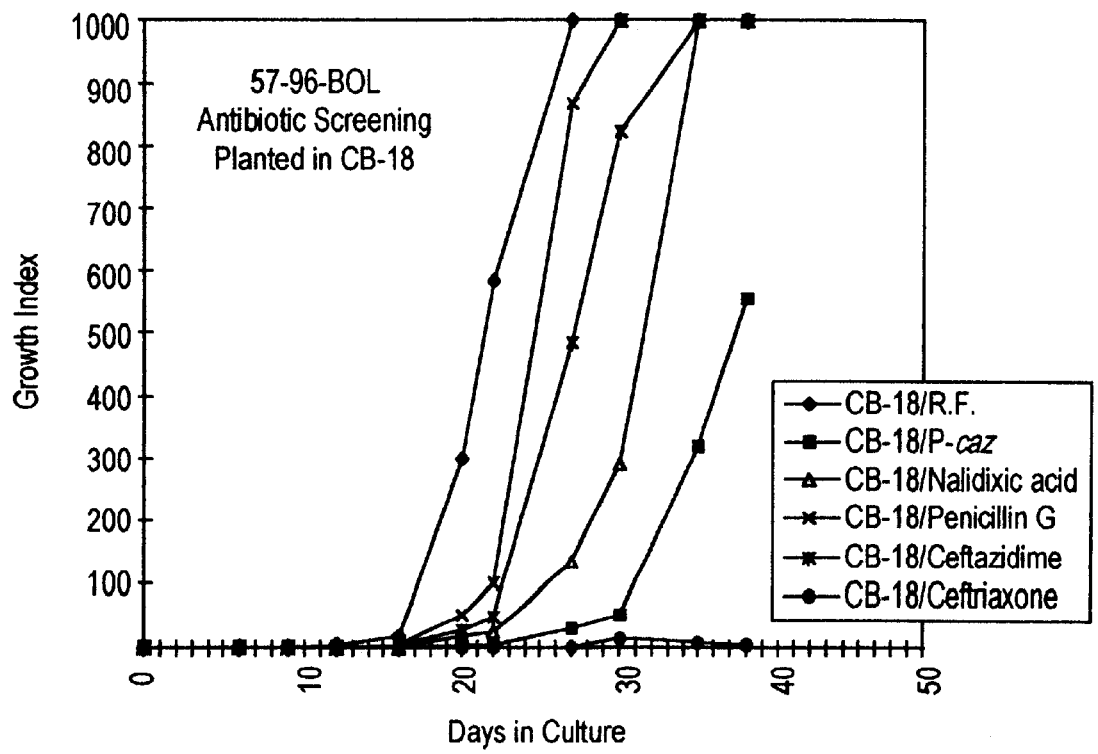
Figure 31:
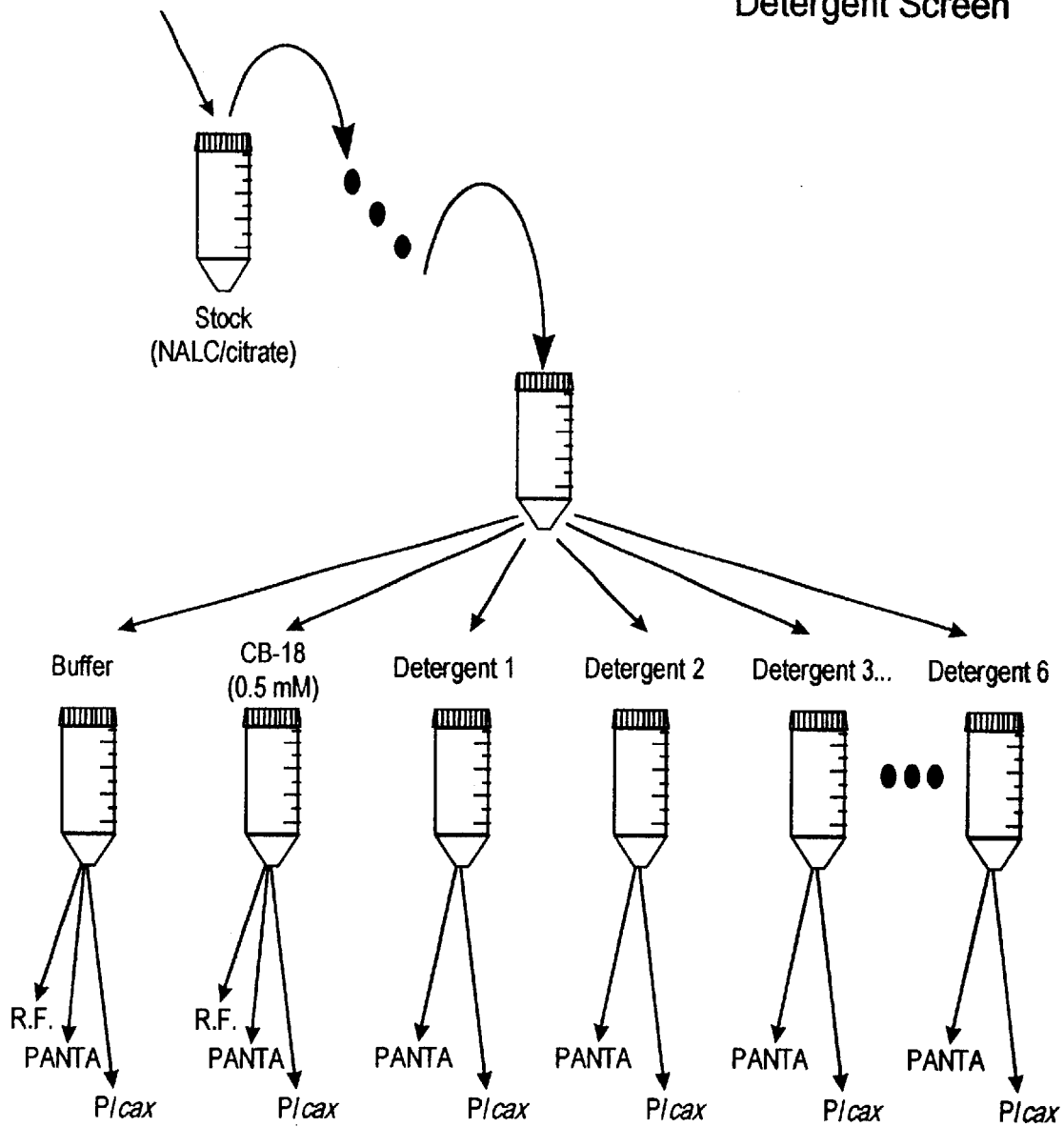

PANTA contains polymyxin B, amphotericin B, nalidixic acid, trimethoprim, and azlocillin. Whereas amphotericin B is designed to control fungal contamination, the remaining antibiotics all have antibacterial activity. Polymyxin B is a polypeptide that interacts with phospholipids to alter permeability. Nalidixic acid is a quinolone that interferers with DNA synthesis (at the level of DNA gyrase.) Trimethoprim is a pyrimidine analog, typically used in conjunction with sulfonamides, and is also known to interfere with DNA synthesis (at the level of dyhydrofolate reductase.) Azlocillin is a penicillin, representing the β-lactam antibiotics, and exerts its effects at the level of cell wall synthesis. Nalidixic acid, trimethoprim, and azlocillin are all reported to have some activity against various species of mycobacteria. The fact that CB-18 could affect growth in combination with PANTA that did not contain caz (Example 3, FIGS. 3F and 3H) showed that this phenomenon was not solely dependent on the presence of ceftazidime, but was instead broadly applicable to different classes of antibiotics (supra). FIGS. 28–30 highlight the breadth of the utility of different classes of antibiotics. It is reasonably expected that this phenomenon would extend to the different classes of antibiotics.

Ceftazidime was originally incorporated into the CB-18/12B/PANTA detection system to control contamination (Example 1), but not at the expense of mycobacterial viability. This determination was made after experiments that examined the effects of different cephalosporins on mycobacterial viability. The PANTA-cephalosporin combinations tested, in addition to ceftazidime, included cefoperazone (cfp), cefotaxime (cft), and ceftriaxone (car) in different combinations (e.g., cfp/cft, cfp/cax, and cfp/cft/cax).

These experiments were conducted using CB-18 at approximately 7–15 μg/ml and different ATCC type strains of M. tuberculosis (ATCC 27294), M. avium (ATCC 25291), M. kansaii (ATCC 12478), M. fortuitum (ATCC 6841), M. xenopi (ATCC 19250), and M. gordonae (ATCC 14470). The CB-18/12B/PANTA/caz combination was the only formulation that showed minimal impact on these isolates during the preliminary studies. For example, the combinations of PANTA with cfp/cft, cfp/cax, and cfp/cft/cax all caused significant delays among most isolates tested. PANTA/caz caused a delay of the M. avium isolate tested, and a significant delay of the M. gordonae isolate tested.

In the CB-18 Pilot Study the CB-18/12B/PANTA/caz system missed 14 smear positive specimens (Table 6). Analysis of these 14 smear positive isolates revealed that 5 were MTB and the other 9 various MOTT species, including 4 MAC, 2 M. fortuitum, and 1 each of M. chelonae, M. szulgai, and 1 M. kawsashi The significant conclusion derived from these data is that the CB-18/12B/PANTA/caz system affects a broad range of mycobacteria, both MTB and MOTT.

The realization that the CB-18 effect was observable in the absence of ceftazidime (Example 3), that is to say that other antibiotics (e.g., both cephalosporins, other components of PANTA, and additional antibiotics) could cause delays in growth of different mycobacteria, and the apparent sensitivity of the system to CB-18 concentrations lead to the experiments of Examples 5 and 6. The experiments of Example 5 tested M. tuberculosis, M. avium complex and M. fortuitum complex isolates with respect to changes in CB-18 concentration, and Example 6 focused on susceptibility patterns of M. tubercuilosis isolates. Table 7 summarized the results of the experiments of Example 5, and FIGS. 10–15 presented the results using the different mycobacterial species. Table 8 summarized the results of the experiments of Example 6, and FIGS. 17–27 presented the results of theM. tuberculosis isolates tested. FIGS. 28–30 show that this phenomenon extended beyond the β-lactams tested. While there were significant differences between species and isolates in the experiments of Examples 5 and 6, all were synergistically affected by the combination of CB-18 and antibiotics to some degree. The M. tuberculosis isolates appeared to be the most sensitive of the mycobacterial species tested, and the rapid growers were impacted to a minor degree, but showed the most synergy when used in combination with antibiotics. The M. avium isolates displayed intermediate responses. Basically, all isolates could be differentiated based on the growth characteristics in the presence of CB-18 and different antibiotics. Therefore, the CB-18 effect was dependent on the isolate and the antibiotic used, and the presence of CB-18 at the appropriate concentration was necessary to differentiate the isolates.

This in turn led to the notion that different betaines might provide a higher degree of sensitivity with respect to differentiating isolates. Example 7 utilized a variety of detergents, in conjunction with either reconstitution fluid (R.F.), PANTA or PANTA/cax in the assay. Table 10 summarized the results of these experiments and FIG. 32B presented the results of several different detergents (in the presence of P-cax only). Therefore, the CB-18 effect is dependent on the dynamic interaction of the isolate, the detergent, and the antibiotic, and therein lies the utility of the CB-18 effect.

Antimicrobial Therapy, Drug Resistance and Permeability

Antibiotics differ with respect to their site of action. For example, Yao, J. D. C. et al., In: Murray, P. R. et al, eds. Manual of Clinical Microbiology, ASM Press, Washington, D.C. (1995) pp.1281–1307 review the different classes of antibacterial agents and report that the range in the sites of action vary from affecting or interfering with different aspects of cell wall and cell membrane synthesis or integrity, protein synthesis, nucleic acids synthesis (e.g., both RNA and DNA precursors), and DNA replication, as well as drugs that simply facilitate mutagenesis.

Bacteria are insensitive (i.e., resistant) to different antibiotics for a variety of reasons. Quintiliani, R. et al., In: Murray, P. R. et al., eds. *Manual of Clinical Microbiology*, ASM Press, Washington, D.C. (1995) pp.1308–1326 (incorporated herein by reference) review several of these mechanisms. In summary, the antibiotic must first enter the cell and then exert its effect at the site of action. The basis for resistence can be due to: (a) the permeability of the organism, (b) the molecular configuration of the site of action might either be incompatible or simply nonexistent in a particular clinical isolate, or (c) the bacteria might modify, destroy or pump the antibiotic from the intracelmlar space. In the first case, if the bacterium is impermeable to the drug, then the antibiotic cannot reach the site of action to exert its influence. In the second instance, if the drug can enter the bacterium, but the site of action (e.g., the 3-D structure of the target site) is such that the antibiotic cannot bind, or if the site of action does not exist (e.g., the structure or enzyme in question is not a part of the expressed constituents), then the bacterium will be unaffected by the drug. In the last instance, if the antibiotic can enter, and the target does exist, then the bacterium can effectively evade the action of the drug by either degrading the antibiotic, modifying the antibiotic to reduce its toxicity, or removing/pumping the antibiotic from the intracellular environment.

Treatment of mycobacterial infections is severely limited (supra), more so than most microorganisms (Inderlied, C. B. et al., In: Murray, P. R. et al., eds. *Manual of Clinical Microbiology*, ASM. Press, Washington, D.C. (1995) pp.1385–1404). This insensitivity is due in part to the impermeable nature of this class of bacteria: the mycobacteria are 1,000 to 10,000 fold less permeable than *Escherichia coli* (Jarlier, V., et al., *Jour. Bact.* 172:1418–1423 (1990) and Nikaido, H., et al, *Res. Microbiol* 142:437–443 (1991)). Connell, N. D. et al. In: *Tuberculosis. Pathogenesis, Protection, and Control.* Bloom, B. R. ed. ASM Press, Washington, D.C. (1994) pp. 333–352 review the permeability characteristics of the mycobacteria and state that "the low permeability of the *M. chelonae* cell wall completely explains the level of resistance of this organism to cephalosporins."

The low permeability is in part responsible for the complex pattern of susceptibility displayed by the mycobacteria. For example, whereas MTB infections can usually be treated effectively with INH and/or PZA, MAC isolates are typically resistant to these drugs. In addition, *M. fortuittim* and *M. chelonae* isolates are typically resistant to all the front line antituberculosis agents (Inderlied, C. B. et al., In: Murray, P. R. et al., eds. *Manual of Clinical Microbiology*, ASM Press, Washington, D.C. (1995) pp.1385–1404). Cynamon, M. H. et al, In: *Drug Susceptibility in the Chemotherapy of Mycobacterial Infectioyzs,* Heifets, L. B. ed. CRC Press, Boston, Mass. (1991), pp.147–159 review studies discussing treatment of infections caused by these rapid growers and report a diverse pattern of susceptibility. For example, in each category of antibiotics reviewed ($\beta$-lactams, sulfonamides, macrolides, aminoglycosides, etc.) a range in susceptibility was described, between a few percent up to 100%, with 30% to 60% being the norm (depending on the drug and its concentration). Heifets, L. B. In: *Drug Susceptibility in the Chemotherapy of Mycobacterial Infections,* Heifets, L. B. ed. CRC Press, Boston, Mass. (1991), pp.13–57 review similar studies on MTB and MAC and discuss diversity in susceptibility, but suggest that the pattern of susceptibility, while still diverse, is not as varied.

While permeability explains a significant portion of the susceptibility patterns of the mycobacteria, these microorganisms appear to have two additional mechanisms that play a significant role in resistance. First, MTB infections appear to be composed of subpopulations of cells. These subpopulations can be classified as: (a) actively growing, (b) semi-dormant—due to the low pH of the macrophage, (c) semi-dormant—with sporadic bursts of metabolism, and (d) dormant (Heifets, L. B. In: *Drug Susceptibility in the Chemotherapy of Mycobacterial Infections,* Heifets, L. B. ed. CRC Press, Boston, Mass. (1991), pp.13–57). Dormancy permits these subpopulations to survive during therapy. The other mechanism appears to be genetic instability. The generation of point mutations causes molecular variability at potential therapeutic target sites. In toto, the variability in susceptibility patterns is a combination of these mechanisms, and the predominant mechanism is probably dependent on the species, and even the isolate itself.

In general, the resistance mechanisms that appear to be most operational in mycobacteria are permeability, regulation of proliferation (e.g., dormancy), and structural variability of the target site(s). Approaches to overcome or bypass resistance must either modify permeability, understand and address proliferation, or modify the chemical structure of the antibiotic to "fit" the target site more appropriately.

In light of this perspective, five pieces of information presented in the Examples herein must be reconciled. First, the mechanism of action of the CB-18 effect is different from that of the quaternary ammonium salts. This latter group of detergents exert a general surface active effect to disrupt the cellular membrane and denature cellular proteins (Hugo, W. B. In: *S.C.I. Monograph no. 19: Surface-Active Agents in Microbiology.* London Soc. Chem. Industry, London (1965) pp. 69–82). FIGS. 7A–7C and 8A–8C compare the action of TMA-18 with CB-18 to confirm that the CB-18 effect is different from that of the action of the quaternary detergents. At high concentrations, however, the betaines appear to mimic the quaternary detergents and cause a general deleterious effect.

Second, there is no post antibiotic effect (PAE). For example, a 90 minute exposure to CB-18 at 383 $\mu$g/ml has no apparent effect on growth characteristics (FIGS. 3C and 3G). If the CB-18 effect is specific, that is to say is not causing a generally deleterious effect, but instead is required at a minimal concentration during active metabolism, then the PAE might be minimal. Isoniazid is an antituberculosis agent that has no PAE (Heifets, L. B. In: *Drug Susceptibility in the Chemotherapy of Mycobacterial Infections,* Heifets, L. B. ed. CRC Press, Boston, Mass. (1991), pp.13–57).

The third point centers around the fact that in some isolates the CB-18 effect is seen in the presence of reconstitution fluid (R.F.) only (i.e., in the absence of antibiotics (FIGS. 10–15)). The fact that this effect is isolate dependent (FIGS. 17–27) strongly suggests that the CB-18 effect has a specific site of action, as opposed to global consequences. In other words, the CB-18 effect is a reflection of the microheterogeneity of susceptibility patterns within mycobacteria, and most especially the *M. tuberculosis* complex.

Fourth, the CB-18 effect is different from that of EDTA (FIGS. 34–35). EDTA alters permeability by extracting and chelating divalent metal cations that stabilize the cell wall structure. Whereas Rastogi, N. et al., *Antimicrob. Agents Chemo.* 34:759–764 (1990) reported that growth in 1 mM EDTA (372.5 μg/ml) was detrimental to the extent that the data could not be used in the "X/Y quotient" analyses performed by these authors. EDTA and CB-18 were both used in the experiments in Example 7 at 17 μg/ml (approximately equi-molar amounts) and were shown to behave differently in the assay of the invention. In addition, Tsubone K., *Jour. Pharm. Sci.* 80:1051–1054 (1991) show that in general there was little or no correlation between the chelating activity of different phosphobetaines and antimicrobial activity. Additionally, Table 10 reviews the different betaines tested. Those carboxybetaines that had an amidopropyl linkage were ineffective relative to carboxybetaines with the same bridge but no amidopropyl linkage (compare Hetaine CLA or Schercotaine WOAB with DeTaine PB and Velvetex OLB). The amidopropyl linkage would not be expected to interfere with chelation between the centers of charge, but would be expected to interfere with the CB-18 effect if the site of action were physiological in nature (e.g., enzyme).

Fifth, Example 7 (FIG. 32B) tested Tween 80 in this assay: Tween 80 had no impact on the 571/573-BAL isolate at 17 μg/ml (13 μM). This was a rather interesting result since several authors have reported that incorporation of Tween 80 into the culture media also causes an induction of susceptibility (Hui, J. et al., *Antimicrob. Agents. Chemo.* 11:773–779 (1977); Yamori, S. et al., *MicrobioL Immunol.* 35:921–926 (1991)). The data herein suggest that the mechanism whereby Tween 80 exerts its effect is different from that of CB-18. For example, at high concentrations of Tween 80 (e.g., 1% (10 mg/ml)) growth was actually optimal, and amounts as high as 10% were not inhibitory (Stinson, M. W. et al., *Am. Rev. Resp. Dis.* 104:717–727 (1971)). In contrast, CB-18 at approximately 3–7 μg/ml caused no alteration in growth, whereas at 54 μg/ml (222 μM) growth of both isolates (ATCC 27294 and 571/573-BAL) was completely suppressed (FIGS. 10A and 11A). The CB-18 effect was observable in a narrow concentration range (between approximately 13 μg/ml and approximately 27 μg/ml, depending on the isolate).

Finally, lecithin can overcome the CB-18 effect. This is in contrast to the teaching of Barry, C. E. et al. (U.S. Pat. No. 5,610,198). Barry, C. E. et al. (U.S. Pat. No. 5.610,198) recite lecithin as an adjuvant in their invention. In the invention described herein, this phospholipid might function to either neutralize CB-18 (similar to its electrostatic interaction with the quaternary salts), or as a competitive inhibitor (interfering with the CB-18 effect at the site of action). Since CB-18 has a net neutral charge, the latter hypothesis seems more viable (i.e., there would be a minimal stable electrostatic interaction). If lipids such as lecithin were acting as competitive inhibitors then this might explain the lack of a PAE.

If CB-18 were being sequestered into lipoidal bodies, as suggested by Thornton WO 95/27076, then the betaine-like detergents would not be available to fuinction as surface active agents. If the mycobacteria were heterogeneous at the site of action of the CB-18 effect, then different clinical isolates would be expected to behave differently in the presence of different betaine-like detergents (Example 7). In addition, if altering permeability facilitated access of the therapeutic to the target site, and there was a heterogeneous population of clinical isolates with respect to the target site of the antibiotic, then variations at this level would also be expected (as seen in Examples 5 and 6). Combinations of betaine-like detergents and different antibiotics would be expected to show significant variability with respect to behavior. It is this dissection of information at two different sites of action that the betaine susceptibility test would provide.

The invention herein may address one or more of these resistance mechanisms (i.e., permeability, dormancy or molecular compatibility). Not intending to be held to the following hypothesis, the following explanation is provided as a means to illustrate the utility of the invention: The delay in growth may be a manifestation of a stimulation of the mechanism responsible for dormancy. For example, since most antibiotics have a natural half-life, if the CB-18 effect were causing a cessation of mycobacterial metabolism until toxic levels of the antibiotic subsided, the CB-18 effect may be used to classify the nature of the clinical isolate in regard to proliferation characteristics. This information would be valuable to the clinician in terms of the drug to use as well as the length of the therapy.

The other mechanism is related to the permeability of the mycobacteria. Not intending on being held to the following hypothesis, the following explanation is provided as a means to illustrate the utility of the invention: The betaine-like detergents may be altering the permeability of the mycobacteria by modifying the composition of mycolic acid conformations. The net result would be an induced susceptibility to antibiotics. The information derived from the invention herein would be valuable to the clinician in terms of which drug(s) to use for the most effective therapy.

The concept that the CB-18 effect may be a result of alterations in the pattern of mycolic acid modifications is based in part on the work of Yuan, Y. et al., *Proc. Natl. Acad. Sci.* 93:12828–12833 (1996) and is examined in detail in Example 9. In summary, modifications to mycolic acids can be directly related to cell wall fluidity. Certain modifications decrease cell wall fluidity, and a drop in cell wall fluidity can be correlated with a reduction in permeability. The low permeability of mycobacteria is thought to play a significant role in antimicrobial resistance (Yuan, Y. et al., *Proc. Natl. Acad. Sci.* 92:6630–6634(1995); Brennan, P. J. et al., *Annu. Rev. Biochem.* 64:29–63 (1995)). Recall that Connell, N. D. et al. In: *Tuberculosis. Pathogenesis, Protection, and Control.* Bloom, B. R. ed. ASM. Press, Washington, D.C. (1994) pp.333–352 attributed the resistance of *M. chelonae* to cephalosporins exclusively to permeability.

Figure 39A:
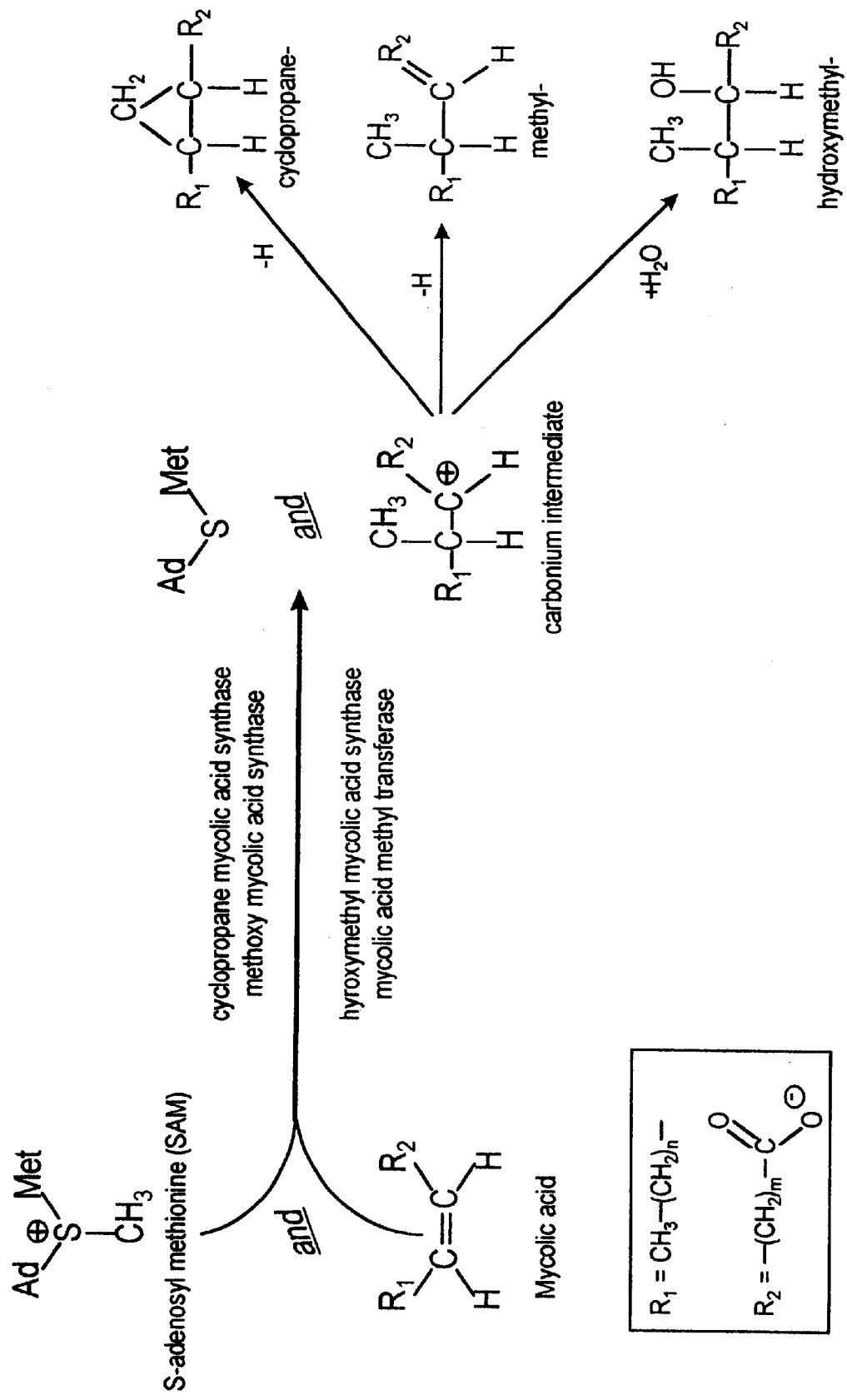

Modifications to mycolic acids occur via a series of related S-adenosyl methionine (SAM) dependent enzymatic reactions (FIG. 39A). Barry, C. E. et al. (U.S. Pat. No. 5,610,198) teaches that thiolated-fatty acid derivatives ("thiatetracosanoic acids") can be used to inhibit these SAM-dependent modifications to mycolic acids (FIG. 39B) to treat infections caused by pathogenic mycobacteria. The transition state structure of the thiatetracosanoic acids resembles a betaine-like detergent (Yuan. Y, et al., *Proc. Natl. Acad. Sci.* 93:12828–12833 (1996)), specifically, a sulphonium-based carboxybetaine (Table 1 and FIG. 39B). The sulphoniumcarboxybetaines would not require enzymatic catalysis for activation but would simply inhibit these SAM-dependent enzymes.

In contrast to the betaine-like detergents of the invention, the thiatetracosanoic acids would be extremely insoluble. In other words, the Krafft temperatures of the thiatetracosanoic acids would be above the physiological norm (e.g., 37° C.). Delivery would be a significant hurdle. The sulphoniumcarboxybetaines would be much more soluble (even when $R_1$=18–20, but especially when $R_4 \geq 3$ (Table 1; Laughlin, R., *Langmuir* 7:842–847 (1991)). The betaine-like structure would directly solve the solubility and, to some degree, the delivery problem. For example, the thiatetracosanoic acids would most probably be in the solid phase if delivered intravenously. Since the betaine would be more soluble, intravenous delivery at low dose would be more feasible due to the lower Krafft temperature of betaines.

Barry, C. E. et al. (U.S. Pat. No. 5,610,198) also discloses that the thiatetracosanoic acids would be specific for slow growing pathogenic mycobacteria. Barry, C. E. et al. (U.S. Pat. No. 5,610,198) firther discloses that only antibiotics that also interfere with mycolic acid synthesis would function synergistically with these thiolated fatty acid derivatives. The invention herein shows that the betaine-like detergents are applicable to a broad range of bacteria containing mycolic acid structures (i.e., corynebacteria, Nocardia, as well as mycobacteria (Example 9)), and that an extensive range of antibiotics can also be utilized in the invention (Examples 5 and 6).

Figure 39B:
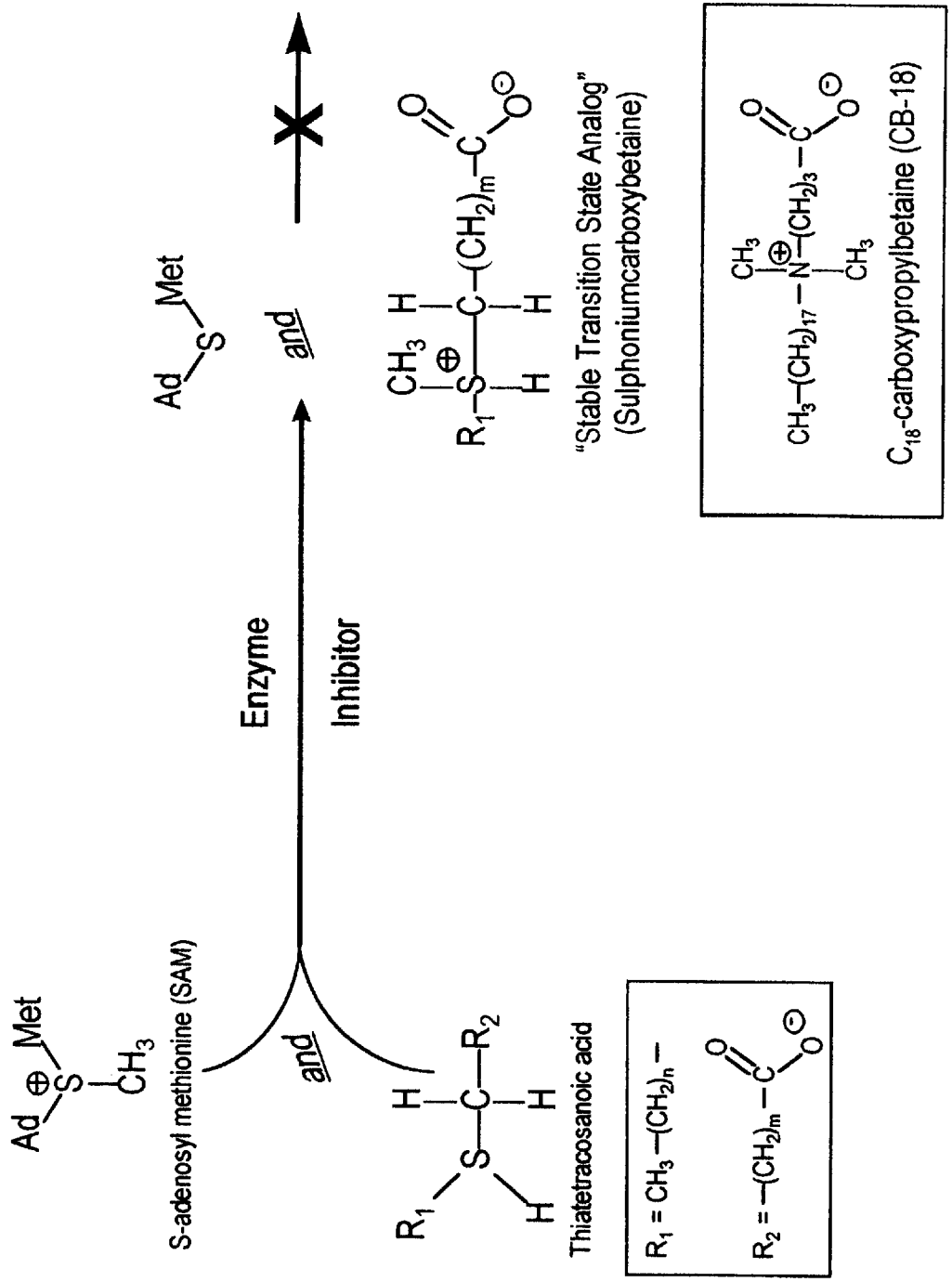
Figure 39C:
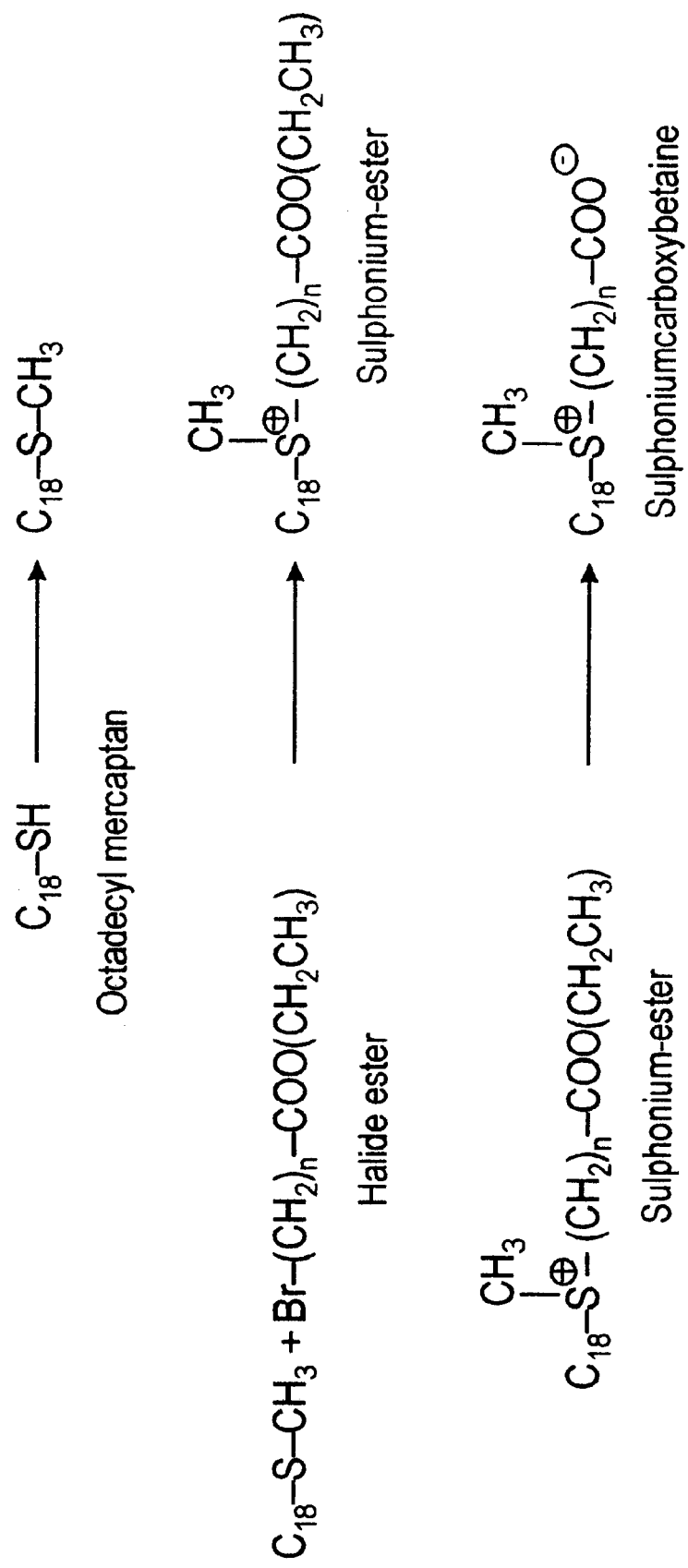

Synthesis of the sulphoniumcarboxybetaine might be according to the synthesis shown in FIG. 39C, but any method to accomplish the same end using methods known in the art would be acceptable (March, *Advanced Organic Chemistry. Reactions, Mehanisms and Structures,* Fourth Ed., John Wiley & Sons, New York, N.Y. (1992); and Fieser, et al., *Reagents for Organic Synthesis* vol. 1–16, John Wiley & Sons, New York, N.Y. (1992) both incorporated herein by reference).

In summary, but not intending to be held to the following explanation, the CB-18 effect appears to be the consequence of the interaction between a betaine-like detergent and a particular site of action. If this interaction were to modify the permeability of bacteria with mycolic acid structures then the net result would be to increase the effective concentration of an antibiotic at its target site. For example, considering the isolates derived from the CB-18 Pilot Study (Tables 7 and 8), if these mycobacteria showed heterogeneity at both the target site (i.e., peptidoglycan synthesis) and at the β-lactamase site, then an even greater degree of discrimination in the betaine susceptibility assay would be anticipated. For example, one scenario would cite a particular isolate that might be susceptible to a given β-lactam, but due to a lack of permeability this isolate might escape the effect of the antibiotic. If betaine-like detergents were able to increase the permeability of this isolate, the β-lactamase may or may not have the capacity to destroy the antibiotic before it exerts it effect. If the β-lactamase from the isolate in question were deficient with respect to an ability to destroy a particular β-lactam structure, altering the permeability might be enough to exert a sufficiently deleterious effect, observed as the CB-18 effect. It would be reasonably expected that different bacteria with mycolic acid structures would have significant structural differences with respect to the sites of action of the three different molecules discussed in this example (β-lactam, betaine-like detergent, and β-lactamase). Therefore, a high degree of discrimination would be possible due to the large number of antibiotics available (especially β-lactams) that can be used in combination with the large number of betaine-like detergents available.

A susceptibility assay according to the invention that opens the door to the use of β-lactams as therapeutic adjuvants in antituberculosis therapy is of significant utility because the most common and best characterized class of antibiotic compounds is by far the β-lactams. Due to the depth and breadth of these antibiotics, the ability to treat mycobacterial infections with these agents would provide significant advantages. Application of the β-lactams in therapeutic regimes designed to treat mycobacterial infections has been tried with limited success. For example, Chambers, H. P. et al., *Antimicro. Agents Chemo.* 39:2620–2624 (1995) examined five clinical isolates of MTB and tested several different classes of β-lactams. Most isolates were resistant to the penicillins and most of the cephalosporins; however, imipenem (a carbapenem) showed some activity. Combining almost all β-lactams with a β-lactamase inhibitor was necessary to achieve significant susceptibility.

As discussed above, β-lactamase inhibitors interfere with the resistance mechanism whereby the organism degrades the antibiotic. This is an example wherein antibiotic therapy addresses a resistance mechanism, and thereby enhances any β-lactam based chemotherapy. The ability to broaden the susceptibility of the mycobacteria to antibiotics, especially the β-lactam antibiotics, by addressing resistance mechanisms has significant potential in effectively treating mycobacterial infections. The invention described herein utilize molecules that address a mechanism effecting bacterial resistance in such a manner that has not heretofore been described. Analysis of isolates 512-JHH (FIG. 24) and 538-JHH (FIG. 25), and realization that CB-18 had a significant impact on an isolate that had been subjected to antituberculin therapy in vivo (Table 9) emphasizes the therapeutic utility of the betaine-like detergents.

Having now fully described the invention, it will be understood by those with skill in the art that the invention may be performed within a wide and equivalent range of conditions, parameters and the like, without affecting the spirit or scope of the invention or any embodiment thereof. All references cited herein are fully incorporated herein by reference.

EXAMPLES

Example 1

CB-18 Processing and Mycobacterial Culture

The inventions described herein were initially conceived as a result of observations made during studies involved with novel methods for processing clinical specimens for the detection of mycobacteria. These procedures were based on the methods of Thornton as described in WO 95/27076 and were designed as a primary processing methodology for the isolation of bacteria with mycolic acid structures, especially mycobacteria, from clinical specimens, and most especially from respiratory specimens. The method of Thornton WO 95/27076 is described below, and manufacture of the reagents for this procedure are described at the end of this Example.

(1) Place 1–10 mls of sputum or bronch-wash in a 50 ml conical tube.

NOTE: While respiratory specimens are the predominant specimen type expected to be used in conjunction with the procedure described here, other specimen types such as water, soil, tissue, fecal and others can be adapted for use in conjunction with the procedure below. Some of these specimens might first be clarified by re-suspending in water or buffer and passing the mixture over a Spin-X II column fitted with a 20–60 micron fit (Corning Costar, Boston, Mass.). Such a column might also contain a matrix, such as Sephadex® (Sephadex G-50®: Pharmacia, Piscataway, N.J.) or an equivalent resin, to enhance purification. Any specimen could then be treated as described below.

(2) To the specimen add an equal volume of 0.5% NALC liquefaction solution (see below: 0.5% NALC/25 mM. sodium citrate) and vortex.

(3) Incubate at room temperature for 10 minutes (vortex at about 5 minutes, and then just before the next step).

(4) Open the tube and add sterile, filtered water to the specimen to a final volume of approximately 35 mls (NOTE: use sterile, filtered water (e.g., GIBCO/BRL, Gaithersburg, Md., Cat. #: 15230-022)).

(5) Add 4 mls of a concentrated solution containing a betaine-like detergent, 10×CB-18 Buffer for example (see below): 10×CB-18=10 mM CB-18, 0.5 M. Tris-HCl pH 8.0, 50 mM. NALC, and 1 mM. NaCl.

(6) Vortex well to completely mix the specimen.

(7) Incubate at 37° C. for 90 minutes with shaking (140 rpm).

(8) Vortex and then centrifuge specimens at 4,000×g for 20 minutes at 30° C.

(9) Decant the tubes completely and add 500 µl of sterile water or buffer to the specimen.

(10) Resuspend the pellet completely and prepare the sediment for detection, such as by acid fast staining (i.e., microscopy), culture, nucleic acids amplification, or immunodiagnostics.

Preliminary studies designed to assess the nature of contaminants breaking through the BACTEC 12B liquid media supplemented with PANTA used discarded respiratory specimens (n=277) from Quest Diagnostics—Baltimore. (NOTE: the BACTEC 12B liquid culture system is one of the standard methods in the art for culturing mycobacteria, and PANTA is an antimicobial supplement containing polymyxin B, azlocillin, nalidixic acid, trimethoprim, and amphotericin B: this culture system is referred to herein as "12B/PANTA" (Becton Dickinson, Cockeysville, Md.)) Specimens were collected and processed with CB-18 according to the procedure above. Approximately 400–500 µl of each sediment was planted on 12B/PANTA. All contaminants were identified by morphology and/or gram stain and then differentiated as either oxidase/catalase, positive or negative. Contaminants were then speciated, and antibiotic sensitivities determined, using MicroScan® panels (Dade, West Sacramento, Calif.). The results are shown in Table 2.

TABLE 2

Identification of BACTEC 12B/PANTA Contaminants (n = 277)

| Group | # | % |
|---|---|---|
| Gram Negative | 48 | 84.2% |
| Gram Positive | 5 | 8.8% |
| Yeast | 3 | 5.3% |
| Fungi | 1 | 1.8% |
| Total | 57 | |

From 40 Patients: Contamination = 14.4%

Table 2 revealed that 57 contaminants were isolated from 40 specimens. The contamination rate on a per specimen basis was 14.4% (40÷277). This suggested that the predominant problem encountered with respiratory specimens processed according to WO 95/27076 (e.g., CB-18) was the occurrence of gram negative organisms (>84%). Approximately 31 (64%) of the 48 gram negative isolates were Enterobacteriaceae. The most common isolates were *Providencia stuartii* (n=13), Pseudomonas species (n=11), and *Proteus mirabilis* (n=7). Therefore, significantly impacting the contamination rate would require a reduction in the incidence of gram negative organisms. The susceptibility data showed that 40 of the 48 gram negative bacteria were sensitive to ceftazidime at 8 µg/ml. As a result of these data and other experiments it was decided that the antibiotic supplement PANTA should be fortified with ceftazidime (8 µg/ml final) in an attempt to control this gram negative contamination (the 12B/PANTA system supplemented with ceftazidime (caz) is referred to herein as "12B/PANTA/caz"). Based on parallel experiments using several ATCC mycobacterial type strains it was thought that ceftazidime would reduce the incidence of gram negative contamination without significantly impacting the Friability of the mycobacteria.

Preparation of 10×CB-18 Buffer (1) 20×Buffer Salts: 1 M Tris-HCl pH 8.0, 2 mM. NaCl

| Tris Base (121.14 gr/mole) | 54.27 gr |
|---|---|
| Tris HCl (157.64 gr/mole) | 87.02 gr |
| NaCl | 0.117 gr |
| Add Water to: | 1 liter |

(i) Place approximately 250 mls of water in a 1 liter graduated cylinder.

(ii) Add the Tris base (Sigma, St. Louis, Mo., Cat. #: T 1503), Tris-HCl (Sigma, St. Louis, Mo., Cat. #: T3253) and NaCl (Sigma, St. Louis, Mo., Cat. #: S 7653) and mix (NOTE: use sterile, filtered water (e.g., GIBCO/BRL, Gaithersburg, Md., Cat. #: 15230-022)).

(iii) Add the remaining water to 1 liter and ensure complete mixing.

(iv) Check the pH by removing a small aliquot. The pH should be ±0.2 pH units.

(v) Filter sterilize (0.22µ filter), divide into 50 ml aliquots, and store at room temperature.

(2) 10×CB-18 Stock Solution: 100 mM CB-18

| *CB-18 (383 gr/mole) | 1.915 gr |
|---|---|
| Isopropanol:Water (1:1) to: | 50 mls |

*CB-18: N,N-dimethyl-N-(n-octadecyl)-N-(3-carboxypropyl) ammonium inner salt (CAS ®No. 78195-27-4)

(i) Mix 25 mls of analytical grade isopropanol (Baxter, McGaw Park, Ill., Cat. #: 3043-1 NY) with 25 mls of water in a graduated cylinderto prepare 50 mls of 1:1, isopropanol:water (NOTE: use sterile, filtered water (e.g., GIBCO/BRL, Gaithersburg, Md., Cat. #: 15230-022)).

(ii) Transfer 25 mls of the Isopropanol:Water (1:1) solution to a 50 ml conical tube.

(iii) Weight-out 1.915 grams of CB-18 and place it in the graduated cylinder with 25 mls of the remaining isopropanol:water (1:1). Mix by swirling.

(iv) Add more of the Isopropanol:Water (1:1) solution, up to about 40, mls and swirl gently. Let the solution sit for about 20 minutes and swirl gently about every 5 minutes.

(v) When the CB-18 has dissolved (about thirty minutes total) bring the final volume up to 50 mls with the Isopropanol:Water (1:1) solution and mix by inversion.

(vi) Divide the solution into two sterile plastic 50 ml conical tubes and store at room temperature.

(3) 10×CB-18 Buffer (i) Determine the number of specimens to be processed, insert this number in the chart below (add one to this number to ensure enough buffer), calculate the final amounts of each component required and prepare the appropriate amount of 10×CB-18 as described below.

| Component | Multiplication Factor | | | Final Amount |
|---|---|---|---|---|
| 20 × Buffer Salts | 2 mls | × | Number | = |
| 100 × CB-18 | 400 µl | × | of | = |
| NALC (163.2 gr/mole) | 0.033 gr | × | Specimens | = |
| Add Water to | 4 mls | × | plus one | = |

(ii) Immediately prior to use combine the 20×Buffer Salts, NALC (Fluka, Ronkonkoma, N.Y., Cat. # 01039), and 100×CB-18 and bring up to volume with sterile, filtered water (NOTE: use sterile, filtered water (e.g., GIBCO/BRL, Gaithersburg, Md., Cat. #: 15230-022)).

NOTE: At anypoint in this procedure if precipitate is present in the buffer, DO NOT USE. The solution should be kept warm during storage and use (e.g., greater than 20° C.). Do not refrigerate this solution.

Preparation of 0.5% NALC Liquefaction Solution (1) 10×Na-Citrate Stock: 0.25 M sodium citrate dihydrate

| Trisodium Citrate dihydrate (294.1 gr/mole) | 7.35 gr |
|---|---|
| Add Water to: | 100 mls |

(i) Place approximately 25 mns of water in a 100 graduated cylinder (NOTE: use sterile, filtered water (e.g., GIBCO/BRL, Gaithersburg, Md., Cat. #: 15230-022)).

(ii) Add the trisodium citrate dihydrate (Sigma, St. Louis, Mo., Cat. #: C 3434) and mix by swirling. Add the remaining water to 100 mls and mix by inversion.

(iii) Sterilize by filtration (0.22µ filter) and aliquot into 50 ml conicals. Store at room temperature.

(2) 0.5% NALC Liquefaction Solution (made fresh daily):

(i) Determine the approximate volume of NALC liquefaction solution required.

(ii) Combine the 10×Na-Citrate stock and NALC (Fluka, Ronkonkoma, N.Y., Cat. #: 01039) in a 50 ml conical tube or graduated cylinder, and bring to the final volume with water (NOTE: use sterile, filtered water (e.g., GIBCO/BRL, Gaithersburg, Md., Cat. #: 15230-022)).

(iii) Use immediately and discard the unused portion.

| Approx. # Specimens | 3–10 | 7–25 | 12–37 | 15–50 |
|---|---|---|---|---|
| 10 × Na-Citrate Stock | 2.5 mls | 5 mls | 7.5 mls | 10 mls |
| NALC (163.2 gr/mole) | 0.12 gr | 0.25 gr. | 0.38 gr. | 0.5 gr. |
| Add Water to: | 25 mls | 50 mls | 75 mls | 100 mls |

Preparation of Ceftzidime Stock and 12B/PANTA/caz (1) Ceftazidime Stock (36 mg/ml)

| Ceftazidime | 72 mg |
|---|---|
| 1 M Na-Bicarbonate | 85.6 µl |
| Add Water to: | 2 mls |

(i) In a 2 ml volumetric flask mix 1 ml of the water and the 1 M sodium bicarbonate (Sigma, St. Louis, Mo.: Cat#: S 6297 (dissolve 8.40 grams of Na-bicarbonate in 100 mls water, sterile filter, and store frozen in 10 ml and 1 ml aliquots)) (NOTE: use sterile, filtered water (e.g., GIBCO/BRL, Gaithersburg, Md., Cat. #: 15230-022)).

(ii) Add the ceftazidime (Sigma, St. Louis, Mo.: Cat#: C 3809) and immediately bring the volume up to 2 mls with water.

(iii) Gently mix by inversion until the solution is clear. DO NOT heat the solution above room temperature (e.g., do not warm the solution in your hands.)

(iv) Immediately aliquot 50 µl portions into 1.5 ml microfuge tubes and immediately store at −70° C. until use.

(2) Fortification and Use of PANTA/caz (i) Remove the lyophilized PANTA and reconstitution fluid (R.F.) from the refrigerator, and one 50 µl aliquot of ceftazidime stock (36 mg/ml) from the freezer.

(ii) When the ceftazidime has melted use a 5 ml syringe and add 1 ml of R.F. to the ceftazidime stock. Mix by drawing into the syringe and expelling one time. Using the syringe, transfer the entire contents to the PANTA bottle.

(iii) Add 4 more milliliters of R.F. to the PANTA bottle (final volume=5 mls). Label "PANTA/caz."

(iv) Add 100 µls of PANTA/caz to each 12B bottle prior to use (add the antibiotic within 2 hours of specimen addition.)

(v) Store the unused portion at −20 C. Discard after 48 hours (e.g., do not freeze-thaw more than 1 time.)

Example 2

CB-18 Pilot Study

CB-18 was used to process respiratory specimens for the detection of Mycobacteria (acid fast bacilli: AFB) in an effort to evaluate the methods of Thornton WO 95/27076. Respiratory specimens (n=573) were split and collected from the TB-laboratories of Quest Diagnostics-Baltimore (BAL), as well as Quest Diagnostics-Teterboro (TBR), Washington, D.C. Bureau of Laboratories (BOL), Johns Hopkins Hospitals (JHH, and the University of Maryland at Baltimore (UMB). The host site split each specimen such that half of each specimen was processed at the site by the standard NALC/NaOH method (Kent, P. T. et al., "Public Health Mycobacteriology," in A Guide for the Level III Laboratory, U.S. Department of Health and Human Service, Centers for Disease Control, (1985) pp. 31–46) and planted on both liquid (either BACTEC 12B or BBL MGIT) and solid media (either 7H11, L-J or SeptiCheck), and the other half of each specimen was sent to the Quest-Baltimore facility where specimens were processed with CB-18 on a daily basis as described in Example 1. The CB-18 sediments were planted on 12B/PANTA/caz and 7H11-selective slants as described above. All smear analyses were performed as per recommended procedures (Kent, P. T. et al., "Public Health Mycobacteriology," in *A Guide for the Level III Laboratory*, U.S. Department of Health and Human Service, Centers for Disease Control, (1985) pp. 57–69). The results of this study are herein referred to as the "CB-18 Pilot Study."

Of the 573 specimens processed, there were 106 AFB culture positive specimens by all methods (i.e., by either NaOH or CB-18, by either liquid or solid culture). There were 8 *M. gordonae* isolates. All were discrepant, smear negative and split equally between the two methods (i.e., the 4 that were isolated by NaOH were missed by CB-18, and vice versa). Since *M. gordonae* isolates are considered contaminants oflimited clinical significance (Wayne, L. G., et al., *Clin. Microbiol. Rev.* 5:1–25 (1992)), they were omitted from the following analyses: Therefore 98 AFB culture positive specimens were analyzed. Table 3 summarizes the culture results in the absence of the *M. gordonae* isolates.

There were 52 concordant positive specimens, 467 concordant negative specimens and 46 discordant specimens. NaOH identified a total of 61 positive specimens for a sensitivity 62.2%. CB-18 identified a total of 89 positive specimens for a sensitivity of 90.8%. CB-18 increased aggregate culture sensitivity approximately 46%.

TABLE 3

Aggregate Culture Results of the CB-18 Pilot Study

|  |  | NALC/NaOH |  |  |
| --- | --- | --- | --- | --- |
| n = 573 |  | + | − |  |
| CB-18 | + | 52 | 37 | 90.8% |
|  | − | 9 | 467 |  |
|  |  | 62.2% |  | Total AFB = 98 |

Of the 98 culture positive specimens, 69 were mycobacteria other than tuberculosis (MOTT), and 29 were MTB. NaOH identified 33 of the MOTT positive specimens, and 28 of the MTB positive specimens. CB-18 identified 64 of the MOTT specimens, but only 25 of the MTB specimens. The culture sensitivity among NaOH processed specimens was 47.8% and 96.6% for MOTT and MTB, respectively. The culture sensitivity among CB-18 processed specimens was 92.8% and 86.2% for MOTT and MTB, respectively. CB-18 increased culture sensitivity among MOTT disease positive specimens by 94.1%, but reduced culture sensitivity among MTB disease positive specimens by 12.1%.

Table 4 shows the results of smear analysis. There were 61 culture positive specimens that were also smear positive by any processing method. There were 18 specimens that had identical smear values by both processing methods, and 19 specimens wherein both methods reported a smear positive result, but the value reported by CB-18 was higher. There were no instances in which NaOH had a higher smear value among smear positive specimens. There were 23 instances wherein CB-18 reported a smear positive result, but NaOH reported a smear negative result. There was only 1 instance in which NaOH reported a smear positive result and CB-18 reported a smear negative result. NaOH identified 38 of the 98 culture positive specimens by smear for a sensitivity of 38.8%, and CB-18 identified 60 by smear for a sensitivity of 61.2%. Therefore, CB-18 increased smear sensitivity by approximately 58%. Table 4 also shows that the increase in smear sensitivity is a consequence of increases among both tuberculous mycobacteria (MTB) and mycobacteria other than tuberculosis (MOTT).

TABLE 4

Smear Analysis of the CB-18 Pilot Study

|  | All | MOTT | MTB |
| --- | --- | --- | --- |
| Identical smear values | 18 | 8 | 10 |
| CB-18 smear value > NaOH smear value | 19 | 9 | 10 |
| NaOH smear value > CB-18 smear value | 0 | 0 | 0 |
| CB-18 smear ⊕ and NaOH smear ⊖ | 23 | 16 | 7 |
| NaOH smear ⊕ and CB-18 smear ⊖ | 1 | 1 | 0 |
| Total culture ⊕ and smear ⊕ | 61 | 34 | 27 |
| Total AFB culture ⊕ in study | 98 | 69 | 29 |
| NaOH smear sensitivity | 38.8% | 26.1% | 69.0% |
| CB-18 smear sensitivity | 61.2% | 42.8% | 93.1% |

While there was an increase in smear sensitivity with CB-18, the specificity of smear analysis was 99.8%, and 96.8% by NALC/NaOH and CB-18, respectively. There were a large number of specimens that were reported as "smear ±" by CB-18 that did not have confirming cultures by CB-18. CDC guidelines (Kent, P. T. et al., "Public Health Mycobacteriology," in *A Guide for the Level III Laboratory*, U.S. Department of Health and Human Service, Centers for Disease Control, (1985) pp. 57–69) instruct laboratories to call these smear±results as "doubtful" in the absence of a confirming culture result.

There were an exceptionally high number of smear±results when specimens were processed by CB-18. Analyzing each method independently, that is to say in lieu of the results of the other processing method, and including these smear±results provides a much different picture. For example, the data of Table 5 revealed that 37 of the 61 specimens that were culture positive by NALC/NaOH, were also smear positive by NALC/NaOH. Of the 89 culture positive CB-18 specimens, 56 were also smear positive by CB-18. The sensitivity and specificity of the NALC/NaOH smear analysis was 60.6% and 99.6%, respectively, and 62.9% and 91.2%, respectively, by CB-18.

Of the 31 smear±results (5+26=31) observed by CB-18, approximately 42% (n=13) had confirming cultures by other methods or from other specimens, or could be associated with previous disease, or had a positive amplification result (i.e., confirming the presence of mycobacterial DNA). (Note: As per CDC guidelines the 16 smear 1+ and 2+ CB-18 culture negative specimens were considered CB-18 smear positive in the analysis of Table 4—hence the initial reduction in specificity (99.8% vs. 96.8% (Table 4)).) In summary, smear specificity was 99.6% and 91.2% by NALC/NaOH and CB-18, respectively, according to the analysis presented in Table 5, even though CB-18 provided an overall increase in culture sensitivity (Table 3).

The results presented in Table 5 suggest that CB-18 processing has no effect on the technique of smear itself. For example, CB-18 did not alter the "stickiness" of the bacterium with respect to adherence to the slide. This is based on the observation that CB-18 increased smear sensitivity, with respect to culture positive specimens, by 58% relative to NALC/NaOH (Table 4); however, each method was approximately equivalent with respect to the number of culture positive specimens that were picked up by smear by that method (Table 5: 60.6% vs. 62.9%). In other words, culture is still the more sensitive diagnostic technique, but CB-18 appears to impact the overall sensitivity of both methods approximately equally.

TABLE 5

Independent Evaluation of the Two Different Processing Methods

| Smear | NALC/NaOH | | CB-18 | |
|---|---|---|---|---|
| Value | AFB ⊕ | AFB ⊖ | AFB ⊕ | AFB ⊖ |
| Negative | 24 | 502 | 33 | 434 |
| ± | 3 | 0 | 5 | 26 |
| 1+ | 7 | 1 | 8 | 14 |
| 2+ | 8 | 1 | 6 | 2 |
| 3+ | 5 | 0 | 7 | 0 |
| 4+ | 14 | 0 | 30 | 0 |
| Total | 61 | 504 | 89 | 476 |
| Smear: | Sensitivity 60.6% | Specificity 99.6% | Sensitivity 62.9% | Specificity 91.2% |

TABLE 6

Comparison of Liquid Culture and Solid Media

| | | Culture Result | | | | Sensitivity | |
|---|---|---|---|---|---|---|---|
| | | Liquid & Solid | Liquid Only | Solid Only | AFB Sum | Liquid | Solid |
| NaOH | Smear ⊕ | 31 | 6 | 0 | 37 | 100% | 83.8% |
| | Smear ⊖ | 14 | 9 | 1 | 24 | 95.8% | 62.5% |
| | Total | 45 | 15 | 1 | 61 | 98.4% | 75.4% |
| CB-18 | Smear ⊕ | 38 | 4 | 14 | 56 | 75.0% | 92.9% |
| | Smear ⊖ | 4 | 11 | 18 | 33 | 45.4% | 66.7% |
| | Total | 42 | 15 | 32 | 89 | 64.0% | 83.1% |

In summary, the number of culture negative and smear positive specimens (i.e., both smear+ and smear±), identified by each method was dramatically different: NALC/NaOH reported only 2 smear positive and culture negative specimens, while CB-18 reported 42 smear positive specimens (including the CB-18 smear±but culture negative specimens: Table 5). The question of the validity of the smear±results (i.e., the loss in smear specificity) is of significant concern. Specifically, if the assumption above is correct (e.g., CB-18 impacts the overall sensitivity of both detection methods approximately equally), then CB-18 has reduced the specificity of smear analysis. This would be of significant concern to the laboratorian. If the assumption is incorrect, and these are valid smear results, indicating that these patients may in fact be infected with mycobacteria, then the sensitivity of CB-18 smear analysis maybe higher than indicated in either Table 4 or Table 5. This later conclusion would be of significant concern to the physician. In order to understand these results, the analyses shown in Table 6 were performed.

The sensitivities of liquid and solid culture of the two different processing methods used in the CB-18 Pilot Study were examined independently (Table 6). The number of AFB culture positive specimens isolated by a given culture method (liquid vs. solid), was analyzed for that processing method (NaOH vs. CB-18). Considering the 61 NaOH culture positive specimens: 45 were positive by both liquid and solid culture, 15 were positive by liquid only, and 1 was positive on solid media only. Examining the 89 CB-18 culture positive specimens: 42 were positive by both liquid and solid culture, 15 were positive by liquid only, and 32 were positive on solid media only. The sensitivity of liquid culture when processed by NaOH and CB-18 was 98.4% and 64.0%, respectively. The sensitivity of solid media when processed by NaOH and CB-18 was 75.4% and 83.1%, respectively.

The expected result is that seen for NaOH processed specimens: liquid culture was approximately 31% more sensitive than culture on solid media. In contrast, when specimens were processed using CB-18 (as described in Example 1), and planted on 12B/PANTA/caz and 7H11-selective slants, the solid media was approximately 30% more sensitive.

There were remarkable and unexpected dichotomies within these results. For example, while aggregate culture sensitivity was increased by approximately 46% (Table 3), the increase was due exclusively to an increase in MOTT isolation (i.e., there was a decrease in MTB culture sensitivity.) In marked contrast to this was the overall increase in smear sensitivity wherein the contributions were derived almost equally from both MOTT and MTB positive specimens (Table 4).

Thornton WO 95/27076 suggested that increased sensitivities were due to (i) a reduction in the deleterious impact of processing relative to NaOH, (ii) an increased efficiency of recovery by centrifugation as a result of compensating the innate buoyancy of the organisms, and (iii) an increased probability of detection due to dispersion of those organisms that cord. Whereas increased culture sensitivity could be due to combinations of all three aspects, increased smear sensitivity could only be due to either dispersion or increased recovery (smear is unrelated to viability). Since MOTT organisms generally do not cord to the same degree as MTB bacteria, the increased smear sensitivity was most probably due to enhanced recovery. Alternatively, viability must intuitively be a significant aspect of culture sensitivity. The dichotomy stems from the fact that the smear data point to enhanced recovery among both MOTT and MTB organisms, but the culture data point to increased viability among MOTT organisms yet decreased viability among MTB organisms.

The reversal in liquid-solid culture sensitivity among CB-18 processed specimens (Table 6) suggested that the dichotomy was a result of the combination of CB-18 with the antibiotics in the PANTA/ceftazidime supplement. For example, comparing the solid culture sensitivity of smear positive and smear negative specimens of the two different processing methods showed a marked similarity. Solid media sensitivity among smear positive specimens was 34% higher than smear negative specimens when processed by NALC/NaOH, and 39% higher when processed by CB-18. The same examination of the liquid culture data showed a minor difference in sensitivity between smear positive and smear negative specimens when processed by NALC/NaOH (e.g., a 4% difference), but a striking difference among the same group processed by CB-18 (e.g., a 65% difference). The 75% liquid culture sensitivity among smear positive specimens processed by CB-18 was unexpected and highly unusual (these 14 specimens consisted of 5-MTB and 9-MOTT: 4-MAC 2-*M. fortuitum,* and 1 each of *M. chelonae, M. szulgai,* and *M. kansasii.*) The 100% sensitivity of liquid culture for NALC/NaOH processed specimens that were smear positive was not serendipitous. Stone, B. L. et al., *Jour. Clin. Micro.* 35:1030–1031 (1997) report that the liquid culture sensitivity of smear positive specimens (processed by NALC/NaOH) was also 99.3% (this was a much larger study: n=439).

There are two conclusions to be drawn from these data. First, the CB-18/12B/PANTA/caz system affected a broad range of mycobacteria. For example, while the 5 missed MTB isolates were highly visible due to their social significance, MTB isolates comprised only 36% (5÷14) of the smear positive-liquid culture negative specimens, and 30% (29÷98) of all AFB isolates in this study. Similarly, MOTT isolates comprised 64% (9÷14) of the smear positive-liquid culture negative specimens, and 70% (69÷98) of all AFB isolates in this study. Since the proportion of isolates affected is the same, this appears to be a broadly applicable phenomenon: the detrimental combination of CB-18 and antibiotics effects MTB and MOTT alike.

Second, the impact of the CB-18/12B/PANTA/caz system may be inoculum dependent. For example, similar to that reported by Eng, R. K., et al., *Antimicrob. Ag. Chemother.* 26:42–47 (1984) for *Pseudomonas aeruginosa,* the minimum inhibitory concentration (MIC) of ceftazidime was increased with increasing inoculum. Since smear is a direct reflection of the number of organisms per unit volume, smear negative specimens would be more affected by the CB-18/12B/PANTA/caz system—hence the 65% difference between the liquid culture sensitivity of smear positive and smear negative specimens.

In this study CB-18 was used at a concentration of 1 mM. (383 $\mu$g/ml). The concentration of CB-18 in specimens planted on BACTEC 12B probably ranged from 35 $\mu$g/ml to 7 $\mu$g/ml, depending on the original consistency of the specimen, the ability of the CB-18 procedure to liquefy the specimen, and the quantity of the "backwash" remaining following decanting (i.e., the original processing fluid). In a worst case scenario (e.g., a thick, heavy sputum) the specimen was not liquefied very well and a large volume of the original processing media remained. Under these circumstances the specimen was essentially planted in processing solution. Adding 400–500 $\mu$l of sediment to the BACTEC 12B bottle with a final volume of ≈4.5 mls provided an ≈11-fold dilution (i.e., 35 $\mu$g/ml). In the best case scenario (e.g., a thin bronchial wash) ≈100 $\mu$l of the original processing media remained. The sediment was then re-suspended in 500 $\mu$l of water providing a ≈5-fold dilution. These specimens would be at approximately 7 $\mu$g/ml. While it was not known what the CB-18 concentration was for a given specimen, the relevant assumption is that CB-18 is homogeneously dissolved in the processing media, and since CB-18 was not washed out, there was a range in concentration for each specimen, somewhere between 7 $\mu$g/ml and 35 $\mu$g/ml.

Solid media is very different from its liquid counterpart. First, a much smaller volume is added to the slant (≈100 $\mu$l). This smaller inoculum partially explains the difference in culture sensitivities. Second, any CB-18 added to the slant would be minimized by capillary action: the detergent would be absorbed into the media, away from the bacteria, thereby minimizing its effect.

In summary, the data above suggest that antibiotics and CB-18 are synergistically deleterious, and this effect broadly affects all mycobacteria.

Example 3

Processing in CB18 vs. Planting in CB18

In an effort to understand the dynamic interactions of CB-18 carried over into the 12B/PANTA/caz culture system, the experiments outlined in FIGS. 1A and 1B were devised (NOTE: FIGS. 1A and 1B refer to the same experiment—two different renderings of the same experiment are provided due to the complexity of the experimental design). Two different isolates were used: the *M. tuberculosis* type strain ATCC 27294 (ATCC, Rockville, Md.), and the clinical isolate 571/573-BAL derived from the CB-18 Pilot Study (NOTE: "571/573-BAL" refers to one of two isolates, both isolates being derived from the same patient, but from two different naive specimens (i.e., 571-BAL and 573-BAL (see Table 8 and compare FIGS. 18 and 19)) submitted on the same day—these two isolates behaved identically in all respects and were used interchangeably in this and the Examples which follow.)

Each isolate was cultivated on either Lowenstein-Jensen (L-J) slants or 7H11-selective slants (7H11-selective slants are fortified with polymyxin B, carbenicillin, amphotericin B and trimethoprim (Becton Dickinson, Cockeysville, Md.)). Cells were scraped off these slants and placed in either buffer or buffer containing 1 mM CB-18 (as described in Example 1), and then diluted 1,000-fold in the same (FIGS. 1A and 1B). Each bacterial stock was then incubated for 90 minutes at 37° C. with shaking (140 rpm) before further dilution. Each bacterial stock was then serially diluted into either buffer or 0.5 mM CB-18 to generate final dilution stocks of 25,000×, 50,000× and 100,000×(relative to the original stock (FIGS. 1A and 1B)). Each dilution series was then planted (400 $\mu$l each) in duplicate in BACTEC 12B bottles supplemented with either PANTA or PANTA which had been fortified with caz such that the final caz concentration was 8 $\mu$g/ml (P/caz). The concentration of CB-18 in these experiments was approximately 17 $\mu$g/ml (somewhere between the 7 $\mu$g/ml and 35 $\mu$g/ml estimated to be in most bottles as discussed in Example 2). Bottles were checked periodically and the growth indices recorded. Growth indices on all six bottles in a given series were averaged and then plotted versus days in culture. The results for ATCC 27294 are shown in FIGS. 2A–2F, and the results for 571/573-BAL are shown in FIGS. 3A–3H. In addition to the data provided in FIGS. 2A–2F, ATCC 27294 was grown under the following two sets of conditions: 7H11-Selective, process in CB-18 (383 $\mu$g/ml), plant in buffer; 7H11-Selective, process in CB-18 (383 $\mu$g/ml), plant in CB-18 (17 $\mu$g/ml CB-18 final) (data not provided).

The ATCC 27294 isolate was generally unaffected by any of the conditions imposed by this experimental paradigm: neither the cultivation conditions (L-J vs. 7H11), nor the antibiotics (PANTA vs. PANTA/caz), nor the processing solution (buffer vs. CB-18), nor the planting solution (buffer vs. CB-18) had a significant impact on the growth characteristics of ATCC 27294 (FIGS. 2A–2F; ATCC 27294 7H11-Selective, process in CB-18 (383 $\mu$g/ml), plant in buffer; ATCC 27294 7H11-Selective, process in CB-18 (383 $\mu$g/ml), plant in CB-18 17 $\mu$g/ml CB-18 final) (data not provided)).

Alternatively, the 571/573-BAL isolate was dramatically impacted by almost all aspects of the experimental scheme. For example, the behavior of 571/573-BAL was not only dependent on how the isolate was prepared for the experiment (L-J vs. 7H11-selective), but behavior was also dependent on the presence of ceftazidime and the composition of the planting solution (e.g., buffer vs. CB-18). In fact, the most significant parameter appeared to be the existence of CB-18 in the planting solution (compare FIGS. 3A with 3B; 3C with 3D; 3E with 3F; and 3G with 3H). Cells that were processed in buffer and then planted in CB-18 did not come in contact with CB-18 until just prior to planting. In FIG. 3F the isolate planted in the presence of P/caz did not grow. In fact, only 3 of the 12 bottles used to generate the P/caz growth curves in FIGS. 3F and 3H actually grew.

Actual processing seemed to have the least impact on growth characteristics. For example, the experiment was designed so the cells could be processed in CB-18, and then diluted such that the concentration of CB-18 in the culture bottle ranged from approximately 0.68 $\mu$g/ml (@25,000x), 0.34 $\mu$g/ml (@50,000x) to 0.17 $\mu$g/ml (@100,000x). There were no significant differences in growth characteristics between these different dilutions. Comparing FIGS. 3A and 3C, with FIGS. 3E and 3G revealed that cells could be processed in CB-18, but as long as the CB-18 concentration in the culture bottle was below approximately 1 $\mu$g/ml, for example, growth was unimpeded. In other words, there is no "post antibiotic effect" with CB-18 (Heifets, L. B. In: *Drug Susceptibility in the Chemotherapy of Mycobacterial Infections,* Heifets, L. B. ed. CRC Press, Boston, Mass. (1991), pp.13–57).

In summary, the data above, in combination with the CB-18 Pilot Study, show that different isolates behave differently, and presentation of these isolates impacts the sensitivity of these isolates (e.g., prior exposure to antibiotics: cells cultivated on 7H11-selective (FIGS. 3E–3H)). Most significantly, however, the presence of a betaine (e.g., CB-18) in the culture media exacerbated the susceptibility of these isolates to antibiotics also present in the culture media.

Example 4

Addition of Lecithin Overcomes the CB-18 Effect: Examination of Low Inoculum, and Comparison to Quaternamy Ammonium Salts The experiment described in Example 3 (FIGS. 1A and 1B) showed that the use of CB-18 as a primary diagnostic tool requires further refinement. For example, either CB-18 needed to be removed from the planting solution, a less toxic betaine should be used, or the effects of CB-18 needed to be neutralized. This led to the notion that the action of CB-18 might be neutralized by lecithin, in a manner analogous to the quaternary ammonium salts (e.g., Zephiran® or benzalkonium chloride) described by Patterson, R. A. *Amer. Jour. Public Health* 46:1429–1430 (1956) and Wayne, L. G. *Amer Rev. Resp. Dis.* 80:912–913 (1959).

The quaternary ammonium salts are thought to have a rather general deleterious effect on bacterial and mycologic organisms. Hugo, W. B. In: *S.C.I. Monograph no. 19: Surface-Active Agents in Microbiology.* London Soc. Chem. Industry, London (1965) pp.69–82 reviews the literature and summarizes the action of the quaternary salts as causing disruption of the cellular membrane and general denaturation (e.g., inactivation) of intracellular proteins.

Figure 4:
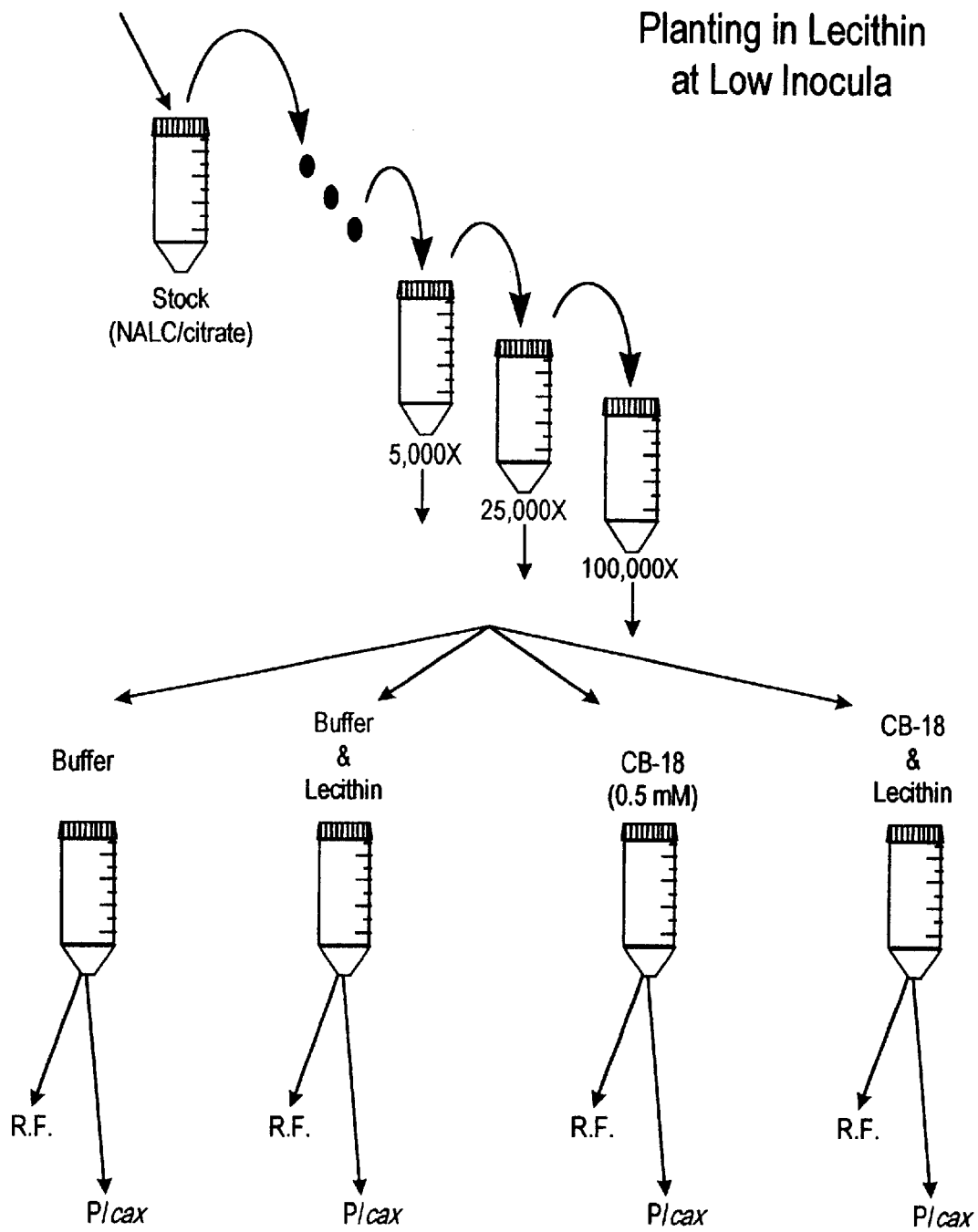
FIG. 4 outlines the experimental design used for planting in lecithin at low inocula. This design was used to examine the ability of lecithin to neutralize the CB-18 effect. The experimental design also examines the CB-18 effect at different inocula.

Patterson, R. A. *Amer. Jour. Public Health* 46:1429–1430 (1956) and Wayne, L. G. *Amer Rev. Resp. Dis.* 80:912–913 (1959) showed that the deleterious effects of the quaternary ammonium salts in mycobacterial culture could be overcome with lecithin (phosphatidylcholine, a phospholipid). FIG. 4 shows the experimental design to test whether lecithin could also overcome the effects of CB-18 sensitization of 571/573-BAL.

In this experiment the 571/573-BAL isolate was cultivated on 7H11-selective media, serially diluted in NALC/ citrate to approximately 1,000x. In an attempt to examine how the inoculum impacted the results of this assay three different stocks were manufactured, one series in buffer and one series in CB-18. Hence, further serial dilutions were made in either buffer or 1.0 mM CB-18 to 2,500x, 12,500x and 50,000x. The planting solutions were manufactured by mixing these three stocks 1:1 with either buffer or a buffered solution of lecithin (Sigma, St. Louis, Mo.; Cat.#: P 5394 (7.5% lecithin was made up as a 100xconcentrate in 100% ethanol (3 grams in 40 mls) and diluted in the Tris buffer of Example 1 immediately prior to use)). The final dilutions of three different planting solutions were approximately 5,000x, 25,000x, and 100,000x. The final concentration of CB-18 and lecithin in the appropriate planting solutions was approximately 0.5 mM. Each series was then planted in quadruplicate (400 $\mu$l each) in BACTEC 12B bottles supplemented with either reconstitution fluid (R.F.) or PANTA that had been supplemented with 8 $\mu$g/ml ceftazidime (P/caz). The final concentration of both lecithin and CB-18 during incubation was approximately 17 $\mu$g/ml. Bottles were checked periodically and the growth indices recorded. Growth indices in a given series were averaged and then plotted versus days in culture.

Aliquots of the three stocks (i.e., 2,500x, 12,500x and 50,000x) were also taken for quantitative culture by plating on 7H10 plates (Becton Dickinson, Cockeysville, Md.). Analysis of the 7H10 plates demonstrated that approximately 165±54 colony forming units (cfu) were placed in each bottle in the 5,000x series, approximately 33±11 cfu were placed in each bottle in the 25,00033 series, and approximately 8±3 cfu were placed in each bottle in the 100,000x series. FIG. 5A presents the 5,000x series planted in either buffer or buffer containing lecithin, and FIG. 5B presents the 5,000x series planted in CB-18 or CB-18 combined with lecithin. FIG. 5C presents the 25,000x series planted in either buffer or buffer containing lecithin, and FIG. 5D presents the 25,000x series planted in CB-18 or CB-18 combined with lecithin. FIG. 5E presents the 100,000x series planted in either buffer or buffer containing lecithin, and FIG. 5F presents the 100,000x series planted in CB-18 or CB-18 combined with lecithin.

Examination of FIGS. 5A, 5C and 5E confirmed that addition of lecithin at this concentration had little if any impact on the sensitivity of the BACTEC 12B assay. In addition, lecithin had the ability to overcome, to some degree, the deleterious effect of the antibiotic formulation (P/caz) in the absence of CB-18. Examination of FIGS. 5B, 5D, and 5F showed that lecithin was able to overcome the detrimental effect of CB-18, both alone and in combination with antibiotics. As the inoculum was reduced from 165±54 cfu to 33±11 cfu to 8±3 cfu the ability of lecithin to overcome the antibiotics, CB-18, or the combination of the two, seemed to diminish. In all cases, however, when lecithin was added as a component of the planting solution all replicate bottles became positive. In contrast, all replicate bottles wherein CB-18 was combined with P/caz were negative (FIGS. 5B, 5D, and 5F). Clearly, lecithin was capable of overcoming the CB-18 effect. Repeated experiments have confirmed these findings.

Quaternary Ammonium Salts

The results presented in FIGS. 5A–5F argued that the mechanism of action of CB-18 was analogous to that of the quaternary ammonium compounds (e.g., the general surface active properties). This conclusion is based on concept that lecithin is neutralizing both the quaternary ammonium detergents and CB-18. Presumably, neutralization is accomplished by the electrostatic interaction of the two lipids. While interaction of the cationic quaternary detergents with the anionic phospholipids seems logical, the betaines have a net neutral charge. The betaine-lecithin interaction would be transient.

Figure 6:
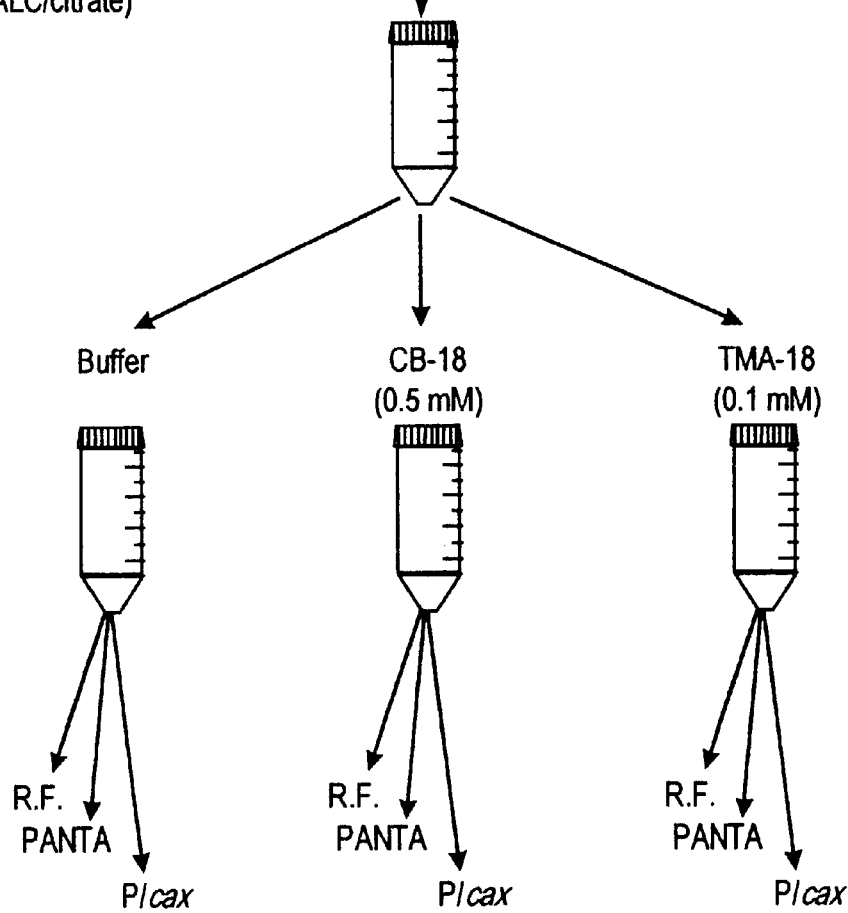
FIG. 6 outlines the experimental design of the CB-18 and TMA-18 titration experiments used to compare the effect of CB-18 with the action of the quaternary ammonium salt trimethyloctadecyl ammonium bromide (TMA-18).

The results of FIGS. 3C and 3G showed that there was no "post antibiotic effect" with cells processed in CB-18 but planted in buffer. If the mechanism of CB-18's action was similar to that of the quaternary salts (i.e., generally deleterious), then some delay would be anticipated. For example, if the CB-18 effect was a consequence of the surface active property of the detergent, then disruption of cellular function would not only have nonspecific long term consequences, but would also be independent of the isolate. In an effort to examine the similarity in the mechanism, CB-18 was assayed in parallel with trimethyloctadecylammonium bromide (TMA-18 (Aldrich, Milwaukee, Wis., Cat.# 35,924-6): made as a 100×stock in 1:1, water:isopropanol similar to that described for CB-18 in Example 1). The experimental design is outlined in FIG. 6.

Figure 7A:
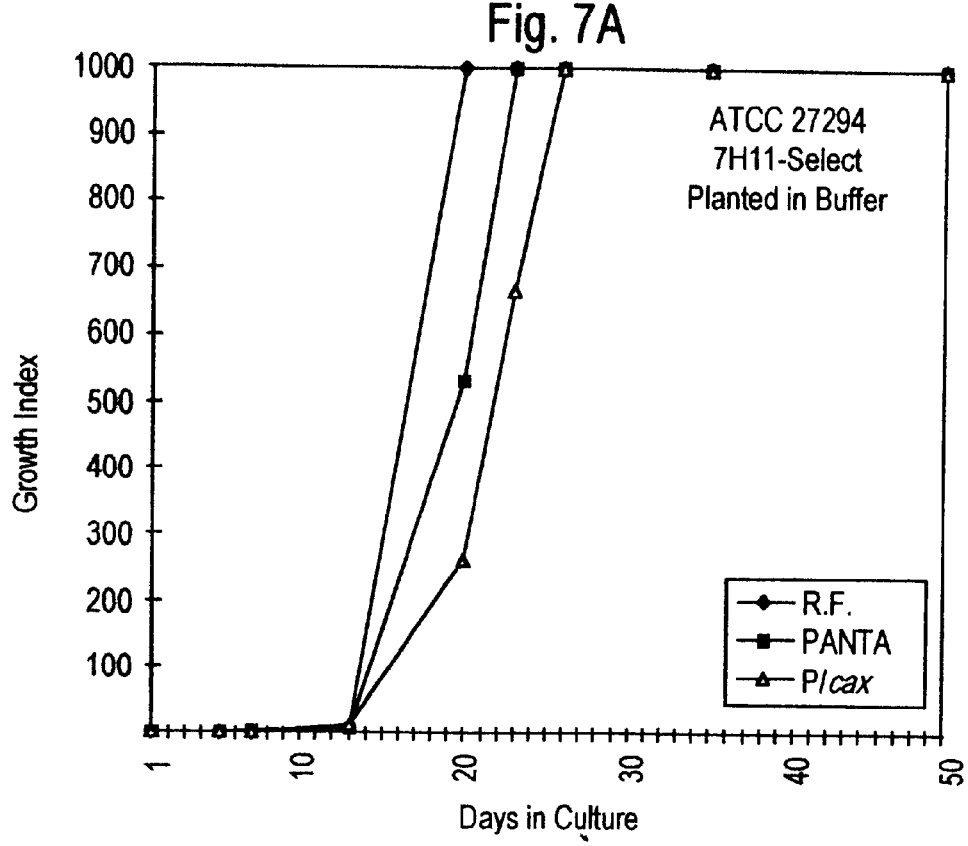
Figure 7B:
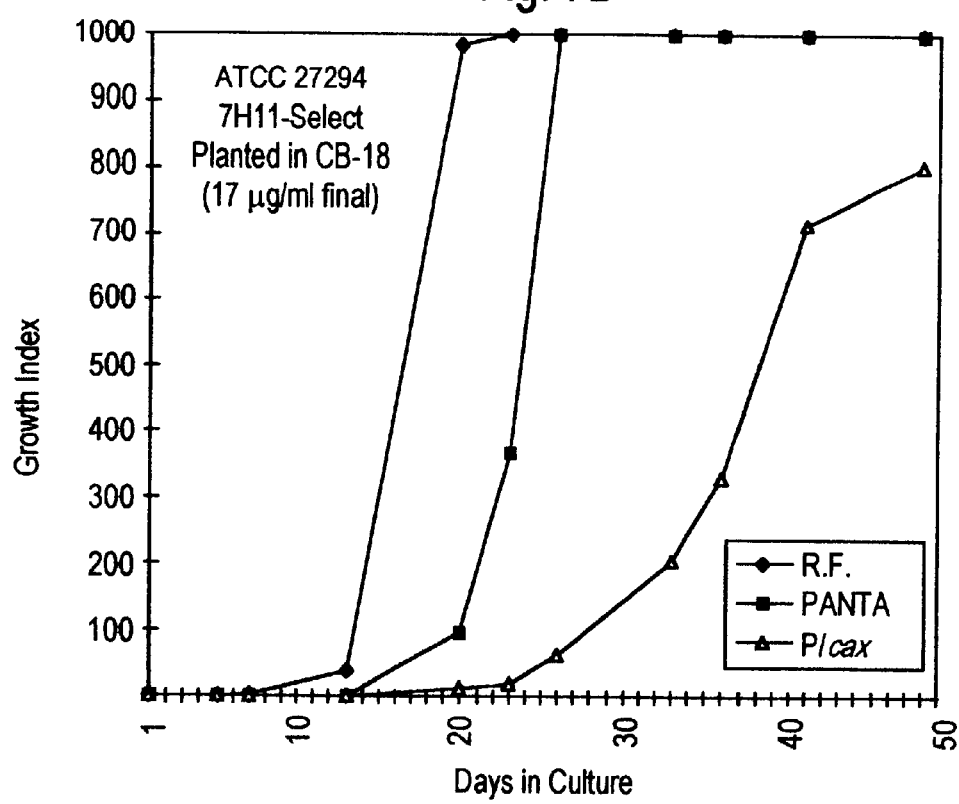

In this experiment both ATCC 27294 and 571/573-BAL were cultivated on 7H11-selective media, and then serially diluted in NALC/citrate to 10,000×. The planting solution (i.e., the final dilution (50,000×)) was manufactured by diluting into either buffer, 0.5 mM CB-18, or 0.1 mM TMA-18 (all concentrations represent the final detergent concentration in the planting solution). Each series was then planted in duplicate (400 μl each) in BACTEC 12B bottles supplemented with either reconstitution fluid (R.F.), PANTA, or PANTA fortified with ceftriaxone (8 μg/ml final: P/cax). The final concentration of CB-18 during incubation was approximately 17 μg/ml. The final concentration of TMA-18 during incubation was approximately 3.4 μg/ml. Bottles were checked periodically and the growth indices recorded. Growth indices in a given series were averaged and then plotted versus days in culture. FIGS. 7A–7C show one experiment wherein ATCC 27294 cells were planted in the different solutions described above, and FIGS. 8A–8C show a parallel experiment wherein 571/573-BAL cells were planted in the same series.

The results using ATCC 27294 show that P/cax had a more deleterious effect than PANTA alone (FIG. 7A), or the PANTA/caz combination (compare FIG. 2A with FIG. 7A). In the presence of 17 μg/ml CB-18 minor delays in PANTA alone became obvious, and the P/cax formulation showed significant delays (FIG. 7B). Culture of ATCC 27294 in the presence of 3.4 μg/ml TMA-18 showed significant delays in all bottles (FIG. 7C).

The behavior of the 571/573-BAL isolate was similar in many respects to the ATCC 27294 isolate, with subtle yet significant differences. For example, in the presence of 17 μg/ml CB-18 delays in all conditions became obvious and the P/cax formulation showed adramnatic delay (FIG. 8B). Culture of 571/573-BAL in the presence of 3.4 μgl/ml TMA-18 was identical to that of ATCC 27294: significant delays were observed in all bottles (FIG. 8C).

The suggestion of the se experiments was that the mechanism whereby CB-18 exerts its effect is different from that of the quatemnary ammonium salts (e.g., TMA-18). For examnple, growth curves of ATCC 27294 and 571/573-BAL, in the absence of any added detergent (compare FIG. 7A with 8A), or in the presence of low concentrations of CB-18 (compare FIG. 10A with 11A), were virtually identical. As the concentration of CB-18 was increased, the isolates could be differentiated (compare FIG. 7B with 8B). As the concentration of CB-18 was further increased, the isolates again appeared to behave similarly: neither could grow in the presence of high concentrations of CB-18 (again comparing FIG. 10A with 11A). This was in marked contrast to the behavior of these two isolates in the presence of TMA-18 (compare FIG. 7C with 8C): the isolates behaved almost identically. If the site of action of CB-18 and TMA-18 were the same, then the isolates would be expected to behave similarly under all conditions. If the site of action of the two detergents were different, then differences in the manner in which the two isolates behave in the respective culture conditions would be expected. It is important to remember that this result was anticipated by the discussions surrounding FIGS. 3C and 3G: CB-18 does not show a post antibiotic effect (Example 3).

Another way to view these data would emphasize that the combination of CB-18 and P/caxc appears to be primarily synergistic. For example, while CB-18 (FIG. 7B) and P/cax (FIG. 7A) have little effect on ATCC 27294 in isolation, the combination of the two is synergistic, not additive. Alternatively, FIGS. 8A and 8B show that P/cax and CB-18 appear to affect 571/573-BAL in isolation, however, the CB-18-P/cax combination, while additive to some degree, is primarily synergistic. In contrast, TMA-18 is bacteriostatic in isolation (FIGS. 7C and 8C) and, when used in combination with antibiotics the result appears to be primarily additive. Additional experiments with CB-18 and TMA-18 on these and other isolates confirm the subtle, but distinct nature of the impact exerted by these two detergents.

Conclusion

A comparison of the results obtained when the ATCC 27294 isolate was cultivated on 7H11 selective slants, processed in CB-18 (383 μg/ml), and planted in CB-18 (17 μg/ml CB-18 final) (data not provided) with 7B (the ATCC 27294 isolate), and a comparison of FIGS. 3H and 8B with 5B, 5D, 5F (the 571/573-BAL isolate), with respect to the susceptibility to antibiotics in the presence of CB-18 raises a significant point. For example, in FIGS. 3H and 8B the 571/573-BAL isolate grew in the presence of CB-18 with antibiotics. In contrast, in FIGS. 5B, 5D, and 5F not a single replicate grew under similar conditions. A priori, these differences might logically be argued to be the result of either variations in the actual CB-18 concentration, the antibiotic concentration, or the inoculum used in a given experiment (see Example 2, and discussions of Table 6 in reference to Eng, R. K., et al., *Antimicrob. Ag. Chemother.* 26:42–47 (1984) and inoculum), or combinations thereof. For example, higher concentrations of CB-18 or antibiotics might have been serendipitously employed in experiments used to generate FIG. 7B, or FIGS. 5B, 5D, and 5F, relative to experiments used to generate the results obtained when the ATCC 27294 isolate was cultivated on 7H11 selective slants, processed in CB-18 (383 μg/ml), and planted in CB-18 (17 μg/ml CB-18 final) (data not provided), or FIGS. 3H and 8B, respectively; or the inoculum in FIGS. 7B, 5B, 5D, and 5F were lower than their respective counterparts. Due to the manner in which CB-18, the antibiotics, and the inoculum were introduced into each bottle (i.e., using a 1 ml syringe), differences in all three variables from bottle to bottle within a given series would be expected and anticipated: the rule rather than the exception. If the culture system employed herein were hypersensitive to any one component, differences such as those described above would become manifest. In the experiment described in FIG. 4 and reported in FIGS. 5A–5F, differences in growth curves were observed between the different inocula. These differences were primarily delays that would be expected with lower input. Variations in the antibiotic concentrations would be minimal relative to variations in CB-18 concentration or inoculum. The culture system appears to be much more elastic with respect to changes in CB-18 concentration.

Example 5

CB18 Titration's: Comparison of MTB, MAC and Rapid Growers

Figure 9:
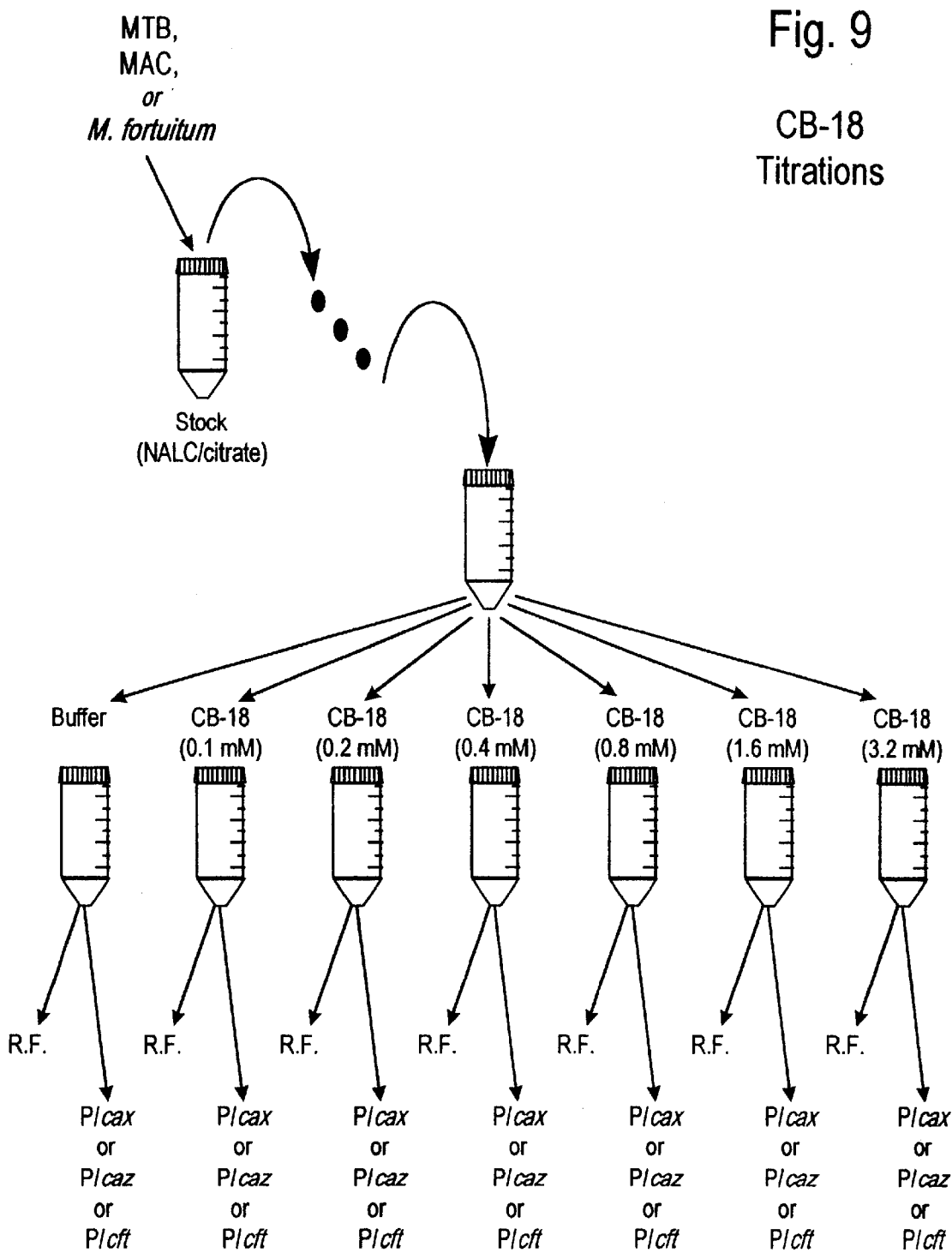
FIG. 9 outlines the experimental design used for CB-18 titrations to examine the CB-18 effect at different concentrations of CB-18 with the different mycobacterial species listed in Table 7.
Figure 12A:
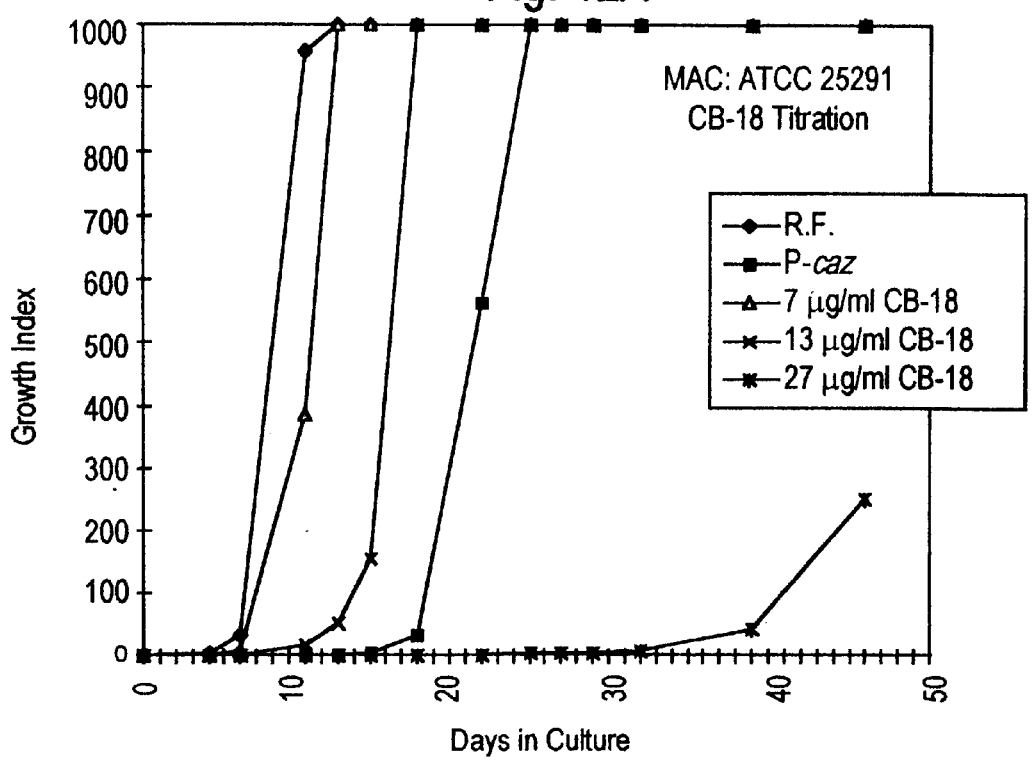
FIGS. 12A and 12B present the growth curves when the *M. avium* isolate ATCC 25291 was tested using the CB-18 titration experiment presented in FIG. 9. Diamonds: R.F.; squares: P-caz; triangles: 7 µg/ml CB-18; "x": 13 µg/ml CB-18; "*" 27 µg/ml CB-18.
Figure 12B:
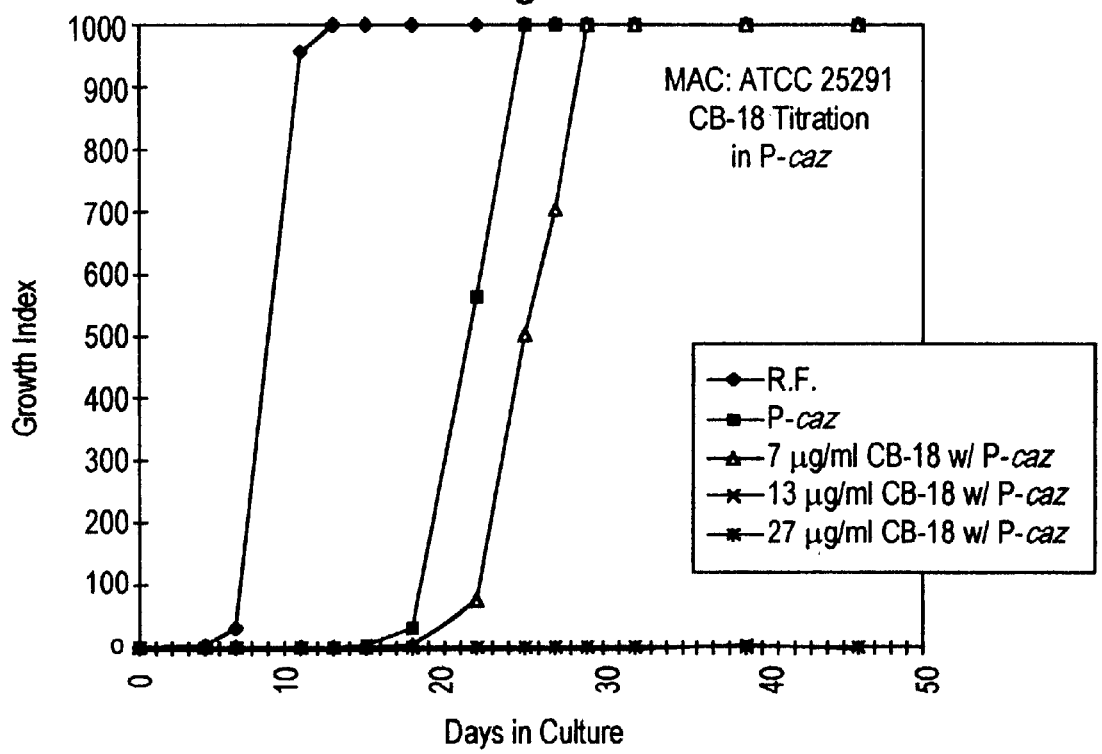

The results of the CB-18 Pilot Study (Example 2) suggested that the CB-18 effect was broadly applicable to a wide range of mycobacterial species (Table 6), and Example 4 suggested that the system was elastic with respect to CB-18 concentration. In an effort to validate this hypothesis the experiment described in FIG. 9 was employed using different mycobacterial species, several of which were derived from the CB-18 Pilot Study.

In this experiment, M. tuberculosis complex, M. avium complex, and M. fortuitum complex isolates were tested. The M. tuberculosis complex isolates tested were ATCC 27294 and 571/573-BAL. The M. avium complex isolates tested were ATCC 25291 and 802-BAL; and the M. fortuitum complex isolates tested were ATCC 6841 and 495-JHH. These characteristics of these isolates and the results of these experiments are summarized in Table 7.

All isolates were cultivated on 7H11-selective media, and then serially diluted in NALC/citrate to 1,000×. The planting solution (i.e., the final dilution (5,000×)) was manufactured by diluting into either buffer, or a series of different CB-18 concentrations. These included 0.1 mM CB-18, 0.2 mM CB-18, 0.4 mM CB-18, 0.8 mM CB-18, 1.6 mM CB-18 or 3.2 mM CB-18. All concentrations represent the final detergent concentration in the planting solution, and not all isolates were tested at all concentrations.

Each series was then planted in triplicate (400 μl each) in BACTEC 12B bottles supplemented with either reconstitution fluid (R.F.), PANTA, or PANTA fortified with either ceftriaxone (8 μg/ml final: P/cax), ceftazidime (8 μg/ml final: P/caz), or cefoxitin (8 μg/ml final: P/cft). *M. tuberculosis* isolates were planted in P-cax, *M. avium* isolates were planted in P-caz, and *M. fortuitum* isolates were planted in P-cft The final concentration of CB-18 during incubation was approximately 3 μg/ml for the 0.1 mM. series, approximately 7 μg/ml for the 0.2 mM. series, approximately 13 μg/ml for the 0.4 mM series, approximately 27 μg/ml for the 0.8 mM series, approximately 54 μg/ml for the 1.6 mM series, and approximately 109 μg/ml for the 3.2 mM series. Bottles were checked periodically and the growth indices recorded. Growth indices in a given series were averaged and then plotted versus days in culture.

FIGS. 10A and 10B show one experiment wherein the *M. tuberculosis* isolate ATCC 27294 was planted in the different solutions described above, and FIGS. 11A and 11B show a parallel experiment wherein the *M. tuberculosis* isolate 571/573-BAL was planted in the same series. FIGS. 12A and 12B show one experiment wherein the *M. avium* isolate ATCC 25291 was planted in the different solutions described above, and FIGS. 13A and 13B show a parallel experiment wherein the *M. avium* isolate 802-BAL was planted in the same series. FIGS. 14A and 14B show one experiment wherein the *M. fortuitum* isolate ATCC 6841 was planted in the different solutions described above, and FIGS. 15A and 15B show a parallel experiment wherein the *M. tuberculosis* isolate 495-JHHL was planted in the same series.

The viability of the *M. tuberculosis* isolate ATCC 27294 dropped off when the concentration of CB-18 approached 54 μg/ml (FIG. 10A), whereas the viability of the *M. tuberculosis* isolate 571/573-BAL dropped off when concentration of CB-18 approached 27 μg/ml (FIG. 11A). When antibiotics were included in the culture media the viability of ATCC 27294 dropped off when concentration of CB-18 approached 27 μg/ml (FIG. 10B), and the viability of 571/573-BAL dropped off when concentration of CB-18 approached 13 μg/ml (FIG. 11B). Clearly the system was very sensitive to changes in CB-18 concentration. Variability from experiment to experiment could easily be explained by this sensitivity.

The viability of the *M. avium* isolate ATCC 25291 dropped off when the concentration of CB-18 approached 27 μg/ml (FIG. 12A), whereas the viability of the *M. avium* complex (MAC) isolate 802-BAL was not affected at the test concentrations (FIG. 13A). When antibiotics were included in the culture media the viability of ATCC 25291 dropped off when the concentration of CB-18 approached 13 μg/ml (FIG. 12B), and the viability of 802-BAL dropped off when the concentration of CB-18 approached 27 μg/ml (FIG. 13B). At 27 μg/ml the curve began to plateau because only one of the three bottles became positive (FIG. 13B). Again, the system was sensitive to changes in CB-18 concentration.

The viability of both *M. fortuitum* isolates (ATCC 6841 and 495-JHH) dropped off when the concentration of CB-18 approached 109 μg/ml (FIGS. 14A and 15A, respectively). When antibiotics were included in the culture media the viability of ATCC 6841 dropped off when the concentration of CB-18 approached 54 μg/ml (FIG. 14B), and the viability of 495-JHH dropped off when the concentration of CB-18 approached 27 μg/ml (FIG. 15B).

The rapid growers as a group seemed more resistant to the action of CB-18 alone, but showed the most synergy when combined with antibiotics. For example, 495-JHH was viable at 109 μg/ml of CB-18, but dropped off between 13 and 27 μg/ml in the presence of P-cft (FIGS. 15A and 15B). Alternatively, 571/573-BAL was viable at 13 μg/ml of CB-18, but viability dropped off between 7 and 13 μg/ml in the presence of P-cax (FIGS. 11A and 11B).

The results with the two rapid growers was an interesting result from the standpoint that Connell, N. D. et al. In: *Tuberculosis. Pathogewlesis, Protection, and Control.* Bloom, B. R. ed. ASM. Press, Washington, D.C. (1994) pp.333–352 attribute resistance to cephalosporins among rapid growers to permeability. If, as suggested in Example 9, CB-18 is in some fashion effecting permeability, this result would have been anticipated.

TABLE 7*

| | | Mycobacterial Species Screened | | | | | | |
|---|---|---|---|---|---|---|---|---|
| | | NALC/NaOH | | | CB-18 | | | |
| | | | Culture | | | Culture | | |
| ID | | Smear | Liquid | Solid | Smear | 12B | 7H11 | Results & Comment |
| ATCC 27294 | MTB | NA | NA | NA | NA | NA | NA | Viability falls off between 27–54 μg/ml with CB-18 alone, and between 13–27 μg/ml in the presence of antibiotics |
| 573-BAL | MTB | 1+ | ⊕28 | ⊖ | 3+ | ⊖ | ⊖/20 | Viability falls off between 13–27 μg/ml with CB-18 alone, and between 7–13 μg/ml in the presence of antibiotics |
| ATCC | *M. av*[1] | NA | NA | NA | NA | NA | NA | Viability falls off between 13–27 μg/ml with CB-18 alone, |

TABLE 7*-continued

| | | Mycobacterial Species Screened | | | | | |
|---|---|---|---|---|---|---|---|
| | | NALC/NaOH | | | CB-18 | | |
| | | | Culture | | | Culture | |
| ID | | Smear | Liquid | Solid | Smear | 12B | 7H11 Results & Comment |
| 25291 802-BAL | MAC | ⊖ | ⊕/10 | ⊕/11 | 1+ | ⊖ | ⊕/20 and between 7–13 μg/ml in the presence of antibiotics Viability is unaffected at levels tested with CB-18 alone, and fall off between 13–27 μg/ml in the presence of antibiotics |
| ATCC 6841 | M. fo$^{q2}$ | NA | NA | NA | NA | NA | NA Viability falls off at levels greater than 109 μg/ml with CB-18 alone, and between 27–54 μg/ml in the presence of antibiotics |
| 495-JHH | M. fo | ⊖ | ⊕/9 | ⊖ | ± | ⊖ | ⊕/14 Viability falls off at levels greater than 109 μg/ml with CB-18 alone, and between 13–27 μg/ml in the presence of antibiotics |

*Smear values were reported as per CDC guidelines. Positive cultures are indicated with a "⊕" symbol followed by a number. This number represents the total time to a positive result in days. Negative cultures are highlighted with a "⊖" symbol. Slants lost to contamlnation are so marked with a "cont." notation, and liquid cultures subjected to redigestion are marked with a " ®" notation. The ATCC 27294 strain was not derived from the CB-18 Pilot Study. As such, the culture results are not applicable ("NA").
[1]M. av is M. avium.
[1]M. fo is M. fortuitum.

There are several points to be made from these data. First, there appears to be a minimum useful concentration of CB-18: low concentrations of CB-18 have no inducing effect, but high concentrations of CB-18 are bactericidal (even in the absence of added antibiotics.) The ability to induce is dependent on the mycobacterial species, as well as the isolate itself.

Example 6

Characterization of MTB Isolates and Antibiotics

The principle conclusion derived from Examples 2, 3 and 5 was that CB-18 is sensitizing some mycobacteria to antibiotics that they would not be susceptible to under normal circumstances. The breadth of this phenomenon, in terms of isolates and antibiotics was thus examined. Several isolates derived from the CB-18 Pilot Study (Example 2) were examined with respect to different β-lactam antibiotics in the presence and absence of CB-18. In a supplementary series of experiments, additional (i.e., non-β-lactam) antibiotics were examined.

Figure 16:
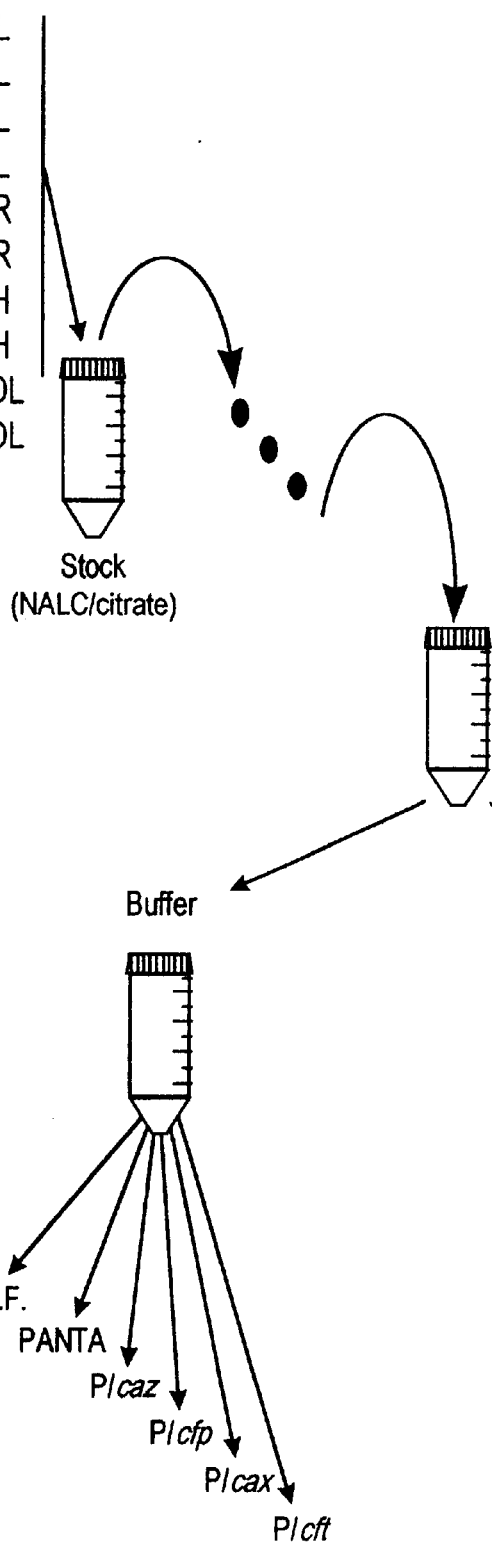
FIG. 16 outlines the MTB isolates vs. antibiotic screen experimental design used to examine the CB-18 effect with different antibiotics on the *M. tuberculosis* isolates listed in Table 8.

FIG. 16 outlines the experimental design used to test different MTB isolates. These isolates (Table 8) were cultivated on 7H11-selective slants and serially diluted in NALC/citrate to approximately 10,000×. The planting solution (i.e., final dilution (approximately 50,000×)) was manufactured by further diluting into either buffer or 0.5 mM CB-18 (final concentration). Each series was then planted in duplicate (400 μl each) in BACTEC 12B bottles supplemented with either reconstitution fluid (R.F.), PANTA, or PANTA which had been fortified with either ceftazidime at 8 μg/ml final ("P/caz"), cefoperazone at 16 μg/nl final ("P/cfp") (Sigma, St. Louis, Mo., Cat#. C-4292: cefoperazone was made up in water at 72 mg/ml and added in a manner similar to that described for ceftazidime (Example 1)), ceftriaxone at 8 μg/ml final ("P/cax") (Sigma, St. Louis, Mo., Cat#. C-5793: ceftriaxone was made up in water at 36 mg/ml and added in a manner similar to that described for ceftazidime (Example 1)), or cefoxitin at 8 μg/ml final ("P/cft") (Sigma, St. Louis, Mo., Cat#. C-4786: cefoxitin was made up in water at 36 mg/ml and added in a manner similar to that described for ceftazidime (Example 1)). Again, the final CB-18 concentration was approximately 17 μg/ml during incubation. Bottles were checked periodically and the growth indices recorded. Growth indices in a given series were averaged and then plotted versus days in culture.

Eleven isolates (including the ATCC 27294 strain) were screened. Table 8 summarizes the 10 clinical isolates employed, and the results of testing. Representative isolates are shown in FIGS. 17–27. There were significant differences in these isolates with respect to behavior in this assay.

TABLE 8*

| | | MTB Isolates Screened | | | | | |
|---|---|---|---|---|---|---|---|
| | | NALC/NaOH | | | CB-18 | | |
| | | | Culture | | | Culture | |
| ID | Smear | Liquid | Solid | Smear | 12B | 7H11 | Results & Comment |
| ATCC 27294 | NA | NA | NA | NA | NA | NA | Minimal, if any, CB-18 induced sensitivity to antibiotics tested, however, cax sensitivity was exacerbated by CB-18. |
| 571-BAL | 1+ | ⊕/28 | ⊕/42 | 1+ | ⊖ | ⊕/cont. | Dramatic CB-18 induced sensitivity to all antibiotics tested (same Pt. as 573-BAL). |
| 573-BAL | 1+ | ⊕/28 | ⊖ | 3+ | ⊖ | ⊕/20 | Dramatic CB-18 induced sensitivity to all antibiotics tested (same Pt. as 571-BAL). |
| 535-BAL | 4+ | ⊕/3 | ⊕/28 | 4+ | ⊕/3 | ⊕/11 | Minimal CB-18 induced effects to antibiotics tested: cax sensitivity was independent of CB-18 |
| 896-BAL | 4+ | ⊕/1 | ⊕/14 | 4+ | ⊕/1 | ⊕/5 | Minimal, if any, CB-18 induced sensitivity to antibiotics tested, however, cax sensitivity was slightly exacerbated by CB-18. Strain is multi drug resistant: INH, RIF & PZA |
| 040-TBR | ⊖ | ⊕/29 | ⊕/42 | 1+ ® | ⊕/14/ | ⊖ | Minor CB-18 induced sensitivity to most antibiotics tested, however, cax sensitivity significantly exacerbated by CB48. |

TABLE 8*-continued

MTB Isolates Screened

| | NALC/NaOH | | | CB-18 | | | |
|---|---|---|---|---|---|---|---|
| | | Culture | | | Culture | | |
| ID | Smear | Liquid | Solid | Smear | 12B | 7H11 | Results & Comment |
| 061-TBR | ⊖ | ⊕/29 | ⊕/35 | 2+ | ⊕/10 | ⊕/19 | Minor, if any, CB-18 induced sensitivity to antibiotics tested, however, car sensitivity was exacerbated by CB-18. Strain is INH resistant |
| 512-JHH | 2+ | ⊕/4 | ⊖ | 4+ | ⊕/3 | ⊕/12 | Minor CB-18 induced sensitivity to most antibiotics tested (same Pt. as 538-JHH) |
| 538-JHH | ⊖ | ⊕/31 | ⊕/33 | 2+ | ⊖ | ⊕/49 | Minor CB-18 induced sensitivity to most antibiotics tested (same Pt. as 512-JHH) |
| 52-96-BOL | 1+ | ⊕/25 | ⊕/27 | 1+ | ⊖ | ⊕/39 | Minor CB-18 induced sensitivity to most antibiotics tested, however, cax sensitivity significantly exacerbated by CB-18. |
| 57-96-BOL | 1+ | ⊕/25 | ⊕/27 | 3+ | ⊖ | ⊕/25 | Moderate sensitivity to most antibiotics, and moderate CB-18 induced sensitivity to most antibiotics as well. Strain is MDR. |

*Smear values were reported as per CDC guidelines. Positive cultures are indicated with a "⊕" symbol followed by a number. This number represents the total time to a positive result in days. Negative cultures are highlighted with a "⊖" symbol. Slants lost to contamination are so marked with a "cont." notation, and liquid cudtures subjected to redigestion are marked with a "®" notation. The ATCC 27294 strain was not derived from the CB-18 Pilot Study. As such, the culture results are not applicable ("NA").

Figure 17A:
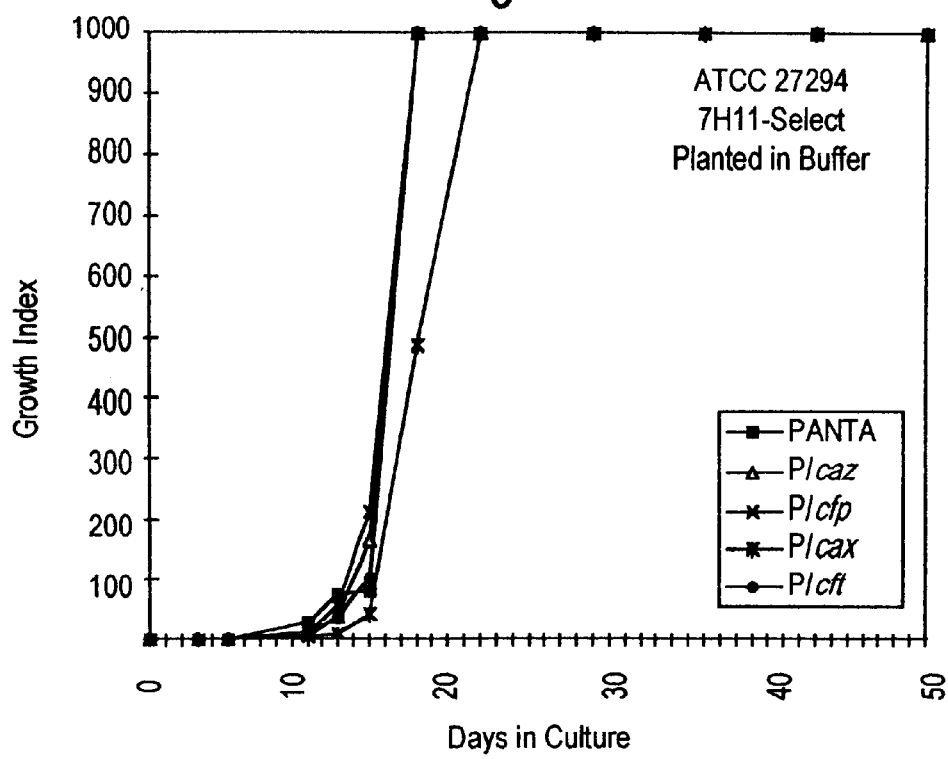
FIGS. 17A and 17B present the growth curves when the *M. tuberculosis* isolate ATCC 27294 was tested using the antibiotic screening experiment presented in FIG. 16. Squares: PANTA; triangles: P-caz;"x": P/cfp; "*" P/cax; circles: P/cft.
Figure 17B:
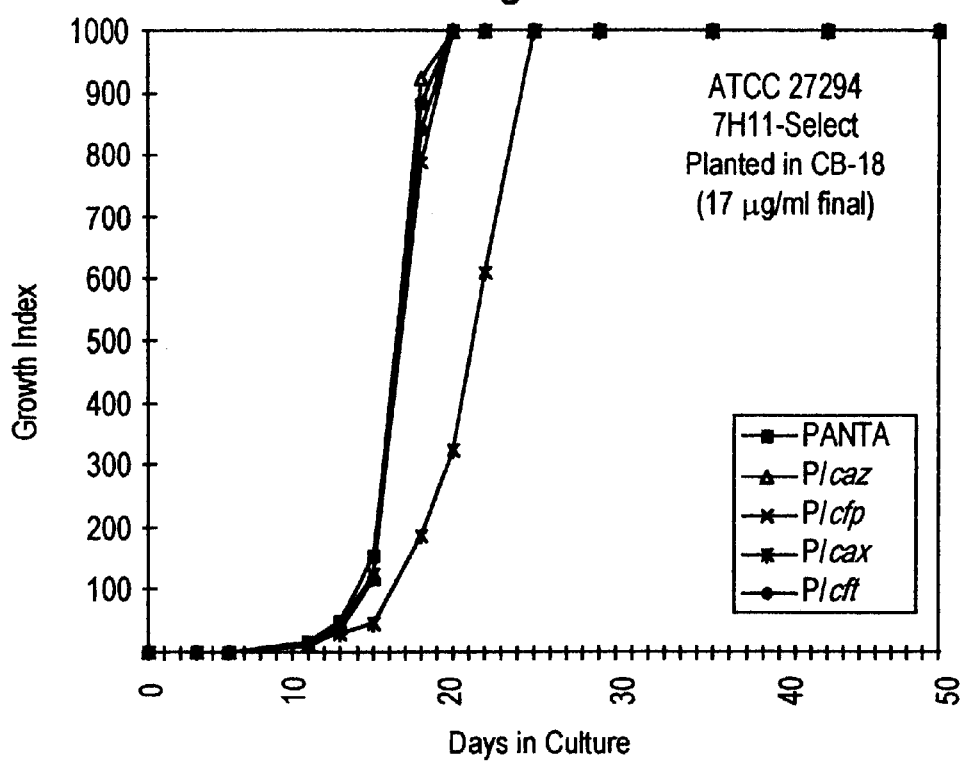
Figure 18A:
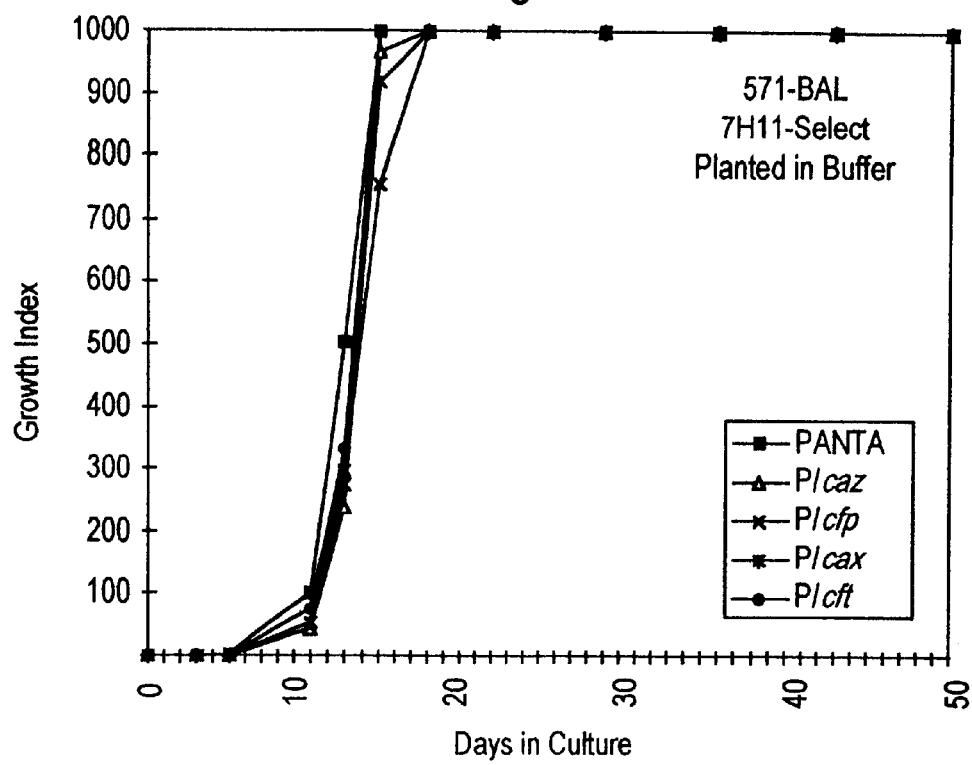
FIGS. 18A and 18B present the growth curves when the *M. tuberculosis* isolate 571-BAL was tested using the antibiotic screening experiment presented in FIG. 16. Squares: PANTA; triangles: P-caz;"x": P/cfp; "*" P/cax; circles: P/cft.
Figure 18B:
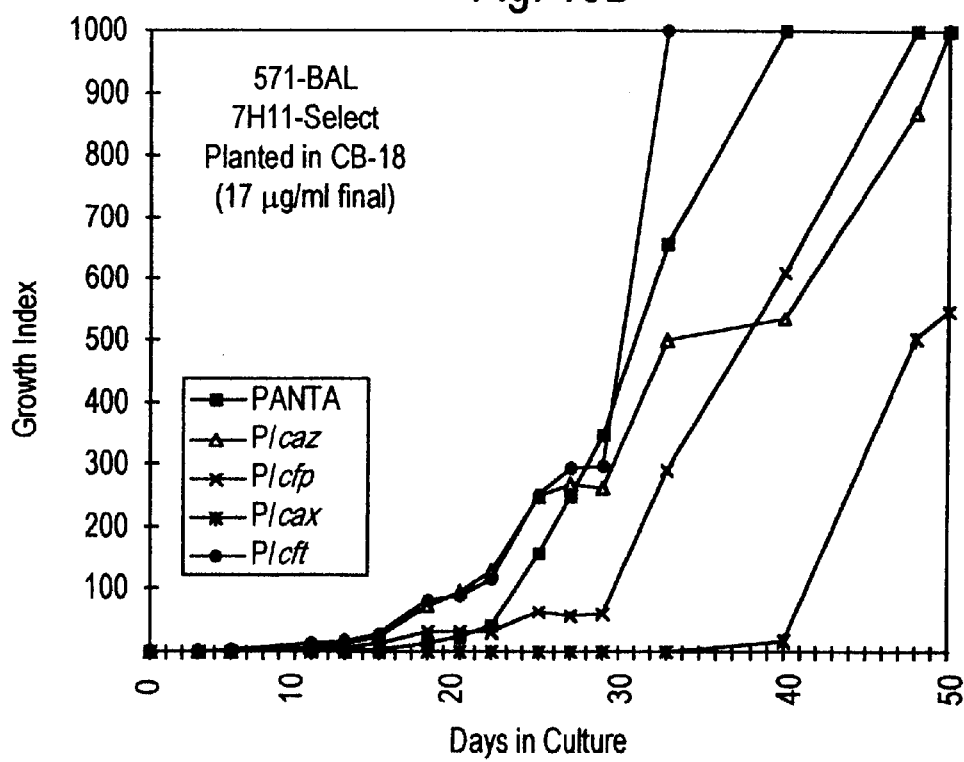
Figure 19A:
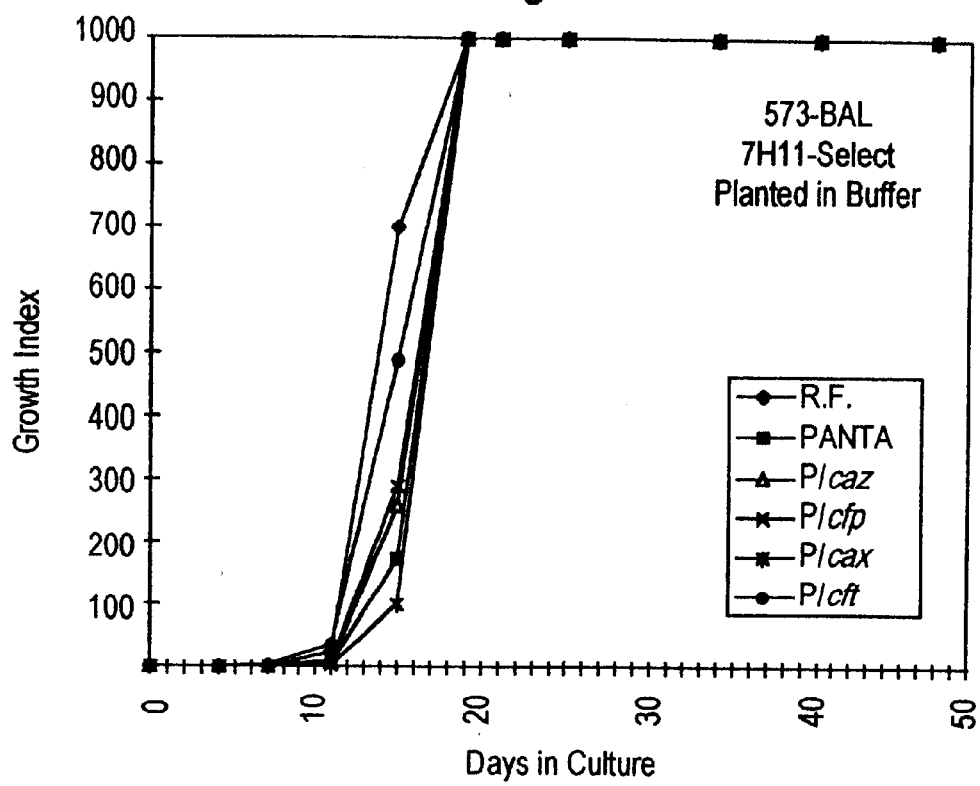
FIGS. 19A and 19B present the growth curves when the *M. tuberculosis* isolate 573-BAL was tested using the antibiotic screening experiment presented in FIG. 16. Diamonds: R.F.; squares: PANTA; triangles: P-caz;"x": P/cft; "*" P/cax; circles: P/cft.
Figure 19B:
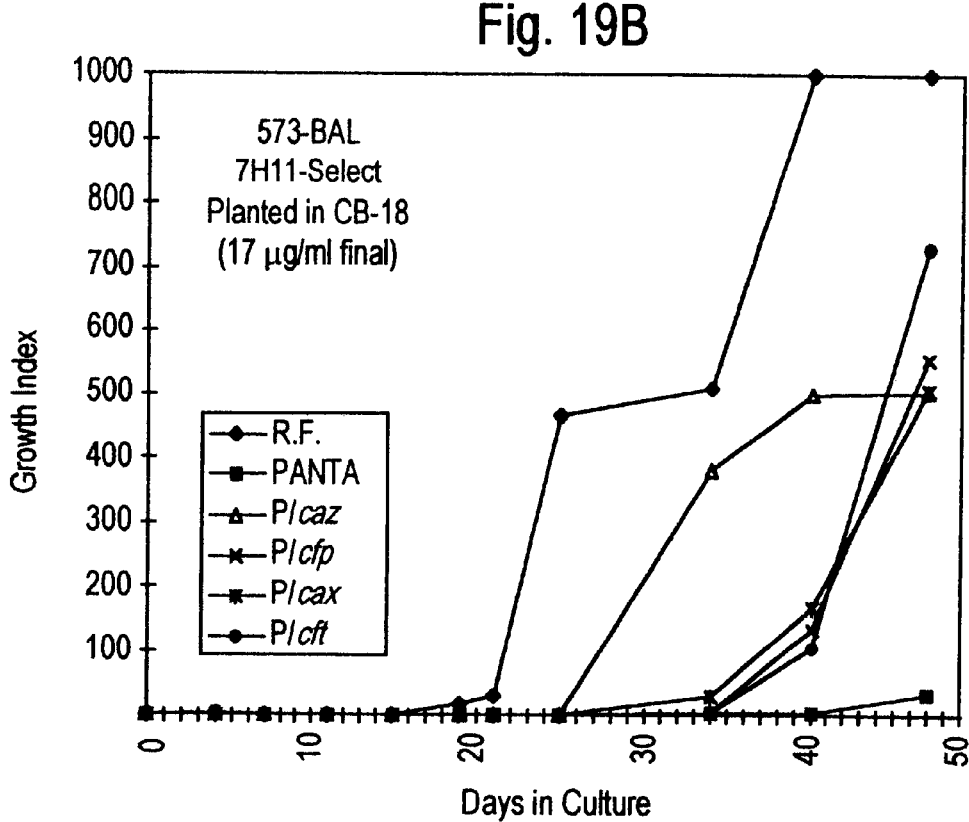

ATCC 27294 showed little or no difference with respect to CB-18 induced susceptibility, with the exception of minor delays when CB-18 was combined with P/cax (FIGS. 17A and 17B). These results were consistent with previous data examining P/caz (compare FIG. 2F with 17B) and Plcax (compare FIG. 7B with 17B). The apparent difference in the induced susceptibility to PANTA observed in FIG. 7B, but not FIG. 17B, is probably a result of variations in CB-18 concentration between experiments as discussed in Example 5.

Both 571-BAL (FIGS. 18A and 18B) and 573-BAL (FIGS. 19A and 19B) again showed remarkable induction of susceptibility for all drugs tested. Only when antibiotics were combined with CB-18 was there a synergistic deleterious effect on 571/573-BAL.

Figure 20A:
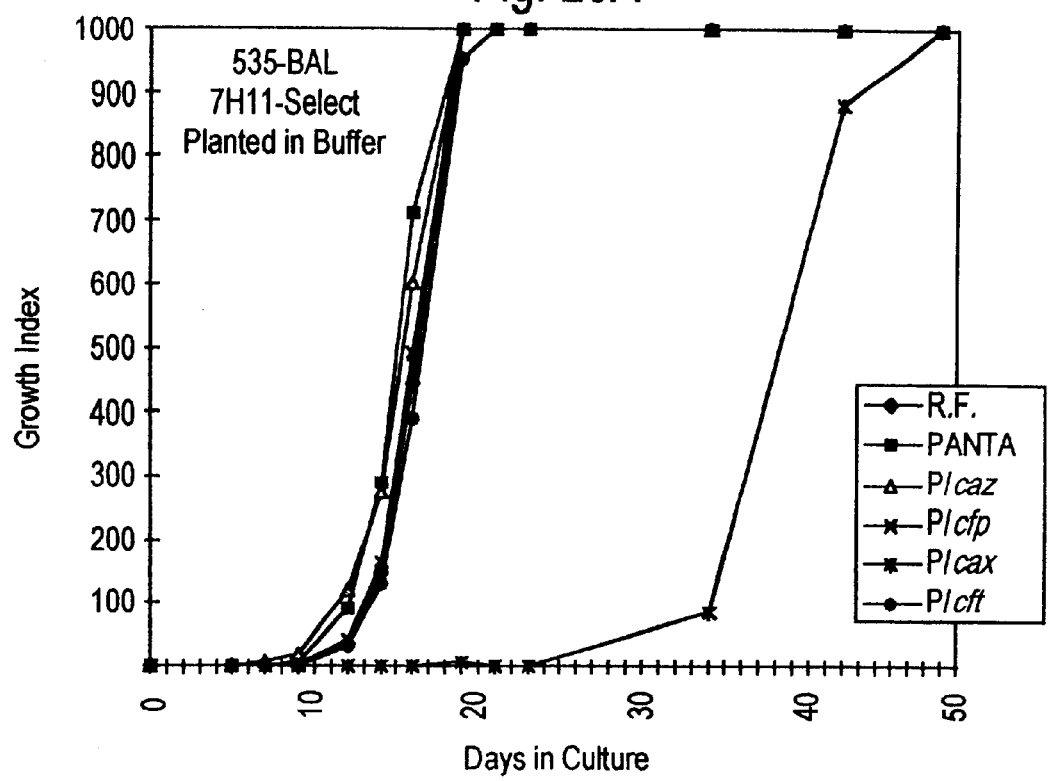
FIGS. 20A and 20B present the growth curves when the *M. tuberculosis* isolate 535-BAL was tested using the antibiotic screening experiment presented in FIG. 16. Diamonds: R.F.; squares: PANTA; triangles: P-caz;"x": P/cfp; "*" P/cax; circles: P/cft.
Figure 20B:
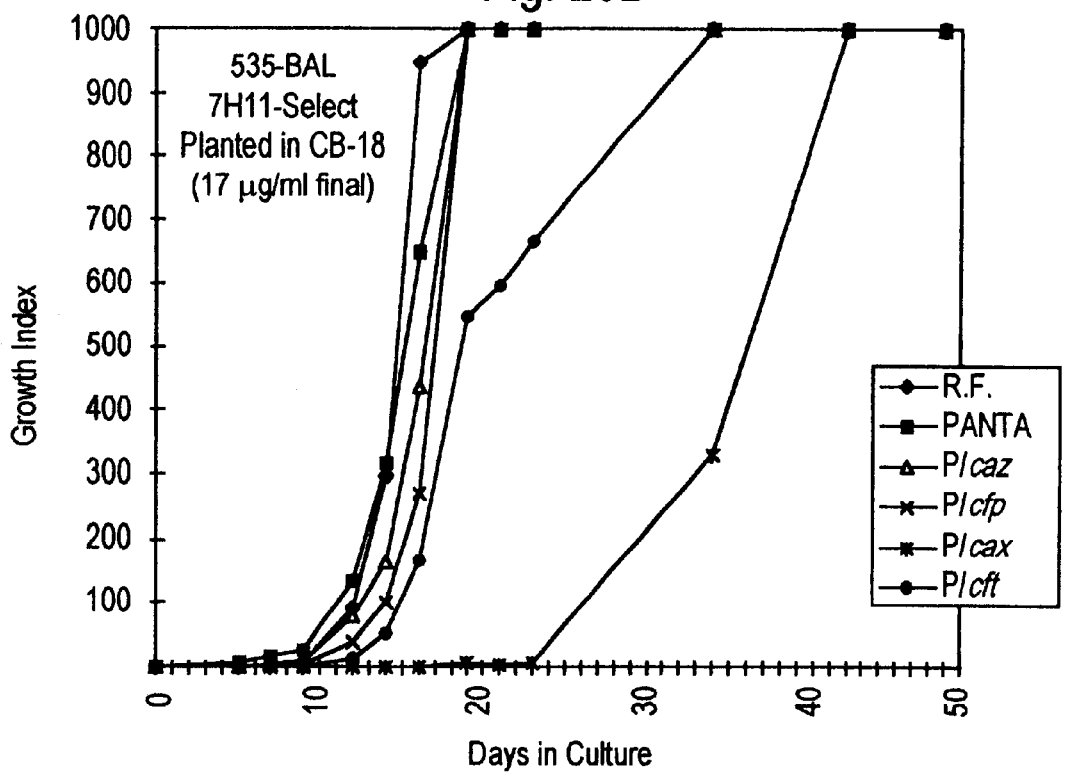
Figure 21A:
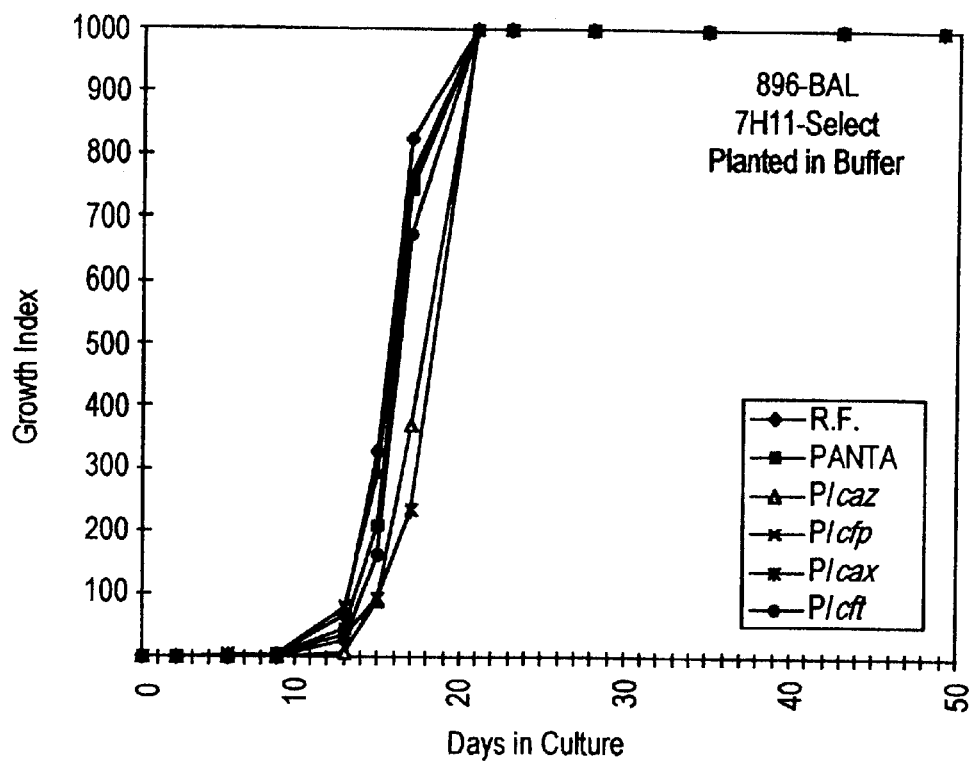
FIGS. 21A and 21B present the growth curves when the *M. tuberculosis* isolate 896-BAL was tested using the antibiotic screening experiment presented in FIG. 16. Diamonds: R.F.; squares: PANTA; triangles: P-caz;"x": P/cfp; "*" P/cax; circles: P/cft.
Figure 21B:
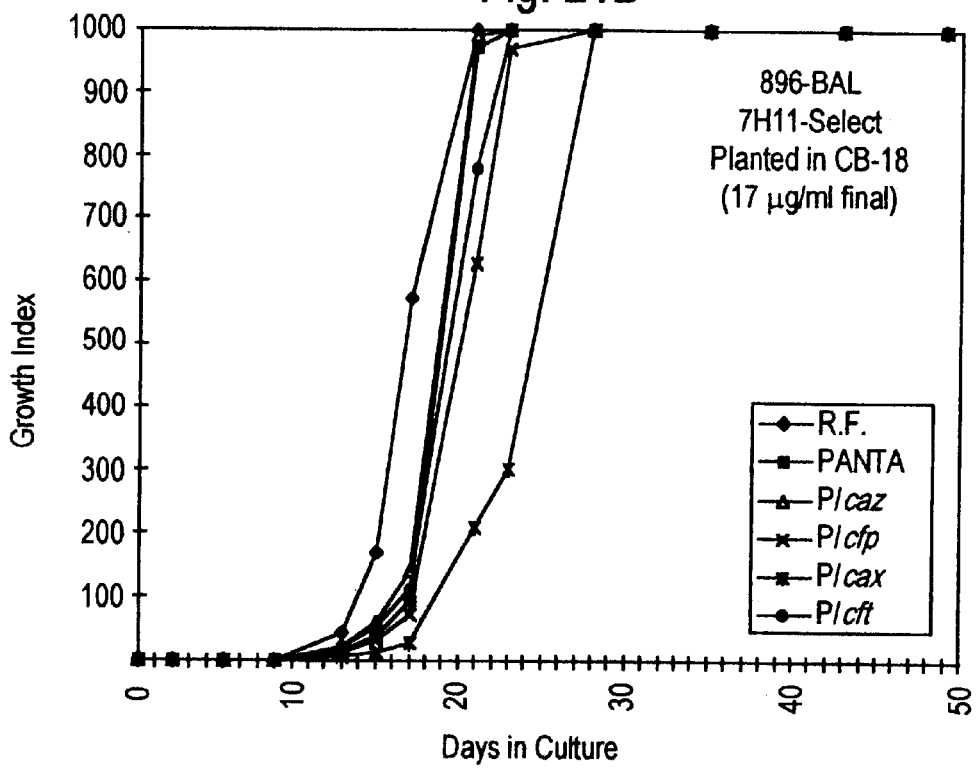
Figure 22A:
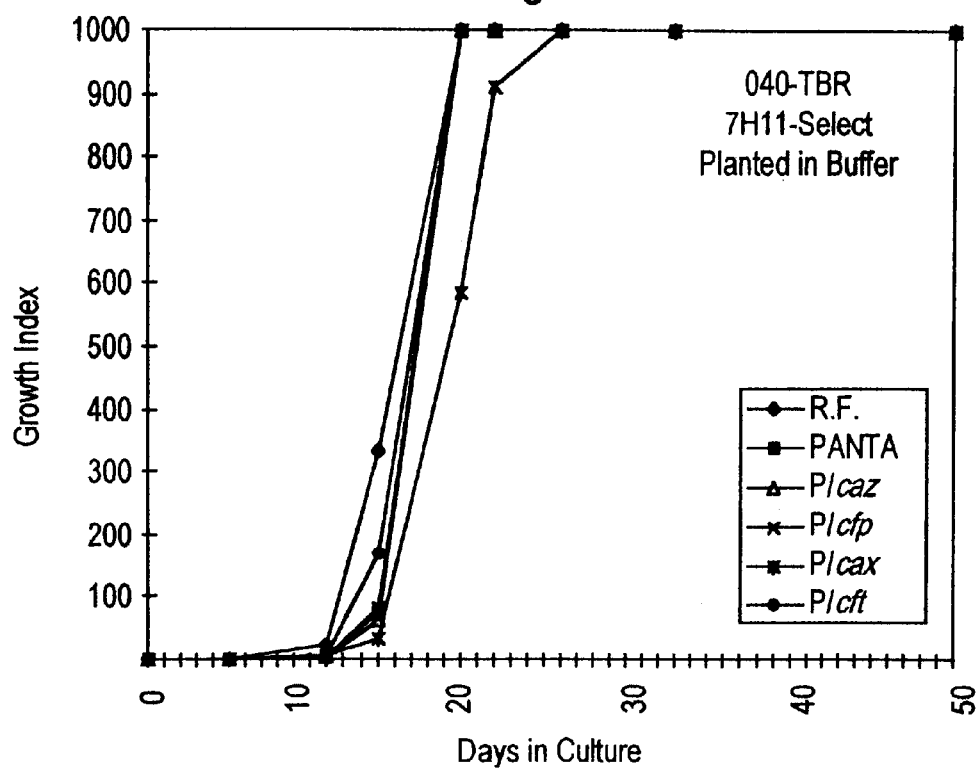
FIGS. 22A and 22B present the growth curves when the *M. tuberculosis* isolate 040-TBR was tested using the antibiotic screening experiment presented in FIG. 16. Diamonds: R.F.; squares: PANTA; triangles: P-caz;"x": P/cfp; "*" P/cax; circles: P/cft.
Figure 22B:
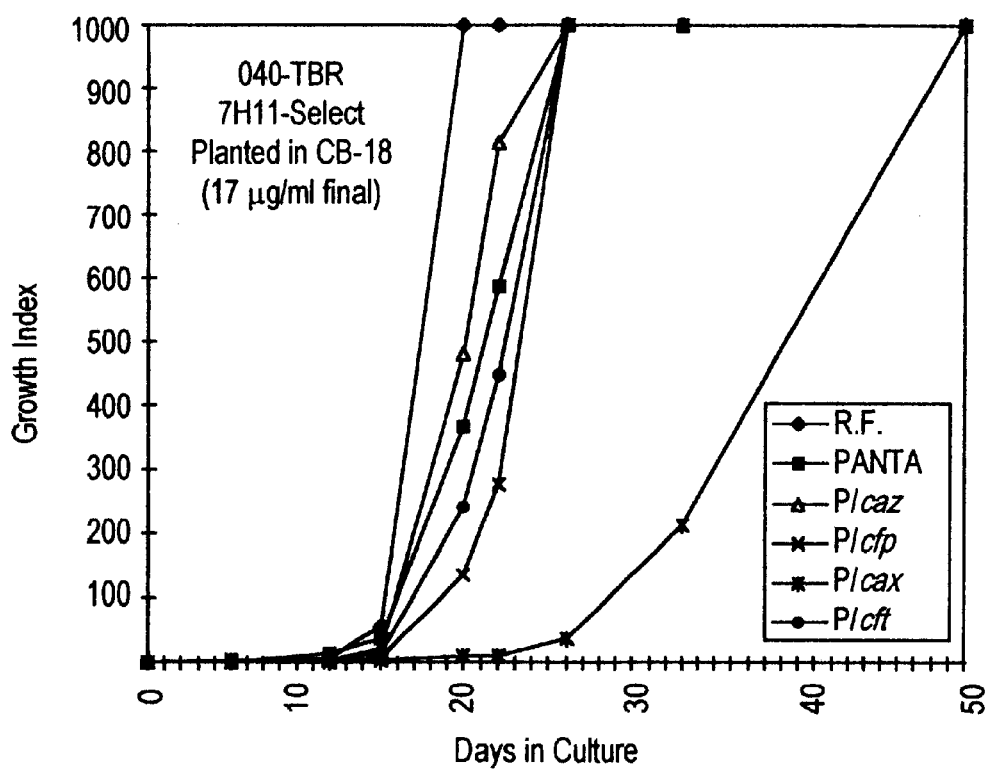
Figure 23A:
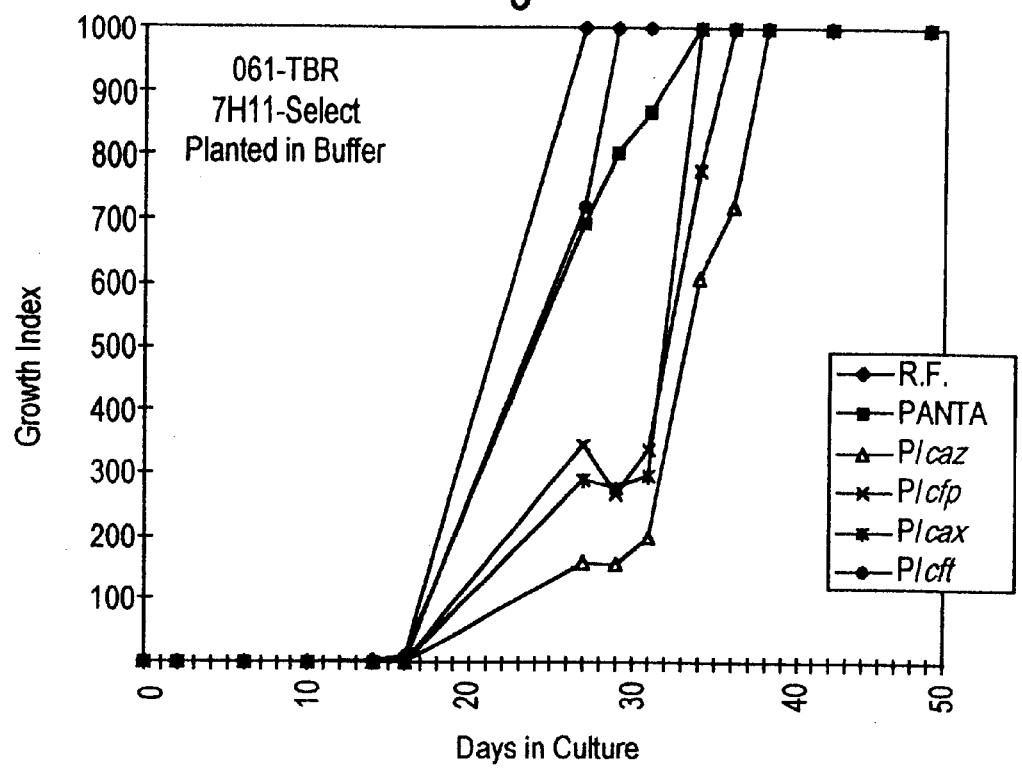
FIGS. 23A and 23B present the growth curves when the *M. tuberculosis* isolate 061-TBR was tested using the antibiotic screening experiment presented in FIG. 16. Diamonds: R.F.; squares: PANTA; triangles: P-caz;"x": P/cfp; "*" P/cax; circles: P/cft.
Figure 23B:
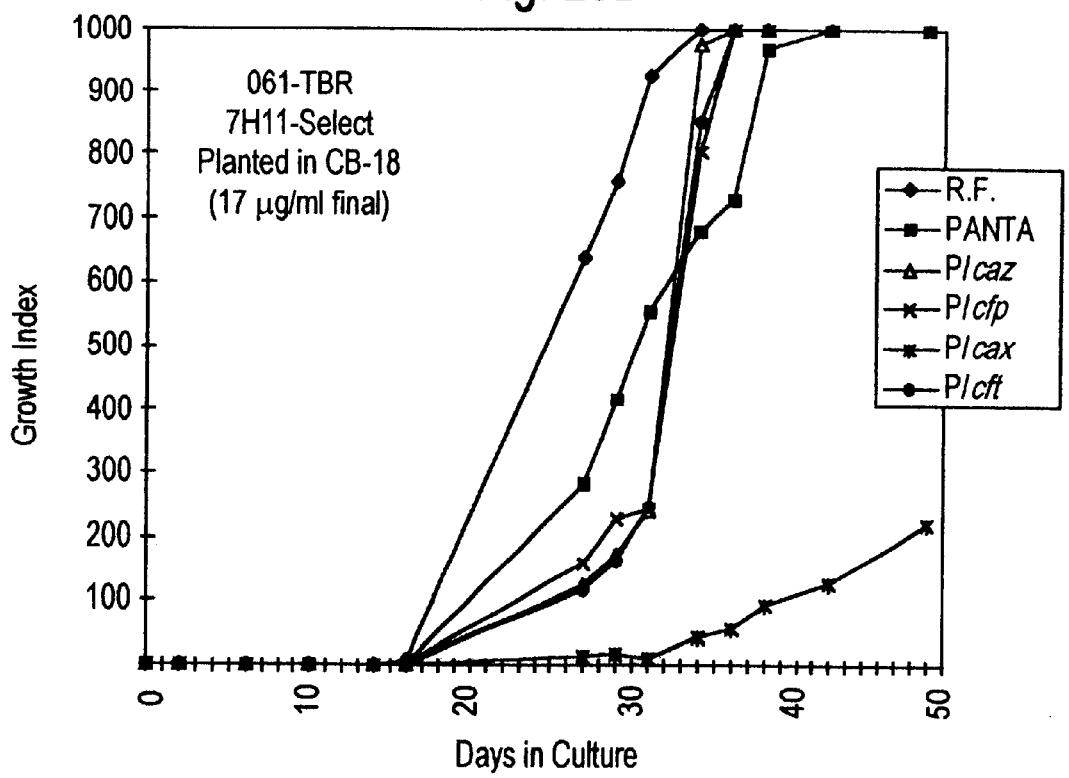
Figure 25A:
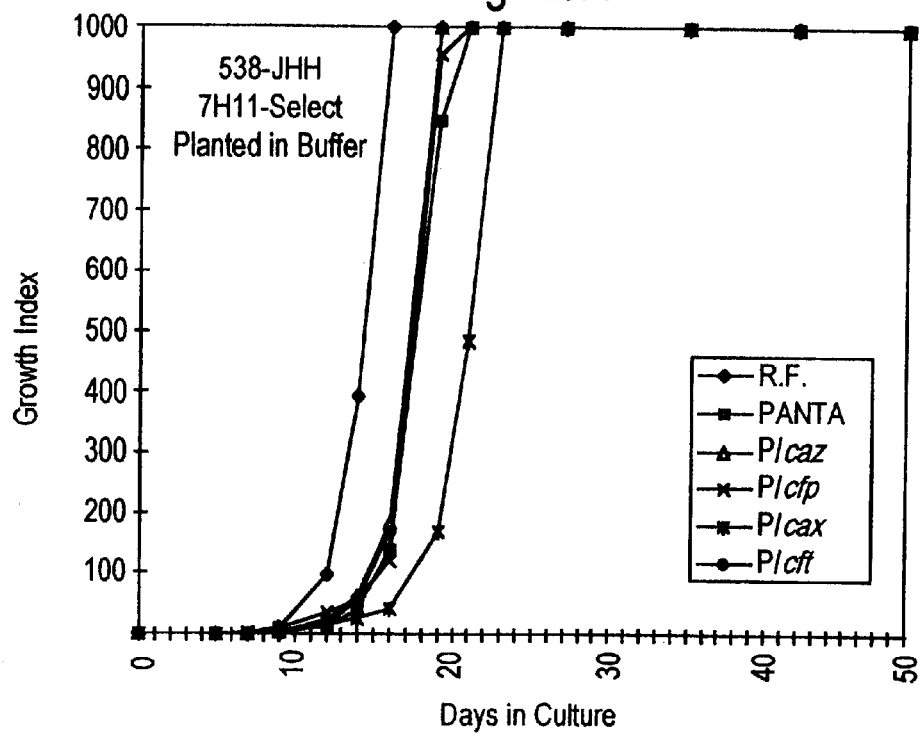
FIGS. 25A and 25B present the growth curves when the *M. tuberculosis* isolate 538-JHH was tested using the antibiotic screening experiment presented in FIG. 16.Diamonds: R.F.; squares: PANTA; triangles: P-caz;"x": P/cfp; "*" P/cax; circles: P/cft.
Figure 25B:
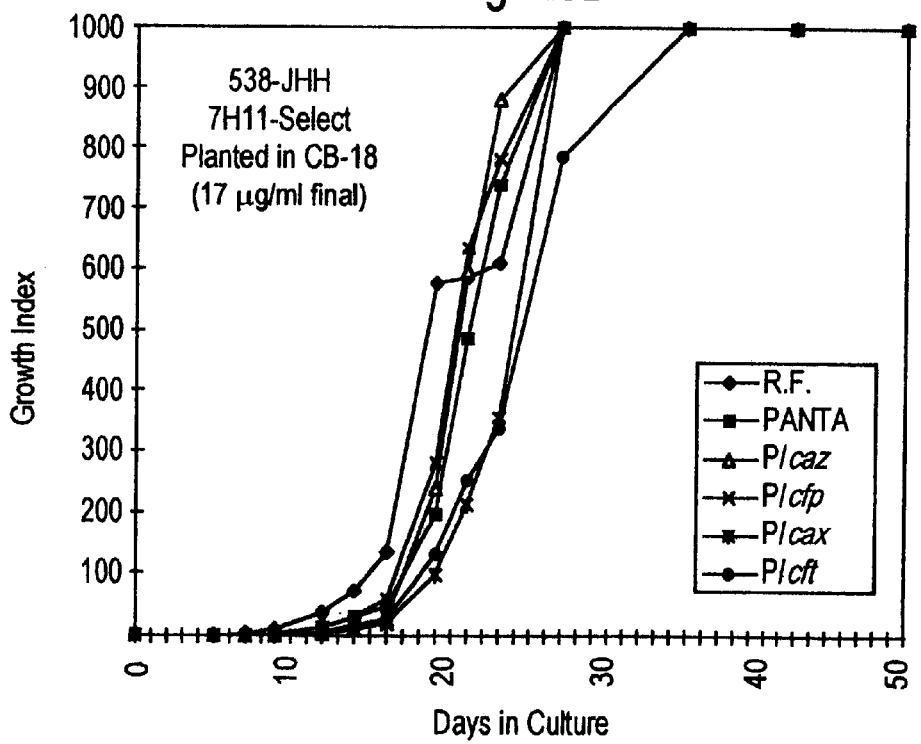

Similar to ATCC 27294, the 535-BAL isolate was unaffected by CB-18 at this concentration, however, this isolate was affected by P-cax (FIGS. 20A and 20B). The behavior of the 896-BAL isolate, which was resistant to INH, RIF and PZA, was also similar to ATCC 27294 (compare FIGS. 17A and 17B with FIGS. 21A and 21B). Isolates 040-TBR and 52-96-BOL were affected by CB-18 to some degree, however, sensitivity to cax was significantly affected by the presence of CB-18 in both isolates (FIGS. 22A and 22B, and FIGS. 26A and 26B, respectively). In contrast, the 061-TBR and 57-96-BOL isolates were affected by all antibiotics in the absence of CB-18, however, the deleterious-effect of the antibiotics was exacerbated in the presence of CB-18 (FIGS. 23A and 23B, and FIGS. 27A and 27B, respectively).

The 512-JHH and 538-JHH pair (FIGS. 24A and 24B, and FIGS. 25A and 25B, respectively) was interesting from the standpoint that in the context of the CB-18 Pilot Study one was naive (512-JHH) when exposed to CB-18, while the other was exposed to CB-18 while on antituberculin therapy (538-JHH). Four specimens were processed from this patient (Table 9). The first specimen was submitted on Feb. 8, 1996, was reported as smear positive within the mandatory 24 hours reporting period, and turned AFB-culture positive within 4 days of submission. The second specimen from this patient (527-JHH) was submitted 10 days following the initial specimen, approximately 1 week following isolation of AFB from the culture bottle, and 5 days after the patient was started on drug therapy. The three specimens submitted following initiation of drug therapy were all CB-18/12B/PANTA/caz-negative, and only two (538-JHH and 5 541-JHH) were positive on the 7H11 slant. While contamination did not play a role in any of these CB-18/12B/PANTA/caz discrepancies, thefactthat 527-JHH had the lowest smear value of the 4 submissions, may explain the discrepant 7H11 result; however, the significant delay of the 538-JHH on solid media (i.e., 49 days) was unusual for a smear positive specimen. While the analogous specimens processed by NALCINaOH were also delayed relative to the initial specimen, CB-18 appeared to significantly impact the viability of this isolate on therapy. This is consistent with the discussion of Example 3, and the series presented in FIG. 3 (compare FIG. 3B with 3F, and FIG. 3D with 3H), and suggests the clinical utility of the betaine-like detergents as therapeutic adjuvants.

TABLE 9*

M. tuberculosis Isolates from One Patient

| | | NALC/NaOH | | | CB-18 | | | |
|---|---|---|---|---|---|---|---|---|
| | | | Culture | | | Culture | | |
| ID | | Smear | Liquid | Solid | Smear | 12B | 7H11 | Comment |
| 512-JHH | MTB | 2+ | ⊕/4 | ⊖ | 4+ | ⊕/3 | ⊕/12 | 2/8/96 - Naive |
| 527-JHH | MTB | ⊖ | ⊕/24 | ⊖ | ± | ⊖ | ⊖ | 2/17/96 - Therapy |
| 538-JHH | MTB | ⊖ | ⊕/31 | ⊕/33 | 2+ | ⊖ | ⊕/49 | 2/27/96 - Therapy |
| 541-JHH | MTB | ⊖ | ⊕/31 | ⊕/33 | 2+ | ⊖ | ⊕/20 | 2/27/96 - Therapy |

TABLE 9*-continued

| | M. tuberculosis Isolates from One Patient | | | | | | |
|---|---|---|---|---|---|---|---|
| | NALC/NaOH | | | CB-18 | | | |
| | | Culture | | | Culture | | |
| ID | Smear | Liquid | Solid | Smear | 12B | 7H11 | Comment |

*Smear values were reported as per CDC guidelines. Positive cultures are indicated with a "⊖" symbol followed by a number. This number represents the total time to a positive result in days. Negative cultures are highlighted with a "⊖" symbol.

The experimental design of FIG. 16 was also used to examine the breadth of the CB-18 effect with respect to other, non-β-lactam antibiotics. In these experiments antibiotics (Sigma, St. Louis, Mo.) were manufactured as stock solutions in water or buffer and then diluted with reconstitution fluid and added to the culture bottles prior to inoculation. Nystatin (100 μg/ml final), polymixin B (300 units final), erthromycin (4 μg/ml final), oleandomycin (2 μg/ml final), penicillin G (8 μg/ml final), nalidixic acid (30 μg/ml final), lincomycin (2 μg/ml final), ceftriaxone (32 μg/ml final), and ceftazidime (16 μg/ml final) (ceftazidime was manufactured in 10% sodium bicarbonate) were tested on ATCC 27294, 571/573-BAL, 061-TBR, 52-96-BOL, and 57-96-BOL. All experiments used R.F. and P-caz as controls, and all bottles wherein CB-18 was added used a final concentration of 17 μg/ml. FIG. 28 presents the results of the 571/573-BAL isolate with erythromycin and ceftriaxone. FIG. 29 presents the results of the 061-TBR isolate with polymyxin B, oleandomycin, lincomycin, naldixic acid, penicillin G, and ceftriaxone. FIG. 30 presents the results of the 57-96-BOL isolate with naldixic acid, penicillin G, ceftazidime and ceftriaxone.

These results indicated that the CB-18 effect was dependent on both the isolate and the antibiotic. Interesting, ceftazidime alone (i.e., in the absence of PANTA), at 16 μg/ml final, was one of the least innocuous compounds.

Conclusion

These results highlight the micro-heterogeneity within the M. tuberculosis complex with respect to antimicrobial susceptibility. While the mechanisms involved in these observations have not been defined, CB-18 appears to permit a high degree of discrimination of *M. tuberculosis* isolates based on susceptibility. This information may be useful to predict more successful therapeutic regimes for treating mycobacterial infections, especially MTB infections. In addition, the fact that CB-18 induces susceptibility suggests that this compound itself may be a useful therapeutic adjuvant.

The "CB-18 effect," that is the ability to induce susceptibility, is dependent on the dynamic interaction of the betaine-like detergent (e.g., CB-18), the antibiotic(s) and the isolate. The most useful concentration of a betaine-like detergent is expected to be dependent on the betaine-like detergent itself and can be determined using the screening methods of the invention.

Example 7

Screening Detergents and Other Betaine-Like Structures

In an effort to extend the findings of Example 6, an assay was developed to screen structural homologues of CB-18. Table 10 lists the detergents used in the assay outlined in FIG. 31. Due to the sensitivity of the 571/573-BAL isolate to susceptibility induction, it was used as the reporter strain in these screening experiments. The 571/573-BAL isolate was cultivated on 7H11-selective slants and was serially diluted in NALC/citrate to approximately 10,000×. The planting solution (i.e., final dilution (approximately 50,000×)) was manufactured by further diluting into either buffer, 0.5 mM CB-18, or the appropriate detergent. All detergents were made up as 100×concentrates in 1:1, isopropanol:water and used as the final diluent in a given experimental series.

The final concentration of each detergent was such that the resulting 12B bottle had a given detergent at a final concentration of approximately 17 μg/ml. Each experimental series was run with buffer and CB-18 planting controls planted in duplicate (400 μl each) in BACTEC 12B bottles supplemented with either reconstitution fluid (R.F.), PANTA, or PANTA supplemented with ceftriaxone at 8 μg/ml final ("P/cax"). Between five and seven detergents were tested at one time. Each diluted detergent containing MTB cells was planted in duplicate (400 μl each) in BACTEC 12B bottles supplemented with either PANTA, or P/cax. Almost all detergents were tested twice. Bottles were checked periodically and the growth indices recorded. Growth indices in a given series were averaged and then plotted versus days in culture.

Table 10 summarizes the detergents examined and the results thereof. The following detergents were obtained from Aldrich Chemical Company (Milwaukee, Wis.): benzyldimethyl-stearyl ammonium chloride (Cat.#: 22,901-6), benzyldimethyl-tetradecyl ammonium chloride (Cat.#: 29,279-6), and octadecyltrimethyl ammonium bromide (Cat.#: 35,924-6). The following detergents were obtained from the Sigma Chemical Company (St. Louis, Mo.): mixed alkyltrimethyl amonium bromide (Cat.#: M-7635), paimitic acid (Cat.#: P-0500), stearic acid (Cat.#: S-4751), CHAPS (Cat.#: C-3023), deoxycholic acid (Cat.#: D-6750), SB-18 ($C_{18}$-sulfopropylbetaine) (Cat.#: O-8004), Brij 97 (oleyl-(poyoxyethylene)$_{10}$) (Cat.#: P-6136), and Brij 56 (cetyl-(poyoxyethylene)$_{10}$) (Cat.#: P-5759). Tween 80 (the polyoxyethylene sorbitanester of oleic acid) (Cat.#: 1334 875) was obtained from Boehringer Mannheim (Indianapolis, Ind.). Custom-made detergents included: $C_{18}$-caboxyethylbetaine, $C_{18}$-sulfobutylbetaine, $C_{16}$-hydroxypropyl-sulfobetaine, $C_{16}$-amidopropyl-sulfatobetaine were synthesized by Ecochem Research, Inc. (Chaska, Minn.), and $C_{16}$-AHTMAP (a reverse betaine) which was obtained as a gift from the KAO Institute of Fundamental Research (Tochigi, Japan). Chembetaine-S (soyamidopropyl-carboxymethylbetaine) was received as a sample from the Chemron Corporation (Paso Robles, Calif.). DeTaine PB (cetyl-carboxymethylbetaine) was obtained as a sample from DeForest, Inc. (Boca Raton, Fla.). Hetaine CLA (canolamidopropyl carboxybetaine) was received as a sample from Heterene, Inc. (Paterson, N.J.).

Rewoteric AM. R-4 (tallow glycinate) was received as a sample from the Sherex Chemical Company (Dublin, Ohio.). Schercotaine IAB (stearylamidopropyl-carboxybetaine) and Schercoatine WOAB (wheat germ amidopropyl-carboxybetaine) were received as samples from Scher Chemicals, Inc. (Clifton, N.J.). Velvetex OLB-50 (oleyl-carboxymethylbetaine) was obtained as a sample from the Henkel Corporation, Emory Group Costa (Hoboken, N.J.). Crosultaine E-30 (erucamidopropyl hydroxypropyl sulfobetaine) was received as a sample from Croda, Inc. (Parsippany, N.J.). Mackamine O2 (oleamine oxide) was obtained as a sample from the McIntyre Group, LTD. (University Park, Ill.).

Figure 32A:
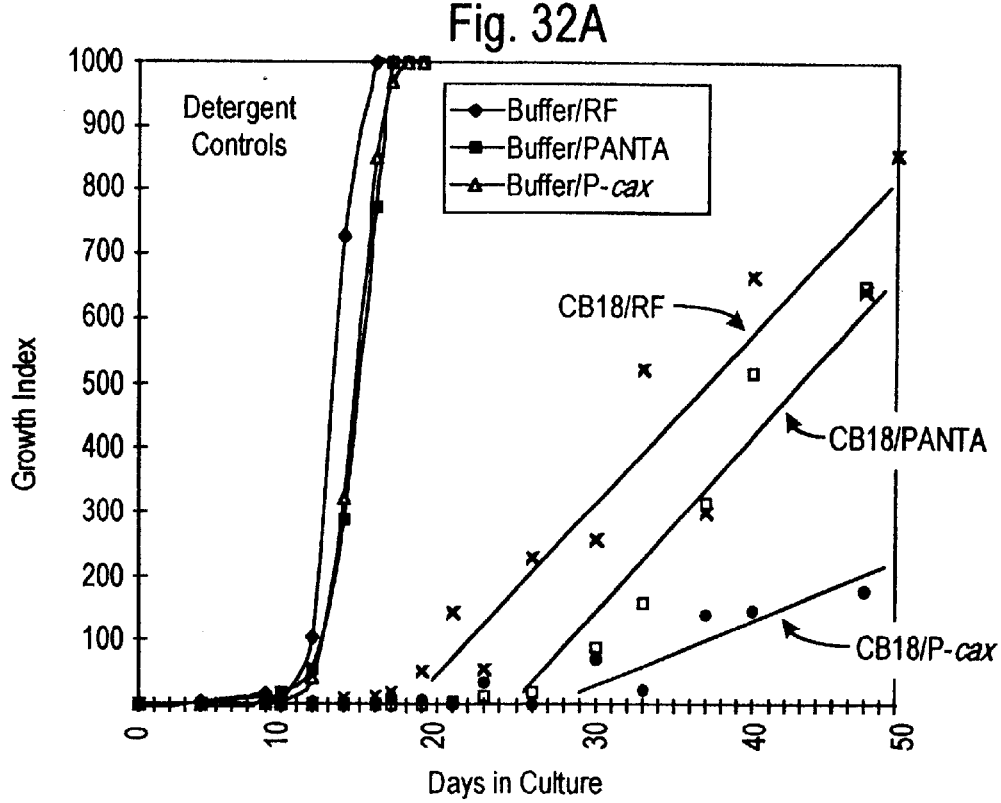
Figure 32B:
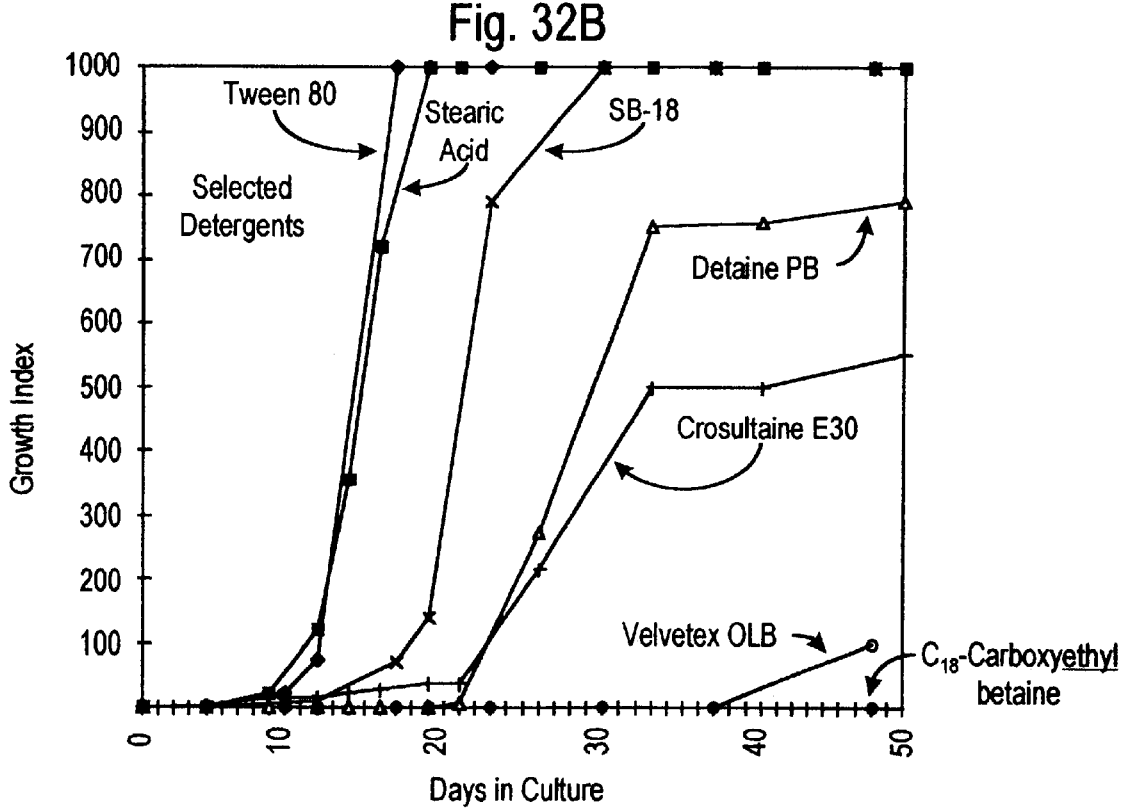

The controls for these experiments are shown in FIG. 32A, and representative detergent results are shown in FIG. 32B. In FIG. 32A duplicate bottles for each control series from all eight experiments were averaged and plotted to show the trend of results relative to the impact of the antibiotics (◆-PANTA, and ▲-P/cax), CB-18 (✗-CB-18 alone), and the combination of the two (□-CB-18/PANTA, and ●-CB-18/P-cax). The growth curves seen in FIG. 32B were based on the average of duplicate bottles from both experiments wherein the cells were planted in the respective detergent in BACTEC 12B bottles that had been supplemented P/cax.

As shown previously, 571/573-BAL is unaffected, or minimally affected, by the presence of either PANTA or P/cax in the absence of CB-18 (compare FIGS. 3A, 3E, 8A and 18A/19A with FIG. 32A). Alternatively, CB-18 alone had an impact on the growth characteristics of the 571/573-BAL strain, and the combination of CB-18 with antibiotics was synergistically deleterious, with P/cax providing the greatest suppression of growth (FIG. 32A: ✗-CB-18 alone, □-CB-18/PANTA, and ●-CB-18/P-cax).

Again, there was remarkable diversity in results with respect to detergent structure. In summary, all quaternary ammonium salts tested were extremely active at this concentration at completely suppressing growth in this assay (Table 10). Alternatively, neither the anionic fatty acids, nor the bile salts tested had any effect on growth.

The only carboxybetaines that showed activity were those that were unmodified. For example, those carboxybetaines wherein an amidopropyl-group was used to link the alkyl chain to the cation ("α" in Table 1) showed no activity in this assay. Alternatively, carboxybetaines without constituents showed a strong ability to suppress growth when combined with antibiotics, especially $C_{18}$-carboxyethylbetaine (the ethyl-bridge homologue of CB-18). Further studies with $C_{18}$-carboxyethylbetaine on ATCC 27294 showed avery narrow range of activity (approximately 7–13 μg/ml). FIGS. 32A and 32B show the variability when simple (i. e., unmodified) carboxybetaines with methylene (Detain PB and Velvetex OLB), ethylene ($C_{18}$-carboxyethylbetaine), and propylene (CB-18) bridges were employed in this assay. This is consistent with the data of Tsubone K. et al., Jour. Pharm. Sci. 80:441–444 (1991) wherein toxicity is correlated with bridge length.

Betaine-like detergents in the "other" category showed mixed results. Neither the reverse betaine nor the sulfato-betaine (e.g., —$SO_4^\ominus$) suppressed growth. Only one of the four sulfobetaines (—$SO_3^\ominus$) (i.e., Crosultaine E30), two of the three nonionic detergents (Brij 56 and Brij 97), and the one amine oxide tested (oleamine oxide) were able to significantly suppress growth (Table 10).

While the apparent bactericidal activity of the amine oxide was anticipated based on the use of these compounds in antimicrobial formulations (Michaels, E. B., U.S. Pat. No. 564,454 and U.S. Pat. No. 641,728), the activity of the Brij compounds and Crosultaine E-30 was gurpfising. Other than Crosultaine E-30, the only other sulfobetaine that appeared to have significant activity in this assay was SB-18. Further studies with SB-18 on 571/573-BAL showed a very broad range of activity (approximately 20–75 μg/ml). The other sulfobetaines all had amidopropyl linkages or hydroxypropyl bridges, indicating that similar to the carboxybetaines, modifications to the backbone structure appear to interfere with the activity described herein. Crosultaine E-30 has both an amidopropyl linkage and a hydroxypropyl bridge. While the Brij compounds do not have modifications to the backbone, these reagents are expected to stimulate growth. Historically, the nonionic detergents have been reported to be contaminated with impurities, and onlywhenpurified stimulate growth (Dubos, R. J. et al., Jour. Exptl. Med. 83:409–423 (1946)). Impurities might explain the results with the Brij detergents and Crosultaine E-30.

These data raised the possibility that the observed effect was caused by an impurity. However, CB-18 as supplied was approximately 98% pure (personal communication, Bob Carlson, Ecochem Research, Inc., Chaska, Minn.). Therefore, any impurity would have to be functional in these assays at approximately 0.34 μg/ml (assuming that 2% of the added CB-18 was an impurity, then 2% of 17 μg/ml would be approximately 0.34 μg/ml). TMA-18 was inhibitory at low concentrations in this assay, ten-times this concentration (FIGS. 7C and 8C). In addition, while many of the commercially available betaines might be contaminated with quaternary salts resulting from synthetic mechanisms (e.g., precursors or synthetic byproducts), the possibility that a quaternary salt would result during the synthesis of CB-18 is highly unlikely (personal communication, Bob Carlson, Ecochem Research, Inc., Chaska, Minn.) Further, the expected side products generated during CB-18 synthesis made according to modified methods of Weers J. et al. Langmuir 7:854–867 (1991), or Kazuo (JP 8125139), would not be expected to be toxic (personal communication, Bob Carlson, Ecochem Research, Inc., Chaska, Minn.)

These experiments (FIG. 32B) also revealed that Tween 80 had no impact on the 571/573-BAL isolate at 17 μg/ml (13 μM). Hui, J. et al., Antimicrob. Agents. Chemo. 11:773–779 (1977) varied Tween 80 concentration and showed that susceptibility induction to rifampin was not achieved until approximately 0.005% (50 μg/ml (38 μM)). More importantly, higher concentrations of Tween 80 (up to 0.05% (500 μg/ml (380 μM)) served only to stimulate growth. Stinson, M. W. et al., Am. Rev. Resp. Dis. 104:717–727 (1971) reported that maximal stimulation was achieved at 1% (10 mg/ml (7.69 mM)), and amounts as high as 10% (100 mg/ml (76.9 mM)) provided no additional advantage, but were not inhibitory. Addition of Tween 80 to the culture media was perhaps the most significant diagnostic advance in mycobacteriology this century because it causes "rapid" growth (Dubos, R. et al., Jour. Expt. Med. 83:409–423 (1946). Yamori, S. et al., Microbiol. Immunol 35:921–926 (1991)) reported changes in susceptibility patterns for some drugs as Tween 80 was titrated from 0% to 0.5% to 2%. The presence of ODAC (a culture supplement containing BSA, NaCl, dextrose, catalase, and oleic acid) caused significant changes in susceptibility in combination with Tween 80. CB-18, on the other hand, caused no alteration in growth at approximately 3–7 μg/ml, but complete suppression of growth at 13–27 μg/ml (FIGS. 10A and 11A).

The conclusion to be drawn from these experiments is that a wide variety of betaine-like detergents is useful in the methods of the invention, and susceptibility induction varies according to betaine-like structure. Each betaine-like detergent must be optimized for use in conjunction with the methods of the invention. An exceptionally high degree of discrimination in differentiating isolates is possible by combining different antibiotics with different betaine-like detergents.

TABLE 10

| DETERGENT | RESULT |
| --- | --- |
| CATIONIC DETERGENTS | |
| Benzyldimethyl-stearyl ammonium chloride | Complete suppression of growth |
| Benzyldimethyl-tetradecyl ammonium chloride | Complete suppression of growth |
| Mixed alkyltrimethyl amonium bromide | Complete suppression of growth |
| Octadecyltrimethyl ammonium bromide | Complete suppression of growth |
| ANIONIC DETERGENTS | |
| Palmitic acid | No effect |
| Stearic acid | No effect |
| BILE SALTS | |
| CHAPS | No effect |
| Deoxycholic acid | No effect |
| CARBOXYBETAINES | |
| $C_{18}$-carboxyethylbetaine | Complete suppression of growth |
| Chembetaine-S (soyamidopropyl-carboxymethylbetaine) | No effect |
| DeTaine PB (cetyl-carboxymethylbetaine) | Strong suppression of growth |
| Hetaine CLA (canolamidopropyl carboxybetaine) | No effect |
| Rewoteric AM R-4 (tallow glycinate) | No effect |
| Schercotaine IAB (stearylamidopropyl-carboxybetaine) | No effect |
| Schercoatine WOAB (wheat germ amidopropyl-carboxybetaine) | No effect |
| Velvetex OLB-50 (oleyl-carboxymethylbetaine) | Very strong suppression of growth |
| OTHER BETAINES | |
| $C_{16}$-AHTMAP (Reverse betaine) | No effect |
| $C_{18}$-sulfobutylbetaine | Slight delay in growth |
| $C_{16}$-hydroxypropyl-sulfobetaine | Slight delay in growth |
| $C_{16}$-amidopropyl-sulfatobetaine | No effect |
| Crosultaine E-30 (erucamidopropyl hydroxypropyl sulfobetaine) | Strong suppression of growth |
| SB-18 ($C_{18}$-sulfopropylbetaine) | Modest suppression |
| Mackamine O2 (oleamine oxide) | Complete suppression of growth |
| NONIONIC DETERGENTS | |
| Tween 80 (polyoxyethylene sorbitanester of oleic acid) | No effect |
| Brij 97 (oleyl-(poyoxyethylene)$_{10}$) | Very strong suppression of growth |
| Brij 56 (cetyl-(poyoxyethylene)$_{10}$) | Very strong suppression of growth |

The CB-18 Effect and EDTA

Example 4 showed that the action of CB-18 was different from that of TMA-18, and FIG. 32B showed that the effect of CB-18 was different from that of Tween 80. The results of testing different betaine-like detergents suggested that unmodified structures might be most useful (Table 10). In an effort to further differentiate the CB-18 effect from other affecters such as metal chelators (e.g., EDTA), the experiments described in FIG. 33 were performed.

EDTA alters permeability in bacteria by extracting and chelating divalent metal cations that stabilize the cell wall structure. Rastogi, N. et al., *Antimicrob. Agents Chemo.* 34:759–764 (1990) reported that attempts to grow mycobacteria in 1 mM. EDTA (372.5 µg/ml) had a significant impact on viability. Given that the betaines are salted-in based on their ability to coordinate water (Tsujii, K. et al., *Jour. Phys. Chem.* 82:1610–1614 (1978)), the possibility was raised that the CB-18 effect was a result of the chelating activity of this compound.

Figure 33:
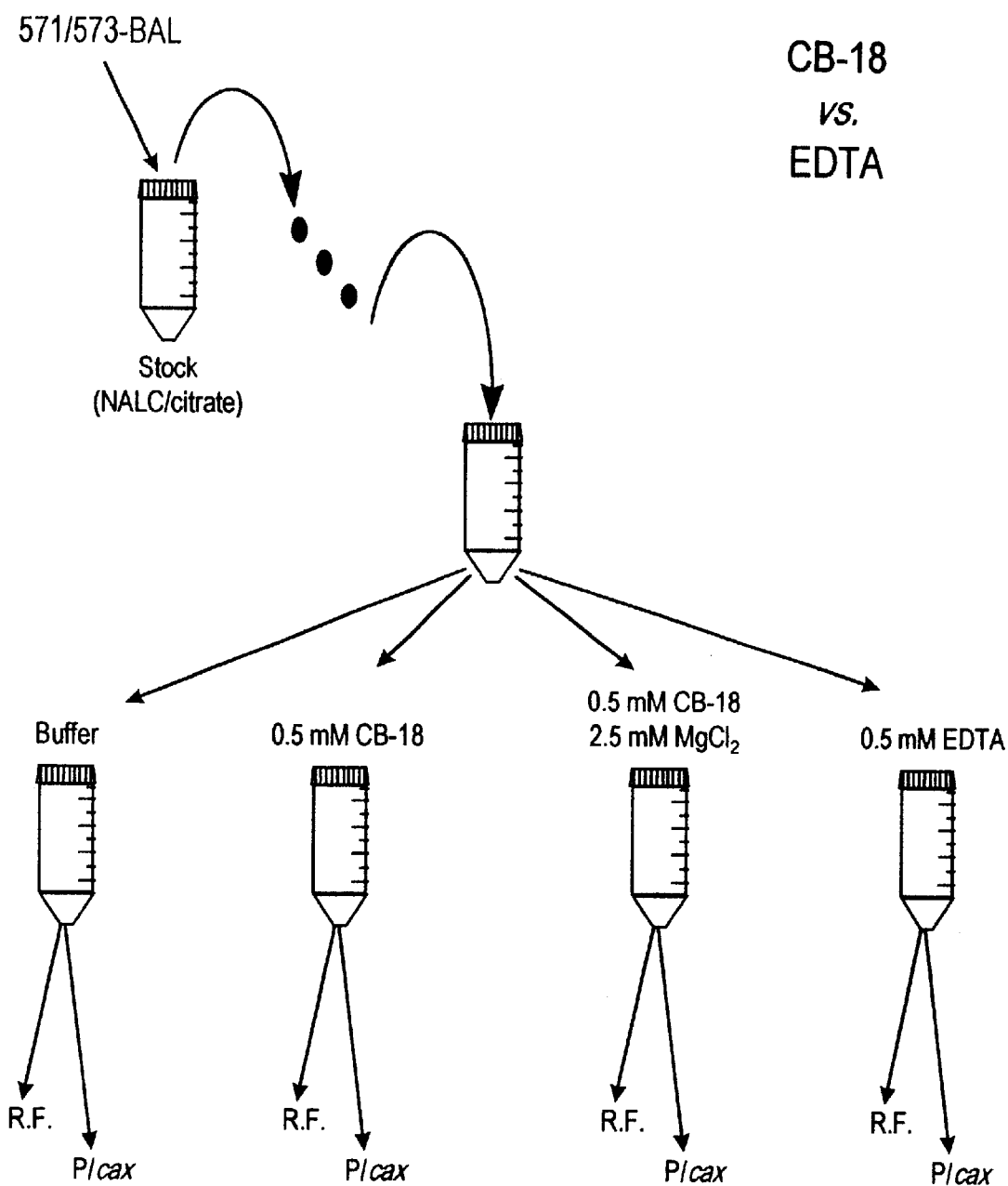
Figure 35A:
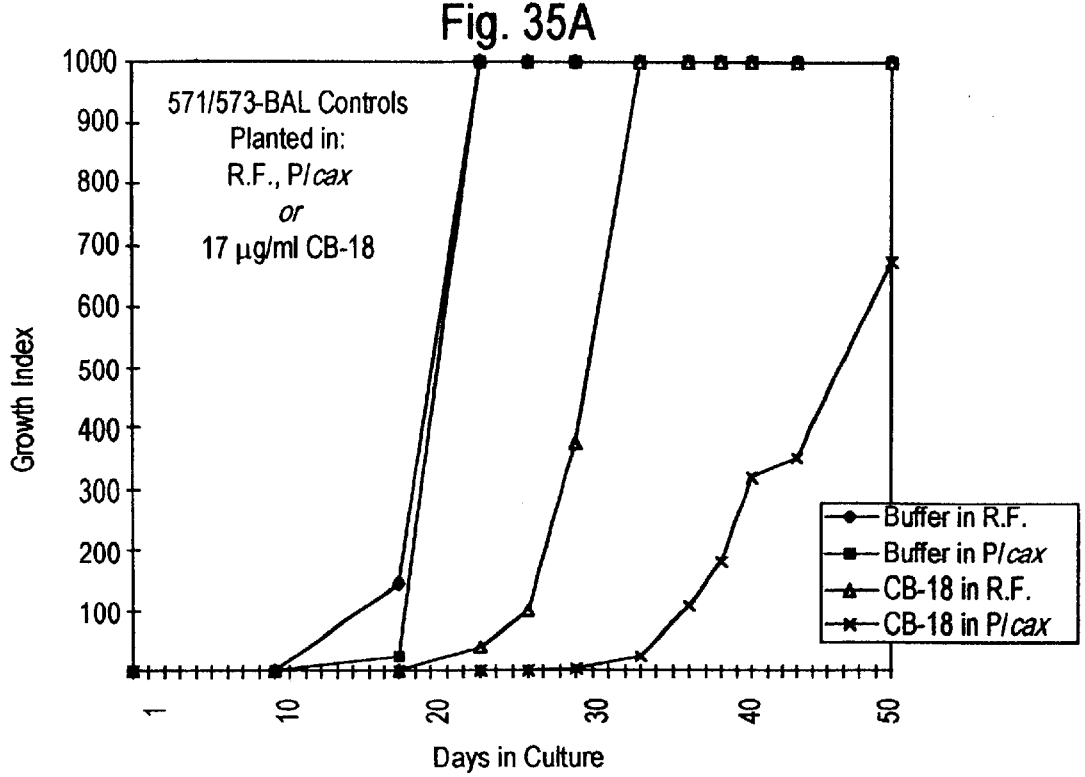

In an effort to differentiate the CB-18 effect from the action of metal chelators such as EDTA, an assay was developed to dissect the action of CB-18 (FIG. 33). The ATCC 27294 and 571/573-BAL isolates were cultivated on 7H11-selective slants and then each was serially diluted in NALC/citrate to approximately 10,000×. The planting solution (i.e., final dilution (approximately 50,000×)) was manufactured by further diluting into either buffer, 0.5 mM CB-18, 0.5 mnM CB-18 containing 2.5 MM. $MgCl_2$, or 0.5 mM. EDTA (Life Technologies, Gaithersburg, Md.). The final concentration of CB-18 and EDTA was approximately 17 µg/ml during incubation, and the concentration of $MgCl_2$ was approximately 85 µg/ml during incubation. Each experimental series was planted in triplicate (400 µl each) in BACTEC 12B bottles supplemented with either reconstitution fluid (R.F.) or PANTA supplemented with ceftriaxone at 8 µg/ml final (P/cax). Bottles were checked periodically and the growth indies recorded. Growth indices in a given series were averaged and then plotted versus days in culture. FIGS. 34A and 34B present the results of the ATCC27294 isolate, and FIGS. 35A and 35B present the results of the 571/573-BAL isolate.

Figure 35B:
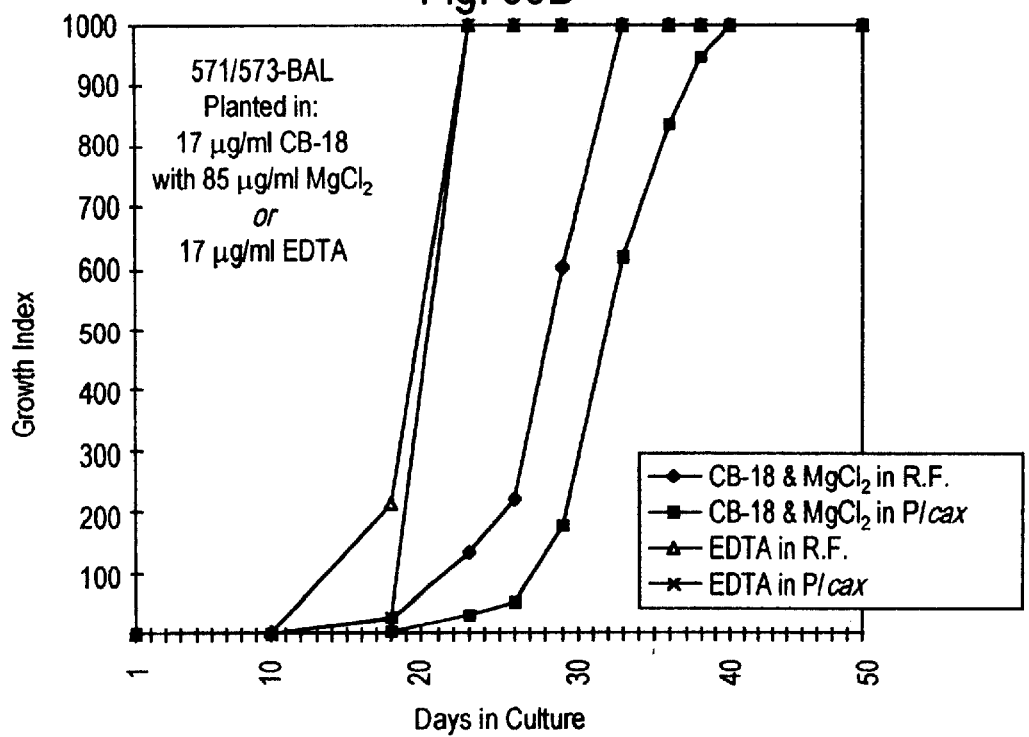

EDTA had no effect on growth characteristics of either isolate at the concentration used (FIGS. 34B and 35B). The concentration of EDTA used in these experiments was almost 22-fold lower than that used by Rastogi, N. et al., *Antimicrob. Agents Chemo.* 34:759–764 (1990) (372 µg/ml vs. 17 µg/ml).

The most interesting aspect of these experiments was the CB-18/$MgCl_2$ combination. The hypothesis behind this arm of the experiment was that if CB-18 was able to chelate $MgCl_2$, then perhaps the action of CB-18 would be neutralized by this interaction (to some degree). Whereas the ATCC 27294 isolate was unaffected by CB-18 alone (FIG. 34A: i.e., in the absence of $MgCl_2$), the 571/573-BAL isolate was suppressed by CB-18 alone (FIG. 35A). Addition of a five-fold molar excess of $MgCl_2$ showed no improvement in the growth character of 571/573-BAL (FIG. 35B). Neither ATCC 27294 nor 571/573-BAL showed an exacerbated delay in the presence of P/cax alone; however, P/cax in the presence of CB-18 was again seen to be synergistically deleterious, more so with the 571/573-BAL isolate (FIGS. 34A and 35A). Addition of $MgCl_2$ to the CB-18/P-cax combination seemed to alleviate, to some degree, the detrimental effects of the CB-18/P-cax combination (FIGS. 34B and 35B), especially the CB-18/P-cax effect on 571/573-BAL. If $MgCl_2$ does not alleviate the CB-18 effect in the absence of P-cax, but $MgCl_2$ diminishes susceptibility in the presence of P-cax, then $MgCl_2$ must be interfering with the action of P-cax. Since ceftriaxone (cax) is sold as the disodium salt, the antibiotic has a net negative charge (i.e., −2) and would be expected to interact with $MgCl_2$.

Tsubone K., *Jour. Pharm. Sci.* 80:1051–1054 (1991) has shown that in general there is little or no correlation between the chelating activity of different phosphobetaines and antimicrobial activity. This is consistent with the observation that the CB-18 effect is not a consequence of chelating metal ions.

Example 8

Mycobacterial Susceptibility Testing and the CB-18 Effect

There are a variety of methods for susceptibility testing. The standard methods currently in use include: (a) disk diffusion tests, (b) broth microdilution, (c) agar gradient, and (d) rapid automated instrument methods. In these methods the concentration of the drug(s) is varied and growth characteristics described. The inoculum size is know to substantially affect the results of susceptibility testing.

Contemporary susceptibility testing in mycobacteriology follows the 1% proportion method as described by Vestal, A. L. Centers for Disease Control, [Dept. Of Health, Education and Welfare publication no. (CDC) 76-8230] pp.97–115 (1975). This is characterized by diluting the control one hundred fold (100x) and comparing the growth in the presence of the antituberculin with the control. If 1% or more of the inoculum is resistant to the drug then the growth of the isolate under investigation will be equal to or greater than the control. If the isolate is susceptible, or if less than 1% of the inoculum is resistant, then the growth will be less than that of the control.

The gold standards in tuberculosis susceptibility testing are the BACTEC® S.I.R.E or BACTECO® PZA tests (Becton Dickinson, Cockeysville, Md.). This is an automated broth method (Snider, D. E., et al, *Am. Rev. Resp. Dis.* 123:402–406 (1981); Siddiqi, S. H., et al., *Jour. Clin. Micro.* 13:908–912 (1981); Vincke, G., et al. *Jour. Antimicrob. Chemther.* 10:351–354 (1982); Roberts, G. D., et al., *Jour. Clin. Micro.* 18:689–696 (1983); and Tarrand, J. J., et al., *Jour. Clin. Micro.* 21:941–946 (1985)). Product labeling states that after the control growth index (GI) exceeds 30 ($GI_{t=0}$), the bottle is read the following day ($G_{t+1}$) and the difference between these two days is determined ($GI_{t+1} - GI_t = \Delta GI_{control}$). The bottles with test drugs are read on these same two days and the $\Delta GI_{drug}$ for the drug is determined in the same manner. If $\Delta GI_{control} > \Delta GI_{drug}$ then the isolate is considered sensitive. If $\Delta GI_{control} \geq \Delta GI_{drug}$ then the isolate is considered borderline. If $\Delta GI_{control} < \Delta GI_{drug}$ then the isolate is considered resistant. Heifets L. *Antimicrob. Agents Chemo.* 40:1759–1767 (1996) states that the GI in the presence of the drug should not exceed 50 during 8 days of cultivation (when the inoculum was between $10^4$ and $10^5$ cfu/ml in the drug containing bottles.)

Figure 36:
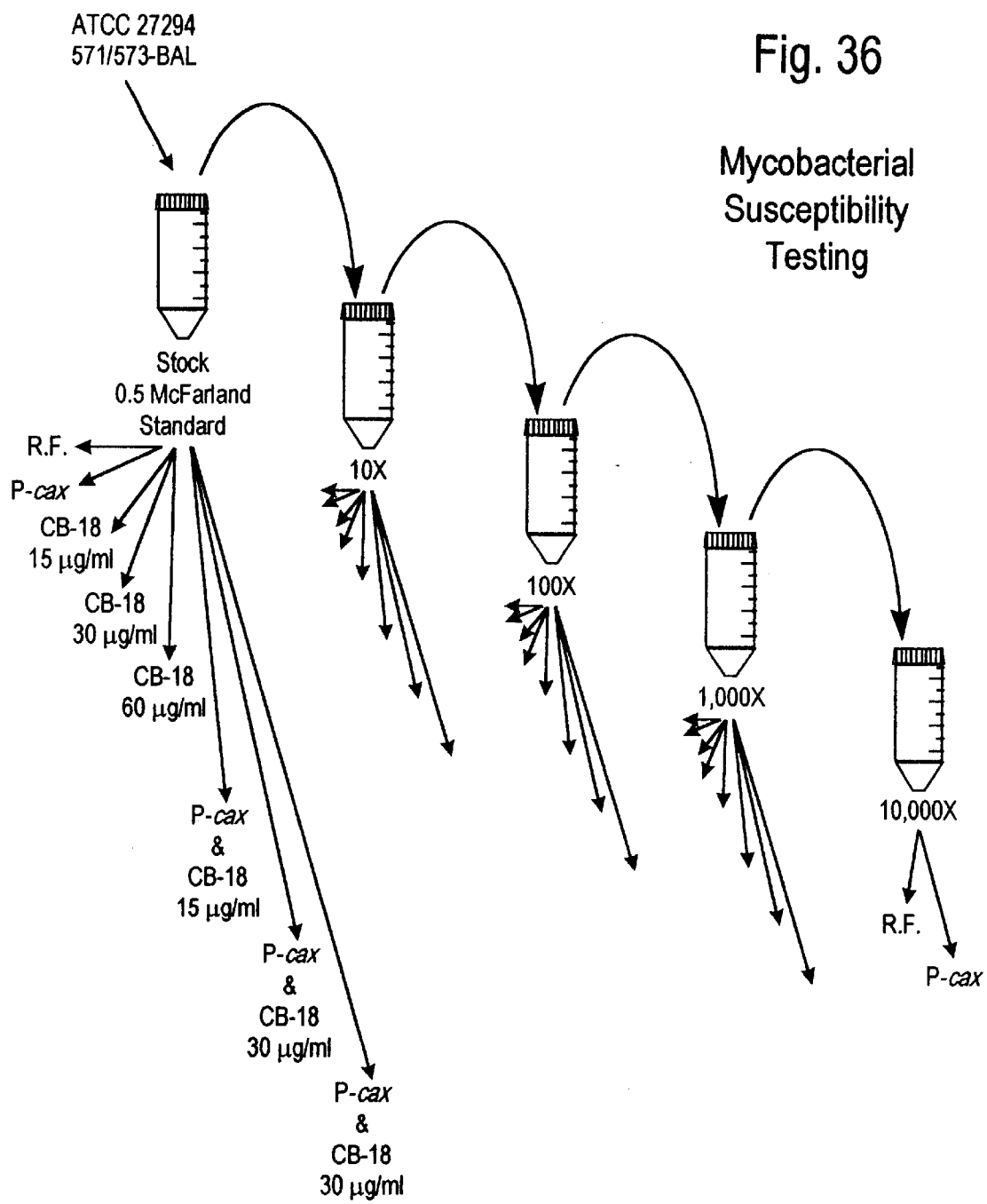
Figure 37C:
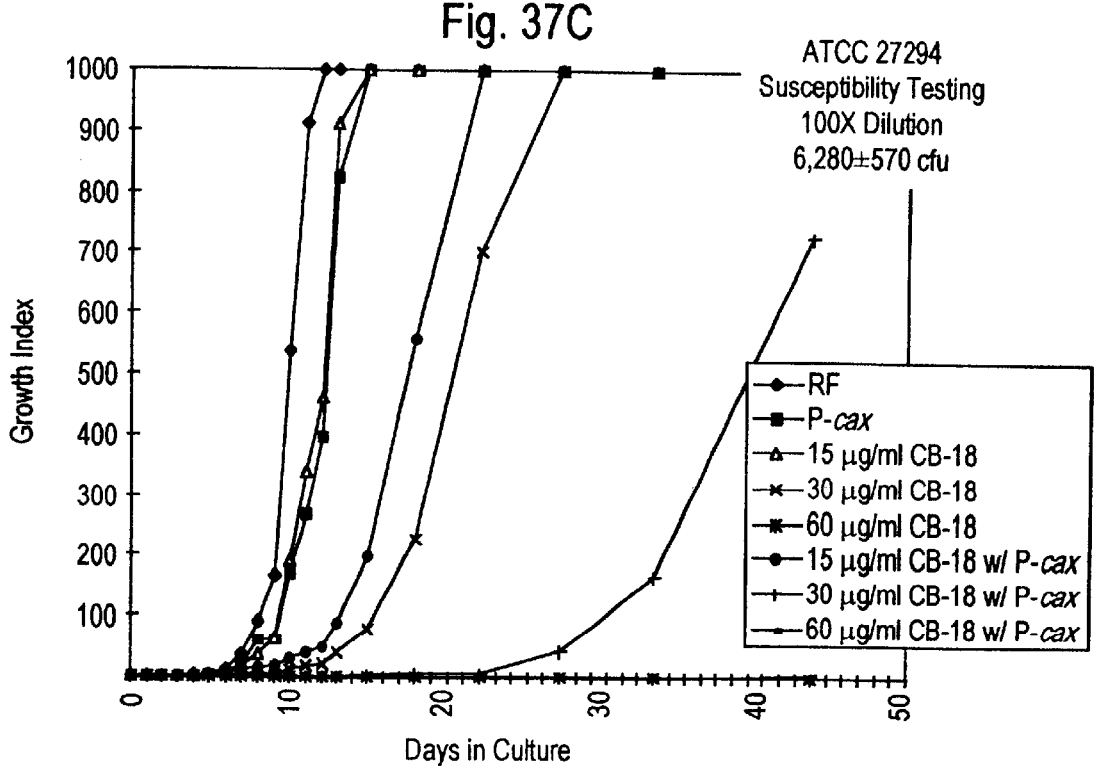
Figure 37D:
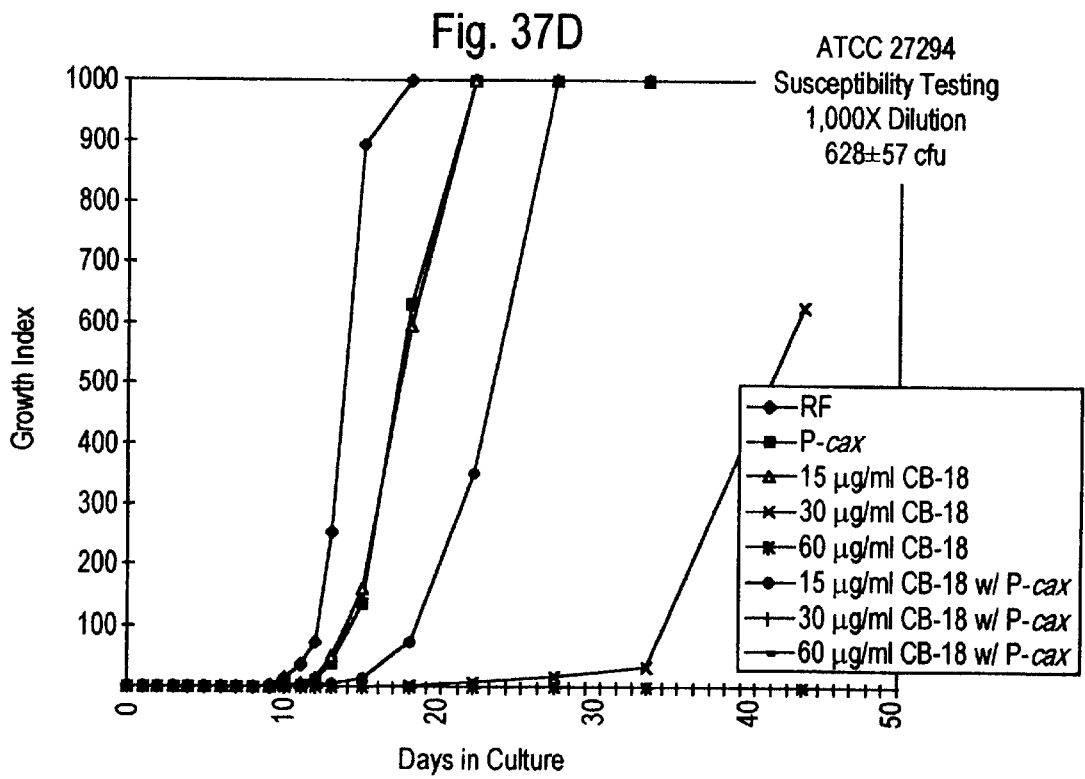

In an attempt to correlate the findings herein with the proportion method used in the S.I.R.E. test, the experiment described in FIG. 36 was performed. This experimental design was constructed to assess the correlation of the current methods of mycobacterial susceptibility testing with the results observed using betaine-like detergents. For example, the control for the MacFarland drug containing bottles would be 100x-R.F. bottle; the control for the 10x-dilution drug bottles would be the 1,000x-R.F. bottle; and the control for the 100x-dilution drug bottles would be the 10,000x-R.F. bottle.

In this experiment both the ATCC 27294 and the 571/573-BAL *M. tuberculosis* isolates were cultivated on 7H11-selective media for 2 weeks. Cells were scraped and suspended in NALC/citrate, sonicated for 60 seconds and then allowed to settle. The solution was adjusted to a 0.5 MacFarland standard and serially diluted in ten-fold steps to 10,000 fold.

Each dilution series, with the exception of the 10,000x dilution, was plated in duplicate to 7H11 for colony counts, and then inoculated in duplicate to bottles containing either R.F., PANTA containing ceftriaxone at 8 µg/ml final (P-cax), CB-18 alone at 15 µg/ml, 30 µg/ml, or 60 µg/ml, or CB-18 in combination with P-cax (CB-18 at 15 µg/ml, 30 µg/ml, or 60 µg/ml). The 10,000xdilution was plated in duplicate to 7H11 and inoculated in duplicate to bottles containing either R.F. or P-cax only.

Colony counts permitted an estimation of the 0.5 MacFarland standard for each isolate. These estimates were then used to approximate the number of cfu inoculated into the 12B bottle at each dilution. The number of cfu planted for each series is shown below. The results of the ATCC 27294 isolate are shown in FIGS. 37A–37E, and the results of the 571/573-BAL isolate are shown in FIGS. 38A–38E.

| | cfu Planted in 12B | |
|---|---|---|
| Dilution | ATCC 27294 | 571/573-BAL |
| 0.5 MacFarland | $6.28 \pm 0.57 \times 10^5$ | $1.11 \pm 0.18 \times 10^6$ |
| 10x | 62,800 ± 5,700 | 111,000 ± 17,900 |
| 100x | 6,280 ± 570 | 11,100 ± 1,790 |
| 1,000x | 628 ± 57 | 1,110 ± 179 |
| 10,000x | 63 ± 6 | 111 ± 18 |

At high input ($>1 \times 10^5$ cfu) growth curves of both the ATCC 27294 type strain and the 571/573-BAL isolate showed unusual patterns (FIGS. 37A and 38A). Even at 30 µg/ml CB-18 the isolates grew unimpeded during the first week. In 30 µg/ml CB-18 containing P-cax, however, both isolates showed unusual delays after the first week. At 60 µg/ml CB-18 (in the presence or absence of antibiotics) both isolates grew, but in an unusual fashion: both initially started to grow, but then tapered off Only the ATCC 27294 isolate ever recovered.

The BACTEC assay uses a $^{14}CO_2$ release assay. Since bottles were read on a daily basis, the $^{14}CO_2$ released as a result of metabolism would be purged from the bottles daily during the first two weeks. The difference in GI from day to day would be a reflection of new $^{14}CO_2$ produced since the last reading. Since the bottles were read on a daily basis for the first two weeks only, a positive GI would indicate growth, but a GI that did not increase exponentially would be indicative of a lack of new growth. After two weeks, the bottles were read every 3–5 days. During this time the GI would cumulative. Regardless, using the $\Delta G$ criteria discussed above, none of the conditions wherein the MacFarland standard was used as the inoculum would have described either isolate as sensitive, nor could they be differentiated. Therefore, inoculating the bottles with more than $10^5$ cfu would be counterproductive, that is to say, not recommended.

Analysis of the 10x-dilutions began to present readable results. Both isolates would have been reported as susceptible at 60 µg/ml CB-18 in the presence of P-cax. Only the 571/573-BAL isolate would have been reported as susceptible at 30 µg/ml CB-18 in the presence of P-cax.

Continuing on in the dilution series showed that at the 100x-dilution the ATCC 27294 isolate would have been deemed susceptible at 30 µg/ml CB-18 in the presence of P-cax. Using this inoculum the 571/573-BAL isolate would have been reported as susceptible at 15 µg/ml CB-18 in the presence of P-cax. Examination of the 1,000x-dilution revealed results identical to the 100x-dilution, but the growth curves of the 571/573-BAL isolate under these last two conditions (i.e., 100x and 1,000x) strongly resembled earlier curves (FIGS. 5A–15F and FIG. 11).

The conclusion to be drawn from these experiments is two fold. First, ATCC 27294 and 571/573-BAL could be differentiated, but not under all conditions. Second, the lower limit of testing would be a single organism, while at the other end, bacterial loads in excess of $10^5$ would overload the system. Input levels between 100 and $10^4$ bacilli produce readable results that permitted differentiation of isolates, and an inoculum between 10³ and 10⁴ bacilli would provide reportable results in a timely fashion.

Examnple 9

Mycobacterial Permeability and the CB-18 Effect

One possibility with regard to the mechanism whereby CB-18 exerts its effect is related to the permeability of the mycobacteria. Not intending on being held to the following hypothesis, the following explanation is provided as a means to illustrate the utility of the invention: The betaine-like detergents may be altering the permeability of the bacteria containing mycolic acid structures thereby causing said bacteria to become more susceptibe to antibiotics. Specifically, the CB-18 effect may be a result of alterations in the distribution of conformations of mycolic acid structures.

This is based primarily on the work of Yuan. Y, et al., *Proc. Natl. Acad. Sci.* 93:12828–12833 (1996). In summary, some mycobacteria have the capacity to vary the fluidity of their cell wall (Lin, J. et al., *Jour. Biol. Chem.* 271:29545–29551 (1996)). This is accomplished either by changing the length of the mycolic acids, changing the composition of the structural conformations of the mycolic acids, or both. In other words, both the length and the structural conformation of the cell wall mycolic acids influence the melting temperature of the cell wall. For example, as the length of the mycolic acids changes, or as the ratio of trans-to-cis double bonds changes, or as the number and/or conformation of cyclopropanes, hydroxylations, methylations and carbonyls changes, so does the melting temperature of the mycolic acids also change (Barry, C. E. et al., *Jour. Biol. Chem.* 271:29545–29551 (1996)). In *M. smegmatis*, for example, when the growth temperature is increased, there is a corresponding increase in the proportion of trans-olefins in the proximal double bond of the mycolic acids, and this in turn is associated with an increase in the melting temperature of these lipids (i.e., a reduction in fluidity). In *M. tuberculosis* and *M. avium* as the proportion of trans cyclopropanes in the proximal position is increased, there is a corresponding increase in the melting temperature of these mycolic acids as well.

The fluidity of the mycobacterial cell wall is thought to play a significant role in permeability, and hence resistance (Yuan, Y. et al., *Proc. Natl. Acad. Sci.* 92:6630–6634 (1995); Brennan, P .J. et al.,*Annu. Rev. Biochem.* 64:29–63 (1995)). The resistance of *M. chelonae* to cephalosporins is thought to be due exclusively to permeability (Connell, N. D. et al. In: *Tuberculosis. Pathogenesis, Protection, and Control.* Bloom, B. R ed. ASM. Press, Washington, D.C. (1994) pp.333–352). For example, Barry, C. E. et al., *Jour. Biol. Chem.* 271:29545–29551 (1996) show that as the fluidity of the *M. smegmatis* cell wall decreased (i.e. as the percentage of trans-olefins was increased), the uptake of both norfloxacin and chenodeoxycholate also decreased. Kaneda, K. et al., *Jour. Gen. Microbiol* 134:2213–2229(1988) show that in highly drug resistant rapid growers most of the proximal double bonds are trans-olefins.

Production of the various mycolic acid conformations is accomplished primarily through a series of structurally related S-adenosyl methionine (SAM) dependent enzymes. Molecular analysis has revealed that there are four structurally related genes in *M. tuberculosis* that encode methoxy mycolic acid synthases (MMAS) that are responsible for many of these modifications (Yuan, Y. et al., *Proc. Natl. Acad. Sci.* 93:12828–12833 (1996)). These four gene products (MMAS-1, MMAS-1, MMAS-3, and MMAS-4) all show strong sequence homology to the *E. coli* cyclopropane fatty acid synthase (CFAS), and the*M. leprae* and *M. tuberculosis* cyclopropane mycolic acid synthases (CMAS-1 and CMAS-2). The implication is that they all share a common mechanism. This mechanism involves SAM. and a carbonium intermediate (FIG. 39A). The different products result from the fact that the different synthases have different electron donors/acceptors at their respective active sites to yield olefins, cyclopropanes, methylations, and combinations of hydroxylations with methylations (Yuan, Y. et al., *Proc. Natl. Acad. Sci.* 93:12828–12833 (1996)).

In U.S. Pat. No. 5,610,198 Barry, C. E. et al. state that "thiatetracosanoic acids" (thiolated-fatty acid derivatives) can be used to inhibit cyclopropanation and oxygenation of mycolic acids in pathogenic mycobacteria via inhibition of these SAM-dependent reactions (FIG. 39B). Four "thiatetracosanoic acids" were tested as evidence of utility. In summary, the mechanism of inhibition for these analogs would involve their participation as substrates for the first half of the synthase's enzymatic reaction (specifically, the transfer of a methyl group from SAM.) Following catalysis, the structure formed would be a "stable transition state analog" (FIG. 39B). In essence, the compound would not be released from the active site and would act as a classic competitive inhibitor. The transition state structure resembles a betaine-like detergent. Specifically, a sulphonium-based carboxybetaine (Table 1 and FIG. 39B): sulphoniumcarboxybetaines would not require enzymatic catalysis for activation, but would directly inhibit SAM-dependent modifications.

Figure 15A:
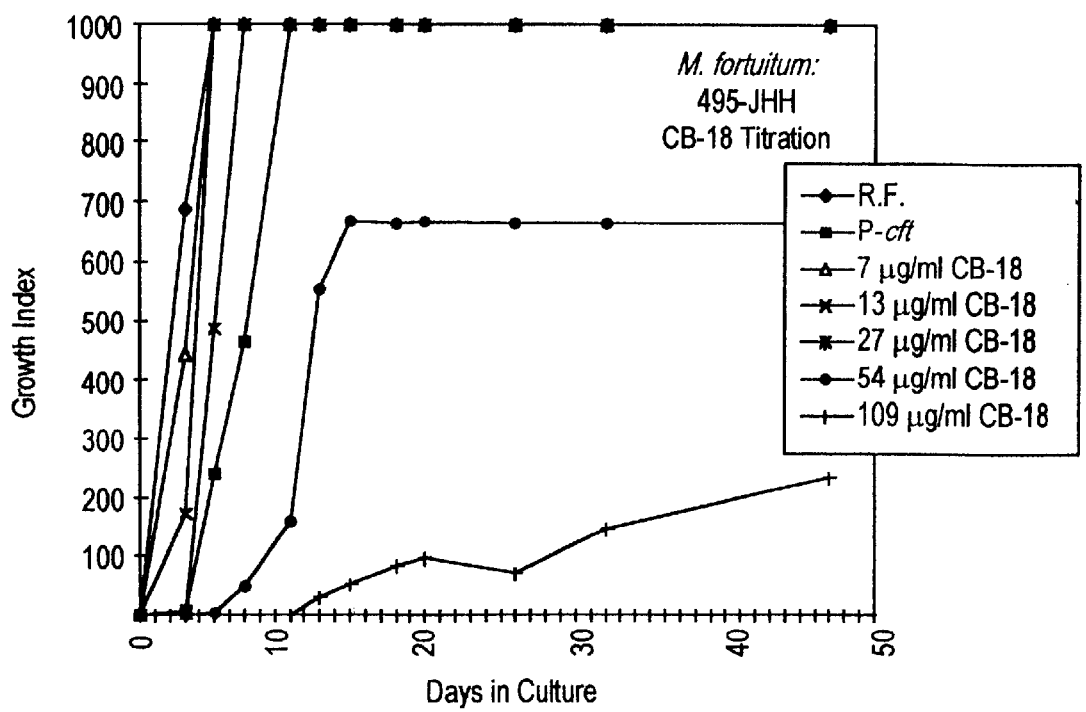
FIGS. 15A and 15B present the growth curves when the *M. fortuitum* complex isolate 495-JHH was tested using the CB-18 titration experiment presented in FIG. 9. Diamonds: R.F.; squares: P-cft; triangles: 7 µg/ml CB-18; "x": 13 µg/ml CB-18; "*" 27 µg/ml CB-18; circles: 54 µg/ml CB-18; vertical hatches: 109 µg/ml CB-18.
Figure 15B:
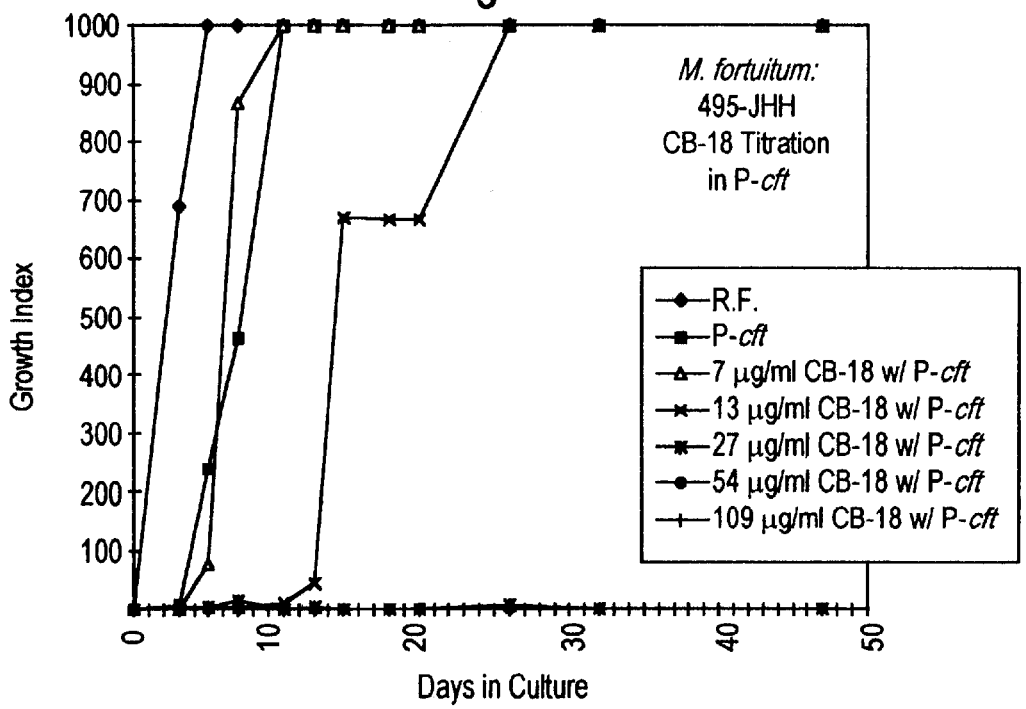

In U.S. Pat. No. 5,610,198 Barry, C. E. et al. also state that these thiatetracosanoic acids were ineffective against saprophytic mycobacteria such as *M. smegmatis*. In contrast to the disclosure of Barry et al. (U.S. Pat. No. 5,610,198), the invention described herein teaches that such saprophytic mycobacteria are susceptible to the action of betaine-like detergents: *M. fortuitum* showed the greatest degree of synergy between CB-18 and the cephalosporin tested. For example, the clinical isolate 495-JHH was unaffected by the presence of cefoxitin, and was able to grow to some degree in the presence of CB-18 at 109 µg/ml (FIG. 15). However, when cefoxitin was combined with as little as 13 µg/ml CB-18 growth was affected to some degree, and completely inhibited at 27 µg/ml CB-18.

Figure 14A:
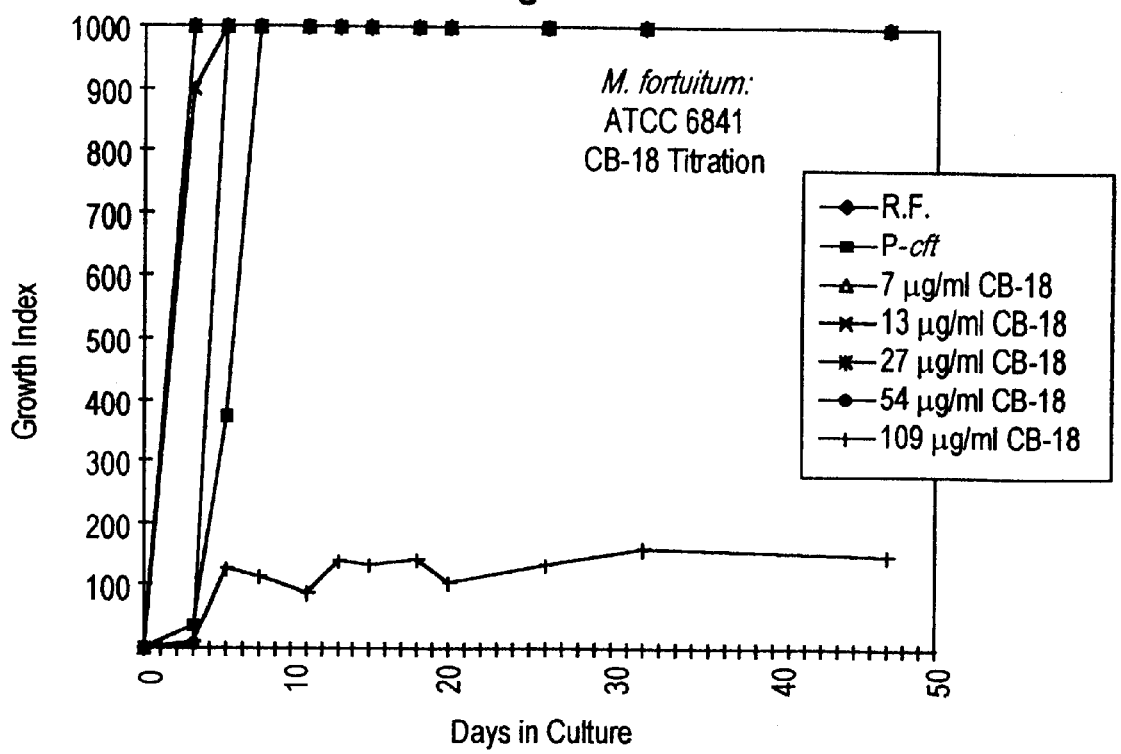
FIGS. 14A and 14B present the growth curves when the *M. fortuitum* isolate ATCC 6841 was tested using the CB-18 titration experiment presented in FIG. 9. Diamonds: R.F.; squares: P-cft; triangles: 7 µg/ml CB-18; "x": 13 µg/ml CB-18; "*" 27 µg/ml CB-18; circles: 54 µg/ml CB-18; vertical hatches: 109 µg/ml CB-18.
Figure 14B:
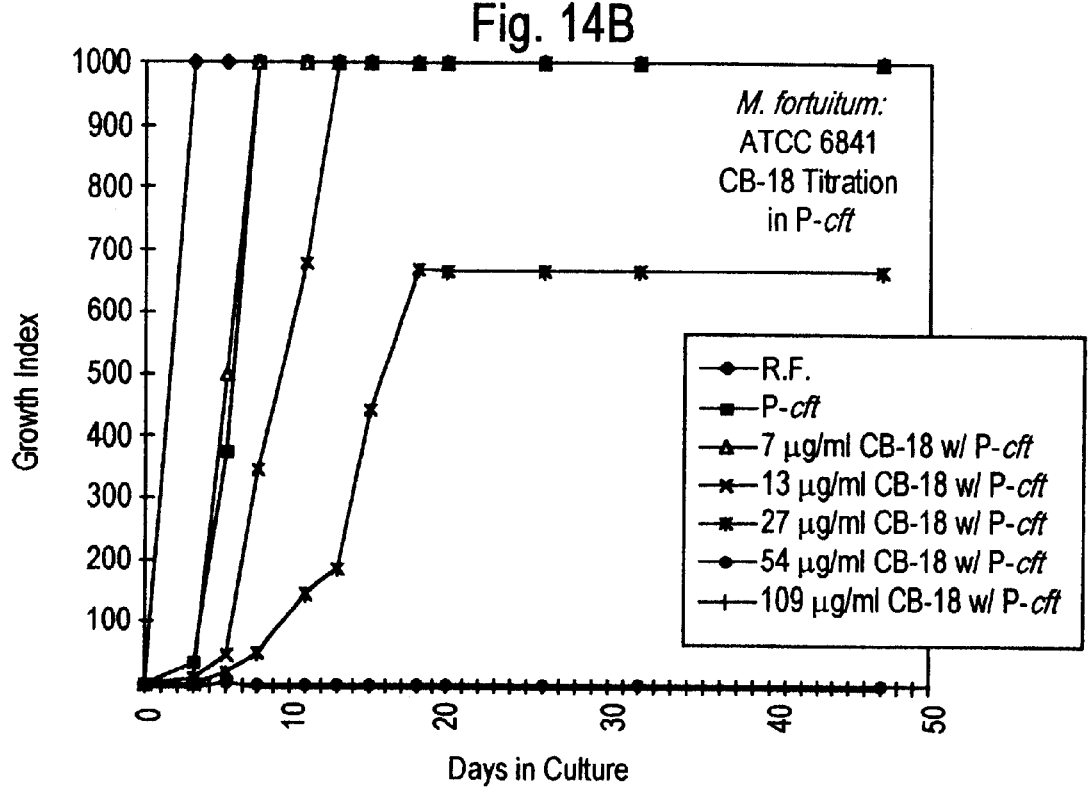

If betaine-like detergents were affecting the permeability of the mycobacteria at the level of cell wall fluidity, through effects on SAM-dependent enzymes, the results of FIGS. 14 and 15 would actually be the expected result. The basis for this expectation stems from the similarity of *M. fortuitum* and *M. smegmatis*. Dobson, G. et al., In: Goodfellow, M. et al., eds. *Chemical Methods in Bacterial Systematics,* Academic Press, London (1985) pp.237–265 and Brennan, P. J. et al.,*Annu. Rev. Biochem.* 64:29–63 (1995) summarize the mycolic acid distribution of the different mycobacterial species and show that the rapid growers (e.g., *M. fortuitum, M. chelonae, M. smegmatis*, etc.) share similar mycolic acid distributions: the primary mycolic acid is the α' type. Liu, J. et al.,*Jour. Biol Chem.* 271:29545–29551 (1996) report that as the growth temperature is increased, the major mycolates in *M. smegmatis* become the $\alpha_1$ and $\alpha_2$ types. The $\alpha_1$ and $\alpha_2$ types are both longer than the α' type (α'=$C_{64}$, and $\alpha_1$ and $\alpha_2$=$C_{78-79}$), and the $\alpha_2$ type posses the proximal trans-olefin, the structure conferring the lowest fluidity, or the least permeable cell wall. The $\alpha_2$ type dominates at the higher temperature (the structures of the α', $\alpha_1$, and $\alpha_2$ mycolic acids are all shown in George, K., et al. *Jour. Biol. Chem.* 270:27292–27298 (1995)).

The significance of these observations becomes apparent when the mechanism proposed by Yuan, Y. et al., *Proc. Natl. Acad. Sci.* 93:12828–12833 (1996) for these SAM-dependent enzymes is reviewed (FIG. 39A): the trans-olefin is the product of a SAM-dependent methylation, and the fluidity is inversely proportional to trans-olefin content. Addition of CB-18 to the culture media might inhibit the formation of the trans-olefin, thereby increasing the fluidity of the cell wall, thus increasing cellular permeability to antibiotics. Once permeability was alleviated, antibiotics could more readily enter the cell. The efficacy of a given antibiotic would then be dependent on the nature of the isolate itself (i.e., the interaction of the antibiotic and the site of the drugs action in the isolate under investigation). The net result would be the observed CB-18 effect.

If SAM-dependent modifications offatty acids were a common mechanism whereby mycobacteria regulated the fluidity of their cell walls, as suggested by Liu, J. et al., *Jour. Biol. Chem.* 271:29545–29551 (1996), then the betaine-like detergents would be expected affect a broad range ofmycolic acid structures, such as, for example, corynemycolates (Durand, E. et al., *Eur. Jour. Biochem.* 93:103–112 (1979)), and hence norcardiomycolates.

While the forgoing discussion rationalizes the extreme synergy observed between cefoxitin and CB-18 in *M. fortuitum* (Table 7), it does not explain the extreme sensitivity of *M. tuberculosis* to the betaine-like detergents (Table 8). For example, growth of the *M. tuberculosis* type strain ATCC 27294 in the absence of antibiotics was impacted to a minor degree at 27 μg/ml CB-18, and completely shut down at 54 μg/ml CB-18. In the presence of antibiotics, growth was affected to a minor degree at 13 μg/ml CB-18, and nonexistent at 27 tg/ml CB-18 (FIG. 10). Growth of the 571/573-BAL *M. tuberculosis* isolate in the absence of antibiotics was impacted to a minor degree at 13 μg/ml CB-18, and completely shut down at 27 μg/ml CB-18. In the presence of antibiotics, growth of this isolate was absent at 13 μg/ml CB-18 (FIG. 11). In contrast to the *M. fortuitum* testing (FIGS. 14 and 15), *M. tuberculosis* was much more sensitive to the betaine-like detergents by themselves.

Apparently, the slow growing mycobacteria, such as *M. tuberculosis,* do not regulate the fluidity of the cell wall as seen in rapidly growing mycobacteria such as *M. smegmatis* (Liu, J. et al., *Jour. Biol. Chem.* 271:29545–29551 (1996)). For example, Takayama, K. et al., *Am. Rev. Respir. Dis.* 118:113–117 (1978) show the extreme sensitivity of *M. tuberculosis* to growth temperatures: at temperatures just several degrees from optimal, mycolic acid synthesis ceases and *M. tuberculosis* is unable to survive. The sensitivity of *M. tuberculosis* to the betaine-like detergents of the invention, or the thiatetracosanoic acids of Barry, C. E. et al. (U.S. Pat. No. 5,610,198), in lieu of antibiotics, might be a consequence of the sensitivity of *M. tuberculosis* isolates to generic interferences of mycolic acid synthesis. For example, while inhibiting cyclopropanation or oxygenation of mycolic acids would effect permeability and, therefore, susceptibility; interference of mycolic acid synthesis in general would have lethal consequences. Induced susceptibility to antibiotics would be observed only at low CB-18 concentrations in the slow growing mycobacteria.

If the site ofaction of the betaine-like detergents were the SAM-dependent synthases in bacteria containing mycolic acid structures, then one would expect to inhibit modifications to the fatty acids (e.g., mycolic acids), and in some instances cause the cessation ofmycolic acid synthesis. Therefore, the betaine-like detergents would only play an ancillary therapeutic role in treatment of rapid growers, but would be expected to have both ancillary and lethal consequences on many slow growing mycobacteria. For example, while the permeability of slow growing mycobacteria incubated with SAM-dependent inhibitors would manifest an induced susceptibility to antibiotics, the deleterious impact on survival due to interference of mycolic acid synthesis would also be a significant, possibly dominating, factor. Rapid growing mycobacteria on the other hand would generally be unaffected by the presence of the betaine-like detergents in isolation, but would show dramatic synergy with antibiotics due to inhibition of the mechanism regulating fluidity.

Barry et al. (U.S. Pat. No. 5,610,198) also state that only anti-mycobacterial drugs, such as isoniazid, ethambutol, streptomycin, rifampin, dapsone, rifabutin, clarithromycin, ciprofloxacin, clofazamine, azithromycin, ethionamide, amikacin or resorcinomycin A, can be used in conjunction with the thiatetracosanoic acids. The invention described herein, and exemplified in Examples 5 and 6, show that in the presence of CB-18 some aspect of bacterial physiology is altered, presumably permeability ala the mechanism discussed herein, to induce susceptibility to a broad range of antibiotics. Therefore, according to the invention, the betaine susceptibility test would utilize the CB-18 effect in conjunction with a variety of antibiotics to identify the natural susceptibility of an isolate being tested, thereby guiding the physician more effectively.

The betaine-like detergents of the invention have significant advantages over the thiatetracosanoic acids of Barry et al. (U.S. Pat. No. 5,610,198). For example, the thiatetracosanoic acids would be extremely insoluble. In other words, the Krafft temperatures of these reagents would be far above the physiological norm. Delivery at the appropriate concentration would be all but impossible. In contrast, the betaine-like detergents used in the invention herein are, for the most part, soluble. For example, Hodge, D. et al., *Langmuir* 7:878–884 (1991) has synthesized a $C_{20}$-carboxyhexylbetaine with a Krafft point of 20° C.

While CB-18 was used herein to characterize the CB-18 effect, it is clear that other betaines are useful in this regard. For example, based upon structure, an alkylsulphoniumcarboxybetaine would be the ideal compound to inhibit mycolic acid modification. The alkylsulphoniumcarboxybetaine could be synthesized by a modified method of Zimmer, R. E. (U.S. Pat. No. 3,560,393). For example, the octadecyl mercaptan could be methylated and the $R_1$—S—$R_2$ purified for modification with the halide ester of the appropriate type (FIG. 39C). Purification by cation exchange chromatography would remove the ester to create the acid.

Example 10

Betaine Susceptibility Panels for Screening Clinical Isolates

Examples 5 and 6 showed that different clinical isolates behaved differently in the context of the assay wherein a single betaine was matched with a number of different antibiotics. Example 6 showed that one clinical isolate behaved differently in the assay wherein different detergents were combined with the P/cax antibiotic formulation. It follows that a betaine susceptibility panel could be developed and refined for the purpose of susceptibility testing.

Such a panel would cross reference different betaines with different antibiotics. The example described herein shows how such a panel could be designed and used for susceptibility testing. This example is provided as a means to illustrate how such a panel could be developed and is not intended to be restrictive of the invention.

Using different betaines, five for example, that give a broad spectrum of results with respect to different clinical isolates, in conjunction with several different antibiotics, five for example, that give a broad spectrum of results with respect to different clinical isolates, comprise the betaine susceptibility panel. For example, define the 5 antibiotics $\alpha$-1, $\alpha$-2, $\alpha$-3, $\alpha$-4, and $\alpha$-5, and define the five betaines as $\beta$-1, $\beta$-2, $\beta$-3, $\beta$-4, and $\beta$-5. The five different betaine-like detergents conditions can be the same detergent at different concentrations, or combinations thereof Similarly, the five different antibiotics can be the same antibiotic at different concentrations, or combinations thereof Table 11 shows how these five betaines can be matched with these five antibiotics to identify the most potent betaine-antibiotic combination(s).

TABLE 11

Betaine Susceptibility Panel

| Antibiotic | Betaine-Like Detergents | | | | | |
|---|---|---|---|---|---|---|
| | $\phi$ | $\beta$-1 | $\beta$-2 | $\beta$-3 | $\beta$-4 | $\beta$-5 |
| $\phi$ | — | $\beta$-1 | $\beta$-2 | $\beta$-3 | $\beta$-4 | $\beta$-5 |
| $\alpha$-1 | $\alpha$-1 | $\alpha$-1/$\beta$-1 | $\alpha$-1/$\beta$-2 | $\alpha$-1/$\beta$-3 | $\alpha$-1/$\beta$-4 | $\alpha$-1/$\beta$-5 |
| $\alpha$-2 | $\alpha$-2 | $\alpha$-2/$\beta$-1 | $\alpha$-2/$\beta$-2 | $\alpha$-2/$\beta$-3 | $\alpha$-2/$\beta$-4 | $\alpha$-2/$\beta$-5 |
| $\alpha$-3 | $\alpha$-3 | $\alpha$-3/$\beta$-1 | $\alpha$-3/$\beta$-2 | $\alpha$-3/$\beta$-3 | $\alpha$-3/$\beta$-4 | $\alpha$-3/$\beta$-5 |
| $\alpha$-4 | $\alpha$-4 | $\alpha$-4/$\beta$-1 | $\alpha$-4/$\beta$-2 | $\alpha$-4/$\beta$-3 | $\alpha$-4/$\beta$-4 | $\alpha$-4/$\beta$-5 |
| $\alpha$-5 | $\alpha$-5 | $\alpha$-5/$\beta$-1 | $\alpha$-5/$\beta$-2 | $\alpha$-5/$\beta$-3 | $\alpha$-5/$\beta$-4 | $\alpha$-5/$\beta$-5 |

Betaine Susceptibility Panels

Use of the betaine panel shown in Table 11 is described below.
(1) Grow the clinical isolate in question in liquid culture (BACTEC 12B, for example) or on solid media (7H11 slants, for example).
(2) Set up the betaine panel. The panel could be set up in a microtiter plate or individual bottles, for example. The betaines and antibiotics could either be lyophilized in the appropriate well or bottle and then reconstituted with growth media, or mixed as individual solutions of antibiotic, betaine, and broth to accomplish the same end. The former would be preferred.
(3) Make a bacterial stock solution in such a manner that the appropriate number of cells (e.g., 100 to 10,000 cfu) are added to each well or tube. Such a stock could be adjusted to the appropriate number of cells by generating a suspension based on the use of MacFarland standards as understood in the art, and then diluting this to the desired endpoint.
(4) Incubate the plate, tubes or bottles for predetermined time(s) and check growth using the method of choice. Detection of growth could be based on $^{14}$C-release (e.g., BACTEC 12B: Becton-Dickinson, Cockeysville, Md.), $O_2$ consumption (ESP Myco System II™, DIFCO Laboratories, Detroit. Mich.), pH changes (MB/BacT®, Organon Teknika, Durham, N.C.), or other standard techniques know in the art, such as tubidity.

Such a panel could also be used to classify clinical isolates. For example, if the mechanism(s) whereby betaines exert their effect to enhance antimicrobial therapy were known, then such information would be informative with respect to enhancing a therapeutic regime, related or unrelated to a betaine-antibiotic combination. Therefore, there are two distinct endpoints. In the first endpoint the betaine susceptibility panel is used as a means to classify the clinical isolate. Such a classification being designed to more effectively prescribe a therapeutic regime unrelated to the use of a betaine as a therapeutic adjuvant. In the second endpoint, the goal of betaine susceptibility testing would be to prescribe the combination of a specific betaine-like detergent(s) with a specific antibiotic(s) (as described in the next Example (Example 11).

Example 11

Use of Betaine-Like Detergents as Therapeutic Adjuvants

As suggested in Example 10, there are two endpoints to susceptibility testing. In one endpoint, the betaine panel is used as a classic susceptibility screen for the purpose of defining the most efficacious therapeutic regime to eliminate the infection, most obviously one of the antibiotics in the panel ofExample 10. In this end point, the therapeutic regime does not include the use of the betaine-like detergent(s) as a therapeutic adjuvant(s).

In the other end point, the therapeutic regime is based on one or more of the antibiotic:betaine-like detergent combinations included in the panel. In this endpoint, the knowledge derived from the results of the panel described in Example 10 are, for example, the end point in and ofitself: this information points the artisan to a specific combination of antibiotic(s) and betaine-like detergent(s). In this instance the betaine must be interfaced with the patient. The purpose of this example is to describe how the betaine(s) is used as a therapeutic adjuvant. This example is provided as a means to illustrate how such a panel could be developed and is not intended to be restrictive of the invention.

The examples and data described herein show that the betaine-like detergents, while having limited antimicrobial efficacy when used in isolation, are most efficacious when used in combination with one or more antibiotics. In order for any antimicrobial therapy to be effective the antibiotic(s) must be delivered to the microorganism. Delivery of the antibiotic per se in the methods of the invention can be via standard methods known in the art for delivery of the antibiotic(s). The purpose ofthis Example is to describe how the betaine(s) might be delivered to the infectious agent. Thus, in a patient receiving the adjuvant treatment according to the method of the invention, if desired, the betaine(s) can be delivered by one method and the antibiotic(s) by another.

Standard methods of delivery of the betaine-like detergent(s) are known in the art and include ingestion, intramuscular injection, intravenous drip, injection at the site of infection, or inhalation. However, the betaine-like detergents are surface active agents that are likely to be not well tolerated by ingestion or intramuscular injection. For example, ingestion oflarge quantities ofa betaine-like detergent would probably result in gastrointestinal distress, and injection of large quantities of betaine would probably result in solubilization of cellular structure, causing irritation at the injection site. When intravenous drip is used, care must be taken with respect to the concentration of the betaine in the blood. While addition of the betaine above the critical micellar concentration (CMC) might be feasible, complications might result if the overall blood level rose above the CMC due to solubilization of blood components. Injection at the site of infection might also be a viable means of delivery;

unfortunately, this may be possible only in rare instances, such as tuberculous lesions or granulotomatous lesions caused by disseminated MAC disease, for example. In a preferred embodiment, the betaine(s) is delivered by inhalation.

Tuberculosis is primarily a respiratory infection. Tuberculous lesions typically appear in 2-carboxy-N-hexadecyl-N,N-dimethyl-benzenemethanaminium, inner salt (CAS®No. 71695-35-7),
tallow glycinate (CAS®No. 70750-46-8),
soyamidopropyl carboxymethylbetaine, and
babassuamidopropyl carboxymethylbetaine.

11. The method of claim 10, wherein said carboxybetaine is N-(3-carboxypropyl)-N,N-dimethyl-1-octadecanaminium, inner salt (CB-18) (CAS®No. 78195-27-4).

12. The method of any one of claims 1–11, wherein said composition comprises two or more betaine-like detergents.

13. The method of claim 1, wherein said antibiotic is a member of a class selected from the group consisting of a β-lactam antibiotic, an aminoglycoside, an aminocyclitol, a quinolone, a tetracycline, a macrolide, a lincosamide, a glycopeptide, a lipopeptide, a polypeptide antibiotic, a sulfonamide, trimethoprim, chloramphenicol, isoniazid, a nitroimidazole, a rifampicin, a nitrofuran, methenamine, and mupirocin.

14. The method of claim 13, wherein said antibiotic is said β-lactam antibiotic.

15. The method of claim 14, wherein said β-lactam antibiotic is selected from the group consisting of penicillin, cephalosporin, monobactam and carbapenem antibiotics.

16. The method of claim 15, wherein said β-lactam antibiotic is said penicillin.

17. The method of claim 16, wherein said penicillin is selected from the group consisting of azlocillin, methicillin, nafcillin, cloxacillin, dicloxacillin, oxacillin, ampicillin, bacampicillin, carbenicillin, ticarcillin, rmiezlocillin and piperacillin.

18. The method of claim 15, wherein said class of antibiotic is said cephalosporin.

19. The method of claim 18, wherein said cephalosporin is selected from the group consisting of cefoxitin, cefoperazone, ceftazidime, ceftriaxone, cefadroxil, cefazolin, cephalexin, cephaloridine, cephalothin, cephapirin, cephradine, cefaclor, cefamandole, cefonicid, ceforanide, cefprozil, cefuroxime, loracarbef, cefmetazole, cefotetan, cefixime, cefotaxime, cefpodoxime, and ceftizoxime.

20. The method of claim 19, wherein said cephalosporin is ceftriaxone.

21. The method of claim 15, wherein said β-lactam antibiotic is said monobactam.

22. The method of claim 21, wherein said monobactam is aztreonam.

23. The method of claim 15, wherein said β-lactam antibiotic is said carbapenem.

24. The method of claim 23, wherein said carbapenem is selected from the group consisting of imipenem, meropenem, panipenem, and biapenem.

25. The method of claim 24, wherein said carbapenem is imipenem.

26. The method of any one of claims 13–25, wherein said composition further comprises a β-lactamase inhibitor.

27. The method of claim 26, wherein said β-lactamase inhibitor is selected from the group consisting of clavulanic acid, sulbactam, and tazobactam.

28. The method of claim 13, wherein said antibiotic is said aminoglycoside or said aminocyclitol.

29. The method of claim 28, wherein said aminoglycoside or aminocyclitol is selected from the group consisting of streptomycin, kanamycin, gentamicin, tobramycin, amikacin, sisomicin, netilmicin, neomycin, framycetin and paromomycin.

30. The method of claim 13, wherein said antibiotic is said quinolone.

31. The method of claim 30, wherein said quinolone is selected from the group consisting of naladixic acid, oxolinic acid, cinoxacin, flumequine, miloxacin, rosoxacin, pipemidic acid, norfloxacin, enoxacin, ciprofloxacin, ofloxacin, lomefloxacin, temafloxacin, fleroxacin, pefloxacin, amifloxacin, sparfloxacin, levofloxacin, clinafloxacin.

32. The method of claim 13, wherein said antibiotic is said tetracycline.

33. The method of claim 13, wherein said antibiotic is said macrolide.

34. The method of claim 33, wherein said macrolide is selected from the group consisting of erthromycin, oleandomycin, spiramycin, josamycin, rosaramicin, clarithromycin, azithromycin, dirithromycin, roxithromycin, flurithromycin, and rokitamycin.

35. The method of claim 13, wherein said antibiotic is said lincosamide.

36. The method of claim 13, wherein said antibiotic is said glycopeptide.

37. The method of claim 13, wherein said antibiotic is said lipopeptide.

38. The method of claim 13, wherein said antibiotic is said polypeptide antibiotic.

39. The method of claim 13, wherein said antibiotic is said sulfonamide.

40. The method of claim 13, wherein said antibiotic is said trimethoprim.

41. The method of claim 13, wherein said composition comprises two or more antibiotics.

42. The method of claim 41, wherein said antibiotics are a sulfonamide and trimethoprim.

43. The method of claim 42, wherein said sulfonamide is sulfamethoxazole.

44. The method of claim 13, wherein said antibiotic is chloramphenicol.

45. The method of claim 13, wherein said antibiotic is isoniazid.

46. The method of claim 13, wherein said antibiotic is anitroimidazole.

47. The method of claim 13, wherein said antibiotic is a nitrofuran.

48. The method of claim 13, wherein said antibiotic is a methenamine.

49. The method of claim 13, wherein said antibiotic is mupirocin.

50. The method of claim 1 wherein said antibiotic is selected the group consisting of amikacin, azithromycin, any β-lactam in combination with any of the β-lactamase inhibitors, capreomycin, cefmetazole, cefoxitin, ciprofloxacin, clarithromycin, clofazamine, cycloserine, dapsone, erythromycin, ethambutol, ethionamide, imipenem, isoniazid, kanamycin, minocycline, ofloxacin, para-amino salicylic acid, prothionamide, pyrazinamide, rifampin, rifabutin, sparfloxacin, sulfamethoxazole with trimethoprim, streptomycin, tetracycline, thiacetazole and viomycil.

51. The method of claim 13, wherein said antibiotic is a rifampicin.

52. The method of claim 51, wherein said rifampicin is selected from the group consisting of rifampin, rifamycin SV, rifamycin B (rifamide), and rifabutin.

53. The method of claim 52, wherein said rifampicin is rifampin.

54. The method of claim 52, wherein said rifampicin is rifabutin.

55. The method of claim 1, wherein said microorganism is a Mycobacterium.

56. The method of claim 55, wherein said Mycobacterium is selected from the group consisting of *M. agri, M. abscessus, M. acetamidolyticum, M. africanum, M. aichiense, M. asiaticum, M. aurum, M. austroafricanum, M. avium, M. bovis, M. bovis* (BCG), *M. chelonae, M. chitae, M. chubuense, M. cookii, M. diernhoferi, M. duvalii, M. fallax, M. farcinogenes, M. flavescens, M. fortuitum, M. gadium, M. gastri, M. gilvum, M. gordonae, M. haemophilum, M. intracellulare, M. kansasii, M. komossense, M. leprae, M. lepraemurium, M. marinum, M. malmoense, M. microti, M. moriokaense, M. neoaurum, M. nonchromogenicum, M. obuense, M. parafortuitum, M. paratuberculosis, M. peregrinum, M. phlei, M. porcinum, M. poriferae, M. pulveris, M. rhodesiae, M. scrofulaceum, M. senegalense, M. shimoidei, M. simiae, M. smegmatis, M. sphagni, M. szulgai, M. terrae, M. thermoresistible, M. tokaiense, M. triviale, M. tuberculosis, M. ulcerans, M. vaccae, M. xenopi.*

57. The method of claim 56, wherein said Mycobacterium is a member of the *Mycobacterium tuberculosis* complex (MTB).

58. The method of claim 57, wherein said microorganism is said *M. tuberculosis.*

59. The method of claim 56, wherein said microorganism is a member of the *Mycobacterium avium* (MAC) complex.

60. The method of claim 56, wherein said microorganism is a member of the MAIS group.

61. The method of claim 56, wherein said microorganism is said *M. ulcerans.*

62. The method of claim 56, wherein said microorganism is said *M. kansasii.*

63. The method of claim 56, wherein said microorganism is said *M. chelonae.*

64. The method of claim 57, wherein said microorganism is said *M. fortuitumn.*

* * * * *